United States Patent [19]
Campbell et al.

[11] Patent Number: 5,405,769
[45] Date of Patent: Apr. 11, 1995

[54] CONSTRUCTION OF THERMOSTABLE MUTANTS OF A LOW MOLECULAR MASS XYLANASE

[75] Inventors: Robert L. Campbell, Orleans; David R. Rose, Markham; Wing L. Sung, Gloucester; Makoto Yaguchi, Ottawa; Warren W. Wakarchuk, Gloucester, all of Canada

[73] Assignee: National Research Council of Canada, Ottawa, Canada

[21] Appl. No.: 44,621

[22] Filed: Apr. 8, 1993

[51] Int. Cl.$^6$ .............................................. C12N 9/24
[52] U.S. Cl. ................................. 435/200; 435/209; 435/188
[58] Field of Search .................. 435/200, 209, 188

[56] References Cited

U.S. PATENT DOCUMENTS 4,931,392  6/1990  Rehner et al. .................. 435/188
4,966,850  10/1990  Yu et al. ........................ 435/200

OTHER PUBLICATIONS

Henrissat, B., et al. (1993) Biochem. J. 293, 781–788.
Gebler, J., et al. (1992) J. Biol. Chem 266, 12559–12561.
Role of Tyrosine-80 in the Stability of Kanamycin Nucleotidyltransferase Analyzed by Site-directed Mutagensis, M. Matsumura, S. Yahanda, S. Yasumura, K. Yutani and S. Aiba, Eur. J. Biochem (1988), 171, 715–720.
Engineering Thermostability in Substilisin BPN' by In Vitro Mutagensis, M. Rollence, D. Filpula, M. Pantoliano, and P. Bryan, (1988) CRC Crit. Rev. Biotech, 8(3), 217–224.
An Engineered Disulfide Bond in Dihydrofolate Reductase, J. Villafranca, E. Howell, S. Oatley, N. Xuong and J. Kraut, Biochemistry (1987), 26, 2182–2189.
Role of Disulfide Cross-Link in the Conformational Stability of a Thermostable Xylanase, U. Tatu, S. Murthy and P. Vithayathil, Journal of Protein Chemistry, vol. 9, No. 5, (1990), pp. 641–646.
Protein Engineering, Editors, Dale L. Oxender and C. Fred Fox, "Some Design Principles for Structurally Stable Proteins", D. Ohlendorf, B. Finzel, P. Weber and F. Salemme, (1987), pp. 165–173.
Protein Engineering of Disulfide Bonds in Subtilisin BPN', C. Mitchinson and J. Wells, Biochemistry (1989), vol. 28, pp. 4807–4815.
In Vivo Formation and Stability of Engineered Disulfide Bonds in Subtilisin, J. Wells and D. Powers, The Journal of Biological Chemistry, vol. 261 (1986) pp. 6564–6570.
Disulfide Bonds and Thermal Stability in T4 Lysozyne, R. Wetzel, L. Perry, W. Baase and W. Becktel, Proc. Natl. Acad. Sci, USA (1988) vol. 85, pp. 401–405.
Dilsulfide Bond Engineered into T4 Lysozyme: Stabilization of the Protein Toward Thermal Inactivation, Perry, L. J., et al., (1984) Science 226, 555–557.

(List continued on next page.)

Primary Examiner—Charles L. Patterson, Jr.
Attorney, Agent, or Firm—Judy A. Erratt

[57] ABSTRACT

The thermostability of the 20,396 dalton *Bacillus circulans* xylanase was increased by site-directed mutagenesis. The thermostability was conferred by the presence of non-native disulfide bridges, and selected N-terminal mutations. The introduction of these non-native disulfide bridges was accomplished by the examination of the three-dimensional structure of the enzyme, and choosing sites where a favorable geometry for a bridge existed. The N-terminal mutations were constructed on the basis of primary sequence comparison with other family G xylanases. The mutant proteins were examined for their ability to retain enzymatic activity after heating as an indication of increased thermostability. These thermotolerant variants are useful as an alternative to chemical bleaching of Kraft pulp in a pre-bleaching step (bio-bleaching). The pre-bleaching involves temperatures higher than that normally used for these enzymes and accordingly these thermotolerant variants can be advantageously used at this step. Thermotolerant xylanases are also of use in the food processing industry.

15 Claims, 28 Drawing Sheets

OTHER PUBLICATIONS

Unpaired Cystein-54 Interferes with the Ability of an Engineered Disulfide to Stablize T4 Lysozyme, L. Perry and R. Wetzel, Biochemistry (1986) vol. 25, pp. 733–739.

Stablization of Xylanse by Random Mutagensis, A. Arase, T. Yomo, I. Urabe, Y. Hata, Y. Katsube and H. Okada, Federation of European Biochemical Societies, vol. 316, (1993), pp. 123–127.

Purification and Properties of Xylanases from the Thermophilic Fungus, *Humicola lanuginosa* (Giffon and Maublanc) Bunce, L. Anand, S. Krishnamurthy and P. Vithayathil, Archives of Biochemistry and Biophysics, vol. 276 (1990), pp. 546–553.

Protein Engineering for Thermostability, Yoshiaki Nosoh and Takeshi Sekiguchi, Tibtech (1990) 8, 16–20.

Amino Acid Sequence of the Low-Molecular-Weight Xylanase from *Trichoderma viride*, M. Yaguchi, C. Roy, M. Ujiie, D. C. Watson and W. Wakarchuk, Xylans and Xylanases, Edited by J. Visser et al, Elsevier Science Publishers (1992) pp. 149–154.

The Use of Enzymes to Decrease the $CI_2$ Requirements in Pulp Bleaching, J. S. Tolan and R. Canovas, Pulp and Paper Canada (1992) 93, 39–42.

Viscosity-Enhancing Bleaching of Hardwood Kraft Pulp with Xylanase from a Cloned Gene, M. G. Paice, R. Bernier Jr., and L. Jurasek, Biotechnology and Bioengineering, vol. 32 (1988), pp. 235–239.

Domains in Microbial $\beta$-1,4-Glycanases: Sequence Conservation, Function, and Enzyme Families, N. R. Gilkes, B. Henrissat, D. G. Kilburn, R. C. Miller Jr. and A. J. Warren, Microbiological Reviews, Jun. (1991), 55(2), 303–315.

Xylanses for the Pulp and Paper Industry, A. Nissen, L. Anker, N. Munk and N. Lange, in Xylane and Xylanases, ed. J. Visser, et al., 1992, Elsevier Sci. Publ. BV., pp. 325–337.

```
BP    1   RTITNNEMGN HSGYDYELWK DYGNT-SMTL NNGGAFSAGW N--NIGNA    45
CA   32   KTITSNEIGV NGGYDYELWK DYGNT-SMTL KNGGAFSCQW S--NIGNA    76
RF    1   SAADQQTRGN VGGYDYEMWN QNGQGQASMN PGAGSFTCSW S--NIENF    46
TR2   1    QTIQPGTGY NNGYFYSYWN DGHGGVTYTN GPGGQFSVNW S--NSGNF    45
TV    1    QTIQPGTGF NNGYFYSYWN DGHGGVTYTN GPGGQFSVNW S--NSGNF    45
TH    1    QTIGPGTGY SNGYYYSYWN DGHAGVTYTN GGGGSFTVNW S--NSGNF    45
SC    1   SGTPSSTGT  DGGYYYSWWT DGAGDATYQN NGGGSYTLTW SG-NNGNL    46
AN    1           S AGINYVQNYN GNLGDFTY-D ESAGTFSMYW EDGVSSDF    37
AT    1             AGINYVQNYN QNLGDFTY-D ESAGTFSMYW EDGVSSDF    37
TR1   1             ASINYDQNYQ TGG-QVSYS- PSNTGFSVNW N--TQDDF    34
SS    1   ATTIT-NETGY D-GMYYSFWT DGGGSVSMTL NGGGSYSTRW T--NCGNF    45
SLB   1   DTVVTTNQEGT NNGYYYSFWT DSQGTVSMNM GSGGQYSTSW R--NTGNF    47
SLC   1   ATTITTNQTGT D-GMYYSFWT DGGGSVSMTL NGGGSYSTQW T--NCGNF    46
BC    1             ASTDYWQNWT DGGGIVNAVN GSGGNYSVNW S--NTGNF    36
BS    1·            ASTDYWQNWT DGGGIVNAVN GSGGNYSVNW S--NTGNF    36

Consensus .........G. ..GYYY..W. DGGG.V.... ..GG.FS..W S..N.GNF

BP   46   LFRK-GKKFD ST-RTHHQLG NISINYNASF N-PSGNSYLC VYGWTQSP    90
CA   77   LFRK-GKKFN DT-QTYKQLG NISVNYDCNY Q-PYGNSYLC VYGWTSSP   121
RF   47   LARM-GKNYD SQKKNYKAFG NIVLTYDVEY T-PRGNSYMC VYGWTRNP    92
TR2  46   VGGK-GWQPG TKNKV----- ---INFS-GS YNPNGNSYLS VYGWSRNP    83
TV   46   VGGK-GWQPG TKNKV----- ---INFS-GS YNPNGNSYLS VYGWSRNP    83
TH   46   VGGK-GWQPG TKNKV----- ---INFS-GS YNPNGNSYLS IYGWSRNP    83
SC   47   VGGK-GWNPG AASRS----- ---ISYS-GT YQPNGNSYLS VYGWTRSS    84
AN   38   VVGL-GWTTG SSNA------ ---ITYSAEY SASGSSSYLA VYGWVNYP    76
AT   38   VVGLGGWTTG SSNA------ ---ITYSAEY SASGSASYLA VYGWVNYP    76
TR1  35   VVGV-GWTTG SSAP------ ---INFGGSF SVNSGTGLLS VYGWSTNP    72
SS   46   VAGK-GWANG GR-RT----- ---VRYT-GW FNPSGNGYGC LYGWTSNP    82
SLB  48   VAGK-GWANG GR-RT----- ---VQYS-GS FNPSGNAYLA LYGWTSNP    84
SLC  47   VAGK-GWSTG DGN------- ---VRYN-GY FNPVGNGYGC LYGWTSNP    82
BC   37   VVGK-GWTTG SPFRT----- ---INYNAGV WAPNGNGYLT LYGWTRSP    75
BS   37   VVGK-GWTTG SPFRT----- ---INYNAGV WAPNGNGYLT LYGWTRSP    75

Consensus V.GK.GW..G .......... ...INY..G. ..P.GNSYL. VYGWT.NP

BP   91   LAEYYIVDSW GTYR-PT--G AYKGSFYADG GTYDIYETTR VNQPSIIG   135
CA  122   LVEYYIVDSW GSWRPP--GG TSKGTITVDG GIYDIYETTR INQPSIQG   167
RF   93   LMEYYIVEGW GDWRPPGNDG EVKGTVSANG NTYDIRKTMR YNQPSLDG   140
TR2  84   LIEYYIVENF GTYN-PSTGA TKLGEVTSDG SVYDIYRTQR VNQPSIIG   130
TV   84   LIEYYIVENF GTYN-PSTGA TKLGEVTSDG SVYDIYRTQR VNQPSIIG   130
TH   84   LIEYYIVENF GTYN-PSTGA TKLGEVTSDG SVYDIYRTQR VNQPSIIG   130
SC   85   LIEYYIVESY GSYD-PSSAA SHKGSVTCNG ATYDILSTWR YNAPSIDG   131
AN   77   GAEYYIVEDY GDYN-PCSSA TSLGTVYSDG STYQVCTDTR INEPSITG   123
AT   77   QAEYYIVEDY GDYN-PCSSA TSLGTVYSDG STYQVCTDTR INEPSITG   123
TR1  73   LVEYYIMEDN HNY--PAQ-G TVKGTVTSDG ATYTIWENTR VNEPSIQG   117
SS   83   LVEYYIVDNW GSYR-PT--G ETRGTVHSDG GTYDIYKTTR YNAPSVEA   127
SLB  85   LVEYYIVDNW GTYR-PT--G EYKGTVTSDG GTYDIYKTTR VNKPSVEG   129
SLC  83   LVEYYIVDNW GSYR-PT--G TYKGTVSSDG GTYDIYQTTR YNAPSVEG   127
BC   76   LIEYVVVDSW GTYR-PT--G TYKGTVKSDG GTYDIYTTTR YNAPSIDG   120
BS   76   LIEYVVVDSW GTYR-PT--G TYKGTVKSDG GTYDIYTTTR YNAPSIDG   120

Consensus L.EYYIVE.W G.YR.P...G T.KGTV.SDG .TYDIY.TTR .N.PSI.G
```

FIGURE 1

```
BP   136   -IATFKQYWS  VRQTKRTS--  ------GTVS  VSAHFRKWES  LGMPM-GK       174
CA   168   -NTTFKQYWS  VRRTKRTS--  ------GTIS  VSKHFAAWES  KGMPL-GK       206
RF   141   -TATFPQYWS  VRQTSGSANN  QTNYMKGTID  VSKHFDAWSA  AGLDMSGT       187
TR2  131   -TATFYQYWS  VRRNHR-S-S  ------GSVN  TANHFNAWAQ  QGLTL-GT       169
TV   131   -TATFYQYWS  VRRTHR-S-S  ------GSVN  TANHFNAWAQ  QGLTL-GT       169
TH   131   -TATFYQYWS  VRRNHR-S-S  ------GSVN  TANHFNAWAS  HGLTL-GT       169
SC   132   -TQTFEQFWS  VRNPKKAPGG  SIS---GTVD  VQCHFDAWKG  LGMNLGSE       175
AN   124   -TSTFTQYFS  VRESTRTS--  ------GTVT  VANHFNFWAQ  HGFGN-SD       162
AT   124   -TSTFTQYFS  VRESTRTS--  ------GTVT  VANHFNFWAH  HGFHN-SD       162
TR1  118   -TATFNQYIS  VRNSPR-T-S  ------GTVT  VQNHFN-WAS  LGLHLGQM       155
SS   128   -PAAFDQYWS  VRQSKVT--S  ------GTIT  TGNHFDAWAR  AGMNMGNF       168
SLB  130   TR-TFDQYWS  VRQSKR-TG-  ------GTIT  TGNHFDAWAR  AGMPLGNF       168
SLC  128   TK-TFQQYWS  VRQSKVTSGS  ------GTIT  TGNHFDAWAR  AGMNMGQF       168
BC   121   DRTTFTQYWS  VRQSKRPTGS  N-----ATIT  FTNHVNAWKS  HGMNLGSN       163
BS   121   DRTTFTQYWS  VRQSKRPTGS  N-----ATIT  FSNHVNAWKS  HGMNLGSN       163

Consensus  .T.TF.QYWS  VR.SKR.S..  ......GTVT  ..NHFNAWA.  .GH.L...

BP   175   MYETAFTVEG  YQSSGSANVM  TNQLFIGN                               201
CA   207   MHETAFNIEG  YQSSGKADVN  SMSINIGK                               233
RF   188   LYEVSLNIEG  YRSNGSANVK  SVSV                                   211
TR2  170   MDYQIVAVEG  YFSSGSASI-  TVS                                    190
TV   170   MDYQIVAVEG  YFSSGSASI-  TVS                                    190
TH   170   MDYQIVAVEG  YFSSGSASI-  TVS                                    190
SC   176   HNYQIVATEG  YQSSGTATI-  TVT                                    197
AN   163   FNYQVMAVEA  WSGAGSASV-  TISS                                   184
AT   163   FNYQVVAVEA  WSGAGSAAV-  TISS                                   184
TR1  157   MNYQVVAVEG  WGGSGSASQ-  SVSN                                   178
SS   167   RYYMIMATEG  YQSSGSSTI-  TVSG                                   189
SLB  169   SYYMIMATEG  YQSSGTSSI-  NVGGTGGGDS  GGATTGAVAA  GAPTVSAG       215
SLC  169   RYYMIMATEG  YQSSGSSNI-  TVSG                                   191
BC   164   WAYQVMATEG  YQSSGSSNV-  TVW                                    185
BS   164   WAYQVMATEG  YQSSGSSNV-  TVW                                    185

Consensus  ..YQ..A.EG  YQSSGSA...  TVS

****************************************************************

BP     Bacillus pumilus
CA     Clostridium acetobutylicum, Xyn B
RF     Ruminococcus flavefaciens
TR2    Trichoderma reesei, XYN II, 21kD, pI 9.0
TV     Trichoderma viride, 20kD
TH     Trichoderma harzianum, 20kD
SC     Schizophyllum commune, Xylanase A
AN     Aspergillus niger, var. awamori
AT     Aspergillus tubigensis, A
TR1    Trichoderma reesei, XYN I, 19kD, pI 5.2
BS     Bacillus subtilis
BC     Bacillus circulans
SLB    Streptomyces lividans, Xln B
SLC    Streptomyces lividans, Xln C
SS     Streptomyces sp. #36a
```

FIGURE 1 CONT'D

```
  1   2   3   4   5   6   7   8   9  10  11  12  13  14  15  16
  A   S   T   D   Y   W   Q   N   W   T   D   G   G   G   I   V
GCT AGC ACA GAC TAC TGG CAA AAT TGG ACT GAT GGG GGC GGT ATA GTA
CGA TCG TGT CTG ATG ACC GTT TTA ACC TGA CTA CCC CCG CCA TAT CAT
 NheI     5'  PCR primer site 17  18  19  20  21  22  23  24  25  26  27  28  29  30  31  32
  N   A   V   N   G   S   G   G   N   Y   S   V   N   W   S   N
AAC GCT GTC AAT GGG TCT GGC GGG AAT TAC AGT GTT AAT TGG TCT AAT
TTG CGA CAG TTA CCC AGA CCG CCC TTA ATG TCA CAA TTA ACC AGA TTA 33  34  35  36  37  38  39  40  41  42  43  44  45  46  47  48
  T   G   N   F   V   V   G   K   G   W   T   T   G   S   P   F
ACC GGA AAT TTT GTT GTT GGT AAA GGT TGG ACT ACA GGT TCG CCA TTT
TGG CCT TTA AAA CAA CAA CCA TTT CCA ACC TGA TGT CCA AGC GGT AAA 49  50  51  52  53  54  55  56  57  58  59  60  61  62  63  64
  R   T   I   N   Y   N   A   G   V   W   A   P   N   G   N   G
AGG ACG ATA AAC TAT AAT GCC GGA GTT TGG GCG CCG AAT GGC AAT GGA
TCC TGC TAT TTG ATA TTA CGG CCT CAA ACC CGC GGC TTA CCG TTA CCT
                                          NarI 65  66  67  68  69  70  71  72  73  74  75  76  77  78  79  80
  Y   L   T   L   Y   G   W   T   R   S   P   L   I   E   Y   Y
TAT TTA ACT TTA TAT GGT TGG ACG AGA TCA CCT CTC ATA GAA TAT TAT
ATA AAT TGA AAT ATA CCA ACC TGC TCT AGT GGA GAG TAT CTT ATA ATA
                                                      SspI 81  82  83  84  85  86  87  88  89  90  91  92  93  94  95  96
  V   V   D   S   W   G   T   Y   R   P   T   G   T   Y   K   G
GTA GTG GAT TCA TGG GGT ACT TAT AGA CCT ACT GGA ACG TAT AAA GGT
CAT CAC CTA AGT ACC CCA TGA ATA TCT GGA TGA CCT TGC ATA TTT CCA 97  98  99 100 101 102 103 104 105 106 107 108 109 110 111 112
  T   V   K   S   D   G   G   T   Y   D   I   Y   T   T   T   R
ACT GTA AAA AGT GAT GGG GGT ACA TAT GAC ATA TAT ACA ACT ACA CGT
TGA CAT TTT TCA CTA CCC CCA TGT ATG CTG TAC ATA TGT TGT TGT GCA
S100C mutagenic primer site   NdeI 113 114 115 116 117 118 119 120 121 122 123 124 125 126 127 128
  Y   N   A   P   S   I   D   G   D   R   T   T   F   T   Q   Y
TAT AAC GCA CCT TCC ATT GAT GGC GAT CGC ACT ACT TTT ACG CAG TAC
ATA TTG CGT GGA AGG TAA CTA CCG CTA GCG TGA TGA AAA TGC GTC ATG
                                 PvuI 129 130 131 132 133 134 135 136 137 138 139 140 141 142 143 144
  W   S   V   R   Q   S   K   R   P   T   G   S   N   A   T   I
TGG AGT GTT CGC CAG TCG AAG AGA CCA ACC GGA AGC AAC GCT ACA ATC
ACC TCA CAA GCG GTC AGC TTC TCT GGT TGG CCT TCG TTG CGA TGT TAG
```

FIGURE 6

```
145 146 147 148 149 150 151 152 153 154 155 156 157 158 159 160
 T   F   S   N   H   V   N   A   W   K   S   H   G   M   N   L
ACT TTC AGC AAT CAT GTG AAC GCA TGG AAG AGC CAT GGA ATG AAT CTG
TGA AAG TCG TTA GTA CAC TTG CGT ACC TTC TCG GTA CCT TAC TTA GAT
                                           NcoI 161 162 163 164 165 166 167 168 169 170 171 172 173 174 175 176
 G   S   N   W   A   Y   Q   V   M   A   T   E   G   Y   Q   S
GGC AGT AAT TGG GCT TAC CAA GTC ATG GCG ACA GAA GGA TAT CAA AGT
CCG TCA TTA ACC CGA ATG GTT CAG TAC CGC TGT CTT CCT ATA GTT TCA
                                               EcoRV 177 178 179 180 181 182 183 184 185 STOP
 S   G   S   S   N   V   T   V   W
AGT GGA AGT TCT AAC GTA ACA GTG TGG TAA CAGATCATCC TTAATCAGGG
TCA CCT TCA AGA TTG CAT TGT CAC ACC ATT GTCTAGTAGG AATTAGTCCC

GTAGCTAACG GCTGCTGAT CGTTCCTTGA GAAGTTTTA TAATCAATGA TTATTAAAAT
CATCGATTGC CGACGACTA GCAAGGAACT CTTCAAAAT ATTAGTTACT AATAATTTTA
                                                  3' PCR primer CGTTAGTAA TGGTTAAAGG TTGTTTTCTA CTAGGTGAAC GGCCTTGGAA TTGCTGGAGG
GCAATCATT ACCAATTTCC AACAAAAGAT GATCCACTTG CCGGAACCTT AACGACCTCC
binding site

TAGGGTATTC TCCATCTGGT TTTT
ATCCCATAAG AGGTAGACCA AAAA
```

FIGURE 6 CONT'D

```
  1    2    3    4    5    6    7    8    9   10   11   12   13   14   15   16
  A    S    T    D    Y    W    Q    N    W    T    D    G    G    G    I    V
GCT  AGC  ACA  GAC  TAC  TGG  CAA  AAT  TGG  ACT  GAT  GGG  GGC  GGT  ATA  GTA
CGA  TCG  TGT  CTG  ATG  ACC  GTT  TTA  ACC  TGA  CTA  CCC  CCG  CCA  TAT  CAT
NheI 17   18   19   20   21   22   23   24   25   26   27   28   29   30   31   32
  N    A    V    N    G    S    G    G    N    Y    S    V    N    W    S    N
AAC  GCT  GTC  AAT  GGG  TCT  GGC  GGG  AAT  TAC  AGT  GTT  AAT  TGG  TCT  AAT
TTG  CGA  CAG  TTA  CCC  AGA  CCG  CCC  TTA  ATG  TCA  CAA  TTA  ACC  AGA  TTA 33   34   35   36   37   38   39   40   41   42   43   44   45   46   47   48
  T    G    N    F    V    V    G    K    G    W    T    T    G    S    P    F
ACC  GGA  AAT  TTT  GTT  GTT  GGT  AAA  GGT  TGG  ACT  ACA  GGT  TCG  CCA  TTT
TGG  CCT  TTA  AAA  CAA  CAA  CCA  TTT  CCA  ACC  TGA  TGT  CCA  AGC  GGT  AAA 49   50   51   52   53   54   55   56   57   58   59   60   61   62   63   64
  R    T    I    N    Y    N    A    G    V    W    A    P    N    G    N    G
AGG  ACG  ATA  AAC  TAT  AAT  GCC  GGA  GTT  TGG  GCG  CCG  AAT  GGC  AAT  GGA
TCC  TGC  TAT  TTG  ATA  TTA  CGG  CCT  CAA  ACC  CGC  GGC  TTA  CCG  TTA  CCT
                                                      NarI 65   66   67   68   69   70   71   72   73   74   75   76   77   78   79   80
  Y    L    T    L    Y    G    W    T    R    S    P    L    I    E    Y    Y
TAT  TTA  ACT  TTA  TAT  GGT  TGG  ACG  AGA  TCA  CCT  CTC  ATA  GAA  TAT  TAT
ATA  AAT  TGA  AAT  ATA  CCA  ACC  TGC  TCT  AGT  GGA  GAG  TAT  CTT  ATA  ATA
                                                                SspI 81   82   83   84   85   86   87   88   89   90   91   92   93   94   95   96
  V    V    D    S    W    G    T    Y    R    P    T    G    T    Y    K    G
GTA  GTG  GAT  TCA  TGG  GGT  ACT  TAT  AGA  CCT  ACT  GGA  ACG  TAT  AAA  GGT
CAT  CAC  CTA  AGT  ACC  CCA  TGA  ATA  TCT  GGA  TGA  CCT  TGC  ATA  TTT  CCA 97   98   99  100  101  102  103  104  105  106  107  108  109  110  111  112
  T    V    K    S    D    G    G    T    Y    D    I    Y    T    T    T    R
ACT  GTA  AAA  AGT  GAT  GGG  GGT  ACA  TAT  GAC  ATC  TAC  ACC  ACC  ACA  AGA
TGA  CAT  TTT  TCA  CTA  CCC  CCA  TGT  ATG  CTG  TAG  ATG  TGG  TGG  TGT  TCT
V908C mutagenic primer site      NdeI 113  114  115  116  117  118  119  120  121  122  123  124  125  126  127  128
  Y    N    A    P    S    I    D    G    D    R    T    T    F    T    Q    Y
TAC  AAC  GCA  CCT  TCC  ATC  GAT  GGC  GAT  CGG  ACC  ACC  TTT  ACT  CAG  TAC
ATG  TTG  CGT  GGA  AGG  TAG  CTA  CCG  CTA  GCC  TGG  TGG  AAA  TGA  GTC  ATG
                         ClaI           PvuI 129  130  131  132  133  134  135  136  137  138  139  140  141  142  143  144
  W    S    V    R    Q    S    K    R    P    T    G    S    N    A    T    I
TGG  AGT  GTT  AGA  CAA  TCT  AAG  CGG  CCG  ACT  GGT  TCG  AAC  GCC  ACC  ATT
ACC  TCA  CAA  TCT  GTT  AGA  TTC  GCC  GGG  TGA  CCA  AGC  TTG  CGG  TGG  TAA
                              EagI/EaeI        BstBI
```

FIGURE 7

```
145 146 147 148 149 150 151 152 153 154 155 156 157 158 159 160
 T   F   T   N   H   V   N   A   W   K   S   H   G   M   N   L
ACG TTC ACC AAT CAC GTG AAT GCA TGG AAA TCC CAC GGT ATG AAC CTA
TGC AAG TGG TTA GTG CAC TTA CGT ACC TTT AGG GAG CCA TAC TTG GAT
                        NsiI                                StyI/
              A152C mutagenic primer site 161 162 163 164 165 166 167 168 169 170 171 172 173 174 175 176
 G   S   N   W   A   Y   Q   V   M   A   T   E   G   Y   Q   S
GGT TCT AAT TGG GCT TAT CAA GTA ATG GCG ACC GAA GGC TAC CAG AGC
CCA AGA TTA ACC CGA ATA GTT CAT TAC CGC TGG CTT CCG ATG GAC TCG
SecI/AvrII 177 178 179 180 181 182 183 184 185 STOP
 S   G   S   S   N   V   T   V   W
TCT GGT TCT TCC AAC GTT ACA GTG TGG TAA AGATCTTGAAGCTT
AGA CCA AGA AGG TTG CAA TGT CAC ACC ATT TCTAGAACTTCGAA
SacI                                     BglII   HindIII
```

FIGURE 7 CONT'D

```
  1   2   3   4   5   6   7   8   9  10  11  12  13  14  15  16
  A   S   T   D   Y   W   Q   N   W   T   D   G   G   G   I   V
GCT AGC ACA GAT TAC TGG CAA AAC TGG ACA GAC GGT GGC GGT ATC GTT
CGA TCG TGT CTA ATG ACC GTT TTG ACC TGT CTG CCA CCG CCA TAG CAA
NheI 17  18  19  20  21  22  23  24  25  26  27  28  29  30  31  32
  N   A   V   N   G   S   G   G   N   Y   S   V   N   W   S   N
AAT GCC GTG AAC GGC TCC GGA GGC AAC TAC AGC GTG AAT TGG TCT AAT
TTA CGG CAC TTG CCG AGG CCT CCG TTG ATG TCG CAC TTA ACC AGA TTA
                    BspEI 33  34  35  36  37  38  39  40  41  42  43  44  45  46  47  48
  T   G   N   F   V   V   G   K   G   W   T   T   G   S   P   F
ACT GGG AAC TTC GTA GTC GGA AAA GGT TGG ACG ACA GGA TCC CCG TTC
TGA CCC TTG AAG CAT CAG CCT TTT CCA ACC TGC TGT CCT AGG GGC AAG
                                                BamHI 49  50  51  52  53  54  55  56  57  58  59  60  61  62  63  64
  R   T   I   N   Y   N   A   G   V   W   A   P   N   G   N   G
CGT ACG ATC AAC TAC AAC GCT GGC GTT TGG GCC CCG AAT GGT AAC GGT
GCA TGC TAG TTG ATG TTG CGA CCG CAA ACC CGG GGC TTA CCA TTG CCA
SplI                                ApaI 65  66  67  68  69  70  71  72  73  74  75  76  77  78  79  80
  Y   L   T   L   Y   G   W   T   R   S   P   L   I   E   Y   Y
TAC CTG ACA CTG TAT GGC TGG ACG CGT TCG CCA CTG ATT GAA TAT TAC
ATG GAC TGT GAC ATA CCG ACC TGC GCA AGC GGT GAC TAA CTT ATA ATG
                            MluI                    SspI 81  82  83  84  85  86  87  88  89  90  91  92  93  94  95  96
  V   V   D   S   W   G   T   Y   R   P   T   G   T   Y   K   G
GTT GTC GAC TCT TGG GGA ACG TAC CGT CCG ACT GGA ACC TAC AAA GGC
CAA CAG CTG AGA ACC CCT TGC ATG GCA GGC TGA CCT TGG ATG TTT CCG
    SalI 97  98  99 100 101 102 103 104 105 106 107 108 109 110 111 112
  T   V   K   S   D   G   G   T   Y   D   I   Y   T   T   T   R
ACA GTC AAA AGC GAT GGT GGT ACC TAC GAC ATC TAC ACC ACC ACA AGA
TGT CAG TTT TCG CTA CCA CCA TGG ATG CTG TAG ATG TGG TGG TGT TCT
                        KpnI 113 114 115 116 117 118 119 120 121 122 123 124 125 126 127 128
  Y   N   A   P   S   I   D   G   D   R   T   T   F   T   Q   Y
TAC AAC GCA CCT TCC ATC GAT GGC GAT CGG ACC ACC TTT ACT CAG TAC
ATG TTG CGT GGA AGG TAG CTA CCG CTA GCC TGG TGG AAA TGA GTC ATG
                    ClaI    PvuI
```

FIGURE 9

```
129 130 131 132 133 134 135 136 137 138 139 140 141 142 143 144
 W   S   V   R   Q   S   K   R   P   T   G   S   N   A   T   I
TGG AGT GTT AGA CAA TCT AAG CGG CCG ACT GGT TCG AAC GCC ACC ATT
ACC TCA CAA TCT GTT AGA TTC GCC GGG TGA CCA AGC TTG CGG TGG TAA
                            EagI/EaeI     BstBI 145 146 147 148 149 150 151 152 153 154 155 156 157 158 159 160
 T   F   T   N   H   V   N   A   W   K   S   H   G   M   N   L
ACG TTC ACC AAT CAC GTG AAT GCA TGG AAA TCC CAC GGT ATG AAC CTA
TGC AAG TGG TTA GTG CAC TTA CGT ACC TTT AGG GTG CCA TAC TTG GAT
                        NsiI                                StyI/

161 162 163 164 165 166 167 168 169 170 171 172 173 174 175 176
 G   S   N   W   A   Y   Q   V   M   A   T   E   G   Y   Q   S
GGT TCT AAT TGG GCT TAT CAA GTA ATG GCG ACC GAA GGC TAC CAG AGC
CCA AGA TTA ACC CGA ATA GTT CAT TAC CGC TGG CTT CCG ATG GTC TCG
SecI/AvrII 177 178 179 180 181 182 183 184 185 STOP
 S   G   S   S   N   V   T   V   W
TCT GGT TCT TCC AAC GTT ACA GTG TGG TAA AGATCTTGAAGCTT
AGA CCA AGA AGG TTG CAA TGT CAC ACC ATT TCTAGAACTTCGAA
SacI                                    BglII   HindIII
```

FIGURE 9 CONT'D

CONSTRUCTION OF THERMOSTABLE MUTANTS OF A LOW MOLECULAR MASS XYLANASE

BACKGROUND AND PRIOR ART

The present invention is directed to a modified xylanase, which shows an improved thermostability when compared to the naturally occurring xylanase. Specifically the present invention is directed to a modified xylanase, wherein said xylanase has increased thermostability and wherein said xylanase is modified through either the introduction of a non-native disulfide bridge, introduction of an N-terminal mutation, or both.

Current strategies for the production of paper use a chemical bleaching step, which is essential for the colour and quality of the paper. Chemical bleaching uses chlorine or chlorine dioxide and produces substantial amounts of by-products, which are environmental pollutants. The bleaching process can be enhanced by using an enzymatic pre-treatment with xylanase (Paice and Jurasek, 1984 Journal of Wood Chemistry and Technology, 4(2):187–198), which lowers the chlorine charge needed to affect bleaching, thereby reducing pollutants. In addition there is less bleaching chemical used, which lowers the chemical costs. New bleaching technology using, oxygen or peroxides with xylanase, are also as effective in brightening the pulp.

The step in the process where the enzyme is applied is after a hot alkali treatment, so that the pulp is very basic and hot. Both of these conditions are sub-optimal for xylanase enzymatic activity. Many pulp mills have the capability to acidify the pulp to a pH which is closer to the pH optimum for the enzyme; however, cooling the pulp would be too energy intensive (expensive) to be used in the mill setting. Therefore, the intrinsic thermostability of the enzymes is a critical parameter for their use in the bio-bleaching processes.

It is therefore desirable, to increase the thermostability of xylanases so that they may find wider application in the pre-treatment of kraft pulp.

Xylanase also has uses in non-pulp applications. Xylanases have been reported to be useful in clarifying juice and wine (Zeikus. J. G., Lee, Y.-E., and Saha, B. C. 1991. ACS Symp. Ser. 460:36–51; Beily, P. 1991. ACS Symp. Ser. 460:408–416; Woodward J. 1984. Top Enzyme Ferment. Biotechnol. 8:9–30), extracting coffee, plant oils and starch (McCleary, B. V. 1986. Int. J. Biol. Macromol. 8:349–354; Beily, P. 1991. ACS Symp. Ser. 460:408–416; Woodward J. 1984. Top Enzyme Ferment. Biotechnol. 8:9–30), for the production of food thickeners (Zeikus. J. G., Lee, Y.-E., and Saha, B. C. 1991. ACS Symp. Ser. 460:36–51), altering texture in bakery products (Maat, J., Roza. M., Verbakel, J., Stam, H., Santos da Silva, M. J., Bosse, M., Egmond, M. R., Hagemans, M. L. D., v. Gorcom, R. F. M., Hessing, J. G. M., v.d. Hodel, C.A.M.J.J., and Rotterdam, C. 1992. In Xylans and xylanases. Visser, J., Beldman, G., Kusters-van Someren, M. A. and Voragen, A. G. J., eds. Elsevier Sci pub., Amsterdam. ISBN 0-444-894-772; McCleary, B. V. 1986. Int. J. Biol. Macromol. 8:349–354), and in the washing of super precision devices and semiconductors (Takayuki, I., Shoji, S. U.S. Pat. No. 5,078,802, issue date 92 Jan. 07). Several of these application could benefit from a thermostable xylanase, for example, food processing at elevated temperatures.

A thermostable xylanase from *Thermoascus aurantiacus* was produced in U.S. Pat. No. 4,966,850 (Yu et al.) from a particular strain of *T. aurantiacus*, while culturing the strain at high temperature culturing conditions, however this enzyme is not a member of the family G xylanases (Gilkes et al. 1991, Microbiol. Reviews 55(2):303–315), which is the subject of this patent.

Arase et al. (FEBS 316:123–127, 1993) report improvements in thermostability of *Bacillus pumilus* xylanase through random mutagenesis of the gene by chemical mutagens. Their improvements in thermostability are minor in comparison to that of the present invention. The prior art most stable mutant maintained 40% residual activity after a short period of 20 minutes at 57° C. This mutant had a low specific activity, equivalent to 19% of the wild type *B. pumilus* xylanase.

Site directed mutagenesis has been used to produce more stable proteins. Disulfide (SS) bonds in proteins restrict the degree of freedom for the unfolded state and thereby stabilize the folded state. The first type of protein stabilization performed by genetic manipulation was the introduction of disulfide bonds. One or two amino acids in the protein are replaced with cysteines; a disulfide bond forms in vivo or in vitro. If the introduced disulfide bond causes no or little tertiary structural change, the cross-links stabilizes the protein. Disulfide bonds have been engineered into T4 lysozyme (T4L) (Perry, L. J. and Wetzel, R. (1984) Science 226, 555–557; Wetzel, R., Perry, L. J. Baase, W. A. and Becktel, W. J. (1988) Proc. Nat. Acad. Sci. USA 85, 401–405), subtilisin (Wells, J. A. and Powers, D. B. (1986) J. Biol. Chem. 261, 6564–6570; Mitchinson, C. and Wells, J. A. (198), dihydrofolate reductase (DHFR) (Villafranca, J. E., Howell, E. E., Oatley, S. J., Xuong, N. and Kraut, J. (1987) Biochemistry 26, 2182–2189), and the Phage λ repressor (C1) (Sauer, R. T., Hehir, K., Stearman, R. S. et al. (1986) Biochemistry 25, 5992–5998) with stabilization occurring in some cases but not others.

For example, in T4L the introduction of SS bonds showed an increase in thermostability of between 6° and 11° C. based on reversible denaturation at pH 2 (Matsumura et al, 1989, Nature 342:291–293). This data does not show how much activity remains after heating the sample, which in a functional sense is what is important for an industrial enzyme. The RNASE H SS bond mutant is also stabilized by 11.8° C. as measured by reversible thermal denaturation, but has no enzymatic activity (Kanaya et al, 1991, Journal of Biological Chemistry 226(10):6038–6044). In DHFR the artificial SS bond contributes to stability of the protein against chemical denaturation, but does not confer thermostability (Villafranca et al, 1987, Biochemistry 26:2182–2189). A similar situation occurs with subtilisin, where 5 different engineered SS bonds do not confer thermostability (Mitchinson and Wells, 1989, Biochemistry 28:4807–4815).

SUMMARY OF INVENTION

According to the present invention there is provided a modified xylanase, wherein said xylanase has increased thermostability and wherein said xylanase is modified through either the introduction of a non-native disulfide bridge, introduction of an N-terminal mutation, or both. No mutations of any type of xylanase have led to improved thermostability as described in the present invention.

In one embodiment of the present invention, the modified xylanase has been modified by the introduction of an intra-molecular disulfide bridge between a cysteine amino acid, which has been introduced on the last strand of sheet III, and a cysteine amino acid, which has been introduced on the alpha helix.

In a further embodiment of the present invention, the modified xylanase has been modified by the introduction of an inter-molecular disulfide bridge between two xylanase molecules, wherein a cysteine amino acid has been introduced in each of said two molecules.

In a further embodiment of the present invention, the modified xylanase has been modified by the introduction of a mutations at the N-terminus of the xylanase.

BRIEF DESCRIPTION OF THE DRAWINGS

FIG. 1 shows the multiple sequence alignment among low molecular weight xylanases. The amino acid sequence corresponding to the low molecular weight xylanases and the corresponding SEQ ID numbers are shown below:

| | |
|---|---|
| Bacillus pumilus | SEQ ID NO: 23 |
| Clostridium acetobutylicum, Xyn B | SEQ ID NO: 24 |
| Ruminococcus flavefaciens | SEQ ID NO: 25 |
| Trichoderma reesei, XYN II, 21kD, pI 9.0 | SEQ ID NO: 26 |
| Trichoderma viride, 20kD | SEQ ID NO: 27 |
| Trichoderma harzianum, 20kD | SEQ ID NO: 28 |
| Schizophyllum commune, Xylanase A | SEQ ID NO: 29 |
| Aspergillus niger, var. awamori | SEQ ID NO: 30 |
| Aspergillus tubigensis A | SEQ ID NO: 31 |
| Trichoderma reesei, XYN I, 19kD, pI 5.2 | SEQ ID NO: 32 |
| Streptomyces sp. #36a | SEQ ID NO: 33 |
| Streptomyces lividans, Xln B | SEQ ID NO: 34 |
| Streptomyces lividans, Xln C | SEQ ID NO: 35 |
| Bacillus circulans | SEQ ID NO: 36 |
| Bacillus subtilis | SEQ ID NO: 37." |

Figure 2:
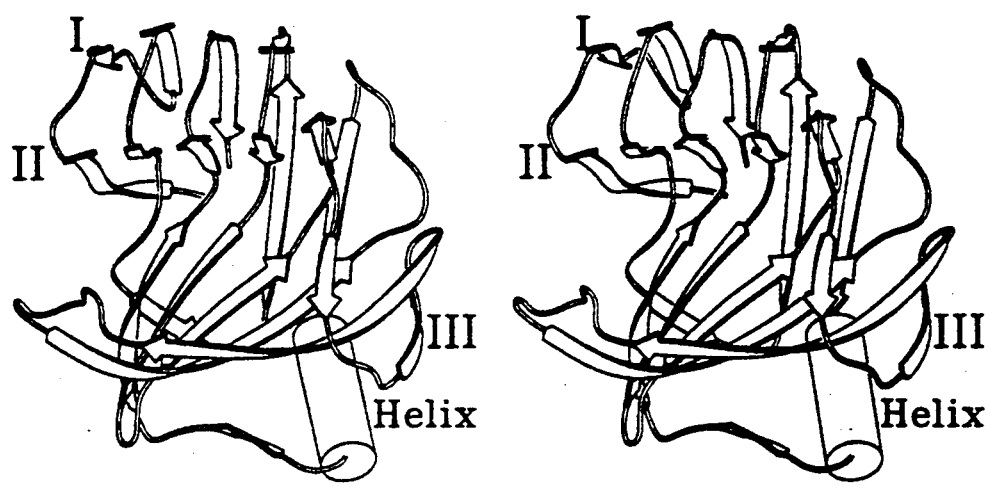

FIG. 2 shows a stereodiagram of the overall fold of the three-dimensional crystal structure of the *Bacillus circulans* xylanase. The strands of beta-sheet are represented by arrows and the alpha-helix is represented by a cylinder. The three beta-sheets referred to in the text are indicated by I, II, and III.

Figure 3:
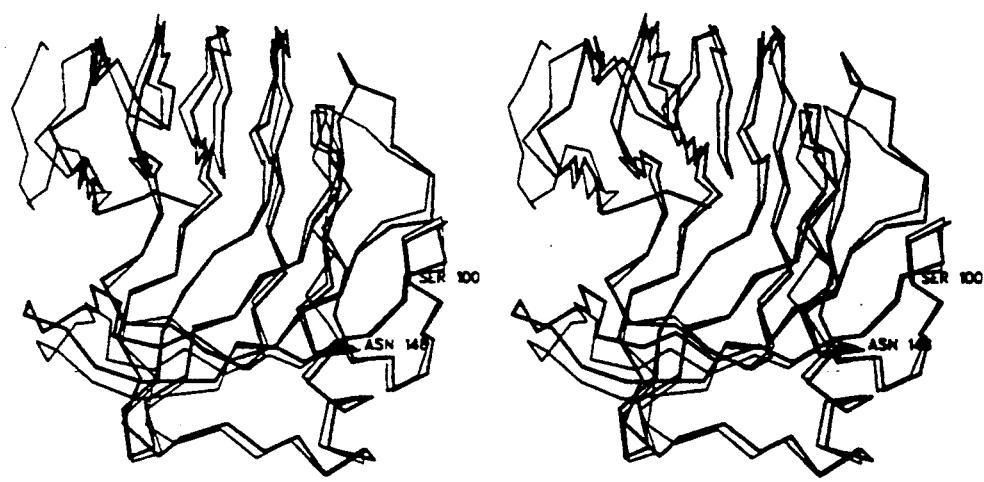

FIG. 3 shows a stereodiagram of the superimposed three-dimensional crystal structures of the xylanases from *B. circulans* and *T. harzianum*. The structures are drawn such that the positions of the alpha-carbons of each amino acid are linked by a straight line. The *B. circulans* structure is drawn in a thick line and the *T. harzianum* structure is drawn in a thin line. The *T. harzianum* xylanase has a slightly more open active site due to different intermolecular crystal contacts.

Figure 4:
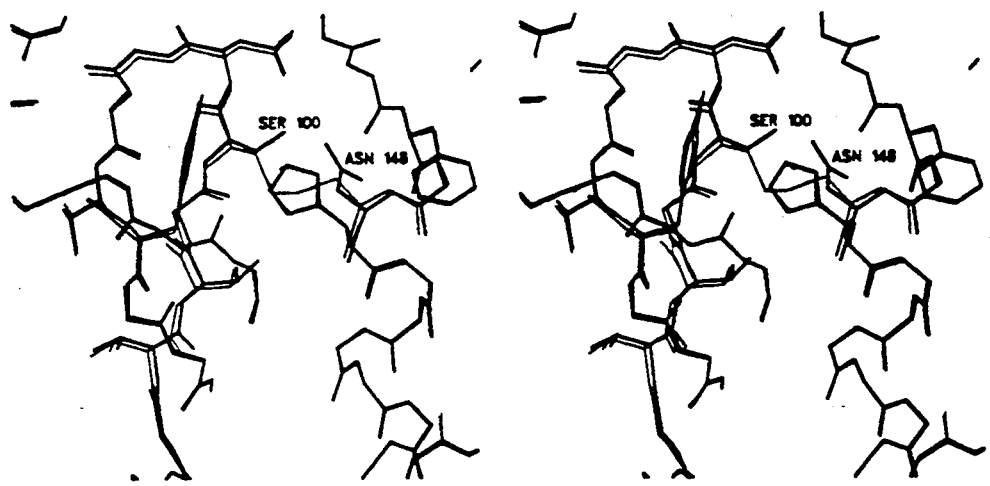

FIG. 4 shows a stereodiagram of the superimposed structures of the wild-type and disulfide-containing mutant (TS1) of the *B. circulans* xylanase in the vicinity of the mutation (residues 100 and 148). The wild-type enzyme is drawn in thick lines and the mutant is drawn in thin lines.

Figure 5:
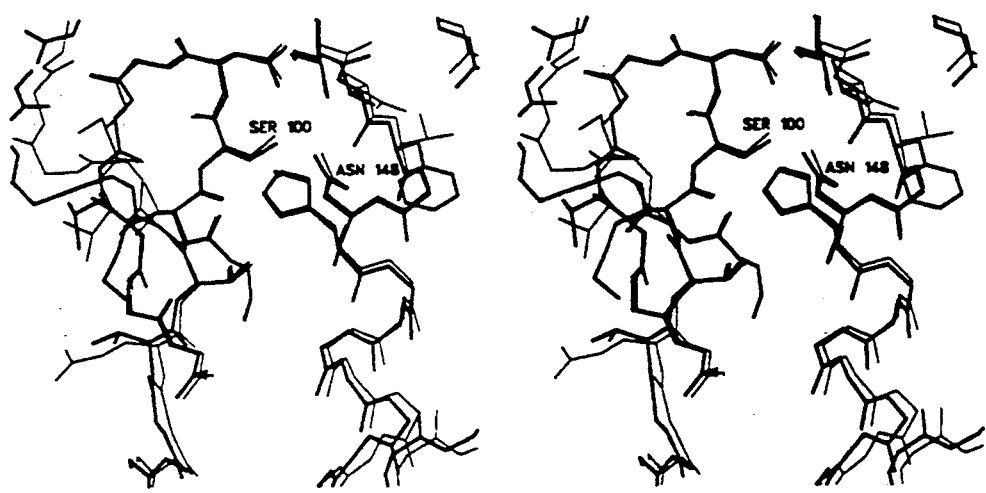

FIG. 5 shows a stereodiagram of the superimposed structures of the xylanases from *B. circulans* and *T. harzianum* in the vicinity of the disulfide bond shown in FIG. 4. The *B. circulans* structure is drawn in a thick line and the *T. harzianum* structure is drawn in a thin line.

FIG. 6 shows the native sequence (SEQ ID NO:1) of the *B. subtills* xylanase gene from plasmid pBSX. The binding sites for the PCR primers and the S100C mutagenic primer are underlined.

FIG. 7 shows the semi-synthetic gene sequence (SEQ ID NO:2) for *B. circulans* xylanases. The sites for UDNA mutagenesis to produce TS2 are shown with underlining.

Figure 8:
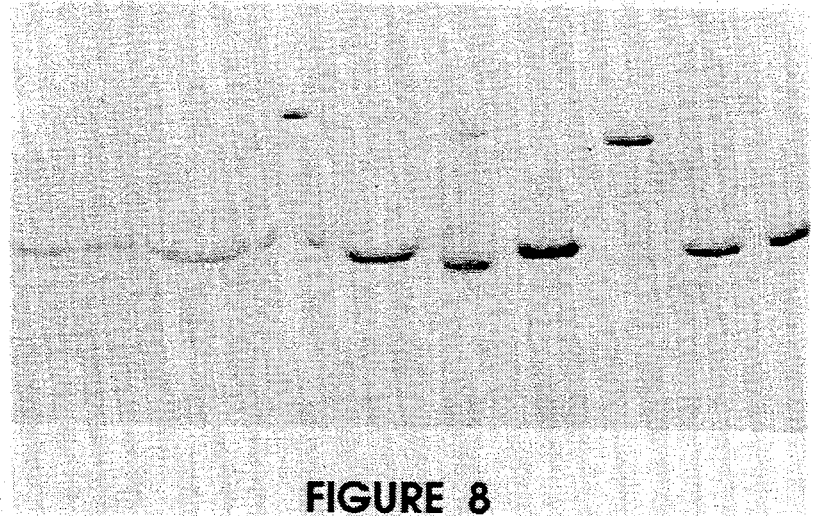

FIG. 8 shows the SDS PAGE results of monomer and dimer fraction from TS4a, TS4M and TS4D. Lane 1 is TS4a monomer fraction, reduced; Lane 2 is as in lane 1 but non-reduced; Lane 3 is TS4a dimer fraction, reduced; Lane 4 is as lane 3 but non-reduced; Lane 5 is TS4M monomer fraction, reduced; Lane 6 is as in lane 5 but non-reduced; Lane 7 is TS4D dimer fraction reduced; Lane 8 is as lane 7 but non-reduced; Lane 9 is BCX wild type reduced; Lane 10 is as in lane 9 but non-reduced. For lanes 1–4, approximately 1 μg of protein was loaded and for the other lanes, approximately 2 μg was loaded.

FIG. 9 shows the complete synthetic gene sequence (SEQ ID NO:3) encoding the *B. circulans* xylanase in the plasmid pXYbc.

Figure 10:
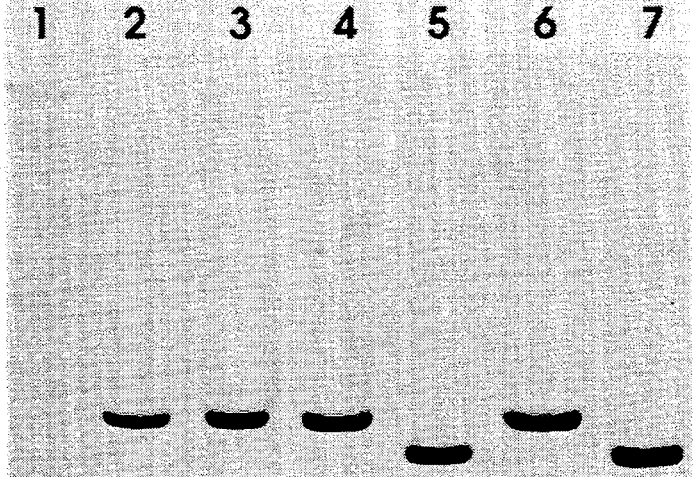

FIG. 10 shows the electrophoretic mobility of the disulfide bridge containing mutants of *B. circulans* xylanase. Lane 1 shows the molecular weight standard, lane 2 is the BCX wild-type, reduced, lane 3 is as in lane 2 but non-reduced, lane 4 is the TS1 mutant, reduced, lane 5 is the TS1 mutant, non-reduced, lane 6 is the TS2 mutant, reduced and lane 7 is a TS2 mutant, non-reduced.

Figure 11:
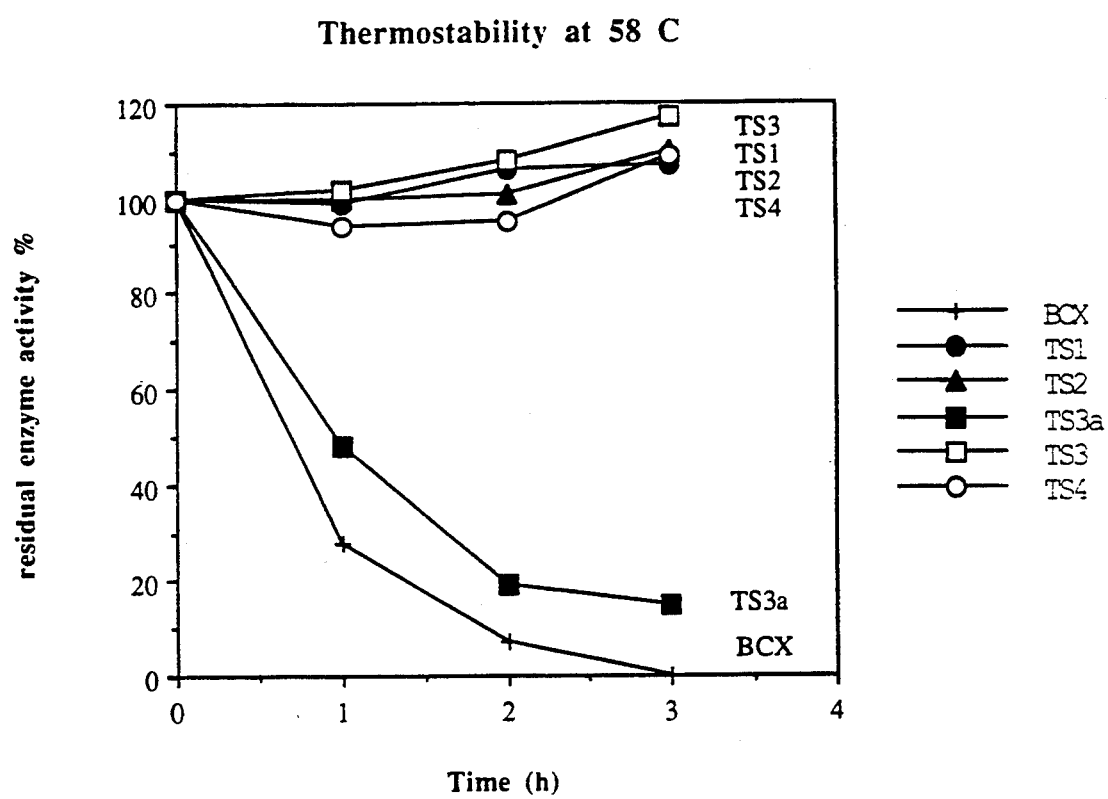

FIG. 11 shows a comparison of the thermostability at 58° C. of various mutants of *B. circulans* xylanase. The curve shown for TS4 is for the mixture of both monomer and dimer.

Figure 12:
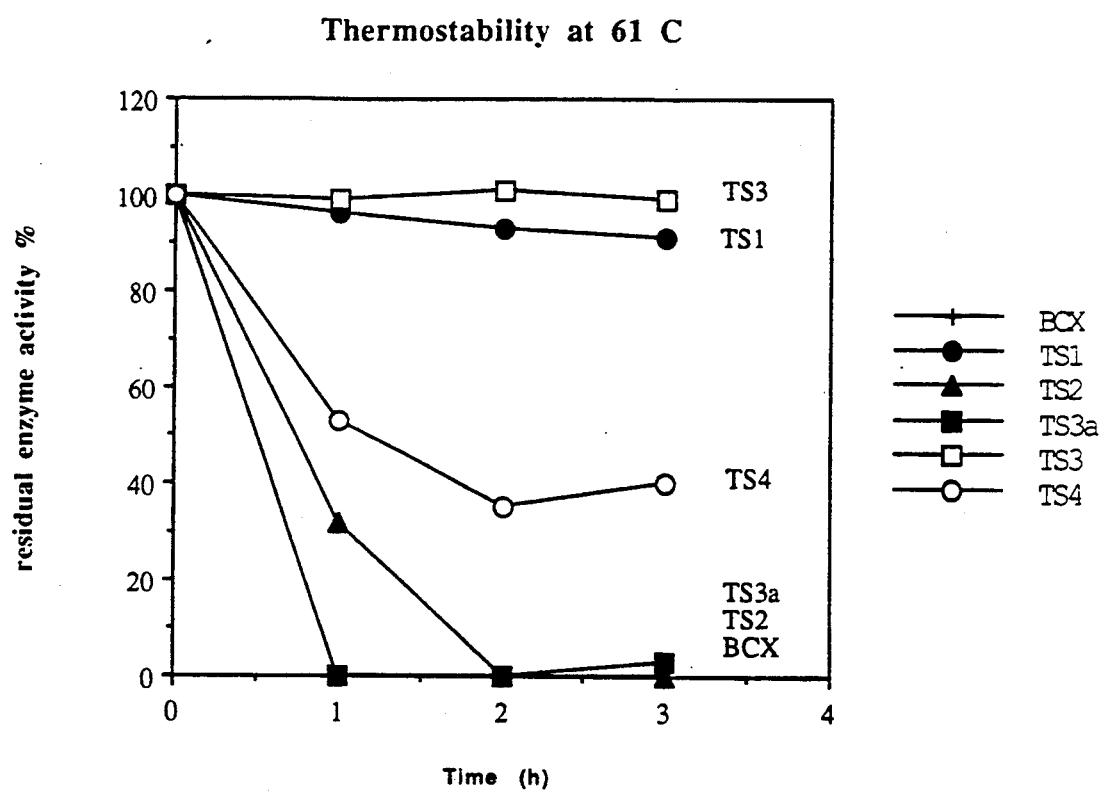

FIG. 12 shows a comparison of the thermostability at 61° C. of various mutants of the *B. circulans* xylanases. The curve shown for TS4 is for the mixture of both monomer and dimer.

Figure 13:
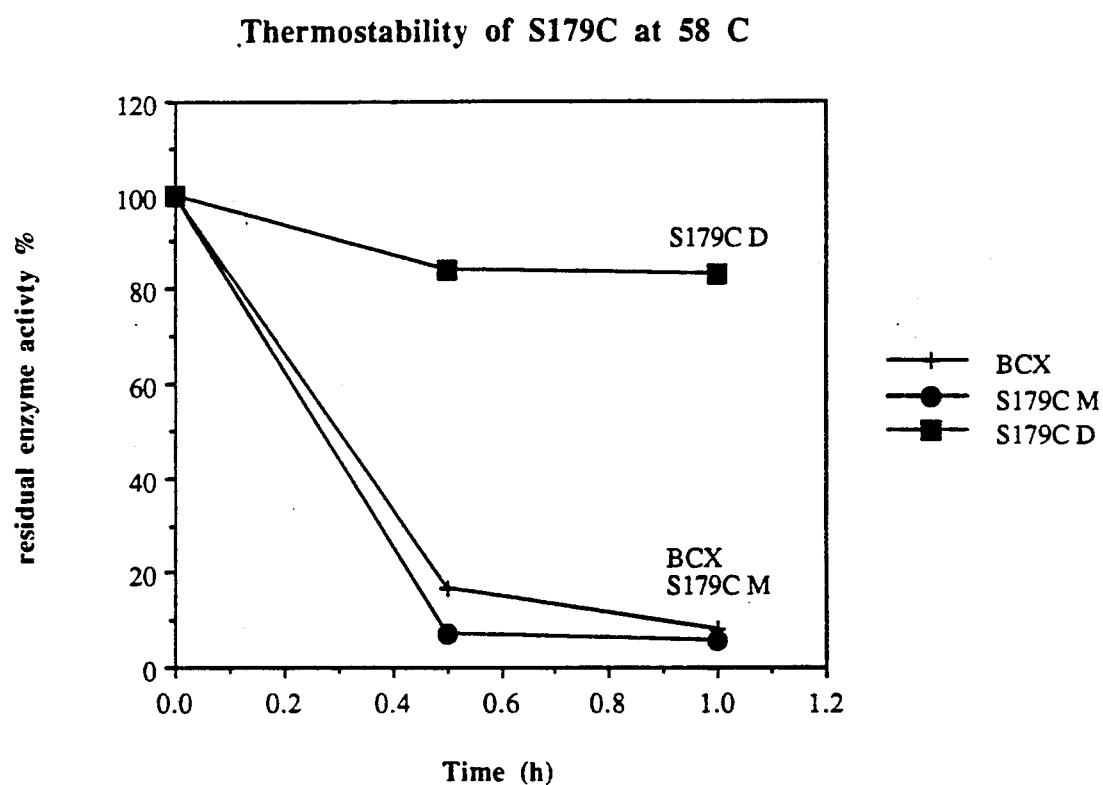

FIG. 13 shows the thermostability of the TS4a (S179C) dimer at 58° C.

Figure 14:
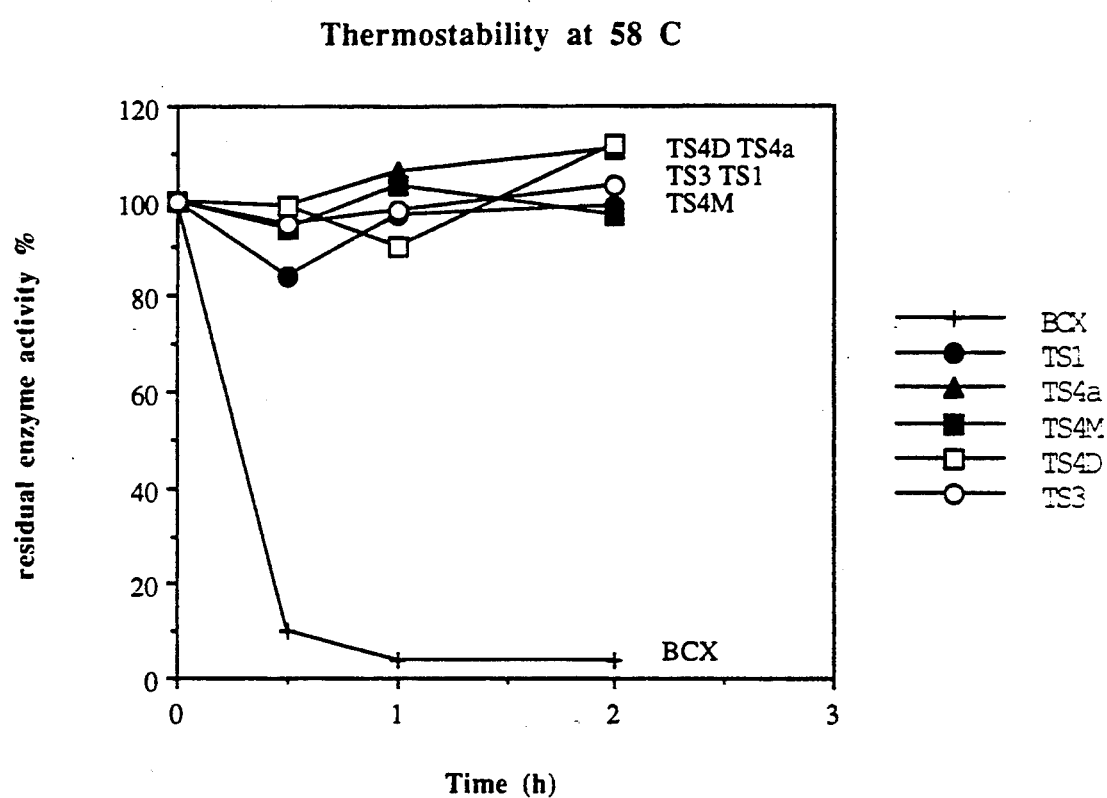

FIG. 14 shows the thermostability at 58° C. of *B. circulans* xylanase mutants TS3 and TS4D, which are combinations of mutants shown in FIGS. 11 and 12.

Figure 15:
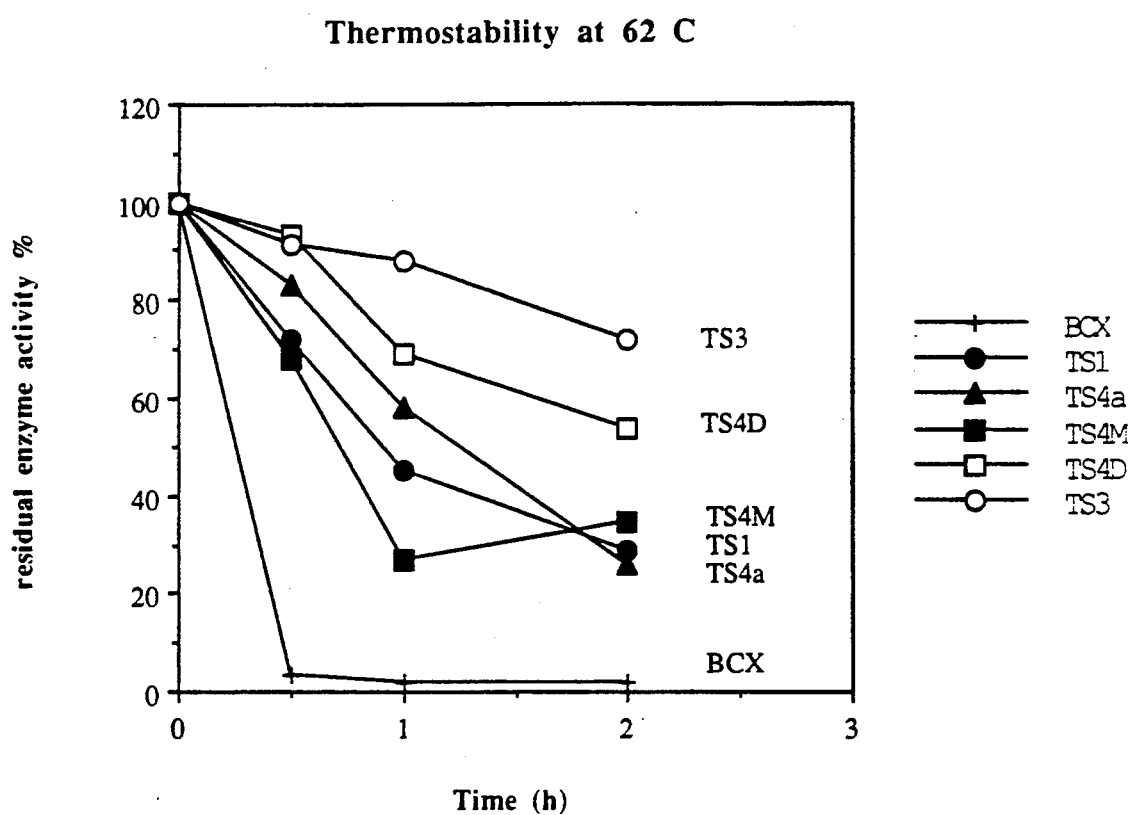

FIG. 15 shows the thermostability at 62° C. of *B. circulans* xylanase mutants TS3 and TS4D, which are combinations of mutants shown in FIGS. 11 and 12.

Figure 16:
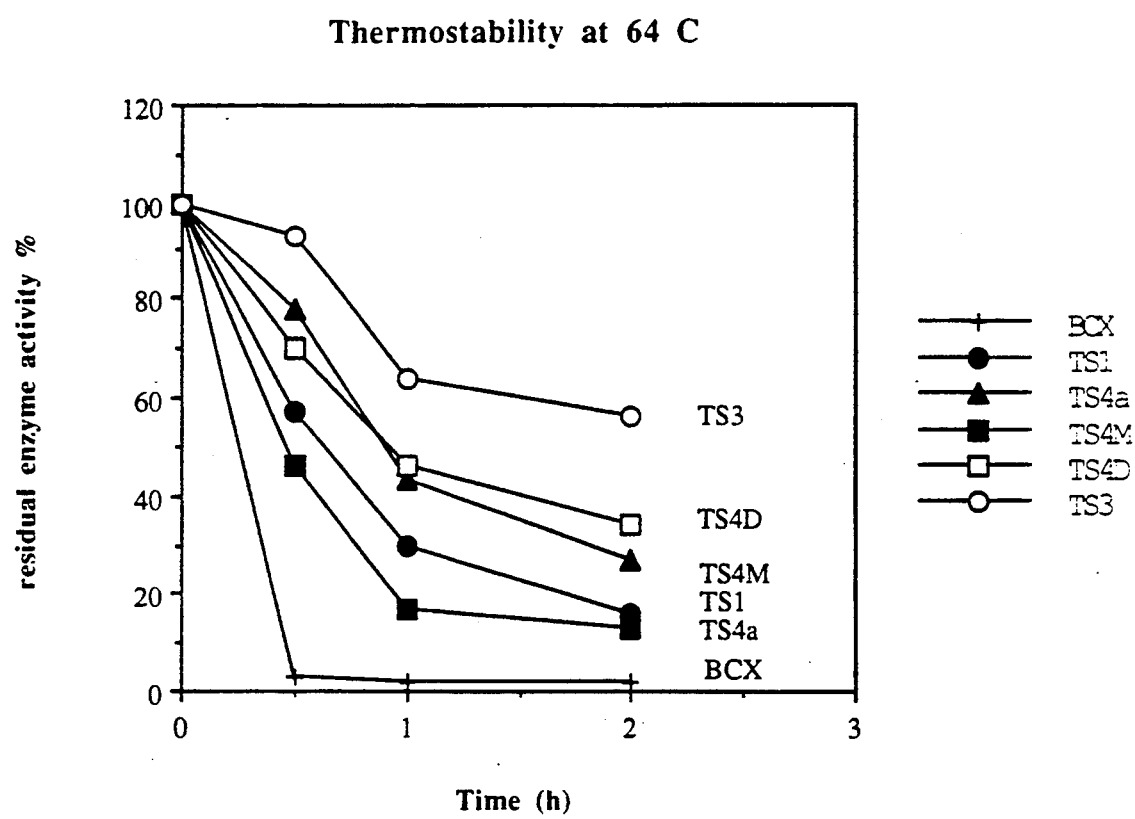

FIG. 16 shows the thermostability at 64° C. of *B. circulans* xylanase mutants TS3 and TS4D, which are combinations of mutations shown in FIGS. 11 and 12.

Figure 17:
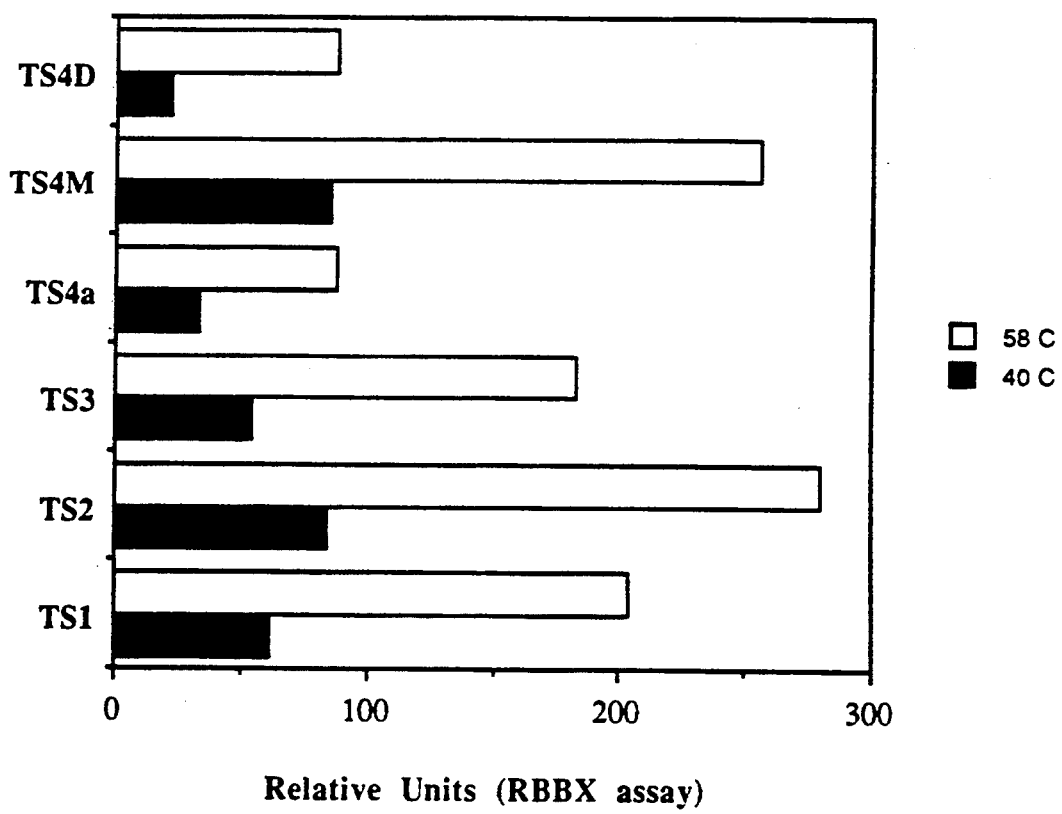

FIG. 17 illustrates the effect of temperature on enzyme activity. With the thermostable xylanase mutants shown, an increase of 18° C. resulted in between 2.6 and 4 fold increase in activity.

Figure 18:
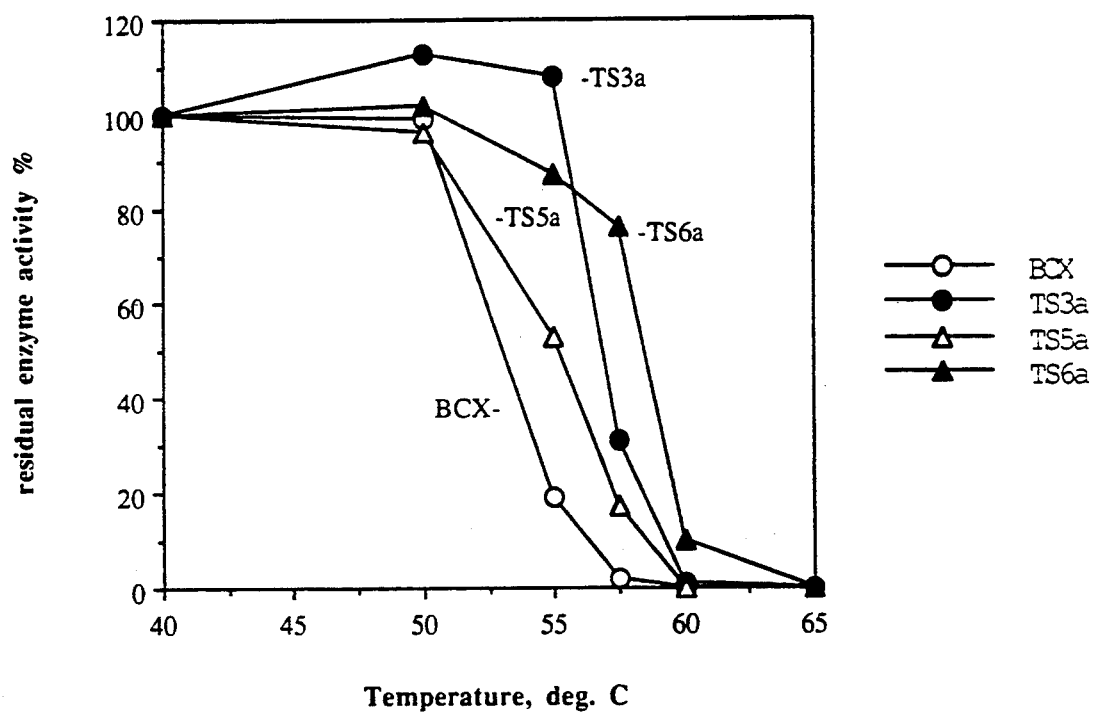

FIG. 18 shows the thermostability of xylanase BCX and mutants wherein xylanase from the wild-type or mutant strains were heated at various temperatures for 30 minutes. After cooling to 20° C. a residual enzymatic activity of the heated samples were determined via the HBAH assay at 40° C.

Figure 19:
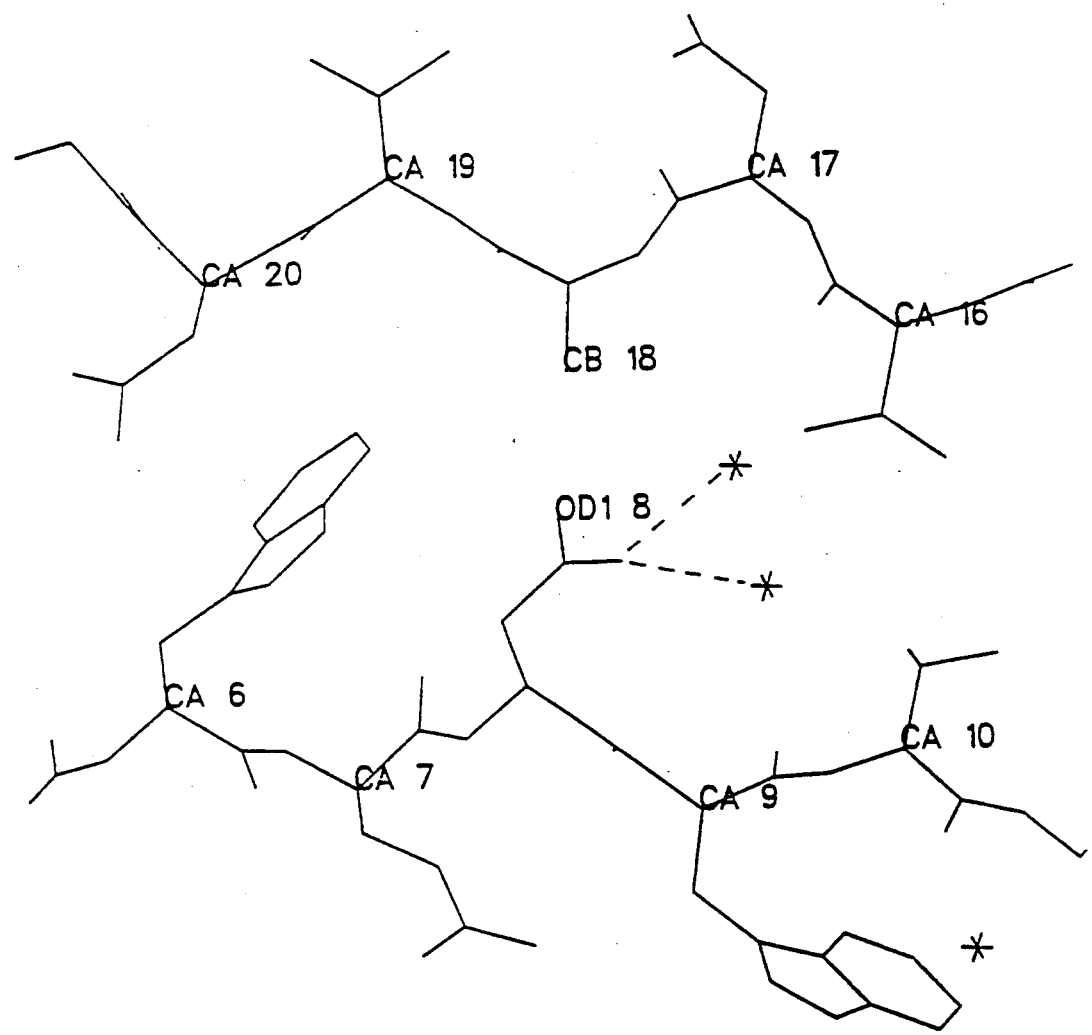

FIG. 19 shows the molecular structure of residue 6–10 and 16–20 of the N-terminus of the wild-type BCX. CA represents the alpha carbon atom of each residue. CB is the beta-carbon atom of the side-chain. OD1 is the delta oxygen atom in the side-chain of asparagine-8. The number next to CA, CB and OD1 designates the residue to which these atoms belong. The two asterisks are the two buried water molecules. The broken lines represent the hydrogen bonds.

Figure 20:
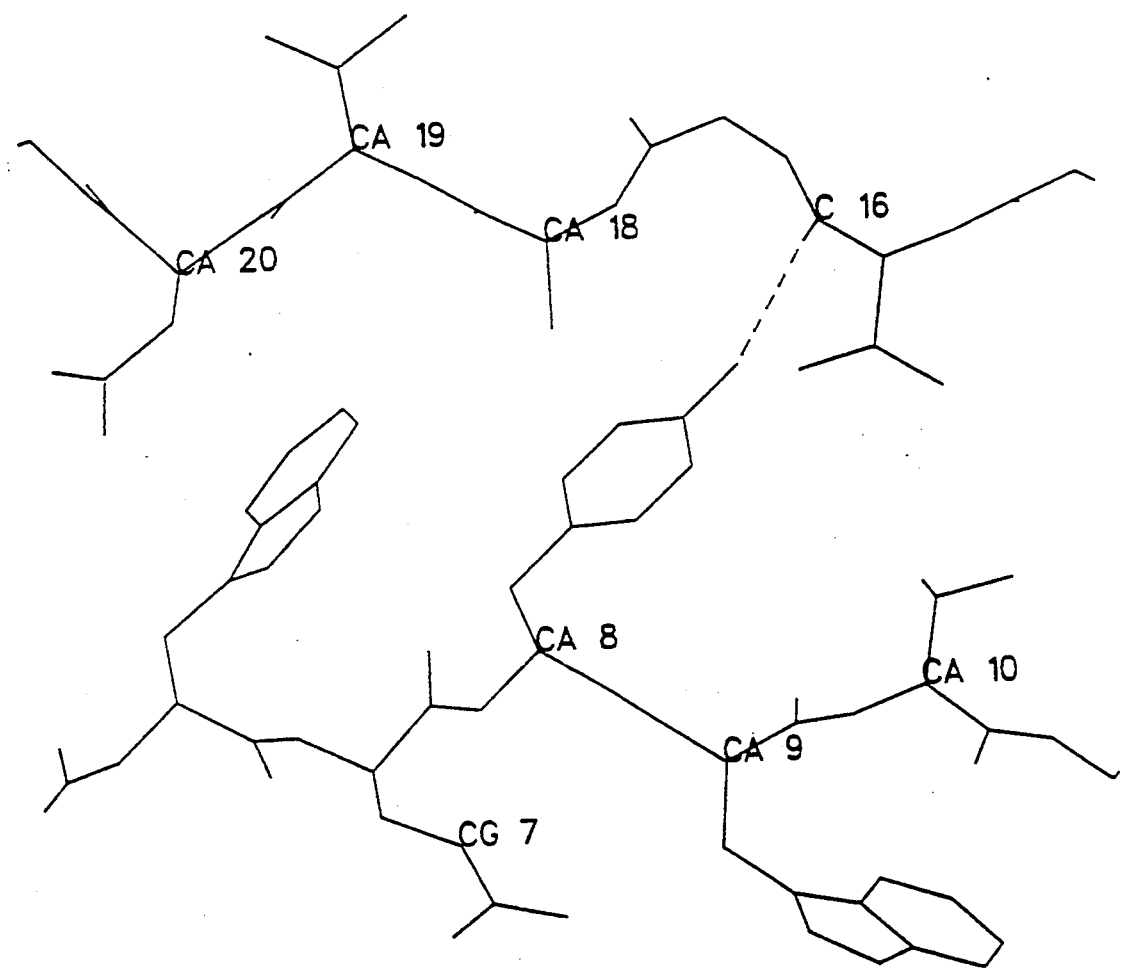

FIG. 20 shows the molecular structure of the same region as FIG. 19, illustrating the postulated effect of the asparagine to tyrosine mutation at residue-8 (TS5a).

Figure 21:
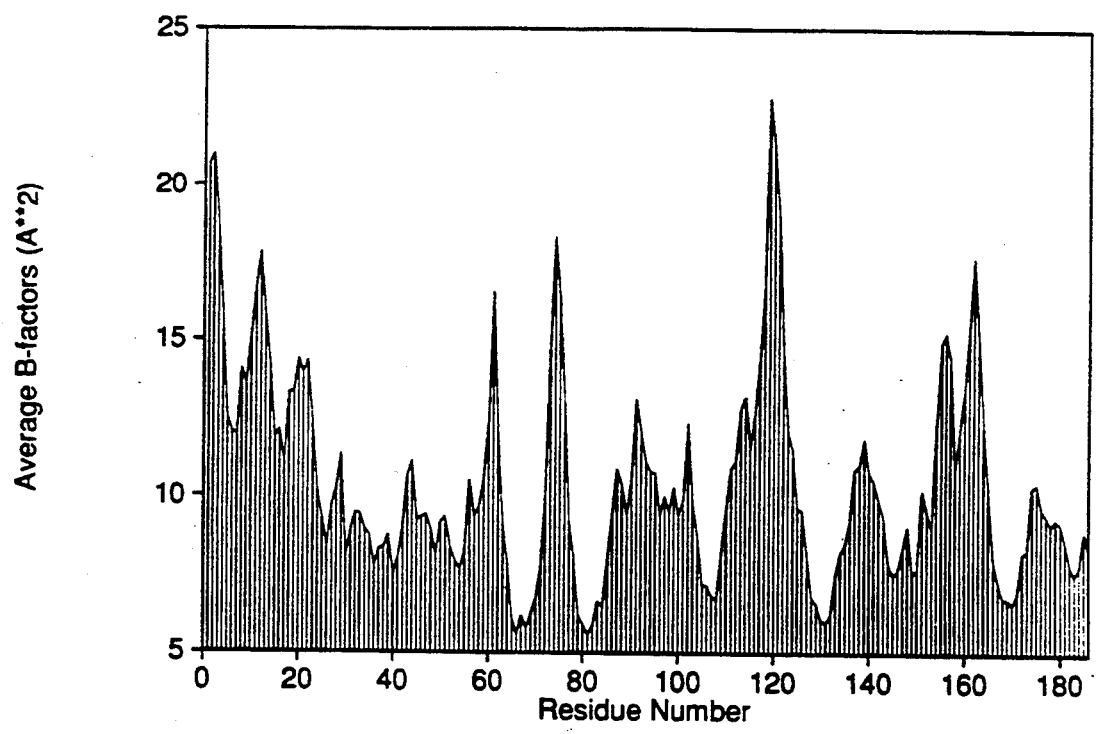

FIG. 21 shows the average main-chain B-factors for the xylanase from *B. circulans*. The B-factor is a measure of the spreading out of electron density. It is thus a measure of the mobility of the atoms in a structure. This plot shows the B-factors (or mobility) averaged over all main-chain atoms in each amino acid. Thus the regions near the amino-terminus and near residue 120 are the most mobile parts of the structure.

Figure 22:
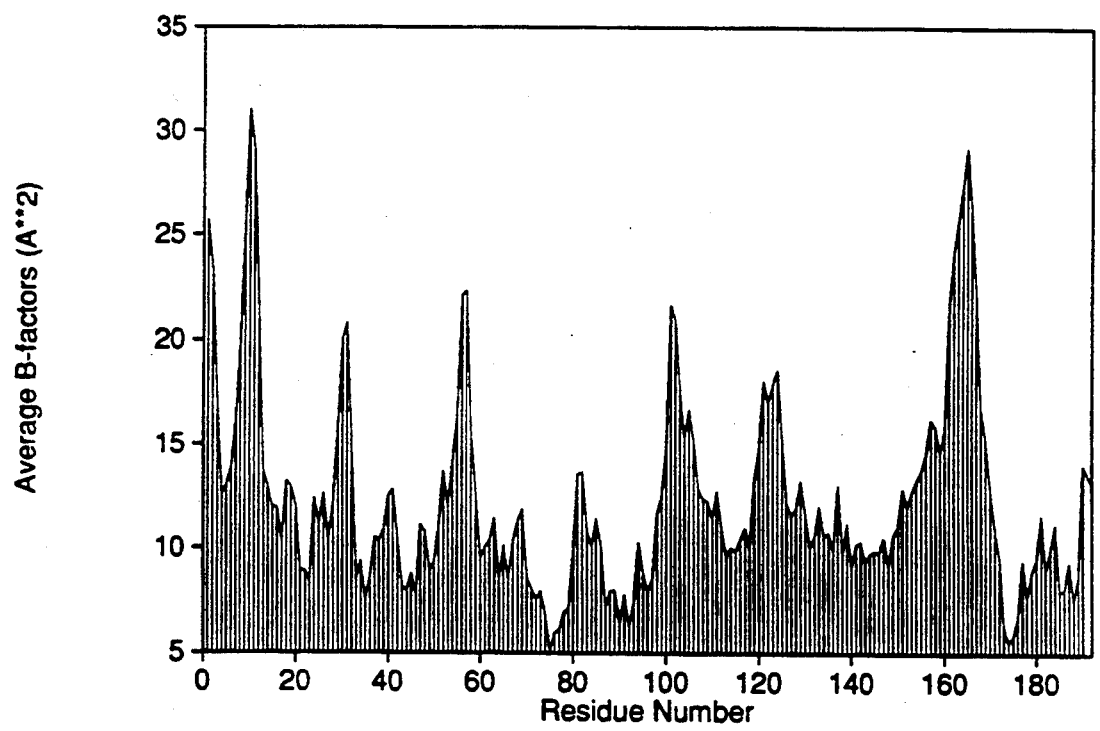

FIG. 22 shows the average main-chain B-factors for the xylanase from *T. harzianum*.

Figure 23:
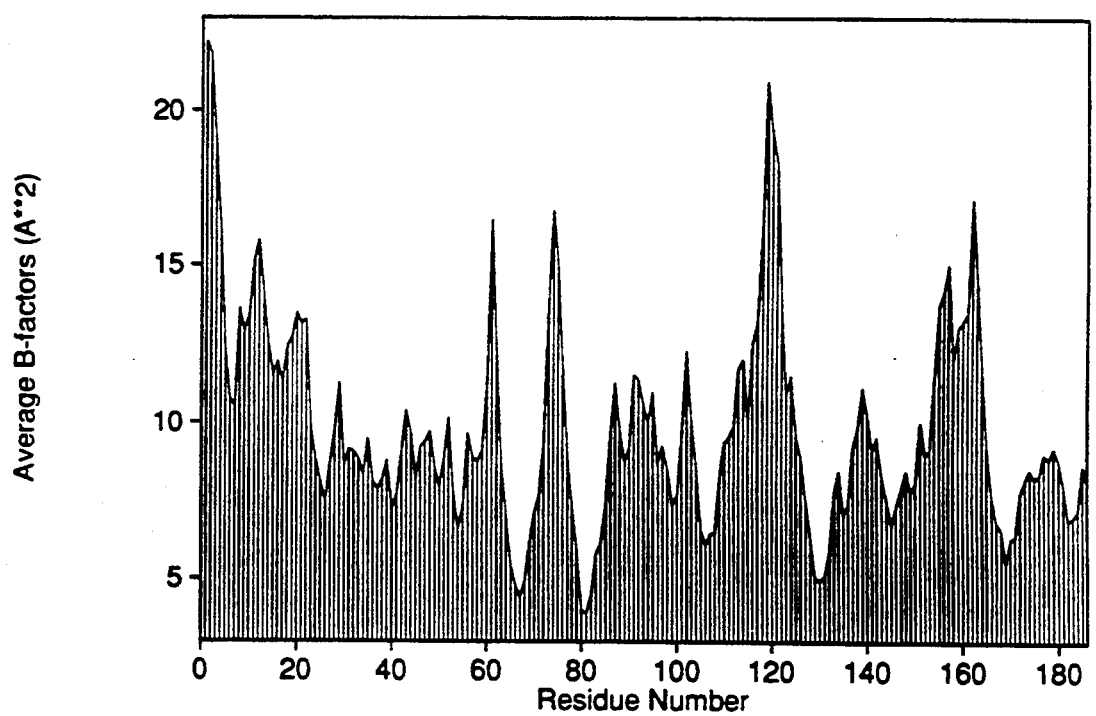

FIG. 23 shows the average main-chain B-factors for the disulfide-containing mutant (TS1) of the xylanase from *B. circulans*.

Figure 24:
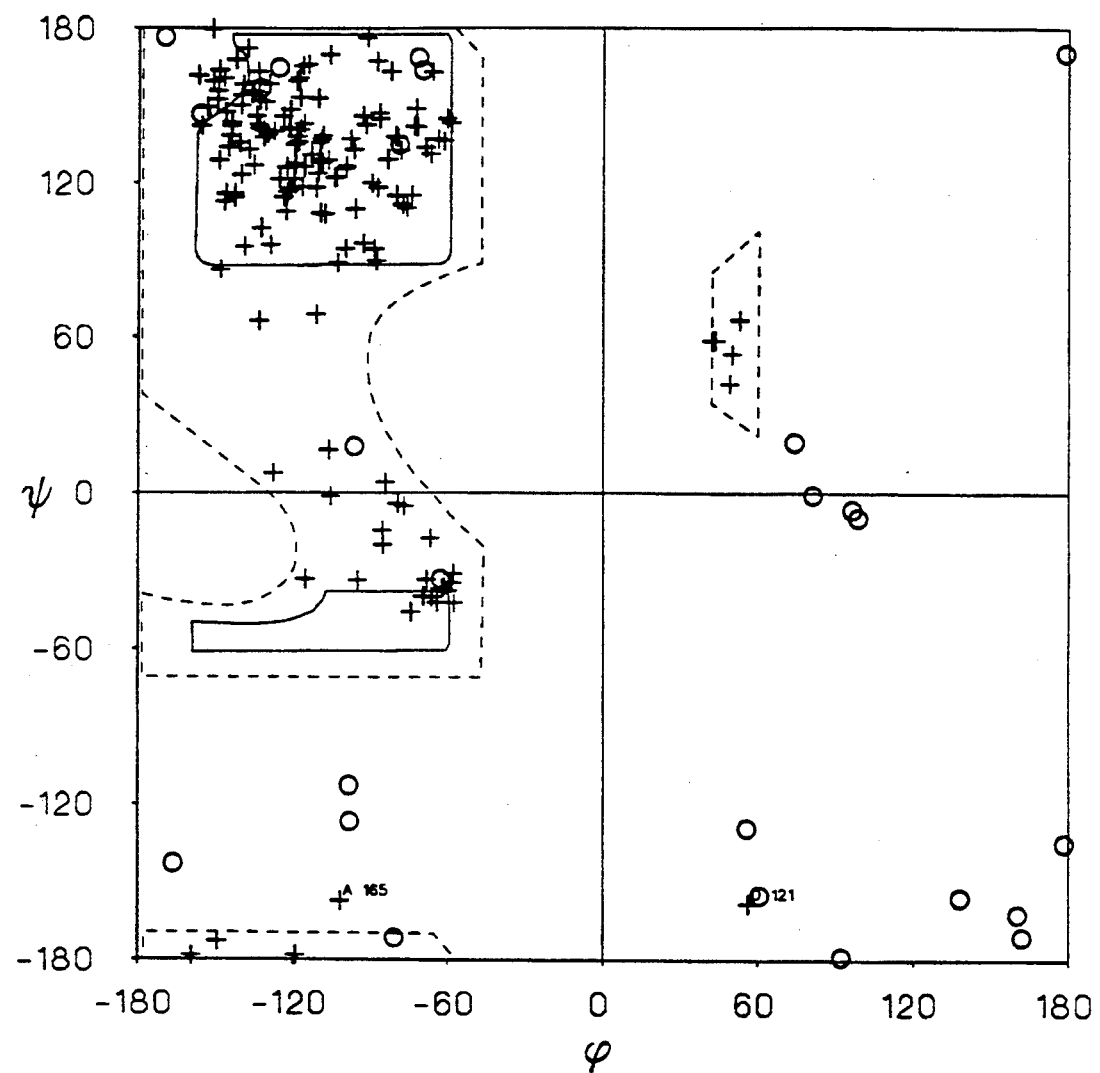

FIG. 24 shows a Ramachandran plot for the xylanase from *B. circulans*. The two residues (D121 and A165) with main-chain dihedral angles outside of normal limits are labelled. Glycines are shown with circles, while all other amino acids are shown with "plus" signs.

Figure 25:
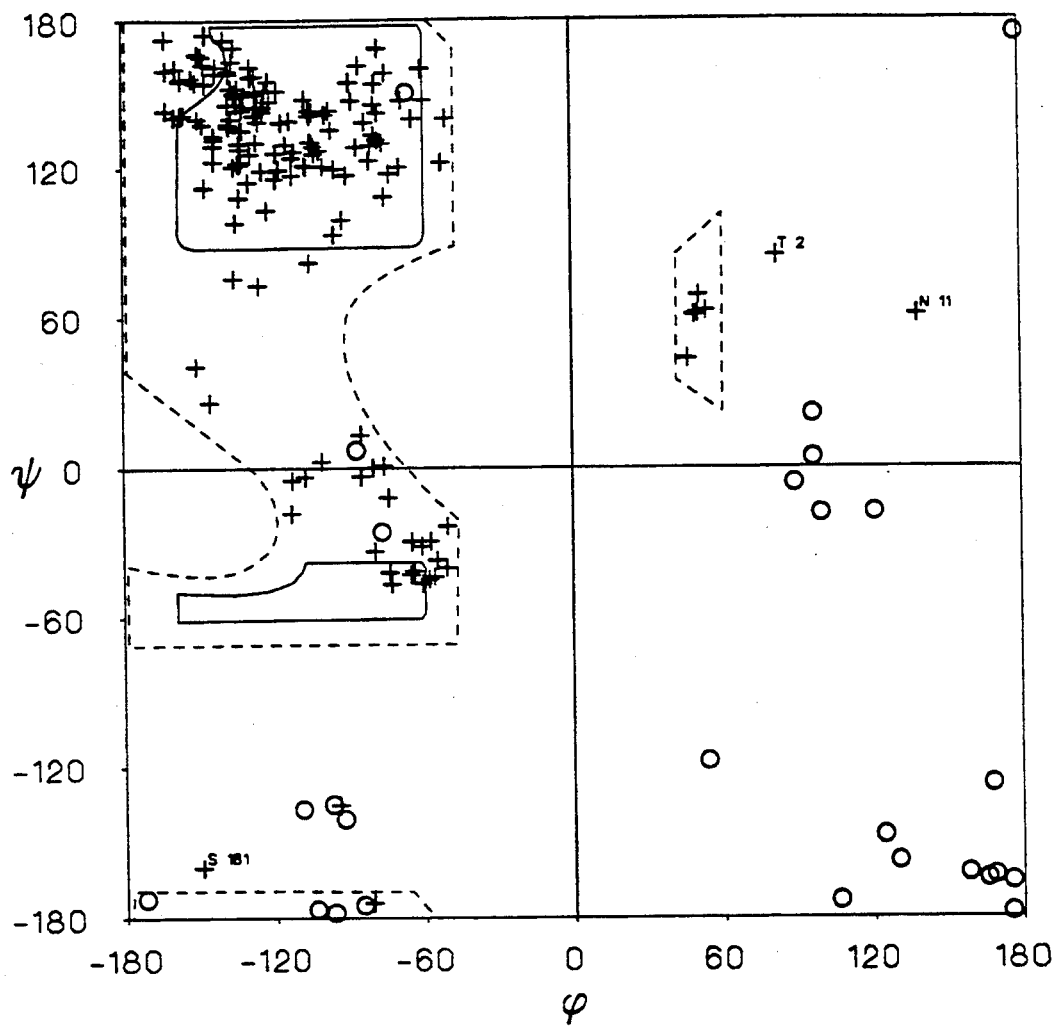

FIG. 25 shows a Ramachandran plot for the xylanase from *T. harzianum*. The three residues (T2, N11 and S181) with main-chain dihedral angles outside of normal limits are labelled. Glycines are shown with circles, while all other amino acids are shown with "plus" signs.

DETAILED DESCRIPTION OF THE INVENTION

The complete amino acid sequence of the low molecular weight xylanase has been determined from a number of different bacterial and fungal sources (M. Yaguchi et al., Amino Acid Sequence of the Low-Molecular-Weight Xylanase from *Trichoderma viride*, Xylans and Xylanases, edited by J. Visser et al, 1992, 149–154). The sequence comparison reported in the reference referred to above has been extended to show the sequence similarities and differences between the bacteria and fungal family G xylanases as listed below.

BACTERIAL

*Bacillus pumilus*
Fukusaki, E., Panbangred, W., Shinmyo, A., Okada, H. FEBS Letters 171:197–201 (1984)

*Clostridium acetobutylicum*, XYN B
Zappe, H., Jones, W. A., Woods, D. R. Nucleic Acids Research 18:2179 (1990)

*Ruminococcus flavefaciens*
Zhang, J., Flint, H. J. EMBL database accession number Z11127 (1992)

Streptomyces sp. No. 36a
Nagashima, M., Okumoto, Y., Okanishi, M. Trends in Actinomycetoligia, 91–96 (1989)

*Streptomyces lividans*, XYN B and XYN C
Shareck, F., Roy, C., Yaguchi, M., Morosoli, R., Kluepfel, D. Gene, 107:75–82 (1991)

*Bacillus circulans*
Yang, R. C. A., MacKenzie, C. R., Narang, R. A. Nucleic Acids Res. 16:7187 (1988)

*Bacillus subtilis*
Paice, M. G., Bourbonnais, R., Desrochers, M., Jurasek, L., Yaguchi, M. Arch. Microbiol. 144:201–206 (1986)

FUNGAL

*Trichoderma reesei*, XYN I and XYN II
Torronene, A., Mach, R. L., Messner, R., Gonzalez, R., Kalkkinen, N., Harkki, A., Kubicek, C.P. Bio/Technology 10:1461–1465 (1992)

*Trichoderma viride*, 20 KD
Yaguchi, M., Roy, C., Ujlie, M., Watson, D.C., Wakarchuk, W. Xylans and Xylanases, ed. by J. Visser et al., Elsevier, pp. 149–154 (1992)

*Trichoderma harzianum*, 20 KD
Yaguchi, M., Roy, C., Watson, D. C., Rollin, F., Tan. L.U.L., Senior, D. J., Saddler, J. N. Xylans and Xylanases, ed. by J. Visser et al., Elsevier, pp. 435–438 (1992)

*Schizophyllum commune*, Xylanase A
Oku, T., Roy, C., Watson, D. C., Wakarchuk, W., Yaguchi, M., Jurasek, L., Paice, M. G. (unpublished)

*Aspergillus niger var. awamori*
Maat, J., Roza, M., Verbakel, J., Stam, H., Santos da Silva, M. J., Egmond, M. R., Hagemans, M.L.D., Gorcom, R.F.M.v., Hessing, J.G.M., Hondel, C.A.M.J.J.v.d., Rotterdam, C.v. Xylans and Xylanases, ed. by J. Visser et al., Elsevier, pp. 349–360 (1992)

*Aspergillus tubigensis*, XYL A
de Graaff, L. H., van den Broeck, H. C., van Ooijan, A.J.J., Visser, J. Xylans and Xylanases, ed. by J. Visser et al., Elsevier, pp. 235–246 (1992)

FIG. 1 shows a multiple sequence alignment among low molecular mass xylanases obtained with GeneWorks version 2.2.1 (IntelliGenetics, Inc., Mountain View, Calif.), which has been manually edited to conform to the structural homology between the xylanases from *B. circulans* and *T. harzianum*. The extended N-terminal sequence of the *C. acetobutylicum* xylanase B (residues 1–31) and the C-terminal sequences of *S. lividans*, xylanase B (residues 216–293) are not shown.

Table 1 shows the amino acid sequence identity (percentage) between different groups of family G xylanases.

TABLE 1

Amino Acid Sequence Identity (%) between the Family G Xylanases

|  | Bacillus pumilus | Bacillus circulans | Trichoderma harzianum | Schizo. commune |
|---|---|---|---|---|
| BACTERLAL | | | | |
| B. pumilus | — | 43 | 46 | 40 |
| C. acetobutylicum | 71 | 42 | 42 | 41 |
| R. flavefaciens | 46 | 36 | 41 | 39 |
| Strept. Sp. 36a | 49 | 57 | 50 | 47 |
| S. lividans, B | 50 | 56 | 51 | 47 |
| S. lividans, C | 49 | 60 | 52 | 51 |
| B. circulans | 43 | — | 51 | 50 |
| B. subtilis | 43 | 99 | 51 | 50 |
| FUNGAL | | | | |
| T. reesei, II | 47 | 51 | 95 | 53 |
| T. viride | 48 | 50 | 94 | 53 |
| T. harzianum | 46 | 51 | — | 54 |
| S. commune | 40 | 50 | 54 | — |
| A. niger awamori | 34 | 42 | 41 | 38 |
| A. tubigensis, A | 34 | 43 | 41 | 37 |
| T. reesei, I | 37 | 46 | 50 | 38 |

The xylanase from *B. circulans* is functionally identical to that from *B. subtilis*, which will be seen later in the Examples. These proteins differ at only one residue and are among the shortest xylanases, with their N-terminus lacking at least 10 amino acid residues compared to other xylanases.

Due to the sequence homology among related xylanases, one could expect that mutations for the introduction of SS bonds, as demonstrated in the examples below for *B. circulans* xylanase, could be extended to other xylanases from bacterial or fungal sources to produce similar effects.

The three-dimensional crystal structure of the *B. circulans* xylanase is represented in FIG. 2. This ribbon representation shows that the structure is composed of three beta-sheets and one alpha-helix. The first two beta-sheets are roughly parallel, while sheet III is at about a 90° angle to sheet II. Sheets I and II are each composed of five strands, while sheet III contains 6 strands. The alpha-helix lies across the back of sheet III and the last two strands of sheet III fold over one edge of the alpha-helix. The active site lies in the cleft between sheets II and III. The x-ray co-ordinates of the structure is given below.

| | | | | | | | | | |
|---|---|---|---|---|---|---|---|---|---|
| ATOM | 1 | CB | ALA | 1 | 32.404 | 42.580 | 22.419 | 1.00 | 19.66 |
| ATOM | 2 | C | ALA | 1 | 34.898 | 42.615 | 22.344 | 1.00 | 20.06 |
| ATOM | 3 | O | ALA | 1 | 35.540 | 41.613 | 22.023 | 1.00 | 20.55 |
| ATOM | 6 | N | ALA | 1 | 33.610 | 42.325 | 20.269 | 1.00 | 18.68 |
| ATOM | 8 | CA | ALA | 1 | 33.627 | 42.997 | 21.599 | 1.00 | 19.67 |
| ATOM | 9 | N | SER | 2 | 35.283 | 43.440 | 23.308 | 1.00 | 20.15 |
| ATOM | 11 | CA | SER | 2 | 36.455 | 43.158 | 24.114 | 1.00 | 20.60 |
| ATOM | 12 | CB | SER | 2 | 37.000 | 44.436 | 24.753 | 1.00 | 22.52 |
| ATOM | 13 | OG | SER | 2 | 37.614 | 45.262 | 23.783 | 1.00 | 25.52 |
| ATOM | 15 | C | SER | 2 | 36.062 | 42.184 | 25.210 | 1.00 | 20.08 |
| ATOM | 16 | O | SER | 2 | 34.967 | 42.270 | 25.786 | 1.00 | 19.93 |
| ATOM | 17 | N | THR | 3 | 36.930 | 41.215 | 25.440 | 1.00 | 18.98 |
| ATOM | 19 | CA | THR | 3 | 36.715 | 40.235 | 26.475 | 1.00 | 18.01 |
| ATOM | 20 | CB | THR | 3 | 37.469 | 38.943 | 26.145 | 1.00 | 18.17 |
| ATOM | 21 | OG1 | THR | 3 | 38.849 | 39.247 | 25.891 | 1.00 | 17.58 |
| ATOM | 23 | CG2 | THR | 3 | 36.860 | 38.273 | 24.920 | 1.00 | 17.34 |
| ATOM | 24 | C | THR | 3 | 37.306 | 40.884 | 27.713 | 1.00 | 17.67 |
| ATOM | 25 | O | THR | 3 | 38.232 | 41.694 | 27.610 | 1.00 | 18.99 |
| ATOM | 26 | N | ASP | 4 | 36.739 | 40.601 | 28.874 | 1.00 | 16.43 |
| ATOM | 28 | CA | ASP | 4 | 37.252 | 41.190 | 30.104 | 1.00 | 16.02 |
| ATOM | 29 | CB | ASP | 4 | 36.284 | 42.252 | 30.644 | 1.00 | 16.80 |
| ATOM | 30 | CG | ASP | 4 | 34.886 | 41.706 | 30.907 | 1.00 | 19.10 |
| ATOM | 31 | OD1 | ASP | 4 | 34.741 | 40.512 | 31.221 | 1.00 | 17.29 |
| ATOM | 32 | OD2 | ASP | 4 | 33.923 | 42.495 | 30.810 | 1.00 | 21.94 |
| ATOM | 33 | C | ASP | 4 | 37.506 | 40.143 | 31.161 | 1.00 | 15.35 |
| ATOM | 34 | O | ASP | 4 | 37.721 | 40.470 | 32.325 | 1.00 | 16.73 |
| ATOM | 35 | N | TYR | 5 | 37.455 | 38.875 | 30.769 | 1.00 | 13.80 |
| ATOM | 37 | CA | TYR | 5 | 37.665 | 37.812 | 31.722 | 1.00 | 12.53 |
| ATOM | 38 | CB | TYR | 5 | 36.318 | 37.186 | 32.119 | 1.00 | 12.90 |
| ATOM | 39 | CG | TYR | 5 | 36.430 | 36.223 | 33.270 | 1.00 | 14.19 |
| ATOM | 40 | CD1 | TYR | 5 | 36.583 | 36.679 | 34.577 | 1.00 | 15.98 |
| ATOM | 41 | CE1 | TYR | 5 | 36.748 | 35.786 | 35.632 | 1.00 | 17.93 |
| ATOM | 42 | CD2 | TYR | 5 | 36.438 | 34.855 | 33.052 | 1.00 | 14.54 |
| ATOM | 43 | CE2 | TYR | 5 | 36.603 | 33.966 | 34.092 | 1.00 | 16.97 |
| ATOM | 44 | CZ | TYR | 5 | 36.762 | 34.431 | 35.379 | 1.00 | 17.23 |
| ATOM | 45 | OH | TYR | 5 | 36.972 | 33.528 | 36.401 | | |

-continued

| | | | | | | | | |
|---|---|---|---|---|---|---|---|---|
| ATOM | 47 | C | TYR | 5 | 38.610 | 36.754 | 31.175 | 1.00 21.34 |
| ATOM | 48 | O | TYR | 5 | 38.539 | 36.387 | 29.996 | 1.00 12.09 |
| ATOM | 49 | N | TRP | 6 | 39.523 | 36.309 | 32.027 | 1.00 11.58 |
| ATOM | 51 | CA | TRP | 6 | 40.498 | 35.270 | 31.691 | 1.00 11.81 |
| ATOM | 52 | CB | TRP | 6 | 41.922 | 35.830 | 31.788 | 1.00 12.62 |
| ATOM | 53 | CG | TRP | 6 | 43.050 | 34.813 | 31.806 | 1.00 12.94 |
| ATOM | 54 | CD2 | TRP | 6 | 43.420 | 33.895 | 30.761 | 1.00 12.88 |
| ATOM | 55 | CE2 | TRP | 6 | 44.595 | 33.232 | 31.184 | 1.00 12.72 |
| ATOM | 56 | CE3 | TRP | 6 | 42.879 | 33.570 | 29.515 | 1.00 13.51 |
| ATOM | 57 | CD1 | TRP | 6 | 43.982 | 34.661 | 32.791 | 1.00 13.01 |
| ATOM | 58 | NE1 | TRP | 6 | 44.912 | 33.718 | 32.425 | 1.00 13.74 |
| ATOM | 60 | CZ2 | TRP | 6 | 45.236 | 32.271 | 30.404 | 1.00 14.48 |
| ATOM | 61 | CZ3 | TRP | 6 | 43.518 | 32.607 | 28.740 | 1.00 13.34 |
| ATOM | 62 | CH2 | TRP | 6 | 44.681 | 31.974 | 29.187 | 1.00 13.00 |
| ATOM | 63 | C | TRP | 6 | 40.292 | 34.122 | 32.670 | 1.00 12.55 |
| ATOM | 64 | O | TRP | 6 | 40.399 | 34.289 | 33.890 | 1.00 12.15 |
| ATOM | 65 | N | GLN | 7 | 39.918 | 32.974 | 32.118 | 1.00 12.46 |
| ATOM | 67 | CA | GLN | 7 | 39.656 | 31.763 | 32.877 | 1.00 12.04 |
| ATOM | 68 | CB | GLN | 7 | 38.380 | 31.105 | 32.332 | 1.00 12.76 |
| ATOM | 69 | CG | GLN | 7 | 38.105 | 29.698 | 32.821 | 1.00 13.89 |
| ATOM | 70 | CD | GLN | 7 | 37.879 | 29.624 | 34.314 | 1.00 16.24 |
| ATOM | 71 | OE1 | GLN | 7 | 37.712 | 30.644 | 34.993 | 1.00 17.99 |
| ATOM | 72 | NE2 | GLN | 7 | 37.867 | 28.411 | 34.838 | 1.00 19.93 |
| ATOM | 75 | C | GLN | 7 | 40.843 | 30.818 | 32.726 | 1.00 20.16 |
| ATOM | 76 | O | GLN | 7 | 41.211 | 30.455 | 31.612 | 1.00 12.58 |
| ATOM | 77 | N | ASN | 8 | 41.471 | 30.451 | 33.837 | 1.00 11.22 |
| ATOM | 79 | CA | ASN | 8 | 42.615 | 29.550 | 33.784 | 1.00 12.68 |
| ATOM | 80 | CB | ASN | 8 | 43.924 | 30.351 | 33.687 | 1.00 13.88 |
| ATOM | 81 | CG | ASN | 8 | 45.166 | 29.462 | 33.674 | 1.00 15.02 |
| ATOM | 82 | OD1 | ASN | 8 | 46.279 | 29.935 | 33.916 | 1.00 16.98 |
| ATOM | 83 | ND2 | ASN | 8 | 44.990 | 28.192 | 33.377 | 1.00 20.52 |
| ATOM | 86 | C | ASN | 8 | 42.604 | 28.712 | 35.045 | 1.00 17.00 |
| ATOM | 87 | O | ASN | 8 | 43.215 | 29.075 | 36.057 | 1.00 14.62 |
| ATOM | 88 | N | TRP | 9 | 41.894 | 27.594 | 34.978 | 1.00 15.63 |
| ATOM | 90 | CA | TRP | 9 | 41.766 | 26.703 | 36.113 | 1.00 14.02 |
| ATOM | 91 | CB | TRP | 9 | 40.300 | 26.630 | 36.562 | 1.00 14.57 |
| ATOM | 92 | CG | TRP | 9 | 40.058 | 25.646 | 37.680 | 1.00 16.93 |
| ATOM | 93 | CD2 | TRP | 9 | 39.703 | 24.260 | 37.548 | 1.00 19.06 |
| ATOM | 94 | CE2 | TRP | 9 | 39.600 | 23.728 | 38.851 | 1.00 19.90 |
| ATOM | 95 | CE3 | TRP | 9 | 39.462 | 23.420 | 36.455 | 1.00 20.63 |
| ATOM | 96 | CD1 | TRP | 9 | 40.151 | 25.888 | 39.025 | 1.00 20.29 |

-continued

| | | | | | | | | |
|---|---|---|---|---|---|---|---|---|
| 1.00 | 20.86 | | | | | | | |
| ATOM | | 97 | NE1 | TRP | 9 | 39.879 | 24.740 | 39.731 |
| 1.00 | 21.73 | | | | | | | |
| ATOM | | 99 | CZ2 | TRP | 9 | 39.268 | 22.397 | 39.090 |
| 1.00 | 20.83 | | | | | | | |
| ATOM | | 100 | CZ3 | TRP | 9 | 39.133 | 22.100 | 36.694 |
| 1.00 | 20.61 | | | | | | | |
| ATOM | | 101 | CH2 | TRP | 9 | 39.038 | 21.600 | 38.003 |
| 1.00 | 20.23 | | | | | | | |
| ATOM | | 102 | C | TRP | 9 | 42.256 | 25.300 | 35.799 |
| 1.00 | 14.32 | | | | | | | |
| ATOM | | 103 | O | TRP | 9 | 41.974 | 24.757 | 34.732 |
| 1.00 | 13.18 | | | | | | | |
| ATOM | | 104 | N | THR | 10 | 42.978 | 24.714 | 36.745 |
| 1.00 | 13.98 | | | | | | | |
| ATOM | | 106 | CA | THR | 10 | 43.461 | 23.352 | 36.609 |
| 1.00 | 14.97 | | | | | | | |
| ATOM | | 107 | CB | THR | 10 | 44.929 | 23.291 | 36.133 |
| 1.00 | 15.94 | | | | | | | |
| ATOM | | 108 | OG1 | THR | 10 | 45.385 | 21.934 | 36.177 |
| 1.00 | 17.17 | | | | | | | |
| ATOM | | 110 | CG2 | THR | 10 | 45.831 | 24.146 | 37.021 |
| 1.00 | 17.26 | | | | | | | |
| ATOM | | 111 | C | THR | 10 | 43.362 | 22.696 | 37.976 |
| 1.00 | 15.04 | | | | | | | |
| ATOM | | 112 | O | THR | 10 | 43.419 | 23.378 | 39.000 |
| 1.00 | 15.78 | | | | | | | |
| ATOM | | 113 | N | ASP | 11 | 43.145 | 21.387 | 38.000 |
| 1.00 | 15.06 | | | | | | | |
| ATOM | | 115 | CA | ASP | 11 | 43.101 | 20.686 | 39.277 |
| 1.00 | 16.34 | | | | | | | |
| ATOM | | 116 | CB | ASP | 11 | 42.200 | 19.448 | 39.228 |
| 1.00 | 16.43 | | | | | | | |
| ATOM | | 117 | CG | ASP | 11 | 42.629 | 18.417 | 38.186 |
| 1.00 | 16.04 | | | | | | | |
| ATOM | | 118 | OD1 | ASP | 11 | 43.738 | 18.498 | 37.612 |
| 1.00 | 16.20 | | | | | | | |
| ATOM | | 119 | OD2 | ASP | 11 | 41.819 | 17.506 | 37.945 |
| 1.00 | 17.65 | | | | | | | |
| ATOM | | 120 | C | ASP | 11 | 44.529 | 20.336 | 39.724 |
| 1.00 | 17.44 | | | | | | | |
| ATOM | | 121 | O | ASP | 11 | 44.723 | 19.661 | 40.731 |
| 1.00 | 18.70 | | | | | | | |
| ATOM | | 122 | N | GLY | 12 | 45.517 | 20.780 | 38.946 |
| 1.00 | 17.45 | | | | | | | |
| ATOM | | 124 | CA | GLY | 12 | 46.913 | 20.547 | 39.287 |
| 1.00 | 17.91 | | | | | | | |
| ATOM | | 125 | C | GLY | 12 | 47.616 | 19.394 | 38.593 |
| 1.00 | 17.48 | | | | | | | |
| ATOM | | 126 | O | GLY | 12 | 48.841 | 19.251 | 38.699 |
| 1.00 | 18.34 | | | | | | | |
| ATOM | | 127 | N | GLY | 13 | 46.862 | 18.568 | 37.881 |
| 1.00 | 16.38 | | | | | | | |
| ATOM | | 129 | CA | GLY | 13 | 47.466 | 17.443 | 37.202 |
| 1.00 | 15.25 | | | | | | | |
| ATOM | | 130 | C | GLY | 13 | 48.141 | 17.771 | 35.887 |
| 1.00 | 15.48 | | | | | | | |
| ATOM | | 131 | O | GLY | 13 | 47.608 | 18.530 | 35.070 |
| 1.00 | 15.97 | | | | | | | |
| ATOM | | 132 | N | GLY | 14 | 49.319 | 17.187 | 35.687 |
| 1.00 | 14.01 | | | | | | | |
| ATOM | | 134 | CA | GLY | 14 | 50.062 | 17.366 | 34.456 |
| 1.00 | 13.22 | | | | | | | |
| ATOM | | 135 | C | GLY | 14 | 50.476 | 18.783 | 34.128 |
| 1.00 | 13.48 | | | | | | | |
| ATOM | | 136 | O | GLY | 14 | 50.581 | 19.642 | 35.009 |
| 1.00 | 15.09 | | | | | | | |
| ATOM | | 137 | N | ILE | 15 | 50.707 | 19.026 | 32.845 |
| 1.00 | 12.64 | | | | | | | |
| ATOM | | 139 | CA | ILE | 15 | 51.145 | 20.327 | 32.387 |
| 1.00 | 13.51 | | | | | | | |
| ATOM | | 140 | CB | ILE | 15 | 52.415 | 20.196 | 31.469 |
| 1.00 | 16.01 | | | | | | | |
| ATOM | | 141 | CG2 | ILE | 15 | 52.750 | 21.523 | 30.777 |
| 1.00 | 16.26 | | | | | | | |
| ATOM | | 142 | CG1 | ILE | 15 | 53.615 | 19.720 | 32.291 |
| 1.00 | 17.95 | | | | | | | |
| ATOM | | 143 | CD1 | ILE | 15 | 53.595 | 18.263 | 32.618 |
| 1.00 | 22.36 | | | | | | | |
| ATOM | | 144 | C | ILE | 15 | 50.054 | 21.032 | 31.604 |
| 1.00 | 11.40 | | | | | | | |
| ATOM | | 145 | O | ILE | 15 | 49.447 | 20.438 | 30.715 |

| | | | | | | | | | |
|---|---|---|---|---|---|---|---|---|---|
| ATOM | 146 | N | VAL | 16 | 49.780 | 22.276 | 31.984 | 1.00 | 11.13 |
| ATOM | 148 | CA | VAL | 16 | 48.811 | 23.124 | 31.291 | 1.00 | 11.65 |
| ATOM | 149 | CB | VAL | 16 | 47.501 | 23.332 | 32.103 | 1.00 | 11.43 |
| ATOM | 150 | CG1 | VAL | 16 | 46.539 | 24.263 | 31.332 | 1.00 | 12.58 |
| ATOM | 151 | CG2 | VAL | 16 | 46.833 | 21.989 | 32.368 | 1.00 | 13.92 |
| ATOM | 152 | C | VAL | 16 | 49.515 | 24.464 | 31.084 | 1.00 | 12.26 |
| ATOM | 153 | O | VAL | 16 | 49.699 | 25.225 | 32.028 | 1.00 | 12.47 |
| ATOM | 154 | N | ASN | 17 | 50.019 | 24.692 | 29.879 | 1.00 | 14.76 |
| ATOM | 156 | CA | ASN | 17 | 50.698 | 25.945 | 29.566 | 1.00 | 11.15 |
| ATOM | 157 | CB | ASN | 17 | 51.909 | 25.681 | 28.660 | 1.00 | 11.18 |
| ATOM | 158 | CG | ASN | 17 | 52.558 | 26.962 | 28.153 | 1.00 | 12.52 |
| ATOM | 159 | OD1 | ASN | 17 | 52.808 | 27.102 | 26.954 | 1.00 | 13.85 |
| ATOM | 160 | ND2 | ASN | 17 | 52.840 | 27.888 | 29.049 | 1.00 | 17.56 |
| ATOM | 163 | C | ASN | 17 | 49.674 | 26.840 | 28.871 | 1.00 | 14.11 |
| ATOM | 164 | O | ASN | 17 | 49.446 | 26.720 | 27.663 | 1.00 | 11.71 |
| ATOM | 165 | N | ALA | 18 | 49.038 | 27.706 | 29.654 | 1.00 | 12.32 |
| ATOM | 167 | CA | ALA | 18 | 48.014 | 28.616 | 29.143 | 1.00 | 11.86 |
| ATOM | 168 | CB | ALA | 18 | 46.831 | 28.682 | 30.114 | 1.00 | 12.70 |
| ATOM | 169 | C | ALA | 18 | 48.601 | 29.999 | 28.941 | 1.00 | 12.87 |
| ATOM | 170 | O | ALA | 18 | 49.201 | 30.566 | 29.856 | 1.00 | 13.74 |
| ATOM | 171 | N | VAL | 19 | 48.415 | 30.551 | 27.751 | 1.00 | 14.88 |
| ATOM | 173 | CA | VAL | 19 | 48.925 | 31.871 | 27.429 | 1.00 | 13.07 |
| ATOM | 174 | CB | VAL | 19 | 49.800 | 31.839 | 26.167 | 1.00 | 13.91 |
| ATOM | 175 | CG1 | VAL | 19 | 50.307 | 33.240 | 25.850 | 1.00 | 14.35 |
| ATOM | 176 | CG2 | VAL | 19 | 50.964 | 30.862 | 26.357 | 1.00 | 15.62 |
| ATOM | 177 | C | VAL | 19 | 47.790 | 32.865 | 27.207 | 1.00 | 16.11 |
| ATOM | 178 | O | VAL | 19 | 46.901 | 32.643 | 26.384 | 1.00 | 13.48 |
| ATOM | 179 | N | ASN | 20 | 47.827 | 33.949 | 27.965 | 1.00 | 12.27 |
| ATOM | 181 | CA | ASN | 20 | 46.843 | 35.016 | 27.877 | 1.00 | 13.30 |
| ATOM | 182 | CB | ASN | 20 | 46.747 | 35.697 | 29.247 | 1.00 | 14.23 |
| ATOM | 183 | CG | ASN | 20 | 45.715 | 36.812 | 29.294 | 1.00 | 14.63 |
| ATOM | 184 | OD1 | ASN | 20 | 45.222 | 37.266 | 28.275 | 1.00 | 16.43 |
| ATOM | 185 | ND2 | ASN | 20 | 45.390 | 37.255 | 30.501 | 1.00 | 16.62 |
| ATOM | 188 | C | ASN | 20 | 47.395 | 35.971 | 26.813 | 1.00 | 18.39 |
| ATOM | 189 | O | ASN | 20 | 48.271 | 36.786 | 27.107 | 1.00 | 15.00 |
| ATOM | 190 | N | GLY | 21 | 46.941 | 35.814 | 25.571 | 1.00 | 15.64 |
| ATOM | 192 | CA | GLY | 21 | 47.432 | 36.642 | 24.481 | 1.00 | 13.96 |
| ATOM | 193 | C | GLY | 21 | 46.799 | 38.013 | 24.356 | 1.00 | 14.20 |
| ATOM | 194 | O | GLY | 21 | 46.039 | 38.438 | 25.223 | 1.00 | 14.39 |
| ATOM | 195 | N | SER | 22 | 47.115 | 38.719 | 23.271 | 1.00 | 14.16 |
| ATOM | 197 | CA | SER | 22 | 46.560 | 40.051 | 23.061 | 1.00 | 14.12 |

-continued

| | | | | | | | | | |
|---|---|---|---|---|---|---|---|---|---|
| | | | | | | | | 1.00 | 15.16 |
| ATOM | 198 | CB | SER | 22 | 47.327 | 40.815 | 21.970 | 1.00 | 17.14 |
| ATOM | 199 | OG | SER | 22 | 47.248 | 40.141 | 20.732 | 1.00 | 22.61 |
| ATOM | 201 | C | SER | 22 | 45.083 | 39.974 | 22.692 | 1.00 | 14.03 |
| ATOM | 202 | O | SER | 22 | 44.634 | 39.007 | 22.060 | 1.00 | 13.62 |
| ATOM | 203 | N | GLY | 23 | 44.339 | 41.001 | 23.090 | 1.00 | 13.56 |
| ATOM | 205 | CA | GLY | 23 | 42.925 | 41.053 | 22.791 | 1.00 | 12.00 |
| ATOM | 206 | C | GLY | 23 | 42.198 | 39.826 | 23.305 | 1.00 | 11.46 |
| ATOM | 207 | O | GLY | 23 | 42.338 | 39.444 | 24.461 | 1.00 | 11.59 |
| ATOM | 208 | N | GLY | 24 | 41.429 | 39.199 | 22.425 | 1.00 | 10.58 |
| ATOM | 210 | CA | GLY | 24 | 40.682 | 38.019 | 22.812 | 1.00 | 9.97 |
| ATOM | 211 | C | GLY | 24 | 41.371 | 36.717 | 22.458 | 1.00 | 10.21 |
| ATOM | 212 | O | GLY | 24 | 40.736 | 35.663 | 22.451 | 1.00 | 9.66 |
| ATOM | 213 | N | ASN | 25 | 42.675 | 36.766 | 22.203 | 1.00 | 9.53 |
| ATOM | 215 | CA | ASN | 25 | 43.413 | 35.559 | 21.846 | 1.00 | 8.48 |
| ATOM | 216 | CB | ASN | 25 | 44.532 | 35.893 | 20.833 | 1.00 | 9.35 |
| ATOM | 217 | CG | ASN | 25 | 45.356 | 34.680 | 20.455 | 1.00 | 10.64 |
| ATOM | 218 | OD1 | ASN | 25 | 46.499 | 34.512 | 20.908 | 1.00 | 12.41 |
| ATOM | 219 | ND2 | ASN | 25 | 44.790 | 33.823 | 19.620 | 1.00 | 10.48 |
| ATOM | 222 | C | ASN | 25 | 44.048 | 34.839 | 23.033 | 1.00 | 8.98 |
| ATOM | 223 | O | ASN | 25 | 44.522 | 35.469 | 23.976 | 1.00 | 9.94 |
| ATOM | 224 | N | TYR | 26 | 44.030 | 33.513 | 22.991 | 1.00 | 8.04 |
| ATOM | 226 | CA | TYR | 26 | 44.696 | 32.715 | 24.016 | 1.00 | 8.17 |
| ATOM | 227 | CB | TYR | 26 | 43.802 | 32.457 | 25.243 | 1.00 | 8.24 |
| ATOM | 228 | CG | TYR | 26 | 42.670 | 31.472 | 25.023 | 1.00 | 8.00 |
| ATOM | 229 | CD1 | TYR | 26 | 41.414 | 31.913 | 24.619 | 1.00 | 9.02 |
| ATOM | 230 | CE1 | TYR | 26 | 40.379 | 31.030 | 24.437 | 1.00 | 8.79 |
| ATOM | 231 | CD2 | TYR | 26 | 42.851 | 30.108 | 25.240 | 1.00 | 8.18 |
| ATOM | 232 | CE2 | TYR | 26 | 41.815 | 29.210 | 25.057 | 1.00 | 9.20 |
| ATOM | 233 | CZ | TYR | 26 | 40.577 | 29.682 | 24.652 | 1.00 | 8.70 |
| ATOM | 234 | OH | TYR | 26 | 39.534 | 28.794 | 24.438 | 1.00 | 9.05 |
| ATOM | 236 | C | TYR | 26 | 45.122 | 31.403 | 23.385 | 1.00 | 9.00 |
| ATOM | 237 | O | TYR | 26 | 44.634 | 31.027 | 22.305 | 1.00 | 8.46 |
| ATOM | 238 | N | SER | 27 | 46.087 | 30.735 | 24.007 | 1.00 | 9.44 |
| ATOM | 240 | CA | SER | 27 | 46.528 | 29.440 | 23.516 | 1.00 | 9.71 |
| ATOM | 241 | CB | SER | 27 | 47.759 | 29.566 | 22.604 | 1.00 | 11.14 |
| ATOM | 242 | OG | SER | 27 | 48.833 | 30.187 | 23.275 | 1.00 | 14.81 |
| ATOM | 244 | C | SER | 27 | 46.809 | 28.543 | 24.701 | 1.00 | 9.94 |
| ATOM | 245 | O | SER | 27 | 46.985 | 29.013 | 25.825 | 1.00 | 10.37 |
| ATOM | 246 | N | VAL | 28 | 46.728 | 27.245 | 24.471 | 1.00 | 9.16 |
| ATOM | 248 | CA | VAL | 28 | 46.994 | 26.271 | 25.520 | 1.00 | 10.37 |
| ATOM | 249 | CB | VAL | 28 | 45.692 | 25.668 | 26.146 | | |

| | | | | | | | | | |
|---|---|---|---|---|---|---|---|---|---|
| ATOM | 250 | CG1 | VAL | 28 | 46.023 | 24.931 | 27.454 | 1.00 | 11.40 |
| ATOM | 251 | CG2 | VAL | 28 | 44.641 | 26.726 | 26.377 | 1.00 | 12.25 |
| ATOM | 252 | C | VAL | 28 | 47.724 | 25.086 | 24.929 | 1.00 | 13.82 |
| ATOM | 253 | O | VAL | 28 | 47.402 | 24.644 | 23.820 | 1.00 | 10.81 |
| ATOM | 254 | N | ASN | 29 | 48.745 | 24.619 | 25.642 | 1.00 | 11.31 |
| ATOM | 256 | CA | ASN | 29 | 49.484 | 23.412 | 25.275 | 1.00 | 10.65 |
| ATOM | 257 | CB | ASN | 29 | 50.977 | 23.683 | 25.060 | 1.00 | 12.10 |
| ATOM | 258 | CG | ASN | 29 | 51.225 | 24.717 | 24.004 | 1.00 | 15.51 |
| ATOM | 259 | OD1 | ASN | 29 | 50.951 | 24.496 | 22.820 | 1.00 | 19.33 |
| ATOM | 260 | ND2 | ASN | 29 | 51.718 | 25.868 | 24.420 | 1.00 | 22.89 |
| ATOM | 263 | C | ASN | 29 | 49.322 | 22.597 | 26.539 | 1.00 | 21.25 |
| ATOM | 264 | O | ASN | 29 | 49.648 | 23.078 | 27.620 | 1.00 | 10.79 |
| ATOM | 265 | N | TRP | 30 | 48.787 | 21.392 | 26.430 | 1.00 | 12.04 |
| ATOM | 267 | CA | TRP | 30 | 48.589 | 20.575 | 27.619 | 1.00 | 9.27 |
| ATOM | 268 | CB | TRP | 30 | 47.115 | 20.598 | 28.066 | 1.00 | 7.76 |
| ATOM | 269 | CG | TRP | 30 | 46.123 | 19.856 | 27.209 | 1.00 | 7.93 |
| ATOM | 270 | CD2 | TRP | 30 | 45.383 | 20.374 | 26.090 | 1.00 | 7.36 |
| ATOM | 271 | CE2 | TRP | 30 | 44.448 | 19.387 | 25.719 | 1.00 | 7.38 |
| ATOM | 272 | CE3 | TRP | 30 | 45.411 | 21.580 | 25.379 | 1.00 | 6.82 |
| ATOM | 273 | CD1 | TRP | 30 | 45.632 | 18.610 | 27.444 | 1.00 | 8.62 |
| ATOM | 274 | NE1 | TRP | 30 | 44.618 | 18.321 | 26.562 | 1.00 | 6.99 |
| ATOM | 276 | CZ2 | TRP | 30 | 43.542 | 19.568 | 24.657 | 1.00 | 7.92 |
| ATOM | 277 | CZ3 | TRP | 30 | 44.510 | 21.759 | 24.330 | 1.00 | 9.07 |
| ATOM | 278 | CH2 | TRP | 30 | 43.592 | 20.757 | 23.982 | 1.00 | 7.97 |
| ATOM | 279 | C | TRP | 30 | 49.112 | 19.166 | 27.431 | 1.00 | 7.80 |
| ATOM | 280 | O | TRP | 30 | 49.151 | 18.641 | 26.305 | 1.00 | 7.73 |
| ATOM | 281 | N | SER | 31 | 49.532 | 18.553 | 28.530 | 1.00 | 8.50 |
| ATOM | 283 | CA | SER | 31 | 50.095 | 17.218 | 28.466 | 1.00 | 8.50 |
| ATOM | 284 | CB | SER | 31 | 51.615 | 17.333 | 28.268 | 1.00 | 9.39 |
| ATOM | 285 | OG | SER | 31 | 52.197 | 16.069 | 28.032 | 1.00 | 11.08 |
| ATOM | 287 | C | SER | 31 | 49.799 | 16.425 | 29.735 | 1.00 | 16.62 |
| ATOM | 288 | O | SER | 31 | 50.040 | 16.912 | 30.846 | 1.00 | 8.65 |
| ATOM | 289 | N | ASN | 32 | 49.246 | 15.224 | 29.556 | 1.00 | 9.67 |
| ATOM | 291 | CA | ASN | 32 | 48.934 | 14.290 | 30.648 | 1.00 | 9.23 |
| ATOM | 292 | CB | ASN | 32 | 50.215 | 13.581 | 31.076 | 1.00 | 9.24 |
| ATOM | 293 | CG | ASN | 32 | 50.856 | 12.828 | 29.931 | 1.00 | 11.30 |
| ATOM | 294 | OD1 | ASN | 32 | 50.311 | 11.835 | 29.448 | 1.00 | 13.54 |
| ATOM | 295 | ND2 | ASN | 32 | 52.010 | 13.300 | 29.487 | 1.00 | 15.18 |
| ATOM | 298 | C | ASN | 32 | 48.306 | 14.979 | 31.844 | 1.00 | 14.28 |
| ATOM | 299 | O | ASN | 32 | 48.778 | 14.870 | 32.975 | 1.00 | 9.76 |
| ATOM | 300 | N | THR | 33 | 47.187 | 15.634 | 31.589 | 1.00 | 10.47 |

| | | | | | | | | | |
|---|---|---|---|---|---|---|---|---|---|
| ATOM | 302 | CA | THR | 33 | 46.510 | 16.413 | 32.613 | 1.00 | 9.79 |
| ATOM | 303 | CB | THR | 33 | 45.734 | 17.580 | 31.943 | 1.00 | 9.75 |
| ATOM | 304 | OG1 | THR | 33 | 44.705 | 17.033 | 31.099 | 1.00 | 10.19 |
| ATOM | 306 | CG2 | THR | 33 | 46.668 | 18.456 | 31.117 | 1.00 | 10.42 |
| ATOM | 307 | C | THR | 33 | 45.471 | 15.679 | 33.450 | 1.00 | 10.04 |
| ATOM | 308 | O | THR | 33 | 45.203 | 14.490 | 33.268 | 1.00 | 9.02 |
| ATOM | 309 | N | GLY | 34 | 44.930 | 16.436 | 34.397 | 1.00 | 9.65 |
| ATOM | 311 | CA | GLY | 34 | 43.804 | 15.992 | 35.187 | 1.00 | 9.55 |
| ATOM | 312 | C | GLY | 34 | 42.716 | 16.743 | 34.416 | 1.00 | 9.51 |
| ATOM | 313 | O | GLY | 34 | 42.654 | 16.646 | 33.183 | 1.00 | 9.70 |
| ATOM | 314 | N | ASN | 35 | 41.924 | 17.563 | 35.098 | 1.00 | 9.59 |
| ATOM | 316 | CA | ASN | 35 | 40.873 | 18.355 | 34.450 | 1.00 | 9.04 |
| ATOM | 317 | CB | ASN | 35 | 39.534 | 18.158 | 35.187 | 1.00 | 9.43 |
| ATOM | 318 | CG | ASN | 35 | 38.361 | 18.897 | 34.531 | 1.00 | 10.15 |
| ATOM | 319 | OD1 | ASN | 35 | 37.501 | 19.427 | 35.232 | 1.00 | 12.88 |
| ATOM | 320 | ND2 | ASN | 35 | 38.301 | 18.905 | 33.204 | 1.00 | 15.72 |
| ATOM | 323 | C | ASN | 35 | 41.290 | 19.823 | 34.496 | 1.00 | 13.33 |
| ATOM | 324 | O | ASN | 35 | 41.876 | 20.282 | 35.476 | 1.00 | 9.12 |
| ATOM | 325 | N | PHE | 36 | 41.061 | 20.545 | 33.406 | 1.00 | 10.17 |
| ATOM | 327 | CA | PHE | 36 | 41.396 | 21.966 | 33.357 | 1.00 | 8.58 |
| ATOM | 328 | CB | PHE | 36 | 42.832 | 22.193 | 32.856 | 1.00 | 7.71 |
| ATOM | 329 | CG | PHE | 36 | 43.018 | 21.898 | 31.389 | 1.00 | 9.56 |
| ATOM | 330 | CD1 | PHE | 36 | 42.835 | 22.898 | 30.434 | 1.00 | 9.71 |
| ATOM | 331 | CD2 | PHE | 36 | 43.322 | 20.618 | 30.959 | 1.00 | 9.80 |
| ATOM | 332 | CE1 | PHE | 36 | 42.947 | 22.618 | 29.082 | 1.00 | 9.86 |
| ATOM | 333 | CE2 | PHE | 36 | 43.437 | 20.335 | 29.600 | 1.00 | 10.32 |
| ATOM | 334 | CZ | PHE | 36 | 43.247 | 21.337 | 28.667 | 1.00 | 11.13 |
| ATOM | 335 | C | PHE | 36 | 40.433 | 22.652 | 32.407 | 1.00 | 10.13 |
| ATOM | 336 | O | PHE | 36 | 39.856 | 22.003 | 31.528 | 1.00 | 7.24 |
| ATOM | 337 | N | VAL | 37 | 40.269 | 23.956 | 32.589 | 1.00 | 8.20 |
| ATOM | 339 | CA | VAL | 37 | 39.405 | 24.776 | 31.739 | 1.00 | 7.92 |
| ATOM | 340 | CB | VAL | 37 | 38.007 | 25.044 | 32.359 | 1.00 | 8.27 |
| ATOM | 341 | CG1 | VAL | 37 | 37.165 | 25.888 | 31.382 | 1.00 | 8.91 |
| ATOM | 342 | CG2 | VAL | 37 | 37.300 | 23.735 | 32.679 | 1.00 | 10.27 |
| ATOM | 343 | C | VAL | 37 | 40.109 | 26.109 | 31.568 | 1.00 | 10.16 |
| ATOM | 344 | O | VAL | 37 | 40.426 | 26.792 | 32.556 | 1.00 | 8.48 |
| ATOM | 345 | N | VAL | 38 | 40.356 | 26.474 | 30.315 | 1.00 | 9.26 |
| ATOM | 347 | CA | VAL | 38 | 41.027 | 27.727 | 29.988 | 1.00 | 7.80 |
| ATOM | 348 | CB | VAL | 38 | 42.445 | 27.453 | 29.421 | 1.00 | 8.41 |
| ATOM | 349 | CG1 | VAL | 38 | 43.098 | 28.748 | 28.947 | 1.00 | 9.47 |
| ATOM | 350 | CG2 | VAL | 38 | 43.305 | 26.766 | 30.470 | 1.00 | 11.38 |

-continued

| | | | | | | | | | |
|---|---|---|---|---|---|---|---|---|---|
| ATOM | 351 | C | VAL | 38 | 40.217 | 28.451 | 28.921 | 1.00 | 10.26 |
| ATOM | 352 | O | VAL | 38 | 39.717 | 27.825 | 28.002 | 1.00 | 8.22 |
| ATOM | 353 | N | GLY | 39 | 40.091 | 29.763 | 29.029 | 1.00 | 9.27 |
| ATOM | 355 | CA | GLY | 39 | 39.344 | 30.479 | 28.013 | 1.00 | 8.83 |
| ATOM | 356 | C | GLY | 39 | 39.214 | 31.960 | 28.280 | 1.00 | 8.67 |
| ATOM | 357 | O | GLY | 39 | 39.600 | 32.449 | 29.348 | 1.00 | 9.03 |
| ATOM | 358 | N | LYS | 40 | 38.703 | 32.676 | 27.287 | 1.00 | 10.05 |
| ATOM | 360 | CA | LYS | 40 | 38.493 | 34.109 | 27.411 | 1.00 | 8.28 |
| ATOM | 361 | CB | LYS | 40 | 39.372 | 34.892 | 26.432 | 1.00 | 7.76 |
| ATOM | 362 | CG | LYS | 40 | 40.787 | 35.076 | 26.926 | 1.00 | 8.70 |
| ATOM | 363 | CD | LYS | 40 | 41.525 | 36.071 | 26.066 | 1.00 | 10.94 |
| ATOM | 364 | CE | LYS | 40 | 42.861 | 36.392 | 26.700 | 1.00 | 10.75 |
| ATOM | 365 | NZ | LYS | 40 | 43.653 | 37.312 | 25.843 | 1.00 | 11.72 |
| ATOM | 369 | C | LYS | 40 | 37.033 | 34.432 | 27.172 | 1.00 | 10.91 |
| ATOM | 370 | O | LYS | 40 | 36.346 | 33.740 | 26.418 | 1.00 | 7.68 |
| ATOM | 371 | N | GLY | 41 | 36.567 | 35.485 | 27.824 | 1.00 | 8.01 |
| ATOM | 373 | CA | GLY | 41 | 35.189 | 35.866 | 27.666 | 1.00 | 7.96 |
| ATOM | 374 | C | GLY | 41 | 34.807 | 37.051 | 28.510 | 1.00 | 8.17 |
| ATOM | 375 | O | GLY | 41 | 35.547 | 38.042 | 28.593 | 1.00 | 8.18 |
| ATOM | 376 | N | TRP | 42 | 33.665 | 36.916 | 29.174 | 1.00 | 8.33 |
| ATOM | 378 | CA | TRP | 42 | 33.093 | 37.988 | 29.977 | 1.00 | 8.49 |
| ATOM | 379 | CB | TRP | 42 | 31.790 | 38.455 | 29.304 | 1.00 | 9.41 |
| ATOM | 380 | CG | TRP | 42 | 32.066 | 38.913 | 27.902 | 1.00 | 10.19 |
| ATOM | 381 | CD2 | TRP | 42 | 32.159 | 38.091 | 26.725 | 1.00 | 10.97 |
| ATOM | 382 | CE2 | TRP | 42 | 32.562 | 38.926 | 25.667 | 1.00 | 11.39 |
| ATOM | 383 | CE3 | TRP | 42 | 31.948 | 36.730 | 26.469 | 1.00 | 12.60 |
| ATOM | 384 | CD1 | TRP | 42 | 32.396 | 40.174 | 27.512 | 1.00 | 11.60 |
| ATOM | 385 | NE1 | TRP | 42 | 32.702 | 40.191 | 26.176 | 1.00 | 12.41 |
| ATOM | 387 | CZ2 | TRP | 42 | 32.761 | 38.447 | 24.369 | 1.00 | 13.46 |
| ATOM | 388 | CZ3 | TRP | 42 | 32.147 | 36.254 | 25.178 | 1.00 | 12.42 |
| ATOM | 389 | CH2 | TRP | 42 | 32.550 | 37.111 | 24.147 | 1.00 | 12.72 |
| ATOM | 390 | C | TRP | 42 | 32.851 | 37.625 | 31.433 | 1.00 | 12.03 |
| ATOM | 391 | O | TRP | 42 | 32.485 | 36.498 | 31.755 | 1.00 | 9.47 |
| ATOM | 392 | N | THR | 43 | 33.084 | 38.597 | 32.309 | 1.00 | 9.69 |
| ATOM | 394 | CA | THR | 43 | 32.924 | 38.423 | 33.744 | 1.00 | 10.28 |
| ATOM | 395 | CB | THR | 43 | 33.385 | 39.688 | 34.487 | 1.00 | 11.31 |
| ATOM | 396 | OG1 | THR | 43 | 34.716 | 40.025 | 34.065 | 1.00 | 13.67 |
| ATOM | 398 | CG2 | THR | 43 | 33.393 | 39.450 | 35.988 | 1.00 | 16.25 |
| ATOM | 399 | C | THR | 43 | 31.477 | 38.108 | 34.115 | 1.00 | 15.27 |
| ATOM | 400 | O | THR | 43 | 31.219 | 37.325 | 35.032 | 1.00 | 11.22 |
| ATOM | 401 | N | THR | 44 | 30.541 | 38.720 | 33.407 | 1.00 | 11.38 |

-continued

| | | | | | | | | | |
|---|---|---|---|---|---|---|---|---|---|
| 1.00 | 11.08 | | | | | | | | |
| ATOM | | 403 | CA | THR | 44 | 29.132 | 38.479 | 33.658 | |
| 1.00 | 11.81 | | | | | | | | |
| ATOM | | 404 | CB | THR | 44 | 28.429 | 39.746 | 34.170 | |
| 1.00 | 13.88 | | | | | | | | |
| ATOM | | 405 | OG1 | THR | 44 | 29.088 | 40.195 | 35.361 | |
| 1.00 | 16.33 | | | | | | | | |
| ATOM | | 407 | CG2 | THR | 44 | 26.973 | 39.451 | 34.497 | |
| 1.00 | 15.15 | | | | | | | | |
| ATOM | | 408 | C | THR | 44 | 28.474 | 37.989 | 32.377 | |
| 1.00 | 10.65 | | | | | | | | |
| ATOM | | 409 | O | THR | 44 | 28.435 | 38.692 | 31.364 | |
| 1.00 | 11.08 | | | | | | | | |
| ATOM | | 410 | N | GLY | 45 | 28.034 | 36.742 | 32.416 | |
| 1.00 | 8.94 | | | | | | | | |
| ATOM | | 412 | CA | GLY | 45 | 27.381 | 36.161 | 31.267 | |
| 1.00 | 9.08 | | | | | | | | |
| ATOM | | 413 | C | GLY | 45 | 26.024 | 36.785 | 31.013 | |
| 1.00 | 8.92 | | | | | | | | |
| ATOM | | 414 | O | GLY | 45 | 25.426 | 37.413 | 31.888 | |
| 1.00 | 10.17 | | | | | | | | |
| ATOM | | 415 | N | SER | 46 | 25.528 | 36.587 | 29.803 | |
| 1.00 | 9.11 | | | | | | | | |
| ATOM | | 417 | CA | SER | 46 | 24.233 | 37.110 | 29.405 | |
| 1.00 | 9.90 | | | | | | | | |
| ATOM | | 418 | CB | SER | 46 | 24.421 | 38.433 | 28.649 | |
| 1.00 | 10.33 | | | | | | | | |
| ATOM | | 419 | OG | SER | 46 | 23.221 | 38.819 | 27.993 | |
| 1.00 | 11.62 | | | | | | | | |
| ATOM | | 421 | C | SER | 46 | 23.556 | 36.106 | 28.484 | |
| 1.00 | 9.38 | | | | | | | | |
| ATOM | | 422 | O | SER | 46 | 24.219 | 35.472 | 27.660 | |
| 1.00 | 9.60 | | | | | | | | |
| ATOM | | 423 | N | PRO | 47 | 22.232 | 35.919 | 28.641 | |
| 1.00 | 9.69 | | | | | | | | |
| ATOM | | 424 | CD | PRO | 47 | 21.363 | 36.467 | 29.703 | |
| 1.00 | 9.98 | | | | | | | | |
| ATOM | | 425 | CA | PRO | 47 | 21.500 | 34.985 | 27.788 | |
| 1.00 | 9.60 | | | | | | | | |
| ATOM | | 426 | CB | PRO | 47 | 20.190 | 34.774 | 28.559 | |
| 1.00 | 10.20 | | | | | | | | |
| ATOM | | 427 | CG | PRO | 47 | 19.978 | 36.084 | 29.224 | |
| 1.00 | 10.28 | | | | | | | | |
| ATOM | | 428 | C | PRO | 47 | 21.264 | 35.599 | 26.395 | |
| 1.00 | 9.80 | | | | | | | | |
| ATOM | | 429 | O | PRO | 47 | 20.771 | 34.915 | 25.492 | |
| 1.00 | 10.61 | | | | | | | | |
| ATOM | | 430 | N | PHE | 48 | 21.644 | 36.872 | 26.223 | |
| 1.00 | 8.32 | | | | | | | | |
| ATOM | | 432 | CA | PHE | 48 | 21.461 | 37.576 | 24.949 | |
| 1.00 | 8.97 | | | | | | | | |
| ATOM | | 433 | CB | PHE | 48 | 20.830 | 38.952 | 25.189 | |
| 1.00 | 10.54 | | | | | | | | |
| ATOM | | 434 | CG | PHE | 48 | 19.587 | 38.903 | 26.020 | |
| 1.00 | 12.40 | | | | | | | | |
| ATOM | | 435 | CD1 | PHE | 48 | 18.507 | 38.142 | 25.610 | |
| 1.00 | 14.30 | | | | | | | | |
| ATOM | | 436 | CD2 | PHE | 48 | 19.527 | 39.558 | 27.239 | |
| 1.00 | 14.43 | | | | | | | | |
| ATOM | | 437 | CE1 | PHE | 48 | 17.379 | 38.028 | 26.410 | |
| 1.00 | 15.31 | | | | | | | | |
| ATOM | | 438 | CE2 | PHE | 48 | 18.400 | 39.448 | 28.043 | |
| 1.00 | 14.37 | | | | | | | | |
| ATOM | | 439 | CZ | PHE | 48 | 17.332 | 38.683 | 27.627 | |
| 1.00 | 14.77 | | | | | | | | |
| ATOM | | 440 | C | PHE | 48 | 22.751 | 37.772 | 24.154 | |
| 1.00 | 9.38 | | | | | | | | |
| ATOM | | 441 | O | PHE | 48 | 22.724 | 38.313 | 23.054 | |
| 1.00 | 9.35 | | | | | | | | |
| ATOM | | 442 | N | ARG | 49 | 23.876 | 37.324 | 24.699 | |
| 1.00 | 8.82 | | | | | | | | |
| ATOM | | 444 | CA | ARG | 49 | 25.152 | 37.512 | 24.019 | |
| 1.00 | 8.97 | | | | | | | | |
| ATOM | | 445 | CB | ARG | 49 | 26.306 | 37.267 | 24.992 | |
| 1.00 | 9.78 | | | | | | | | |
| ATOM | | 446 | CG | ARG | 49 | 27.663 | 37.691 | 24.421 | |
| 1.00 | 10.95 | | | | | | | | |
| ATOM | | 447 | CD | ARG | 49 | 28.794 | 37.437 | 25.386 | |
| 1.00 | 12.16 | | | | | | | | |
| ATOM | | 448 | NE | ARG | 49 | 28.529 | 37.971 | 26.716 | |
| 1.00 | 17.17 | | | | | | | | |
| ATOM | | 450 | CZ | ARG | 49 | 28.663 | 39.245 | 27.065 | |

| | Serial | Atom | Res | Seq | X | Y | Z | Occ | B |
|---|---|---|---|---|---|---|---|---|---|
| | | | | | | | | 1.00 | 16.53 |
| ATOM | 451 | NH1 | ARG | 49 | 29.062 | 40.153 | 26.188 | 1.00 | 19.05 |
| ATOM | 454 | NH2 | ARG | 49 | 28.418 | 39.606 | 28.314 | 1.00 | 18.90 |
| ATOM | 457 | C | ARG | 49 | 25.349 | 36.630 | 22.800 | 1.00 | 7.49 |
| ATOM | 458 | O | ARG | 49 | 24.889 | 35.491 | 22.773 | 1.00 | 8.16 |
| ATOM | 459 | N | THR | 50 | 25.986 | 37.184 | 21.772 | 1.00 | 7.58 |
| ATOM | 461 | CA | THR | 50 | 26.325 | 36.426 | 20.574 | 1.00 | 8.69 |
| ATOM | 462 | CB | THR | 50 | 25.873 | 37.143 | 19.293 | 1.00 | 9.20 |
| ATOM | 463 | OG1 | THR | 50 | 24.453 | 37.318 | 19.334 | 1.00 | 10.54 |
| ATOM | 465 | CG2 | THR | 50 | 26.236 | 36.330 | 18.071 | 1.00 | 10.59 |
| ATOM | 466 | C | THR | 50 | 27.849 | 36.345 | 20.636 | 1.00 | 9.39 |
| ATOM | 467 | O | THR | 50 | 28.535 | 37.373 | 20.662 | 1.00 | 10.80 |
| ATOM | 468 | N | ILE | 51 | 28.358 | 35.128 | 20.762 | 1.00 | 8.53 |
| ATOM | 470 | CA | ILE | 51 | 29.789 | 34.895 | 20.881 | 1.00 | 9.68 |
| ATOM | 471 | CB | ILE | 51 | 30.074 | 33.748 | 21.897 | 1.00 | 9.85 |
| ATOM | 472 | CG2 | ILE | 51 | 31.567 | 33.462 | 21.984 | 1.00 | 11.72 |
| ATOM | 473 | CG1 | ILE | 51 | 29.548 | 34.118 | 23.297 | 1.00 | 11.54 |
| ATOM | 474 | CD1 | ILE | 51 | 28.097 | 33.689 | 23.565 | 1.00 | 11.67 |
| ATOM | 475 | C | ILE | 51 | 30.422 | 34.577 | 19.535 | 1.00 | 9.84 |
| ATOM | 476 | O | ILE | 51 | 29.891 | 33.784 | 18.753 | 1.00 | 9.89 |
| ATOM | 477 | N | ASN | 52 | 31.541 | 35.231 | 19.252 | 1.00 | 9.72 |
| ATOM | 479 | CA | ASN | 52 | 32.265 | 35.007 | 18.002 | 1.00 | 9.63 |
| ATOM | 480 | CB | ASN | 52 | 32.512 | 36.323 | 17.268 | 1.00 | 12.27 |
| ATOM | 481 | CG | ASN | 52 | 31.239 | 37.060 | 16.956 | 1.00 | 16.92 |
| ATOM | 482 | OD1 | ASN | 52 | 30.579 | 36.770 | 15.960 | 1.00 | 20.42 |
| ATOM | 483 | ND2 | ASN | 52 | 30.869 | 38.004 | 17.817 | 1.00 | 18.67 |
| ATOM | 486 | C | ASN | 52 | 33.618 | 34.430 | 18.359 | 1.00 | 8.99 |
| ATOM | 487 | O | ASN | 52 | 34.216 | 34.813 | 19.369 | 1.00 | 8.30 |
| ATOM | 488 | N | TYR | 53 | 34.101 | 33.502 | 17.546 | 1.00 | 8.54 |
| ATOM | 490 | CA | TYR | 53 | 35.417 | 32.938 | 17.805 | 1.00 | 8.38 |
| ATOM | 491 | CB | TYR | 53 | 35.383 | 31.888 | 18.931 | 1.00 | 8.90 |
| ATOM | 492 | CG | TYR | 53 | 34.816 | 30.545 | 18.510 | 1.00 | 8.55 |
| ATOM | 493 | CD1 | TYR | 53 | 35.652 | 29.541 | 18.013 | 1.00 | 8.13 |
| ATOM | 494 | CE1 | TYR | 53 | 35.142 | 28.318 | 17.595 | 1.00 | 7.11 |
| ATOM | 495 | CD2 | TYR | 53 | 33.446 | 30.286 | 18.582 | 1.00 | 8.30 |
| ATOM | 496 | CE2 | TYR | 53 | 32.924 | 29.062 | 18.164 | 1.00 | 7.39 |
| ATOM | 497 | CZ | TYR | 53 | 33.771 | 28.085 | 17.670 | 1.00 | 7.17 |
| ATOM | 498 | OH | TYR | 53 | 33.270 | 26.875 | 17.235 | 1.00 | 8.09 |
| ATOM | 500 | C | TYR | 53 | 35.995 | 32.333 | 16.549 | 1.00 | 8.13 |
| ATOM | 501 | O | TYR | 53 | 35.289 | 32.095 | 15.567 | 1.00 | 8.60 |
| ATOM | 502 | N | ASN | 54 | 37.305 | 32.146 | 16.568 | 1.00 | 7.89 |
| ATOM | 504 | CA | ASN | 54 | 38.011 | 31.525 | 15.466 | | |

| | | | | | | | |
|---|---|---|---|---|---|---|---|
| 1.00 | 8.58 | | | | | | |
| ATOM | | 505 | CB | ASN | 54 | 38.628 | 32.583 | 14.532 |
| 1.00 | 8.69 | | | | | | |
| ATOM | | 506 | CG | ASN | 54 | 39.273 | 31.967 | 13.291 |
| 1.00 | 9.70 | | | | | | |
| ATOM | | 507 | OD1 | ASN | 54 | 39.001 | 32.391 | 12.157 |
| 1.00 | 11.48 | | | | | | |
| ATOM | | 508 | ND2 | ASN | 54 | 40.133 | 30.989 | 13.490 |
| 1.00 | 8.91 | | | | | | |
| ATOM | | 511 | C | ASN | 54 | 39.106 | 30.705 | 16.137 |
| 1.00 | 8.10 | | | | | | |
| ATOM | | 512 | O | ASN | 54 | 39.984 | 31.262 | 16.807 |
| 1.00 | 7.97 | | | | | | |
| ATOM | | 513 | N | ALA | 55 | 39.010 | 29.386 | 16.031 |
| 1.00 | 7.16 | | | | | | |
| ATOM | | 515 | CA | ALA | 55 | 40.028 | 28.510 | 16.607 |
| 1.00 | 8.25 | | | | | | |
| ATOM | | 516 | CB | ALA | 55 | 39.406 | 27.201 | 17.109 |
| 1.00 | 9.23 | | | | | | |
| ATOM | | 517 | C | ALA | 55 | 41.090 | 28.235 | 15.529 |
| 1.00 | 9.13 | | | | | | |
| ATOM | | 518 | O | ALA | 55 | 40.897 | 27.380 | 14.656 |
| 1.00 | 9.17 | | | | | | |
| ATOM | | 519 | N | GLY | 56 | 42.176 | 29.000 | 15.569 |
| 1.00 | 9.32 | | | | | | |
| ATOM | | 521 | CA | GLY | 56 | 43.254 | 28.829 | 14.606 |
| 1.00 | 10.02 | | | | | | |
| ATOM | | 522 | C | GLY | 56 | 43.912 | 27.459 | 14.705 |
| 1.00 | 11.23 | | | | | | |
| ATOM | | 523 | O | GLY | 56 | 44.430 | 26.928 | 13.716 |
| 1.00 | 11.91 | | | | | | |
| ATOM | | 524 | N | VAL | 57 | 43.933 | 26.900 | 15.910 |
| 1.00 | 9.79 | | | | | | |
| ATOM | | 526 | CA | VAL | 57 | 44.483 | 25.572 | 16.150 |
| 1.00 | 9.61 | | | | | | |
| ATOM | | 527 | CB | VAL | 57 | 45.869 | 25.628 | 16.856 |
| 1.00 | 10.77 | | | | | | |
| ATOM | | 528 | CG1 | VAL | 57 | 46.378 | 24.211 | 17.158 |
| 1.00 | 10.95 | | | | | | |
| ATOM | | 529 | CG2 | VAL | 57 | 46.873 | 26.378 | 15.998 |
| 1.00 | 12.00 | | | | | | |
| ATOM | | 530 | C | VAL | 57 | 43.530 | 24.837 | 17.086 |
| 1.00 | 9.35 | | | | | | |
| ATOM | | 531 | O | VAL | 57 | 43.121 | 25.388 | 18.118 |
| 1.00 | 8.73 | | | | | | |
| ATOM | | 532 | N | TRP | 58 | 43.104 | 23.644 | 16.682 |
| 1.00 | 9.21 | | | | | | |
| ATOM | | 534 | CA | TRP | 58 | 42.258 | 22.797 | 17.520 |
| 1.00 | 9.14 | | | | | | |
| ATOM | | 535 | CB | TRP | 58 | 40.771 | 22.855 | 17.137 |
| 1.00 | 8.81 | | | | | | |
| ATOM | | 536 | CG | TRP | 58 | 39.950 | 21.927 | 17.984 |
| 1.00 | 8.75 | | | | | | |
| ATOM | | 537 | CD2 | TRP | 58 | 39.906 | 21.883 | 19.421 |
| 1.00 | 8.67 | | | | | | |
| ATOM | | 538 | CE2 | TRP | 58 | 39.101 | 20.778 | 19.781 |
| 1.00 | 9.27 | | | | | | |
| ATOM | | 539 | CE3 | TRP | 58 | 40.478 | 22.662 | 20.434 |
| 1.00 | 8.89 | | | | | | |
| ATOM | | 540 | CD1 | TRP | 58 | 39.177 | 20.883 | 17.550 |
| 1.00 | 9.50 | | | | | | |
| ATOM | | 541 | NE1 | TRP | 58 | 38.670 | 20.189 | 18.620 |
| 1.00 | 10.22 | | | | | | |
| ATOM | | 543 | CZ2 | TRP | 58 | 38.854 | 20.434 | 21.113 |
| 1.00 | 9.53 | | | | | | |
| ATOM | | 544 | CZ3 | TRP | 58 | 40.234 | 22.321 | 21.756 |
| 1.00 | 9.53 | | | | | | |
| ATOM | | 545 | CH2 | TRP | 58 | 39.428 | 21.214 | 22.083 |
| 1.00 | 10.28 | | | | | | |
| ATOM | | 546 | C | TRP | 58 | 42.841 | 21.418 | 17.283 |
| 1.00 | 9.95 | | | | | | |
| ATOM | | 547 | O | TRP | 58 | 42.496 | 20.741 | 16.323 |
| 1.00 | 10.38 | | | | | | |
| ATOM | | 548 | N | ALA | 59 | 43.732 | 21.011 | 18.177 |
| 1.00 | 9.50 | | | | | | |
| ATOM | | 550 | CA | ALA | 59 | 44.443 | 19.750 | 18.031 |
| 1.00 | 10.62 | | | | | | |
| ATOM | | 551 | CB | ALA | 59 | 45.850 | 20.038 | 17.520 |
| 1.00 | 11.24 | | | | | | |
| ATOM | | 552 | C | ALA | 59 | 44.503 | 18.893 | 19.295 |
| 1.00 | 11.50 | | | | | | |
| ATOM | | 553 | O | ALA | 59 | 45.574 | 18.702 | 19.893 |

| Record | Serial | Atom | Residue | ResNum | X | Y | Z | Occ | B |
|---|---|---|---|---|---|---|---|---|---|
| ATOM | 554 | N | PRO | 60 | 43.345 | 18.417 | 19.763 | 1.00 | 11.67 |
| ATOM | 555 | CD | PRO | 60 | 41.964 | 18.696 | 19.313 | 1.00 | 11.64 |
| ATOM | 556 | CA | PRO | 60 | 43.355 | 17.582 | 20.963 | 1.00 | 12.34 |
| ATOM | 557 | CB | PRO | 60 | 41.878 | 17.587 | 21.386 | 1.00 | 12.06 |
| ATOM | 558 | CG | PRO | 60 | 41.157 | 17.657 | 20.069 | 1.00 | 12.35 |
| ATOM | 559 | C | PRO | 60 | 43.827 | 16.165 | 20.610 | 1.00 | 12.25 |
| ATOM | 560 | O | PRO | 60 | 43.472 | 15.638 | 19.559 | 1.00 | 13.28 |
| ATOM | 561 | N | ASN | 61 | 44.655 | 15.580 | 21.470 | 1.00 | 14.06 |
| ATOM | 563 | CA | ASN | 61 | 45.150 | 14.208 | 21.309 | 1.00 | 13.72 |
| ATOM | 564 | CB | ASN | 61 | 46.663 | 14.142 | 21.519 | 1.00 | 16.04 |
| ATOM | 565 | CG | ASN | 61 | 47.422 | 14.081 | 20.239 | 1.00 | 17.34 |
| ATOM | 566 | OD1 | ASN | 61 | 46.846 | 14.130 | 19.159 | 1.00 | 19.52 |
| ATOM | 567 | ND2 | ASN | 61 | 48.733 | 13.960 | 20.342 | 1.00 | 22.18 |
| ATOM | 570 | C | ASN | 61 | 44.502 | 13.396 | 22.418 | 1.00 | 21.75 |
| ATOM | 571 | O | ASN | 61 | 45.193 | 12.805 | 23.265 | 1.00 | 17.14 |
| ATOM | 572 | N | GLY | 62 | 43.181 | 13.442 | 22.478 | 1.00 | 20.86 |
| ATOM | 574 | CA | GLY | 62 | 42.460 | 12.724 | 23.505 | 1.00 | 14.28 |
| ATOM | 575 | C | GLY | 62 | 41.195 | 13.489 | 23.824 | 1.00 | 12.24 |
| ATOM | 576 | O | GLY | 62 | 40.695 | 14.229 | 22.976 | 1.00 | 11.02 |
| ATOM | 577 | N | ASN | 63 | 40.733 | 13.379 | 25.064 | 1.00 | 11.20 |
| ATOM | 579 | CA | ASN | 63 | 39.501 | 14.033 | 25.508 | 1.00 | 9.94 |
| ATOM | 580 | CB | ASN | 63 | 38.994 | 13.326 | 26.769 | 1.00 | 9.74 |
| ATOM | 581 | CG | ASN | 63 | 37.598 | 13.776 | 27.201 | 1.00 | 11.20 |
| ATOM | 582 | OD1 | ASN | 63 | 37.040 | 13.221 | 28.147 | 1.00 | 12.59 |
| ATOM | 583 | ND2 | ASN | 63 | 37.033 | 14.768 | 26.529 | 1.00 | 17.15 |
| ATOM | 586 | C | ASN | 63 | 39.673 | 15.531 | 25.764 | 1.00 | 13.79 |
| ATOM | 587 | O | ASN | 63 | 40.365 | 15.937 | 26.697 | 1.00 | 9.16 |
| ATOM | 588 | N | GLY | 64 | 39.040 | 16.339 | 24.919 | 1.00 | 9.76 |
| ATOM | 590 | CA | GLY | 64 | 39.092 | 17.787 | 25.045 | 1.00 | 8.41 |
| ATOM | 591 | C | GLY | 64 | 37.887 | 18.376 | 24.327 | 1.00 | 8.11 |
| ATOM | 592 | O | GLY | 64 | 37.430 | 17.794 | 23.339 | 1.00 | 7.55 |
| ATOM | 593 | N | TYR | 65 | 37.366 | 19.496 | 24.830 | 1.00 | 7.74 |
| ATOM | 595 | CA | TYR | 65 | 36.198 | 20.172 | 24.242 | 1.00 | 7.16 |
| ATOM | 596 | CB | TYR | 65 | 35.032 | 20.281 | 25.249 | 1.00 | 5.64 |
| ATOM | 597 | CG | TYR | 65 | 34.628 | 19.022 | 25.992 | 1.00 | 6.56 |
| ATOM | 598 | CD1 | TYR | 65 | 34.618 | 17.780 | 25.369 | 1.00 | 8.02 |
| ATOM | 599 | CE1 | TYR | 65 | 34.220 | 16.645 | 26.048 | 1.00 | 8.25 |
| ATOM | 600 | CD2 | TYR | 65 | 34.222 | 19.090 | 27.324 | 1.00 | 9.23 |
| ATOM | 601 | CE2 | TYR | 65 | 33.816 | 17.959 | 28.012 | 1.00 | 8.95 |
| ATOM | 602 | CZ | TYR | 65 | 33.817 | 16.739 | 27.370 | 1.00 | 9.90 |
| ATOM | 603 | OH | TYR | 65 | 33.412 | 15.599 | 28.045 | 1.00 | 10.73 |

| | | | | | | | | |
|---|---|---|---|---|---|---|---|---|
| ATOM | 605 | C | TYR | 65 | 36.520 | 21.619 | 23.866 | 1.00 12.55 |
| ATOM | 606 | O | TYR | 65 | 37.244 | 22.316 | 24.588 | 1.00 6.29 |
| ATOM | 607 | N | LEU | 66 | 35.970 | 22.063 | 22.743 | 1.00 7.00 |
| ATOM | 609 | CA | LEU | 66 | 36.083 | 23.445 | 22.283 | 1.00 5.38 |
| ATOM | 610 | CB | LEU | 66 | 36.442 | 23.495 | 20.799 | 1.00 5.78 |
| ATOM | 611 | CG | LEU | 66 | 36.461 | 24.907 | 20.208 | 1.00 7.24 |
| ATOM | 612 | CD1 | LEU | 66 | 37.475 | 25.780 | 20.976 | 1.00 7.92 |
| ATOM | 613 | CD2 | LEU | 66 | 36.803 | 24.829 | 18.727 | 1.00 10.09 |
| ATOM | 614 | C | LEU | 66 | 34.622 | 23.830 | 22.525 | 1.00 9.90 |
| ATOM | 615 | O | LEU | 66 | 33.722 | 23.435 | 21.758 | 1.00 6.54 |
| ATOM | 616 | N | THR | 67 | 34.389 | 24.653 | 23.542 | 1.00 5.88 |
| ATOM | 618 | CA | THR | 67 | 33.017 | 24.899 | 23.964 | 1.00 6.32 |
| ATOM | 619 | CB | THR | 67 | 32.687 | 23.771 | 25.014 | 1.00 6.62 |
| ATOM | 620 | OG1 | THR | 67 | 31.338 | 23.878 | 25.482 | 1.00 5.96 |
| ATOM | 622 | CG2 | THR | 67 | 33.641 | 23.834 | 26.239 | 1.00 6.25 |
| ATOM | 623 | C | THR | 67 | 32.757 | 26.231 | 24.650 | 1.00 6.12 |
| ATOM | 624 | O | THR | 67 | 33.651 | 26.792 | 25.281 | 1.00 5.91 |
| ATOM | 625 | N | LEU | 68 | 31.541 | 26.756 | 24.496 | 1.00 5.87 |
| ATOM | 627 | CA | LEU | 68 | 31.141 | 27.950 | 25.232 | 1.00 5.49 |
| ATOM | 628 | CB | LEU | 68 | 29.806 | 28.488 | 24.741 | 1.00 5.70 |
| ATOM | 629 | CG | LEU | 68 | 29.314 | 29.725 | 25.491 | 1.00 7.05 |
| ATOM | 630 | CD1 | LEU | 68 | 30.210 | 30.922 | 25.209 | 1.00 8.06 |
| ATOM | 631 | CD2 | LEU | 68 | 27.874 | 30.009 | 25.092 | 1.00 10.31 |
| ATOM | 632 | C | LEU | 68 | 30.961 | 27.334 | 26.626 | 1.00 10.13 |
| ATOM | 633 | O | LEU | 68 | 30.436 | 26.212 | 26.765 | 1.00 6.24 |
| ATOM | 634 | N | TYR | 69 | 31.357 | 28.062 | 27.656 | 1.00 6.15 |
| ATOM | 636 | CA | TYR | 69 | 31.323 | 27.516 | 28.997 | 1.00 5.92 |
| ATOM | 637 | CB | TYR | 69 | 32.733 | 26.961 | 29.292 | 1.00 6.43 |
| ATOM | 638 | CG | TYR | 69 | 32.942 | 26.431 | 30.685 | 1.00 7.92 |
| ATOM | 639 | CD1 | TYR | 69 | 32.482 | 25.170 | 31.039 | 1.00 7.81 |
| ATOM | 640 | CE1 | TYR | 69 | 32.650 | 24.689 | 32.315 | 1.00 8.51 |
| ATOM | 641 | CD2 | TYR | 69 | 33.586 | 27.199 | 31.652 | 1.00 9.90 |
| ATOM | 642 | CE2 | TYR | 69 | 33.756 | 26.727 | 32.931 | 1.00 8.54 |
| ATOM | 643 | CZ | TYR | 69 | 33.282 | 25.472 | 33.258 | 1.00 8.83 |
| ATOM | 644 | OH | TYR | 69 | 33.410 | 25.015 | 34.551 | 1.00 8.64 |
| ATOM | 646 | C | TYR | 69 | 30.964 | 28.601 | 29.989 | 1.00 10.08 |
| ATOM | 647 | O | TYR | 69 | 31.456 | 29.723 | 29.898 | 1.00 6.66 |
| ATOM | 648 | N | GLY | 70 | 30.119 | 28.274 | 30.957 | 1.00 6.52 |
| ATOM | 650 | CA | GLY | 70 | 29.770 | 29.283 | 31.935 | 1.00 5.93 |
| ATOM | 651 | C | GLY | 70 | 29.001 | 28.724 | 33.108 | 1.00 7.20 |
| ATOM | 652 | O | GLY | 70 | 28.698 | 27.530 | 33.167 | 1.00 6.61 |

-continued

| | | | | | | | | | |
|---|---|---|---|---|---|---|---|---|---|
| ATOM | 653 | N | TRP | 71 | 28.699 | 29.602 | 34.054 | 1.00 | 6.24 |
| ATOM | 655 | CA | TRP | 71 | 27.953 | 29.215 | 35.240 | 1.00 | 7.21 |
| ATOM | 656 | CB | TRP | 71 | 28.865 | 29.170 | 36.478 | 1.00 | 7.25 |
| ATOM | 657 | CG | TRP | 71 | 29.887 | 28.097 | 36.524 | 1.00 | 8.08 |
| ATOM | 658 | CD2 | TRP | 71 | 29.803 | 26.869 | 37.253 | 1.00 | 9.15 |
| ATOM | 659 | CE2 | TRP | 71 | 31.016 | 26.176 | 37.049 | 1.00 | 9.01 |
| ATOM | 660 | CE3 | TRP | 71 | 28.818 | 26.283 | 38.057 | 1.00 | 9.87 |
| ATOM | 661 | CD1 | TRP | 71 | 31.112 | 28.106 | 35.920 | 1.00 | 10.02 |
| ATOM | 662 | NE1 | TRP | 71 | 31.793 | 26.952 | 36.228 | 1.00 | 8.19 |
| ATOM | 664 | CZ2 | TRP | 71 | 31.271 | 24.925 | 37.621 | 1.00 | 9.71 |
| ATOM | 665 | CZ3 | TRP | 71 | 29.068 | 25.043 | 38.621 | 1.00 | 10.26 |
| ATOM | 666 | CH2 | TRP | 71 | 30.286 | 24.375 | 38.401 | 1.00 | 11.63 |
| ATOM | 667 | C | TRP | 71 | 26.893 | 30.220 | 35.620 | 1.00 | 11.11 |
| ATOM | 668 | O | TRP | 71 | 26.976 | 31.401 | 35.273 | 1.00 | 7.86 |
| ATOM | 669 | N | THR | 72 | 25.895 | 29.725 | 36.340 | 1.00 | 7.90 |
| ATOM | 671 | CA | THR | 72 | 24.907 | 30.593 | 36.960 | 1.00 | 9.00 |
| ATOM | 672 | CB | THR | 72 | 23.473 | 30.521 | 36.379 | 1.00 | 9.70 |
| ATOM | 673 | OG1 | THR | 72 | 22.939 | 29.204 | 36.544 | 1.00 | 10.06 |
| ATOM | 675 | CG2 | THR | 72 | 23.431 | 30.955 | 34.929 | 1.00 | 10.75 |
| ATOM | 676 | C | THR | 72 | 24.837 | 30.066 | 38.389 | 1.00 | 9.49 |
| ATOM | 677 | O | THR | 72 | 25.246 | 28.926 | 38.670 | 1.00 | 11.21 |
| ATOM | 678 | N | ARG | 73 | 24.362 | 30.914 | 39.289 | 1.00 | 10.30 |
| ATOM | 680 | CA | ARG | 73 | 24.156 | 30.555 | 40.687 | 1.00 | 13.21 |
| ATOM | 681 | CB | ARG | 73 | 24.932 | 31.488 | 41.621 | 1.00 | 15.05 |
| ATOM | 682 | CG | ARG | 73 | 26.430 | 31.290 | 41.596 | 1.00 | 16.77 |
| ATOM | 683 | CD | ARG | 73 | 27.103 | 32.107 | 42.682 | 1.00 | 18.20 |
| ATOM | 684 | NE | ARG | 73 | 28.538 | 31.835 | 42.766 | 1.00 | 19.22 |
| ATOM | 686 | CZ | ARG | 73 | 29.466 | 32.495 | 42.079 | 1.00 | 21.45 |
| ATOM | 687 | NH1 | ARG | 73 | 29.118 | 33.465 | 41.247 | 1.00 | 22.40 |
| ATOM | 690 | NH2 | ARG | 73 | 30.748 | 32.209 | 42.247 | 1.00 | 24.34 |
| ATOM | 693 | C | ARG | 73 | 22.658 | 30.745 | 40.901 | 1.00 | 23.90 |
| ATOM | 694 | O | ARG | 73 | 22.001 | 31.435 | 40.114 | 1.00 | 15.76 |
| ATOM | 695 | N | SER | 74 | 22.125 | 30.124 | 41.949 | 1.00 | 15.54 |
| ATOM | 697 | CA | SER | 74 | 20.701 | 30.215 | 42.283 | 1.00 | 17.09 |
| ATOM | 698 | CB | SER | 74 | 20.370 | 31.620 | 42.798 | 1.00 | 18.69 |
| ATOM | 699 | OG | SER | 74 | 21.282 | 31.998 | 43.817 | 1.00 | 19.69 |
| ATOM | 701 | C | SER | 74 | 19.759 | 29.838 | 41.126 | 1.00 | 24.14 |
| ATOM | 702 | O | SER | 74 | 18.998 | 30.673 | 40.625 | 1.00 | 17.91 |
| ATOM | 703 | N | PRO | 75 | 19.793 | 28.572 | 40.693 | 1.00 | 18.35 |
| ATOM | 704 | CD | PRO | 75 | 18.753 | 28.012 | 39.810 | 1.00 | 17.77 |
| ATOM | 705 | CA | PRO | 75 | 20.653 | 27.508 | 41.224 | 1.00 | 18.55 |

-continued

| | | | | | | | | |
|---|---|---|---|---|---|---|---|---|
| 1.00 | 17.24 | | | | | | | |
| ATOM | | 706 | CB | PRO | 75 | 19.828 | 26.253 | 40.969 |
| 1.00 | 18.06 | | | | | | | |
| ATOM | | 707 | CG | PRO | 75 | 19.175 | 26.565 | 39.666 |
| 1.00 | 18.68 | | | | | | | |
| ATOM | | 708 | C | PRO | 75 | 21.999 | 27.423 | 40.515 |
| 1.00 | 16.14 | | | | | | | |
| ATOM | | 709 | O | PRO | 75 | 22.231 | 28.081 | 39.492 |
| 1.00 | 15.03 | | | | | | | |
| ATOM | | 710 | N | LEU | 76 | 22.875 | 26.608 | 41.080 |
| 1.00 | 14.58 | | | | | | | |
| ATOM | | 712 | CA | LEU | 76 | 24.207 | 26.389 | 40.547 |
| 1.00 | 14.02 | | | | | | | |
| ATOM | | 713 | CB | LEU | 76 | 25.063 | 25.722 | 41.623 |
| 1.00 | 16.02 | | | | | | | |
| ATOM | | 714 | CG | LEU | 76 | 26.575 | 25.774 | 41.487 |
| 1.00 | 18.13 | | | | | | | |
| ATOM | | 715 | CD1 | LEU | 76 | 27.047 | 27.219 | 41.526 |
| 1.00 | 18.22 | | | | | | | |
| ATOM | | 716 | CD2 | LEU | 76 | 27.197 | 24.970 | 42.626 |
| 1.00 | 18.98 | | | | | | | |
| ATOM | | 717 | C | LEU | 76 | 24.112 | 25.488 | 39.312 |
| 1.00 | 12.79 | | | | | | | |
| ATOM | | 718 | O | LEU | 76 | 23.722 | 24.323 | 39.412 |
| 1.00 | 12.48 | | | | | | | |
| ATOM | | 719 | N | ILE | 77 | 24.482 | 26.025 | 38.151 |
| 1.00 | 11.37 | | | | | | | |
| ATOM | | 721 | CA | ILE | 77 | 24.431 | 25.266 | 36.902 |
| 1.00 | 10.64 | | | | | | | |
| ATOM | | 722 | CB | ILE | 77 | 23.188 | 25.655 | 36.054 |
| 1.00 | 11.91 | | | | | | | |
| ATOM | | 723 | CG2 | ILE | 77 | 23.253 | 24.994 | 34.686 |
| 1.00 | 11.77 | | | | | | | |
| ATOM | | 724 | CG1 | ILE | 77 | 21.898 | 25.234 | 36.769 |
| 1.00 | 12.91 | | | | | | | |
| ATOM | | 725 | CD1 | ILE | 77 | 20.656 | 25.787 | 36.160 |
| 1.00 | 14.88 | | | | | | | |
| ATOM | | 726 | C | ILE | 77 | 25.676 | 25.555 | 36.068 |
| 1.00 | 8.64 | | | | | | | |
| ATOM | | 727 | O | ILE | 77 | 26.084 | 26.712 | 35.948 |
| 1.00 | 8.92 | | | | | | | |
| ATOM | | 728 | N | GLU | 78 | 26.319 | 24.502 | 35.574 |
| 1.00 | 7.66 | | | | | | | |
| ATOM | | 730 | CA | GLU | 78 | 27.503 | 24.621 | 34.720 |
| 1.00 | 7.21 | | | | | | | |
| ATOM | | 731 | CB | GLU | 78 | 28.536 | 23.573 | 35.134 |
| 1.00 | 7.73 | | | | | | | |
| ATOM | | 732 | CG | GLU | 78 | 29.868 | 23.635 | 34.372 |
| 1.00 | 9.08 | | | | | | | |
| ATOM | | 733 | CD | GLU | 78 | 30.835 | 22.544 | 34.805 |
| 1.00 | 10.20 | | | | | | | |
| ATOM | | 734 | OE1 | GLU | 78 | 32.050 | 22.814 | 34.932 |
| 1.00 | 10.78 | | | | | | | |
| ATOM | | 735 | OE2 | GLU | 78 | 30.395 | 21.407 | 35.026 |
| 1.00 | 10.70 | | | | | | | |
| ATOM | | 736 | C | GLU | 78 | 26.961 | 24.315 | 33.322 |
| 1.00 | 7.93 | | | | | | | |
| ATOM | | 737 | O | GLU | 78 | 26.391 | 23.240 | 33.112 |
| 1.00 | 9.13 | | | | | | | |
| ATOM | | 738 | N | TYR | 79 | 27.119 | 25.229 | 32.369 |
| 1.00 | 7.30 | | | | | | | |
| ATOM | | 740 | CA | TYR | 79 | 26.562 | 24.982 | 31.046 |
| 1.00 | 6.18 | | | | | | | |
| ATOM | | 741 | CB | TYR | 79 | 25.422 | 25.963 | 30.737 |
| 1.00 | 6.50 | | | | | | | |
| ATOM | | 742 | CG | TYR | 79 | 25.844 | 27.414 | 30.631 |
| 1.00 | 6.96 | | | | | | | |
| ATOM | | 743 | CD1 | TYR | 79 | 26.466 | 27.896 | 29.479 |
| 1.00 | 6.30 | | | | | | | |
| ATOM | | 744 | CE1 | TYR | 79 | 26.861 | 29.215 | 29.376 |
| 1.00 | 7.02 | | | | | | | |
| ATOM | | 745 | CD2 | TYR | 79 | 25.626 | 28.299 | 31.681 |
| 1.00 | 7.12 | | | | | | | |
| ATOM | | 746 | CE2 | TYR | 79 | 26.019 | 29.633 | 31.584 |
| 1.00 | 7.44 | | | | | | | |
| ATOM | | 747 | CZ | TYR | 79 | 26.636 | 30.079 | 30.427 |
| 1.00 | 7.25 | | | | | | | |
| ATOM | | 748 | OH | TYR | 79 | 27.042 | 31.388 | 30.303 |
| 1.00 | 8.96 | | | | | | | |
| ATOM | | 750 | C | TYR | 79 | 27.605 | 24.969 | 29.939 |
| 1.00 | 7.01 | | | | | | | |
| ATOM | | 751 | O | TYR | 79 | 28.658 | 25.619 | 30.044 |

-continued

| | | | | | | | |
|---|---|---|---|---|---|---|---|
| 1.00 | 5.99 | | | | | | |
| ATOM | | 752 | N | TYR | 80 | 27.235 | 24.315 | 28.840 |
| 1.00 | 6.31 | | | | | | |
| ATOM | | 754 | CA | TYR | 80 | 28.112 | 24.128 | 27.692 |
| 1.00 | 5.86 | | | | | | |
| ATOM | | 755 | CB | TYR | 80 | 28.667 | 22.695 | 27.722 |
| 1.00 | 5.72 | | | | | | |
| ATOM | | 756 | CG | TYR | 80 | 29.620 | 22.352 | 28.827 |
| 1.00 | 5.27 | | | | | | |
| ATOM | | 757 | CD1 | TYR | 80 | 29.159 | 21.881 | 30.055 |
| 1.00 | 7.53 | | | | | | |
| ATOM | | 758 | CE1 | TYR | 80 | 30.042 | 21.465 | 31.032 |
| 1.00 | 7.89 | | | | | | |
| ATOM | | 759 | CD2 | TYR | 80 | 30.983 | 22.403 | 28.608 |
| 1.00 | 7.64 | | | | | | |
| ATOM | | 760 | CE2 | TYR | 80 | 31.865 | 21.995 | 29.566 |
| 1.00 | 8.52 | | | | | | |
| ATOM | | 761 | CZ | TYR | 80 | 31.394 | 21.523 | 30.776 |
| 1.00 | 9.81 | | | | | | |
| ATOM | | 762 | OH | TYR | 80 | 32.297 | 21.100 | 31.725 |
| 1.00 | 10.19 | | | | | | |
| ATOM | | 764 | C | TYR | 80 | 27.413 | 24.207 | 26.346 |
| 1.00 | 6.25 | | | | | | |
| ATOM | | 765 | O | TYR | 80 | 26.268 | 23.762 | 26.216 |
| 1.00 | 6.36 | | | | | | |
| ATOM | | 766 | N | VAL | 81 | 28.111 | 24.755 | 25.354 |
| 1.00 | 5.60 | | | | | | |
| ATOM | | 768 | CA | VAL | 81 | 27.650 | 24.709 | 23.956 |
| 1.00 | 4.96 | | | | | | |
| ATOM | | 769 | CB | VAL | 81 | 27.189 | 26.044 | 23.369 |
| 1.00 | 6.50 | | | | | | |
| ATOM | | 770 | CG1 | VAL | 81 | 26.812 | 25.814 | 21.903 |
| 1.00 | 6.96 | | | | | | |
| ATOM | | 771 | CG2 | VAL | 81 | 25.955 | 26.567 | 24.133 |
| 1.00 | 7.32 | | | | | | |
| ATOM | | 772 | C | VAL | 81 | 28.915 | 24.204 | 23.252 |
| 1.00 | 5.73 | | | | | | |
| ATOM | | 773 | O | VAL | 81 | 29.854 | 24.963 | 22.970 |
| 1.00 | 5.99 | | | | | | |
| ATOM | | 774 | N | VAL | 82 | 28.957 | 22.897 | 23.048 |
| 1.00 | 4.96 | | | | | | |
| ATOM | | 776 | CA | VAL | 82 | 30.123 | 22.242 | 22.470 |
| 1.00 | 5.85 | | | | | | |
| ATOM | | 777 | CB | VAL | 82 | 30.246 | 20.785 | 23.010 |
| 1.00 | 5.93 | | | | | | |
| ATOM | | 778 | CG1 | VAL | 82 | 31.540 | 20.140 | 22.517 |
| 1.00 | 7.63 | | | | | | |
| ATOM | | 779 | CG2 | VAL | 82 | 30.205 | 20.766 | 24.539 |
| 1.00 | 6.83 | | | | | | |
| ATOM | | 780 | C | VAL | 82 | 30.119 | 22.221 | 20.951 |
| 1.00 | 6.61 | | | | | | |
| ATOM | | 781 | O | VAL | 82 | 29.261 | 21.582 | 20.348 |
| 1.00 | 6.74 | | | | | | |
| ATOM | | 782 | N | ASP | 83 | 31.119 | 22.864 | 20.340 |
| 1.00 | 6.11 | | | | | | |
| ATOM | | 784 | CA | ASP | 83 | 31.237 | 22.909 | 18.874 |
| 1.00 | 6.12 | | | | | | |
| ATOM | | 785 | CB | ASP | 83 | 31.679 | 24.290 | 18.395 |
| 1.00 | 5.67 | | | | | | |
| ATOM | | 786 | CG | ASP | 83 | 30.504 | 25.196 | 18.052 |
| 1.00 | 6.35 | | | | | | |
| ATOM | | 787 | OD1 | ASP | 83 | 30.737 | 26.382 | 17.772 |
| 1.00 | 7.42 | | | | | | |
| ATOM | | 788 | OD2 | ASP | 83 | 29.350 | 24.720 | 18.044 |
| 1.00 | 7.63 | | | | | | |
| ATOM | | 789 | C | ASP | 83 | 32.160 | 21.835 | 18.312 |
| 1.00 | 6.63 | | | | | | |
| ATOM | | 790 | O | ASP | 83 | 31.995 | 21.399 | 17.175 |
| 1.00 | 7.51 | | | | | | |
| ATOM | | 791 | N | SER | 84 | 33.188 | 21.479 | 19.069 |
| 1.00 | 6.29 | | | | | | |
| ATOM | | 793 | CA | SER | 84 | 34.085 | 20.424 | 18.641 |
| 1.00 | 6.74 | | | | | | |
| ATOM | | 794 | CB | SER | 84 | 35.198 | 20.933 | 17.727 |
| 1.00 | 6.37 | | | | | | |
| ATOM | | 795 | OG | SER | 84 | 35.909 | 19.816 | 17.225 |
| 1.00 | 6.88 | | | | | | |
| ATOM | | 797 | C | SER | 84 | 34.655 | 19.706 | 19.851 |
| 1.00 | 6.53 | | | | | | |
| ATOM | | 798 | O | SER | 84 | 34.527 | 20.167 | 20.988 |
| 1.00 | 6.69 | | | | | | |
| ATOM | | 799 | N | TRP | 85 | 35.236 | 18.545 | 19.606 |

-continued

| | | | | | | | | | |
|---|---|---|---|---|---|---|---|---|---|
| | | | | | | | | 1.00 | 6.77 |
| ATOM | 801 | CA | TRP | 85 | 35.780 | 17.732 | 20.675 | 1.00 | 7.16 |
| ATOM | 802 | CB | TRP | 85 | 34.667 | 16.856 | 21.276 | 1.00 | 7.31 |
| ATOM | 803 | CG | TRP | 85 | 33.955 | 15.981 | 20.279 | 1.00 | 8.40 |
| ATOM | 804 | CD2 | TRP | 85 | 32.790 | 16.319 | 19.504 | 1.00 | 8.19 |
| ATOM | 805 | CE2 | TRP | 85 | 32.500 | 15.209 | 18.683 | 1.00 | 8.37 |
| ATOM | 806 | CE3 | TRP | 85 | 31.970 | 17.449 | 19.425 | 1.00 | 8.60 |
| ATOM | 807 | CD1 | TRP | 85 | 34.303 | 14.711 | 19.911 | 1.00 | 9.75 |
| ATOM | 808 | NE1 | TRP | 85 | 33.434 | 14.243 | 18.950 | 1.00 | 10.01 |
| ATOM | 810 | CZ2 | TRP | 85 | 31.428 | 15.198 | 17.793 | 1.00 | 8.41 |
| ATOM | 811 | CZ3 | TRP | 85 | 30.905 | 17.432 | 18.537 | 1.00 | 9.35 |
| ATOM | 812 | CH2 | TRP | 85 | 30.649 | 16.313 | 17.737 | 1.00 | 9.03 |
| ATOM | 813 | C | TRP | 85 | 36.914 | 16.881 | 20.127 | 1.00 | 8.11 |
| ATOM | 814 | O | TRP | 85 | 37.254 | 16.976 | 18.939 | 1.00 | 8.43 |
| ATOM | 815 | N | GLY | 86 | 37.518 | 16.094 | 21.006 | 1.00 | 8.18 |
| ATOM | 817 | CA | GLY | 86 | 38.603 | 15.225 | 20.609 | 1.00 | 8.41 |
| ATOM | 818 | C | GLY | 86 | 38.137 | 13.815 | 20.335 | 1.00 | 9.11 |
| ATOM | 819 | O | GLY | 86 | 37.402 | 13.561 | 19.381 | 1.00 | 10.63 |
| ATOM | 820 | N | THR | 87 | 38.534 | 12.895 | 21.197 | 1.00 | 9.04 |
| ATOM | 822 | CA | THR | 87 | 38.185 | 11.491 | 21.029 | 1.00 | 10.41 |
| ATOM | 823 | CB | THR | 87 | 39.277 | 10.586 | 21.643 | 1.00 | 10.21 |
| ATOM | 824 | OG1 | THR | 87 | 39.518 | 10.996 | 22.996 | 1.00 | 12.01 |
| ATOM | 826 | CG2 | THR | 87 | 40.579 | 10.676 | 20.842 | 1.00 | 11.49 |
| ATOM | 827 | C | THR | 87 | 36.852 | 11.086 | 21.637 | 1.00 | 11.00 |
| ATOM | 828 | O | THR | 87 | 36.345 | 9.997 | 21.350 | 1.00 | 12.97 |
| ATOM | 829 | N | TYR | 88 | 36.286 | 11.949 | 22.473 | 1.00 | 11.01 |
| ATOM | 831 | CA | TYR | 88 | 35.033 | 11.641 | 23.165 | 1.00 | 11.59 |
| ATOM | 832 | CB | TYR | 88 | 35.323 | 11.459 | 24.669 | 1.00 | 12.77 |
| ATOM | 833 | CG | TYR | 88 | 34.096 | 11.360 | 25.553 | 1.00 | 15.23 |
| ATOM | 834 | CD1 | TYR | 88 | 33.282 | 10.236 | 25.521 | 1.00 | 17.59 |
| ATOM | 835 | CE1 | TYR | 88 | 32.116 | 10.177 | 26.273 | 1.00 | 18.52 |
| ATOM | 836 | CD2 | TYR | 88 | 33.720 | 12.419 | 26.372 | 1.00 | 16.34 |
| ATOM | 837 | CE2 | TYR | 88 | 32.566 | 12.368 | 27.127 | 1.00 | 17.85 |
| ATOM | 838 | CZ | TYR | 88 | 31.763 | 11.250 | 27.071 | 1.00 | 19.24 |
| ATOM | 839 | OH | TYR | 88 | 30.583 | 11.222 | 27.789 | 1.00 | 21.51 |
| ATOM | 841 | C | TYR | 88 | 33.970 | 12.713 | 22.981 | 1.00 | 10.42 |
| ATOM | 842 | O | TYR | 88 | 34.211 | 13.886 | 23.290 | 1.00 | 9.91 |
| ATOM | 843 | N | ARG | 89 | 32.812 | 12.325 | 22.450 | 1.00 | 10.21 |
| ATOM | 845 | CA | ARG | 89 | 31.717 | 13.277 | 22.278 | 1.00 | 9.91 |
| ATOM | 846 | CB | ARG | 89 | 30.852 | 12.918 | 21.063 | 1.00 | 9.65 |
| ATOM | 847 | CG | ARG | 89 | 29.751 | 13.920 | 20.805 | 1.00 | 8.70 |
| ATOM | 848 | CD | ARG | 89 | 28.867 | 13.540 | 19.623 | | |

| | | | | | | | | | |
|---|---|---|---|---|---|---|---|---|---|
| ATOM | 849 | NE | ARG | 89 | 27.824 | 14.550 | 19.439 | 1.00 | 8.30 |
| ATOM | 851 | CZ | ARG | 89 | 26.565 | 14.414 | 19.857 | 1.00 | 8.00 |
| ATOM | 852 | NH1 | ARG | 89 | 26.170 | 13.300 | 20.460 | 1.00 | 7.35 |
| ATOM | 855 | NH2 | ARG | 89 | 25.729 | 15.435 | 19.750 | 1.00 | 8.01 |
| ATOM | 858 | C | ARG | 89 | 30.886 | 13.218 | 23.563 | 1.00 | 8.94 |
| ATOM | 859 | O | ARG | 89 | 30.381 | 12.157 | 23.936 | 1.00 | 9.57 |
| ATOM | 860 | N | PRO | 90 | 30.766 | 14.348 | 24.276 | 1.00 | 9.70 |
| ATOM | 861 | CD | PRO | 90 | 31.298 | 15.695 | 23.987 | 1.00 | 9.28 |
| ATOM | 862 | CA | PRO | 90 | 29.984 | 14.337 | 25.514 | 1.00 | 10.13 |
| ATOM | 863 | CB | PRO | 90 | 30.311 | 15.695 | 26.139 | 1.00 | 10.21 |
| ATOM | 864 | CG | PRO | 90 | 30.543 | 16.570 | 24.965 | 1.00 | 10.53 |
| ATOM | 865 | C | PRO | 90 | 28.486 | 14.136 | 25.294 | 1.00 | 10.45 |
| ATOM | 866 | O | PRO | 90 | 27.890 | 14.725 | 24.385 | 1.00 | 11.31 |
| ATOM | 867 | N | THR | 91 | 27.890 | 13.263 | 26.096 | 1.00 | 12.21 |
| ATOM | 869 | CA | THR | 91 | 26.459 | 13.001 | 25.995 | 1.00 | 10.98 |
| ATOM | 870 | CB | THR | 91 | 26.144 | 11.723 | 25.167 | 1.00 | 13.17 |
| ATOM | 871 | OG1 | THR | 91 | 26.655 | 10.563 | 25.841 | 1.00 | 13.69 |
| ATOM | 873 | CG2 | THR | 91 | 26.757 | 11.814 | 23.754 | 1.00 | 16.21 |
| ATOM | 874 | C | THR | 91 | 25.885 | 12.875 | 27.406 | 1.00 | 13.50 |
| ATOM | 875 | O | THR | 91 | 26.626 | 12.903 | 28.392 | 1.00 | 13.53 |
| ATOM | 876 | N | GLY | 92 | 24.566 | 12.783 | 27.505 | 1.00 | 15.22 |
| ATOM | 878 | CA | GLY | 92 | 23.915 | 12.659 | 28.798 | 1.00 | 12.71 |
| ATOM | 879 | C | GLY | 92 | 22.488 | 12.240 | 28.541 | 1.00 | 12.21 |
| ATOM | 880 | O | GLY | 92 | 22.232 | 11.459 | 27.617 | 1.00 | 12.62 |
| ATOM | 881 | N | THR | 93 | 21.558 | 12.754 | 29.343 | 1.00 | 12.73 |
| ATOM | 883 | CA | THR | 93 | 20.143 | 12.442 | 29.175 | 1.00 | 11.34 |
| ATOM | 884 | CB | THR | 93 | 19.380 | 12.724 | 30.480 | 1.00 | 12.11 |
| ATOM | 885 | OG1 | THR | 93 | 19.941 | 11.922 | 31.528 | 1.00 | 13.13 |
| ATOM | 887 | CG2 | THR | 93 | 17.897 | 12.397 | 30.328 | 1.00 | 14.32 |
| ATOM | 888 | C | THR | 93 | 19.606 | 13.311 | 28.039 | 1.00 | 14.22 |
| ATOM | 889 | O | THR | 93 | 19.596 | 14.538 | 28.139 | 1.00 | 10.68 |
| ATOM | 890 | N | TYR | 94 | 19.191 | 12.668 | 26.951 | 1.00 | 10.38 |
| ATOM | 892 | CA | TYR | 94 | 18.691 | 13.369 | 25.775 | 1.00 | 10.81 |
| ATOM | 893 | CB | TYR | 94 | 18.532 | 12.381 | 24.619 | 1.00 | 10.59 |
| ATOM | 894 | CG | TYR | 94 | 18.014 | 13.008 | 23.347 | 1.00 | 11.92 |
| ATOM | 895 | CD1 | TYR | 94 | 18.857 | 13.720 | 22.506 | 1.00 | 11.53 |
| ATOM | 896 | CE1 | TYR | 94 | 18.389 | 14.279 | 21.338 | 1.00 | 11.77 |
| ATOM | 897 | CD2 | TYR | 94 | 16.679 | 12.880 | 22.980 | 1.00 | 12.66 |
| ATOM | 898 | CE2 | TYR | 94 | 16.203 | 13.441 | 21.815 | 1.00 | 13.30 |
| ATOM | 899 | CZ | TYR | 94 | 17.062 | 14.137 | 20.999 | 1.00 | 13.21 |
| ATOM | 900 | OH | TYR | 94 | 16.578 | 14.699 | 19.841 | 1.00 | 12.85 |

-continued

| | | ATOM | serial | name | res | resnum | x | y | z |
|---|---|---|---|---|---|---|---|---|---|
| 1.00 | 14.74 | | | | | | | | |
| | | ATOM | 902 | C | TYR | 94 | 17.368 | 14.096 | 26.021 |
| 1.00 | 10.66 | | | | | | | | |
| | | ATOM | 903 | O | TYR | 94 | 16.401 | 13.504 | 26.520 |
| 1.00 | 11.11 | | | | | | | | |
| | | ATOM | 904 | N | LYS | 95 | 17.325 | 15.364 | 25.630 |
| 1.00 | 9.08 | | | | | | | | |
| | | ATOM | 906 | CA | LYS | 95 | 16.147 | 16.196 | 25.797 |
| 1.00 | 10.06 | | | | | | | | |
| | | ATOM | 907 | CB | LYS | 95 | 16.506 | 17.444 | 26.603 |
| 1.00 | 11.36 | | | | | | | | |
| | | ATOM | 908 | CG | LYS | 95 | 16.932 | 17.158 | 28.041 |
| 1.00 | 14.99 | | | | | | | | |
| | | ATOM | 909 | CD | LYS | 95 | 15.789 | 16.499 | 28.813 |
| 1.00 | 18.59 | | | | | | | | |
| | | ATOM | 910 | CE | LYS | 95 | 16.174 | 16.186 | 30.242 |
| 1.00 | 21.65 | | | | | | | | |
| | | ATOM | 911 | NZ | LYS | 95 | 16.400 | 17.443 | 31.010 |
| 1.00 | 25.67 | | | | | | | | |
| | | ATOM | 915 | C | LYS | 95 | 15.521 | 16.619 | 24.475 |
| 1.00 | 10.70 | | | | | | | | |
| | | ATOM | 916 | O | LYS | 95 | 14.304 | 16.785 | 24.391 |
| 1.00 | 12.09 | | | | | | | | |
| | | ATOM | 917 | N | GLY | 96 | 16.335 | 16.811 | 23.443 |
| 1.00 | 9.78 | | | | | | | | |
| | | ATOM | 919 | CA | GLY | 96 | 15.815 | 17.253 | 22.157 |
| 1.00 | 9.58 | | | | | | | | |
| | | ATOM | 920 | C | GLY | 96 | 16.954 | 17.851 | 21.353 |
| 1.00 | 9.11 | | | | | | | | |
| | | ATOM | 921 | O | GLY | 96 | 18.110 | 17.579 | 21.661 |
| 1.00 | 8.59 | | | | | | | | |
| | | ATOM | 922 | N | THR | 97 | 16.643 | 18.634 | 20.325 |
| 1.00 | 9.24 | | | | | | | | |
| | | ATOM | 924 | CA | THR | 97 | 17.679 | 19.261 | 19.502 |
| 1.00 | 9.19 | | | | | | | | |
| | | ATOM | 925 | CB | THR | 97 | 17.809 | 18.608 | 18.108 |
| 1.00 | 9.68 | | | | | | | | |
| | | ATOM | 926 | OG1 | THR | 97 | 16.580 | 18.770 | 17.373 |
| 1.00 | 11.79 | | | | | | | | |
| | | ATOM | 928 | CG2 | THR | 97 | 18.149 | 17.139 | 18.227 |
| 1.00 | 9.87 | | | | | | | | |
| | | ATOM | 929 | C | THR | 97 | 17.345 | 20.720 | 19.263 |
| 1.00 | 10.16 | | | | | | | | |
| | | ATOM | 930 | O | THR | 97 | 16.209 | 21.163 | 19.500 |
| 1.00 | 11.30 | | | | | | | | |
| | | ATOM | 931 | N | VAL | 98 | 18.349 | 21.469 | 18.823 |
| 1.00 | 9.56 | | | | | | | | |
| | | ATOM | 933 | CA | VAL | 98 | 18.180 | 22.870 | 18.485 |
| 1.00 | 9.74 | | | | | | | | |
| | | ATOM | 934 | CB | VAL | 98 | 18.474 | 23.828 | 19.678 |
| 1.00 | 10.00 | | | | | | | | |
| | | ATOM | 935 | CG1 | VAL | 98 | 19.875 | 23.611 | 20.225 |
| 1.00 | 11.15 | | | | | | | | |
| | | ATOM | 936 | CG2 | VAL | 98 | 18.307 | 25.281 | 19.234 |
| 1.00 | 11.62 | | | | | | | | |
| | | ATOM | 937 | C | VAL | 98 | 19.113 | 23.160 | 17.320 |
| 1.00 | 9.97 | | | | | | | | |
| | | ATOM | 938 | O | VAL | 98 | 20.249 | 22.673 | 17.278 |
| 1.00 | 9.52 | | | | | | | | |
| | | ATOM | 939 | N | LYS | 99 | 18.595 | 23.865 | 16.325 |
| 1.00 | 9.83 | | | | | | | | |
| | | ATOM | 941 | CA | LYS | 99 | 19.383 | 24.233 | 15.163 |
| 1.00 | 10.87 | | | | | | | | |
| | | ATOM | 942 | CB | LYS | 99 | 18.547 | 24.121 | 13.882 |
| 1.00 | 13.94 | | | | | | | | |
| | | ATOM | 943 | CG | LYS | 99 | 17.927 | 22.740 | 13.647 |
| 1.00 | 20.06 | | | | | | | | |
| | | ATOM | 944 | CD | LYS | 99 | 16.757 | 22.479 | 14.622 |
| 1.00 | 25.68 | | | | | | | | |
| | | ATOM | 945 | CE | LYS | 99 | 16.131 | 21.091 | 14.473 |
| 1.00 | 27.88 | | | | | | | | |
| | | ATOM | 946 | NZ | LYS | 99 | 17.076 | 19.984 | 14.795 |
| 1.00 | 30.08 | | | | | | | | |
| | | ATOM | 950 | C | LYS | 99 | 19.796 | 25.673 | 15.396 |
| 1.00 | 10.19 | | | | | | | | |
| | | ATOM | 951 | O | LYS | 99 | 18.963 | 26.525 | 15.738 |
| 1.00 | 10.66 | | | | | | | | |
| | | ATOM | 952 | N | SER | 100 | 21.091 | 25.949 | 15.281 |
| 1.00 | 9.03 | | | | | | | | |
| | | ATOM | 954 | CA | SER | 100 | 21.570 | 27.305 | 15.492 |
| 1.00 | 8.92 | | | | | | | | |
| | | ATOM | 955 | CB | SER | 100 | 21.770 | 27.559 | 17.003 |

| | | | | | | | | | |
|---|---|---|---|---|---|---|---|---|---|
| 1.00 | 9.53 | | | | | | | | |
| ATOM | | 956 | OG | SER | 100 | 22.036 | 28.925 | 17.285 | |
| 1.00 | 10.19 | | | | | | | | |
| ATOM | | 958 | C | SER | 100 | 22.897 | 27.481 | 14.769 | |
| 1.00 | 9.22 | | | | | | | | |
| ATOM | | 959 | O | SER | 100 | 23.717 | 26.553 | 14.734 | |
| 1.00 | 9.67 | | | | | | | | |
| ATOM | | 960 | N | ASP | 101 | 23.102 | 28.667 | 14.201 | |
| 1.00 | 8.58 | | | | | | | | |
| ATOM | | 962 | CA | ASP | 101 | 24.360 | 28.991 | 13.530 | |
| 1.00 | 9.53 | | | | | | | | |
| ATOM | | 963 | CB | ASP | 101 | 25.439 | 29.292 | 14.577 | |
| 1.00 | 8.59 | | | | | | | | |
| ATOM | | 964 | CG | ASP | 101 | 24.966 | 30.278 | 15.615 | |
| 1.00 | 9.23 | | | | | | | | |
| ATOM | | 965 | OD1 | ASP | 101 | 24.632 | 29.849 | 16.740 | |
| 1.00 | 8.01 | | | | | | | | |
| ATOM | | 966 | OD2 | ASP | 101 | 24.891 | 31.481 | 15.300 | |
| 1.00 | 11.33 | | | | | | | | |
| ATOM | | 967 | C | ASP | 101 | 24.872 | 27.940 | 12.547 | |
| 1.00 | 10.53 | | | | | | | | |
| ATOM | | 968 | O | ASP | 101 | 26.063 | 27.625 | 12.533 | |
| 1.00 | 11.20 | | | | | | | | |
| ATOM | | 969 | N | GLY | 102 | 23.957 | 27.394 | 11.746 | |
| 1.00 | 10.95 | | | | | | | | |
| ATOM | | 971 | CA | GLY | 102 | 24.323 | 26.415 | 10.740 | |
| 1.00 | 11.74 | | | | | | | | |
| ATOM | | 972 | C | GLY | 102 | 24.522 | 24.991 | 11.203 | |
| 1.00 | 12.03 | | | | | | | | |
| ATOM | | 973 | O | GLY | 102 | 24.849 | 24.130 | 10.387 | |
| 1.00 | 15.13 | | | | | | | | |
| ATOM | | 974 | N | GLY | 103 | 24.331 | 24.720 | 12.489 | |
| 1.00 | 10.73 | | | | | | | | |
| ATOM | | 976 | CA | GLY | 103 | 24.520 | 23.366 | 12.968 | |
| 1.00 | 9.93 | | | | | | | | |
| ATOM | | 977 | C | GLY | 103 | 23.331 | 22.865 | 13.753 | |
| 1.00 | 8.93 | | | | | | | | |
| ATOM | | 978 | O | GLY | 103 | 22.442 | 23.643 | 14.096 | |
| 1.00 | 9.85 | | | | | | | | |
| ATOM | | 979 | N | THR | 104 | 23.272 | 21.554 | 13.952 | |
| 1.00 | 8.69 | | | | | | | | |
| ATOM | | 981 | CA | THR | 104 | 22.207 | 20.950 | 14.753 | |
| 1.00 | 8.72 | | | | | | | | |
| ATOM | | 982 | CB | THR | 104 | 21.513 | 19.802 | 14.014 | |
| 1.00 | 10.36 | | | | | | | | |
| ATOM | | 983 | OG1 | THR | 104 | 20.972 | 20.313 | 12.788 | |
| 1.00 | 13.06 | | | | | | | | |
| ATOM | | 985 | CG2 | THR | 104 | 20.379 | 19.211 | 14.873 | |
| 1.00 | 10.48 | | | | | | | | |
| ATOM | | 986 | C | THR | 104 | 22.887 | 20.429 | 16.020 | |
| 1.00 | 8.40 | | | | | | | | |
| ATOM | | 987 | O | THR | 104 | 23.919 | 19.741 | 15.948 | |
| 1.00 | 8.43 | | | | | | | | |
| ATOM | | 988 | N | TYR | 105 | 22.312 | 20.766 | 17.167 | |
| 1.00 | 6.69 | | | | | | | | |
| ATOM | | 990 | CA | TYR | 105 | 22.869 | 20.382 | 18.453 | |
| 1.00 | 7.22 | | | | | | | | |
| ATOM | | 991 | CB | TYR | 105 | 23.138 | 21.636 | 19.296 | |
| 1.00 | 6.90 | | | | | | | | |
| ATOM | | 992 | CG | TYR | 105 | 24.168 | 22.602 | 18.740 | |
| 1.00 | 7.17 | | | | | | | | |
| ATOM | | 993 | CD1 | TYR | 105 | 23.853 | 23.459 | 17.693 | |
| 1.00 | 7.56 | | | | | | | | |
| ATOM | | 994 | CE1 | TYR | 105 | 24.777 | 24.367 | 17.210 | |
| 1.00 | 7.90 | | | | | | | | |
| ATOM | | 995 | CD2 | TYR | 105 | 25.447 | 22.677 | 19.292 | |
| 1.00 | 6.18 | | | | | | | | |
| ATOM | | 996 | CE2 | TYR | 105 | 26.379 | 23.585 | 18.818 | |
| 1.00 | 7.32 | | | | | | | | |
| ATOM | | 997 | CZ | TYR | 105 | 26.036 | 24.425 | 17.779 | |
| 1.00 | 7.75 | | | | | | | | |
| ATOM | | 998 | OH | TYR | 105 | 26.940 | 25.358 | 17.306 | |
| 1.00 | 8.32 | | | | | | | | |
| ATOM | | 1000 | C | TYR | 105 | 21.907 | 19.505 | 19.240 | |
| 1.00 | 7.65 | | | | | | | | |
| ATOM | | 1001 | O | TYR | 105 | 20.703 | 19.742 | 19.233 | |
| 1.00 | 8.32 | | | | | | | | |
| ATOM | | 1002 | N | ASP | 106 | 22.436 | 18.470 | 19.877 | |
| 1.00 | 7.03 | | | | | | | | |
| ATOM | | 1004 | CA | ASP | 106 | 21.621 | 17.629 | 20.744 | |
| 1.00 | 7.19 | | | | | | | | |
| ATOM | | 1005 | CB | ASP | 106 | 22.232 | 16.242 | 20.895 | |

-continued

| | | | | | | | | | |
|---|---|---|---|---|---|---|---|---|---|
| ATOM | 1006 | CG | ASP | 106 | 22.135 | 15.434 | 19.635 | 1.00 | 7.44 |
| ATOM | 1007 | OD1 | ASP | 106 | 23.134 | 14.788 | 19.269 | 1.00 | 8.29 |
| ATOM | 1008 | OD2 | ASP | 106 | 21.051 | 15.468 | 19.011 | 1.00 | 8.93 |
| ATOM | 1009 | C | ASP | 106 | 21.650 | 18.319 | 22.100 | 1.00 | 8.87 |
| ATOM | 1010 | O | ASP | 106 | 22.678 | 18.897 | 22.489 | 1.00 | 6.52 |
| ATOM | 1011 | N | ILE | 107 | 20.545 | 18.254 | 22.830 | 1.00 | 8.85 |
| ATOM | 1013 | CA | ILE | 107 | 20.456 | 18.862 | 24.154 | 1.00 | 6.54 |
| ATOM | 1014 | CB | ILE | 107 | 19.151 | 19.675 | 24.297 | 1.00 | 7.09 |
| ATOM | 1015 | CG2 | ILE | 107 | 19.023 | 20.234 | 25.710 | 1.00 | 7.73 |
| ATOM | 1016 | CG1 | ILE | 107 | 19.117 | 20.790 | 23.249 | 1.00 | 6.87 |
| ATOM | 1017 | CD1 | ILE | 107 | 17.748 | 21.473 | 23.124 | 1.00 | 8.04 |
| ATOM | 1018 | C | ILE | 107 | 20.491 | 17.755 | 25.205 | 1.00 | 9.19 |
| ATOM | 1019 | O | ILE | 107 | 19.722 | 16.789 | 25.123 | 1.00 | 7.06 |
| ATOM | 1020 | N | TYR | 108 | 21.389 | 17.880 | 26.173 | 1.00 | 7.22 |
| ATOM | 1022 | CA | TYR | 108 | 21.515 | 16.882 | 27.232 | 1.00 | 6.95 |
| ATOM | 1023 | CB | TYR | 108 | 22.811 | 16.077 | 27.090 | 1.00 | 7.18 |
| ATOM | 1024 | CG | TYR | 108 | 23.013 | 15.341 | 25.794 | 1.00 | 7.59 |
| ATOM | 1025 | CD1 | TYR | 108 | 23.988 | 15.753 | 24.887 | 1.00 | 8.26 |
| ATOM | 1026 | CE1 | TYR | 108 | 24.213 | 15.060 | 23.719 | 1.00 | 8.13 |
| ATOM | 1027 | CD2 | TYR | 108 | 22.267 | 14.208 | 25.493 | 1.00 | 8.60 |
| ATOM | 1028 | CE2 | TYR | 108 | 22.486 | 13.502 | 24.324 | 1.00 | 8.68 |
| ATOM | 1029 | CZ | TYR | 108 | 23.458 | 13.933 | 23.441 | 1.00 | 8.88 |
| ATOM | 1030 | OH | TYR | 108 | 23.681 | 13.242 | 22.276 | 1.00 | 9.66 |
| ATOM | 1032 | C | TYR | 108 | 21.617 | 17.506 | 28.607 | 1.00 | 9.55 |
| ATOM | 1033 | O | TYR | 108 | 22.041 | 18.662 | 28.748 | 1.00 | 7.18 |
| ATOM | 1034 | N | THR | 109 | 21.259 | 16.721 | 29.620 | 1.00 | 6.50 |
| ATOM | 1036 | CA | THR | 109 | 21.465 | 17.144 | 31.003 | 1.00 | 7.71 |
| ATOM | 1037 | CB | THR | 109 | 20.173 | 17.372 | 31.831 | 1.00 | 8.74 |
| ATOM | 1038 | OG1 | THR | 109 | 19.393 | 16.169 | 31.862 | 1.00 | 9.86 |
| ATOM | 1040 | CG2 | THR | 109 | 19.371 | 18.521 | 31.276 | 1.00 | 11.56 |
| ATOM | 1041 | C | THR | 109 | 22.241 | 16.028 | 31.670 | 1.00 | 12.46 |
| ATOM | 1042 | O | THR | 109 | 22.121 | 14.849 | 31.295 | 1.00 | 8.80 |
| ATOM | 1043 | N | THR | 110 | 23.095 | 16.412 | 32.606 | 1.00 | 8.91 |
| ATOM | 1045 | CA | THR | 110 | 23.876 | 15.470 | 33.401 | 1.00 | 8.78 |
| ATOM | 1046 | CB | THR | 110 | 25.327 | 15.244 | 32.854 | 1.00 | 10.13 |
| ATOM | 1047 | OG1 | THR | 110 | 26.021 | 16.493 | 32.771 | 1.00 | 10.63 |
| ATOM | 1049 | CG2 | THR | 110 | 25.316 | 14.558 | 31.483 | 1.00 | 10.44 |
| ATOM | 1050 | C | THR | 110 | 23.972 | 16.094 | 34.792 | 1.00 | 10.74 |
| ATOM | 1051 | O | THR | 110 | 23.632 | 17.264 | 34.990 | 1.00 | 9.98 |
| ATOM | 1052 | N | THR | 111 | 24.451 | 15.312 | 35.747 | 1.00 | 10.66 |
| ATOM | 1054 | CA | THR | 111 | 24.620 | 15.777 | 37.114 | 1.00 | 10.72 |

| | | | | | | | | | |
|---|---|---|---|---|---|---|---|---|---|
| | | | | | | | | 1.00 | 11.19 |
| ATOM | 1055 | CB | THR | 111 | 23.582 | 15.125 | 38.047 | 1.00 | 13.02 |
| ATOM | 1056 | OG1 | THR | 111 | 22.270 | 15.388 | 37.539 | 1.00 | 15.05 |
| ATOM | 1058 | CG2 | THR | 111 | 23.695 | 15.684 | 39.476 | 1.00 | 13.84 |
| ATOM | 1059 | C | THR | 111 | 26.015 | 15.372 | 37.566 | 1.00 | 11.62 |
| ATOM | 1060 | O | THR | 111 | 26.505 | 14.306 | 37.199 | 1.00 | 11.90 |
| ATOM | 1061 | N | ARG | 112 | 26.674 | 16.269 | 38.290 | 1.00 | 10.81 |
| ATOM | 1063 | CA | ARG | 112 | 28.002 | 16.016 | 38.839 | 1.00 | 11.90 |
| ATOM | 1064 | CB | ARG | 112 | 28.930 | 17.201 | 38.558 | 1.00 | 14.38 |
| ATOM | 1065 | CG | ARG | 112 | 29.291 | 17.330 | 37.103 | 1.00 | 16.14 |
| ATOM | 1066 | CD | ARG | 112 | 30.426 | 16.404 | 36.731 | 1.00 | 19.66 |
| ATOM | 1067 | NE | ARG | 112 | 31.707 | 17.057 | 36.981 | 1.00 | 23.60 |
| ATOM | 1069 | CZ | ARG | 112 | 32.767 | 16.477 | 37.542 | 1.00 | 25.66 |
| ATOM | 1070 | NH1 | ARG | 112 | 32.724 | 15.204 | 37.927 | 1.00 | 27.05 |
| ATOM | 1073 | NH2 | ARG | 112 | 33.867 | 17.193 | 37.756 | 1.00 | 27.17 |
| ATOM | 1076 | C | ARG | 112 | 27.819 | 15.843 | 40.344 | 1.00 | 11.36 |
| ATOM | 1077 | O | ARG | 112 | 27.071 | 16.595 | 40.978 | 1.00 | 11.70 |
| ATOM | 1078 | N | TYR | 113 | 28.465 | 14.829 | 40.900 | 1.00 | 11.50 |
| ATOM | 1080 | CA | TYR | 113 | 28.366 | 14.530 | 42.323 | 1.00 | 12.45 |
| ATOM | 1081 | CB | TYR | 113 | 27.883 | 13.090 | 42.519 | 1.00 | 12.53 |
| ATOM | 1082 | CG | TYR | 113 | 26.550 | 12.818 | 41.855 | 1.00 | 13.06 |
| ATOM | 1083 | CD1 | TYR | 113 | 25.356 | 13.014 | 42.547 | 1.00 | 13.72 |
| ATOM | 1084 | CE1 | TYR | 113 | 24.139 | 12.792 | 41.945 | 1.00 | 13.98 |
| ATOM | 1085 | CD2 | TYR | 113 | 26.489 | 12.389 | 40.536 | 1.00 | 13.33 |
| ATOM | 1086 | CE2 | TYR | 113 | 25.267 | 12.162 | 39.920 | 1.00 | 13.75 |
| ATOM | 1087 | CZ | TYR | 113 | 24.099 | 12.365 | 40.635 | 1.00 | 13.86 |
| ATOM | 1088 | OH | TYR | 113 | 22.884 | 12.113 | 40.036 | 1.00 | 15.43 |
| ATOM | 1090 | C | TYR | 113 | 29.702 | 14.724 | 43.032 | 1.00 | 13.26 |
| ATOM | 1091 | O | TYR | 113 | 30.718 | 14.139 | 42.625 | 1.00 | 13.92 |
| ATOM | 1092 | N | ASN | 114 | 29.678 | 15.537 | 44.088 | 1.00 | 13.07 |
| ATOM | 1094 | CA | ASN | 114 | 30.861 | 15.840 | 44.901 | 1.00 | 12.98 |
| ATOM | 1095 | CB | ASN | 114 | 31.251 | 14.610 | 45.723 | 1.00 | 14.43 |
| ATOM | 1096 | CG | ASN | 114 | 32.206 | 14.942 | 46.855 | 1.00 | 15.38 |
| ATOM | 1097 | OD1 | ASN | 114 | 32.035 | 15.938 | 47.562 | 1.00 | 17.02 |
| ATOM | 1098 | ND2 | ASN | 114 | 33.191 | 14.085 | 47.057 | 1.00 | 17.49 |
| ATOM | 1101 | c | ASN | 114 | 32.017 | 16.274 | 44.000 | 1.00 | 13.11 |
| ATOM | 1102 | O | ASN | 114 | 33.127 | 15.736 | 44.073 | 1.00 | 13.52 |
| ATOM | 1103 | N | ALA | 115 | 31.743 | 17.264 | 43.162 | 1.00 | 11.72 |
| ATOM | 1105 | CA | ALA | 115 | 32.726 | 17.764 | 42.208 | 1.00 | 11.90 |
| ATOM | 1106 | CB | ALA | 115 | 32.176 | 17.594 | 40.786 | 1.00 | 12.69 |
| ATOM | 1107 | C | ALA | 115 | 33.037 | 19.231 | 42.471 | 1.00 | 11.91 |
| ATOM | 1108 | O | ALA | 115 | 32.214 | 19.955 | 43.039 | | |

| | | | | | | | | |
|---|---|---|---|---|---|---|---|---|
| ATOM | 1109 | N | PRO | 116 | 34.232 | 19.693 | 42.055 | 1.00 11.60 |
| ATOM | 1110 | CD | PRO | 116 | 35.306 | 18.936 | 41.388 | 1.00 12.08 |
| ATOM | 1111 | CA | PRO | 116 | 34.619 | 21.092 | 42.258 | 1.00 12.97 |
| ATOM | 1112 | CB | PRO | 116 | 36.022 | 21.158 | 41.642 | 1.00 12.75 |
| ATOM | 1113 | CG | PRO | 116 | 36.525 | 19.757 | 41.718 | 1.00 13.29 |
| ATOM | 1114 | C | PRO | 116 | 33.666 | 22.013 | 41.496 | 1.00 14.85 |
| ATOM | 1115 | O | PRO | 116 | 33.319 | 21.745 | 40.339 | 1.00 13.38 |
| ATOM | 1116 | N | SER | 117 | 33.228 | 23.084 | 42.142 | 1.00 13.48 |
| ATOM | 1118 | CA | SER | 117 | 32.339 | 24.019 | 41.482 | 1.00 13.65 |
| ATOM | 1119 | CB | SER | 117 | 31.012 | 24.124 | 42.231 | 1.00 14.63 |
| ATOM | 1120 | OG | SER | 117 | 31.158 | 24.930 | 43.385 | 1.00 15.34 |
| ATOM | 1122 | C | SER | 117 | 33.022 | 25.379 | 41.436 | 1.00 17.33 |
| ATOM | 1123 | O | SER | 117 | 34.129 | 25.553 | 41.960 | 1.00 14.80 |
| ATOM | 1124 | N | ILE | 118 | 32.328 | 26.348 | 40.853 | 1.00 14.72 |
| ATOM | 1126 | CA | ILE | 118 | 32.837 | 27.703 | 40.728 | 1.00 14.62 |
| ATOM | 1127 | CB | ILE | 118 | 31.813 | 28.600 | 39.976 | 1.00 16.31 |
| ATOM | 1128 | CG2 | ILE | 118 | 30.488 | 28.670 | 40.731 | 1.00 15.37 |
| ATOM | 1129 | CG1 | ILE | 118 | 32.392 | 29.993 | 39.741 | 1.00 14.25 |
| ATOM | 1130 | CD1 | ILE | 118 | 31.520 | 30.875 | 38.868 | 1.00 16.02 |
| ATOM | 1131 | C | ILE | 118 | 33.206 | 28.321 | 42.080 | 1.00 16.65 |
| ATOM | 1132 | O | ILE | 118 | 34.183 | 29.055 | 42.174 | 1.00 17.92 |
| ATOM | 1133 | N | ASP | 119 | 32.455 | 27.974 | 43.123 | 1.00 18.87 |
| ATOM | 1135 | CA | ASP | 119 | 32.674 | 28.507 | 44.472 | 1.00 20.29 |
| ATOM | 1136 | CB | ASP | 119 | 31.415 | 28.308 | 45.327 | 1.00 22.48 |
| ATOM | 1137 | CG | ASP | 119 | 30.283 | 29.248 | 44.952 | 1.00 24.91 |
| ATOM | 1138 | OD1 | ASP | 119 | 30.568 | 30.400 | 44.566 | 1.00 26.95 |
| ATOM | 1139 | OD2 | ASP | 119 | 29.106 | 28.830 | 45.071 | 1.00 27.78 |
| ATOM | 1140 | C | ASP | 119 | 33.834 | 27.866 | 45.226 | 1.00 29.45 |
| ATOM | 1141 | O | ASP | 119 | 34.165 | 28.300 | 46.339 | 1.00 23.22 |
| ATOM | 1142 | N | GLY | 120 | 34.450 | 26.844 | 44.640 | 1.00 24.26 |
| ATOM | 1144 | CA | GLY | 120 | 35.519 | 26.148 | 45.332 | 1.00 21.95 |
| ATOM | 1145 | C | GLY | 120 | 34.867 | 24.995 | 46.081 | 1.00 21.06 |
| ATOM | 1146 | O | GLY | 120 | 33.639 | 24.838 | 46.041 | 1.00 20.24 |
| ATOM | 1147 | N | ASP | 121 | 35.663 | 24.198 | 46.780 | 1.00 21.54 |
| ATOM | 1149 | CA | ASP | 121 | 35.151 | 23.043 | 47.515 | 1.00 18.87 |
| ATOM | 1150 | CB | ASP | 121 | 34.292 | 23.489 | 48.709 | 1.00 17.79 |
| ATOM | 1151 | CG | ASP | 121 | 35.128 | 24.177 | 49.781 | 1.00 16.14 |
| ATOM | 1152 | OD1 | ASP | 121 | 36.279 | 23.733 | 49.983 | 1.00 16.04 |
| ATOM | 1153 | OD2 | ASP | 121 | 34.660 | 25.169 | 50.381 | 1.00 16.20 |
| ATOM | 1154 | C | ASP | 121 | 34.431 | 22.078 | 46.565 | 1.00 15.66 |
| ATOM | 1155 | O | ASP | 121 | 34.707 | 22.097 | 45.360 | 1.00 17.56 |

-continued

| | | | | | | | | | |
|---|---|---|---|---|---|---|---|---|---|
| | | | | | | | | 1.00 | 20.27 |
| ATOM | 1156 | N | ARG | 122 | 33.541 | 21.233 | 47.071 | 1.00 | 15.49 |
| ATOM | 1158 | CA | ARG | 122 | 32.868 | 20.264 | 46.211 | 1.00 | 14.33 |
| ATOM | 1159 | CB | ARG | 122 | 33.468 | 18.871 | 46.417 | 1.00 | 15.98 |
| ATOM | 1160 | CG | ARG | 122 | 34.987 | 18.856 | 46.370 | 1.00 | 22.01 |
| ATOM | 1161 | CD | ARG | 122 | 35.555 | 17.493 | 46.647 | 1.00 | 25.64 |
| ATOM | 1162 | NE | ARG | 122 | 35.516 | 16.674 | 45.446 | 1.00 | 30.29 |
| ATOM | 1164 | CZ | ARG | 122 | 36.541 | 15.960 | 44.996 | 1.00 | 32.24 |
| ATOM | 1165 | NH1 | ARG | 122 | 37.699 | 15.959 | 45.650 | 1.00 | 33.69 |
| ATOM | 1168 | NH2 | ARG | 122 | 36.411 | 15.255 | 43.880 | 1.00 | 34.20 |
| ATOM | 1171 | C | ARG | 122 | 31.386 | 20.210 | 46.513 | 1.00 | 12.98 |
| ATOM | 1172 | O | ARG | 122 | 30.978 | 20.389 | 47.657 | 1.00 | 13.04 |
| ATOM | 1173 | N | THR | 123 | 30.579 | 19.961 | 45.492 | 1.00 | 11.93 |
| ATOM | 1175 | CA | THR | 123 | 29.144 | 19.878 | 45.705 | 1.00 | 11.52 |
| ATOM | 1176 | CB | THR | 123 | 28.517 | 21.287 | 45.856 | 1.00 | 12.34 |
| ATOM | 1177 | OG1 | THR | 123 | 27.219 | 21.171 | 46.455 | 1.00 | 13.52 |
| ATOM | 1179 | CG2 | THR | 123 | 28.408 | 22.004 | 44.503 | 1.00 | 12.64 |
| ATOM | 1180 | C | THR | 123 | 28.507 | 19.108 | 44.558 | 1.00 | 11.60 |
| ATOM | 1181 | O | THR | 123 | 29.212 | 18.577 | 43.694 | 1.00 | 12.00 |
| ATOM | 1182 | N | THR | 124 | 27.187 | 18.988 | 44.592 | 1.00 | 10.11 |
| ATOM | 1184 | CA | THR | 124 | 26.451 | 18.283 | 43.548 | 1.00 | 11.46 |
| ATOM | 1185 | CB | THR | 124 | 25.470 | 17.273 | 44.172 | 1.00 | 11.44 |
| ATOM | 1186 | OG1 | THR | 124 | 26.212 | 16.222 | 44.818 | 1.00 | 13.54 |
| ATOM | 1188 | CG2 | THR | 124 | 24.564 | 16.679 | 43.105 | 1.00 | 12.97 |
| ATOM | 1189 | C | THR | 124 | 25.691 | 19.343 | 42.738 | 1.00 | 11.64 |
| ATOM | 1190 | O | THR | 124 | 25.013 | 20.201 | 43.307 | 1.00 | 12.44 |
| ATOM | 1191 | N | PHE | 125 | 25.841 | 19.321 | 41.420 | 1.00 | 10.02 |
| ATOM | 1193 | CA | PHE | 125 | 25.172 | 20.310 | 40.581 | 1.00 | 9.87 |
| ATOM | 1194 | CB | PHE | 125 | 26.040 | 21.581 | 40.430 | 1.00 | 10.39 |
| ATOM | 1195 | CG | PHE | 125 | 27.430 | 21.321 | 39.899 | 1.00 | 10.80 |
| ATOM | 1196 | CD1 | PHE | 125 | 28.486 | 21.072 | 40.771 | 1.00 | 10.51 |
| ATOM | 1197 | CD2 | PHE | 125 | 27.681 | 21.298 | 38.526 | 1.00 | 10.72 |
| ATOM | 1198 | CE1 | PHE | 125 | 29.760 | 20.801 | 40.290 | 1.00 | 10.49 |
| ATOM | 1199 | CE2 | PHE | 125 | 28.956 | 21.027 | 38.037 | 1.00 | 11.56 |
| ATOM | 1200 | CZ | PHE | 125 | 29.991 | 20.779 | 38.911 | 1.00 | 10.93 |
| ATOM | 1201 | C | PHE | 125 | 24.813 | 19.744 | 39.216 | 1.00 | 9.17 |
| ATOM | 1202 | O | PHE | 125 | 25.350 | 18.720 | 38.791 | 1.00 | 9.91 |
| ATOM | 1203 | N | THR | 126 | 23.886 | 20.418 | 38.547 | 1.00 | 9.93 |
| ATOM | 1205 | CA | THR | 126 | 23.431 | 20.026 | 37.222 | 1.00 | 10.19 |
| ATOM | 1206 | CB | THR | 126 | 21.949 | 20.388 | 37.041 | 1.00 | 13.09 |
| ATOM | 1207 | OG1 | THR | 126 | 21.192 | 19.813 | 38.113 | 1.00 | 15.71 |
| ATOM | 1209 | CG2 | THR | 126 | 21.416 | 19.847 | 35.715 | | |

-continued

| | | | | | | | |
|---|---|---|---|---|---|---|---|
| 1.00 | 15.34 | | | | | | |
| ATOM | | 1210 | C | THR | 126 | 24.223 | 20.729 | 36.122 |
| 1.00 | 9.09 | | | | | | |
| ATOM | | 1211 | O | THR | 126 | 24.701 | 21.857 | 36.305 |
| 1.00 | 9.18 | | | | | | |
| ATOM | | 1212 | N | GLN | 127 | 24.389 | 20.028 | 35.005 |
| 1.00 | 8.52 | | | | | | |
| ATOM | | 1214 | CA | GLN | 127 | 25.075 | 20.560 | 33.832 |
| 1.00 | 7.83 | | | | | | |
| ATOM | | 1215 | CB | GLN | 127 | 26.264 | 19.683 | 33.444 |
| 1.00 | 7.94 | | | | | | |
| ATOM | | 1216 | CG | GLN | 127 | 27.314 | 19.489 | 34.527 |
| 1.00 | 8.42 | | | | | | |
| ATOM | | 1217 | CD | GLN | 127 | 28.410 | 18.547 | 34.080 |
| 1.00 | 9.41 | | | | | | |
| ATOM | | 1218 | OE1 | GLN | 127 | 28.173 | 17.364 | 33.849 |
| 1.00 | 11.46 | | | | | | |
| ATOM | | 1219 | NE2 | GLN | 127 | 29.599 | 19.072 | 33.903 |
| 1.00 | 9.24 | | | | | | |
| ATOM | | 1222 | C | GLN | 127 | 24.082 | 20.546 | 32.671 |
| 1.00 | 8.00 | | | | | | |
| ATOM | | 1223 | O | GLN | 127 | 23.335 | 19.570 | 32.500 |
| 1.00 | 9.01 | | | | | | |
| ATOM | | 1224 | N | TYR | 128 | 24.050 | 21.637 | 31.915 |
| 1.00 | 7.47 | | | | | | |
| ATOM | | 1226 | CA | TYR | 128 | 23.193 | 21.747 | 30.725 |
| 1.00 | 7.08 | | | | | | |
| ATOM | | 1227 | CB | TYR | 128 | 22.446 | 23.076 | 30.678 |
| 1.00 | 7.17 | | | | | | |
| ATOM | | 1228 | CG | TYR | 128 | 21.337 | 23.250 | 31.683 |
| 1.00 | 7.55 | | | | | | |
| ATOM | | 1229 | CD1 | TYR | 128 | 20.883 | 22.185 | 32.458 |
| 1.00 | 8.48 | | | | | | |
| ATOM | | 1230 | CE1 | TYR | 128 | 19.866 | 22.370 | 33.389 |
| 1.00 | 9.54 | | | | | | |
| ATOM | | 1231 | CD2 | TYR | 128 | 20.748 | 24.495 | 31.859 |
| 1.00 | 8.26 | | | | | | |
| ATOM | | 1232 | CE2 | TYR | 128 | 19.737 | 24.686 | 32.784 |
| 1.00 | 8.94 | | | | | | |
| ATOM | | 1233 | CZ | TYR | 128 | 19.304 | 23.625 | 33.543 |
| 1.00 | 8.68 | | | | | | |
| ATOM | | 1234 | OH | TYR | 128 | 18.303 | 23.828 | 34.475 |
| 1.00 | 10.00 | | | | | | |
| ATOM | | 1236 | C | TYR | 128 | 24.143 | 21.720 | 29.539 |
| 1.00 | 6.99 | | | | | | |
| ATOM | | 1237 | O | TYR | 128 | 25.161 | 22.422 | 29.550 |
| 1.00 | 7.10 | | | | | | |
| ATOM | | 1238 | N | TRP | 129 | 23.786 | 20.956 | 28.511 |
| 1.00 | 6.30 | | | | | | |
| ATOM | | 1240 | CA | TRP | 129 | 24.626 | 20.849 | 27.320 |
| 1.00 | 6.02 | | | | | | |
| ATOM | | 1241 | CB | TRP | 129 | 25.266 | 19.455 | 27.203 |
| 1.00 | 6.55 | | | | | | |
| ATOM | | 1242 | CG | TRP | 129 | 26.025 | 18.930 | 28.374 |
| 1.00 | 7.49 | | | | | | |
| ATOM | | 1243 | CD2 | TRP | 129 | 27.451 | 18.787 | 28.477 |
| 1.00 | 7.83 | | | | | | |
| ATOM | | 1244 | CE2 | TRP | 129 | 27.722 | 18.209 | 29.731 |
| 1.00 | 8.17 | | | | | | |
| ATOM | | 1245 | CE3 | TRP | 129 | 28.522 | 19.086 | 27.622 |
| 1.00 | 7.59 | | | | | | |
| ATOM | | 1246 | CD1 | TRP | 129 | 25.506 | 18.444 | 29.541 |
| 1.00 | 8.08 | | | | | | |
| ATOM | | 1247 | NE1 | TRP | 129 | 26.517 | 18.009 | 30.362 |
| 1.00 | 8.78 | | | | | | |
| ATOM | | 1249 | CZ2 | TRP | 129 | 29.028 | 17.921 | 30.156 |
| 1.00 | 8.09 | | | | | | |
| ATOM | | 1250 | CZ3 | TRP | 129 | 29.806 | 18.797 | 28.044 |
| 1.00 | 7.89 | | | | | | |
| ATOM | | 1251 | CH2 | TRP | 129 | 30.049 | 18.221 | 29.297 |
| 1.00 | 8.85 | | | | | | |
| ATOM | | 1252 | C | TRP | 129 | 23.879 | 20.976 | 26.010 |
| 1.00 | 6.91 | | | | | | |
| ATOM | | 1253 | O | TRP | 129 | 22.750 | 20.503 | 25.891 |
| 1.00 | 6.88 | | | | | | |
| ATOM | | 1254 | N | SER | 130 | 24.532 | 21.630 | 25.051 |
| 1.00 | 6.19 | | | | | | |
| ATOM | | 1256 | CA | SER | 130 | 24.101 | 21.652 | 23.655 |
| 1.00 | 5.86 | | | | | | |
| ATOM | | 1257 | CB | SER | 130 | 23.813 | 23.049 | 23.120 |
| 1.00 | 7.32 | | | | | | |
| ATOM | | 1258 | OG | SER | 130 | 22.470 | 23.416 | 23.404 |

-continued

| | | | | | | | | |
|---|---|---|---|---|---|---|---|---|
| ATOM | 1260 | C | SER | 130 | 25.385 | 21.110 | 23.022 | 1.00 7.36 |
| ATOM | 1261 | O | SER | 130 | 26.447 | 21.723 | 23.188 | 1.00 5.75 |
| ATOM | 1262 | N | VAL | 131 | 25.313 | 19.945 | 22.387 | 1.00 7.07 |
| ATOM | 1264 | CA | VAL | 131 | 26.490 | 19.328 | 21.762 | 1.00 5.14 |
| ATOM | 1265 | CB | VAL | 131 | 26.797 | 17.953 | 22.401 | 1.00 6.25 |
| ATOM | 1266 | CG1 | VAL | 131 | 28.104 | 17.379 | 21.836 | 1.00 6.01 |
| ATOM | 1267 | CG2 | VAL | 131 | 26.910 | 18.089 | 23.913 | 1.00 7.33 |
| ATOM | 1268 | C | VAL | 131 | 26.230 | 19.155 | 20.269 | 1.00 8.18 |
| ATOM | 1269 | O | VAL | 131 | 25.270 | 18.491 | 19.868 | 1.00 6.01 |
| ATOM | 1270 | N | ARG | 132 | 27.075 | 19.755 | 19.433 | 1.00 7.09 |
| ATOM | 1272 | CA | ARG | 132 | 26.877 | 19.667 | 17.989 | 1.00 6.07 |
| ATOM | 1273 | CB | ARG | 132 | 27.971 | 20.447 | 17.262 | 1.00 5.80 |
| ATOM | 1274 | CG | ARG | 132 | 27.492 | 21.119 | 15.982 | 1.00 6.74 |
| ATOM | 1275 | CD | ARG | 132 | 28.601 | 22.044 | 15.465 | 1.00 7.33 |
| ATOM | 1276 | NE | ARG | 132 | 28.257 | 22.750 | 14.230 | 1.00 7.95 |
| ATOM | 1278 | CZ | ARG | 132 | 28.405 | 22.248 | 13.007 | 1.00 10.15 |
| ATOM | 1279 | NH1 | ARG | 132 | 28.883 | 21.020 | 12.830 | 1.00 9.87 |
| ATOM | 1282 | NH2 | ARG | 132 | 28.098 | 22.993 | 11.956 | 1.00 9.74 |
| ATOM | 1285 | C | ARG | 132 | 26.867 | 18.194 | 17.560 | 1.00 11.62 |
| ATOM | 1286 | O | ARG | 132 | 27.605 | 17.374 | 18.110 | 1.00 5.99 |
| ATOM | 1287 | N | GLN | 133 | 26.022 | 17.849 | 16.590 | 1.00 6.38 |
| ATOM | 1289 | CA | GLN | 133 | 25.941 | 16.457 | 16.156 | 1.00 7.04 |
| ATOM | 1290 | CB | GLN | 133 | 24.677 | 16.213 | 15.328 | 1.00 7.51 |
| ATOM | 1291 | CG | GLN | 133 | 23.402 | 16.324 | 16.174 | 1.00 8.04 |
| ATOM | 1292 | CD | GLN | 133 | 22.125 | 15.987 | 15.413 | 1.00 8.11 |
| ATOM | 1293 | OE1 | GLN | 133 | 21.084 | 15.701 | 16.022 | 1.00 9.11 |
| ATOM | 1294 | NE2 | GLN | 133 | 22.193 | 16.014 | 14.095 | 1.00 12.22 |
| ATOM | 1297 | C | GLN | 133 | 27.191 | 15.996 | 15.421 | 1.00 8.08 |
| ATOM | 1298 | O | GLN | 133 | 27.554 | 14.821 | 15.497 | 1.00 7.25 |
| ATOM | 1299 | N | SER | 134 | 27.830 | 16.927 | 14.713 | 1.00 8.01 |
| ATOM | 1301 | CA | SER | 134 | 29.084 | 16.677 | 13.986 | 1.00 7.38 |
| ATOM | 1302 | CB | SER | 134 | 28.839 | 16.670 | 12.467 | 1.00 8.47 |
| ATOM | 1303 | OG | SER | 134 | 28.295 | 17.904 | 12.025 | 1.00 10.32 |
| ATOM | 1305 | C | SER | 134 | 30.024 | 17.825 | 14.382 | 1.00 11.99 |
| ATOM | 1306 | O | SER | 134 | 29.552 | 18.911 | 14.738 | 1.00 8.30 |
| ATOM | 1307 | N | LYS | 135 | 31.336 | 17.588 | 14.353 | 1.00 7.97 |
| ATOM | 1309 | CA | LYS | 135 | 32.288 | 18.633 | 14.722 | 1.00 7.49 |
| ATOM | 1310 | CB | LYS | 135 | 33.733 | 18.098 | 14.730 | 1.00 7.91 |
| ATOM | 1311 | CG | LYS | 135 | 33.968 | 16.992 | 15.737 | 1.00 7.88 |
| ATOM | 1312 | CD | LYS | 135 | 35.408 | 16.520 | 15.771 | 1.00 9.26 |
| ATOM | 1313 | CE | LYS | 135 | 35.552 | 15.304 | 16.668 | 1.00 10.17 |

-continued

| | | | | | | | | | |
|---|---|---|---|---|---|---|---|---|---|
| ATOM | 1314 | NZ | LYS | 135 | 36.989 | 14.926 | 16.843 | 1.00 | 10.79 |
| ATOM | 1318 | C | LYS | 135 | 32.217 | 19.823 | 13.783 | 1.00 | 13.41 |
| ATOM | 1319 | O | LYS | 135 | 32.134 | 19.664 | 12.554 | 1.00 | 8.47 |
| ATOM | 1320 | N | ARG | 136 | 32.239 | 21.023 | 14.353 | 1.00 | 10.44 |
| ATOM | 1322 | CA | ARG | 136 | 32.227 | 22.225 | 13.548 | 1.00 | 8.73 |
| ATOM | 1323 | CB | ARG | 136 | 31.842 | 23.431 | 14.397 | 1.00 | 8.79 |
| ATOM | 1324 | CG | ARG | 136 | 31.469 | 24.661 | 13.597 | 1.00 | 8.71 |
| ATOM | 1325 | CD | ARG | 136 | 30.960 | 25.755 | 14.519 | 1.00 | 8.96 |
| ATOM | 1326 | NE | ARG | 136 | 30.367 | 26.877 | 13.797 | 1.00 | 8.67 |
| ATOM | 1328 | CZ | ARG | 136 | 29.614 | 27.817 | 14.361 | 1.00 | 8.17 |
| ATOM | 1329 | NH1 | ARG | 136 | 29.354 | 27.777 | 15.661 | 1.00 | 7.64 |
| ATOM | 1332 | NH2 | ARG | 136 | 29.121 | 28.807 | 13.631 | 1.00 | 8.13 |
| ATOM | 1335 | C | ARG | 136 | 33.650 | 22.412 | 13.027 | 1.00 | 8.82 |
| ATOM | 1336 | O | ARG | 136 | 34.609 | 22.278 | 13.785 | 1.00 | 9.51 |
| ATOM | 1337 | N | PRO | 137 | 33.810 | 22.679 | 11.720 | 1.00 | 9.99 |
| ATOM | 1338 | CD | PRO | 137 | 32.814 | 22.730 | 10.637 | 1.00 | 10.43 |
| ATOM | 1339 | CA | PRO | 137 | 35.172 | 22.877 | 11.193 | 1.00 | 10.71 |
| ATOM | 1340 | CB | PRO | 137 | 34.916 | 23.225 | 9.728 | 1.00 | 11.19 |
| ATOM | 1341 | CG | PRO | 137 | 33.665 | 22.488 | 9.420 | 1.00 | 12.07 |
| ATOM | 1342 | C | PRO | 137 | 35.810 | 24.072 | 11.917 | 1.00 | 11.96 |
| ATOM | 1343 | O | PRO | 137 | 35.110 | 25.007 | 12.320 | 1.00 | 10.74 |
| ATOM | 1344 | N | THR | 138 | 37.114 | 24.023 | 12.139 | 1.00 | 12.54 |
| ATOM | 1346 | CA | THR | 138 | 37.795 | 25.116 | 12.811 | 1.00 | 10.87 |
| ATOM | 1347 | CB | THR | 138 | 38.652 | 24.604 | 13.982 | 1.00 | 11.05 |
| ATOM | 1348 | OG1 | THR | 138 | 39.583 | 23.616 | 13.512 | 1.00 | 11.69 |
| ATOM | 1350 | CG2 | THR | 138 | 37.746 | 24.000 | 15.070 | 1.00 | 12.49 |
| ATOM | 1351 | C | THR | 138 | 38.650 | 25.904 | 11.826 | 1.00 | 11.85 |
| ATOM | 1352 | O | THR | 138 | 38.816 | 25.493 | 10.675 | 1.00 | 10.93 |
| ATOM | 1353 | N | GLY | 139 | 39.132 | 27.061 | 12.259 | 1.00 | 12.46 |
| ATOM | 1355 | CA | GLY | 139 | 39.954 | 27.889 | 11.397 | 1.00 | 10.76 |
| ATOM | 1356 | C | GLY | 139 | 39.157 | 29.004 | 10.743 | 1.00 | 11.16 |
| ATOM | 1357 | O | GLY | 139 | 39.730 | 29.873 | 10.085 | 1.00 | 12.00 |
| ATOM | 1358 | N | SER | 140 | 37.839 | 28.981 | 10.930 | 1.00 | 14.10 |
| ATOM | 1360 | CA | SER | 140 | 36.954 | 29.996 | 10.375 | 1.00 | 11.25 |
| ATOM | 1361 | CB | SER | 140 | 35.857 | 29.343 | 9.538 | 1.00 | 11.51 |
| ATOM | 1362 | OG | SER | 140 | 36.404 | 28.701 | 8.403 | 1.00 | 13.27 |
| ATOM | 1364 | C | SER | 140 | 36.293 | 30.823 | 11.468 | 1.00 | 17.64 |
| ATOM | 1365 | O | SER | 140 | 36.369 | 30.485 | 12.657 | 1.00 | 9.96 |
| ATOM | 1366 | N | ASN | 141 | 35.697 | 31.937 | 11.064 | 1.00 | 10.71 |
| ATOM | 1368 | CA | ASN | 141 | 34.988 | 32.815 | 11.988 | 1.00 | 9.76 |
| ATOM | 1369 | CB | ASN | 141 | 34.774 | 34.193 | 11.357 | 1.00 | 10.29 |

-continued

| | | | | | | | | | |
|---|---|---|---|---|---|---|---|---|---|
| | | | | | | | | 1.00 | 11.11 |
| ATOM | 1370 | CG | ASN | 141 | 36.068 | 34.965 | 11.187 | 1.00 | 12.89 |
| ATOM | 1371 | OD1 | ASN | 141 | 37.056 | 34.714 | 11.885 | 1.00 | 11.87 |
| ATOM | 1372 | ND2 | ASN | 141 | 36.066 | 35.914 | 10.270 | 1.00 | 14.96 |
| ATOM | 1375 | C | ASN | 141 | 33.645 | 32.158 | 12.283 | 1.00 | 10.47 |
| ATOM | 1376 | O | ASN | 141 | 32.787 | 32.050 | 11.399 | 1.00 | 11.70 |
| ATOM | 1377 | N | ALA | 142 | 33.477 | 31.712 | 13.523 | 1.00 | 9.61 |
| ATOM | 1379 | CA | ALA | 142 | 32.265 | 31.022 | 13.945 | 1.00 | 9.98 |
| ATOM | 1380 | CB | ALA | 142 | 32.629 | 29.707 | 14.600 | 1.00 | 9.88 |
| ATOM | 1381 | C | ALA | 142 | 31.457 | 31.875 | 14.903 | 1.00 | 10.25 |
| ATOM | 1382 | O | AIA | 142 | 32.001 | 32.719 | 15.618 | 1.00 | 11.29 |
| ATOM | 1383 | N | THR | 143 | 30.155 | 31.627 | 14.927 | 1.00 | 9.82 |
| ATOM | 1385 | CA | THR | 143 | 29.246 | 32.357 | 15.788 | 1.00 | 9.36 |
| ATOM | 1386 | CB | THR | 143 | 28.277 | 33.232 | 14.953 | 1.00 | 11.22 |
| ATOM | 1387 | OG1 | THR | 143 | 29.033 | 34.077 | 14.069 | 1.00 | 14.26 |
| ATOM | 1389 | CG2 | THR | 143 | 27.412 | 34.092 | 15.847 | 1.00 | 12.93 |
| ATOM | 1390 | C | THR | 143 | 28.389 | 31.394 | 16.596 | 1.00 | 9.04 |
| ATOM | 1391 | O | THR | 143 | 28.011 | 30.319 | 16.114 | 1.00 | 8.71 |
| ATOM | 1392 | N | ILE | 144 | 28.179 | 31.740 | 17.859 | 1.00 | 7.22 |
| ATOM | 1394 | CA | ILE | 144 | 27.297 | 30.977 | 18.725 | 1.00 | 7.94 |
| ATOM | 1395 | CB | ILE | 144 | 28.030 | 30.341 | 19.930 | 1.00 | 7.57 |
| ATOM | 1396 | CG2 | ILE | 144 | 26.998 | 29.785 | 20.946 | 1.00 | 8.85 |
| ATOM | 1397 | CG1 | ILE | 144 | 28.951 | 29.218 | 19.445 | 1.00 | 8.51 |
| ATOM | 1398 | CD1 | ILE | 144 | 29.793 | 28.590 | 20.549 | 1.00 | 8.96 |
| ATOM | 1399 | C | ILE | 144 | 26.262 | 31.992 | 19.213 | 1.00 | 7.28 |
| ATOM | 1400 | O | ILE | 144 | 26.592 | 32.926 | 19.951 | 1.00 | 7.79 |
| ATOM | 1401 | N | THR | 145 | 25.033 | 31.857 | 18.721 | 1.00 | 7.04 |
| ATOM | 1403 | CA | THR | 145 | 23.929 | 32.739 | 19.102 | 1.00 | 7.58 |
| ATOM | 1404 | CB | THR | 145 | 22.930 | 32.837 | 17.950 | 1.00 | 7.57 |
| ATOM | 1405 | OG1 | THR | 145 | 23.616 | 33.323 | 16.786 | 1.00 | 9.20 |
| ATOM | 1407 | CG2 | THR | 145 | 21.813 | 33.805 | 18.295 | 1.00 | 9.33 |
| ATOM | 1408 | C | THR | 145 | 23.331 | 32.077 | 20.345 | 1.00 | 7.68 |
| ATOM | 1409 | O | THR | 145 | 22.444 | 31.214 | 20.262 | 1.00 | 7.61 |
| ATOM | 1410 | N | PHE | 146 | 23.861 | 32.470 | 21.500 | 1.00 | 7.43 |
| ATOM | 1412 | CA | PHE | 146 | 23.486 | 31.856 | 22.761 | 1.00 | 7.32 |
| ATOM | 1413 | CB | PHE | 146 | 24.361 | 32.397 | 23.893 | 1.00 | 7.88 |
| ATOM | 1414 | CG | PHE | 146 | 24.232 | 31.635 | 25.189 | 1.00 | 7.47 |
| ATOM | 1415 | CD1 | PHE | 146 | 24.328 | 30.247 | 25.221 | 1.00 | 8.42 |
| ATOM | 1416 | CD2 | PHE | 146 | 24.032 | 32.318 | 26.380 | 1.00 | 9.10 |
| ATOM | 1417 | CE1 | PHE | 146 | 24.231 | 29.560 | 26.429 | 1.00 | 10.17 |
| ATOM | 1418 | CE2 | PHE | 146 | 23.934 | 31.636 | 27.589 | 1.00 | 9.57 |
| ATOM | 1419 | CZ | PHE | 146 | 24.034 | 30.259 | 27.611 | | |

-continued

| | | | | | | | | | |
|---|---|---|---|---|---|---|---|---|---|
| ATOM | 1420 | C | PHE | 146 | 22.016 | 31.897 | 23.106 | 1.00 | 9.43 |
| ATOM | 1421 | O | PHE | 146 | 21.493 | 30.937 | 23.682 | 1.00 | 7.62 |
| ATOM | 1422 | N | THR | 147 | 21.330 | 32.950 | 22.677 | 1.00 | 7.42 |
| ATOM | 1424 | CA | THR | 147 | 19.907 | 33.059 | 22.958 | 1.00 | 7.24 |
| ATOM | 1425 | CB | THR | 147 | 19.331 | 34.382 | 22.419 | 1.00 | 8.68 |
| ATOM | 1426 | OG1 | THR | 147 | 17.947 | 34.473 | 22.777 | 1.00 | 9.43 |
| ATOM | 1428 | CG2 | THR | 147 | 19.433 | 34.429 | 20.930 | 1.00 | 17.10 |
| ATOM | 1429 | C | THR | 147 | 19.109 | 31.868 | 22.396 | 1.00 | 10.81 |
| ATOM | 1430 | O | THR | 147 | 18.140 | 31.429 | 23.017 | 1.00 | 8.55 |
| ATOM | 1431 | N | ASN | 148 | 19.526 | 31.325 | 21.250 | 1.00 | 8.97 |
| ATOM | 1433 | CA | ASN | 148 | 18.829 | 30.176 | 20.655 | 1.00 | 8.27 |
| ATOM | 1434 | CB | ASN | 148 | 19.423 | 29.784 | 19.302 | 1.00 | 9.32 |
| ATOM | 1435 | CG | ASN | 148 | 19.127 | 30.791 | 18.202 | 1.00 | 10.43 |
| ATOM | 1436 | OD1 | ASN | 148 | 19.860 | 30.861 | 17.201 | 1.00 | 13.00 |
| ATOM | 1437 | ND2 | ASN | 148 | 18.069 | 31.569 | 18.367 | 1.00 | 15.35 |
| ATOM | 1440 | C | ASN | 148 | 18.909 | 28.967 | 21.574 | 1.00 | 11.66 |
| ATOM | 1441 | O | ASN | 148 | 17.949 | 28.202 | 21.697 | 1.00 | 8.82 |
| ATOM | 1442 | N | HIS | 149 | 20.056 | 28.804 | 22.232 | 1.00 | 9.19 |
| ATOM | 1444 | CA | HIS | 149 | 20.264 | 27.693 | 23.149 | 1.00 | 8.08 |
| ATOM | 1445 | CB | HIS | 149 | 21.755 | 27.507 | 23.426 | 1.00 | 7.07 |
| ATOM | 1446 | CG | HIS | 149 | 22.521 | 27.095 | 22.208 | 1.00 | 6.26 |
| ATOM | 1447 | CD2 | HIS | 149 | 23.157 | 27.828 | 21.262 | 1.00 | 6.45 |
| ATOM | 1448 | ND1 | HIS | 149 | 22.654 | 25.776 | 21.826 | 1.00 | 7.33 |
| ATOM | 1450 | CE1 | HIS | 149 | 23.339 | 25.716 | 20.697 | 1.00 | 7.11 |
| ATOM | 1451 | NE2 | HIS | 149 | 23.655 | 26.947 | 20.335 | 1.00 | 7.85 |
| ATOM | 1453 | C | HIS | 149 | 19.477 | 27.883 | 24.430 | 1.00 | 7.63 |
| ATOM | 1454 | O | HIS | 149 | 18.780 | 26.971 | 24.863 | 1.00 | 7.20 |
| ATOM | 1455 | N | VAL | 150 | 19.552 | 29.080 | 25.005 | 1.00 | 8.12 |
| ATOM | 1457 | CA | VAL | 150 | 18.813 | 29.393 | 26.223 | 1.00 | 7.02 |
| ATOM | 1458 | CB | VAL | 150 | 19.044 | 30.858 | 26.632 | 1.00 | 7.84 |
| ATOM | 1459 | CG1 | VAL | 150 | 18.131 | 31.239 | 27.801 | 1.00 | 7.77 |
| ATOM | 1460 | CG2 | VAL | 150 | 20.515 | 31.052 | 27.014 | 1.00 | 8.91 |
| ATOM | 1461 | C | VAL | 150 | 17.313 | 29.139 | 26.017 | 1.00 | 8.40 |
| ATOM | 1462 | O | VAL | 150 | 16.661 | 28.489 | 26.848 | 1.00 | 8.70 |
| ATOM | 1463 | N | ASN | 151 | 16.794 | 29.575 | 24.875 | 1.00 | 9.04 |
| ATOM | 1465 | CA | ASN | 151 | 15.379 | 29.396 | 24.577 | 1.00 | 9.29 |
| ATOM | 1466 | CB | ASN | 151 | 14.967 | 30.276 | 23.397 | 1.00 | 11.27 |
| ATOM | 1467 | CG | ASN | 151 | 14.954 | 31.754 | 23.767 | 1.00 | 13.99 |
| ATOM | 1468 | OD1 | ASN | 151 | 14.736 | 32.099 | 24.932 | 1.00 | 17.23 |
| ATOM | 1469 | ND2 | ASN | 151 | 15.210 | 32.624 | 22.797 | 1.00 | 22.12 |
| ATOM | 1472 | C | ASN | 151 | 14.993 | 27.933 | 24.372 | 1.00 | 19.31 |

-continued

| | | | | | | | | | |
|---|---|---|---|---|---|---|---|---|---|
| ATOM | 1473 | O | ASN | 151 | 13.957 | 27.484 | 24.875 | 1.00 | 10.65 |
| ATOM | 1474 | N | ALA | 152 | 15.828 | 27.180 | 23.660 | 1.00 | 11.12 |
| ATOM | 1476 | CA | ALA | 152 | 15.563 | 25.754 | 23.459 | 1.00 | 9.31 |
| ATOM | 1477 | CB | ALA | 152 | 16.560 | 25.156 | 22.476 | 1.00 | 8.90 |
| ATOM | 1478 | C | ALA | 152 | 15.629 | 25.011 | 24.797 | 1.00 | 10.29 |
| ATOM | 1479 | O | ALA | 152 | 14.812 | 24.121 | 25.066 | 1.00 | 9.31 |
| ATOM | 1480 | N | TRP | 153 | 16.589 | 25.372 | 25.642 | 1.00 | 9.03 |
| ATOM | 1482 | CA | TRP | 153 | 16.723 | 24.728 | 26.941 | 1.00 | 8.56 |
| ATOM | 1483 | CB | TRP | 153 | 17.970 | 25.239 | 27.677 | 1.00 | 8.90 |
| ATOM | 1484 | CG | TRP | 153 | 19.290 | 24.835 | 27.040 | 1.00 | 8.55 |
| ATOM | 1485 | CD2 | TRP | 153 | 20.590 | 25.321 | 27.401 | 1.00 | 8.34 |
| ATOM | 1486 | CE2 | TRP | 153 | 21.528 | 24.676 | 26.560 | 1.00 | 8.15 |
| ATOM | 1487 | CE3 | TRP | 153 | 21.054 | 26.243 | 28.350 | 1.00 | 7.87 |
| ATOM | 1488 | CD1 | TRP | 153 | 19.480 | 23.940 | 26.022 | 1.00 | 8.65 |
| ATOM | 1489 | NE1 | TRP | 153 | 20.829 | 23.836 | 25.729 | 1.00 | 8.62 |
| ATOM | 1491 | CZ2 | TRP | 153 | 22.905 | 24.925 | 26.642 | 1.00 | 8.65 |
| ATOM | 1492 | CZ3 | TRP | 153 | 22.420 | 26.491 | 28.429 | 1.00 | 7.85 |
| ATOM | 1493 | CH2 | TRP | 153 | 23.327 | 25.834 | 27.581 | 1.00 | 8.42 |
| ATOM | 1494 | C | TRP | 153 | 15.479 | 25.002 | 27.787 | 1.00 | 8.96 |
| ATOM | 1495 | O | TRP | 153 | 14.936 | 24.096 | 28.422 | 1.00 | 9.72 |
| ATOM | 1496 | N | LYS | 154 | 15.012 | 26.245 | 27.753 | 1.00 | 10.06 |
| ATOM | 1498 | CA | LYS | 154 | 13.834 | 26.636 | 28.514 | 1.00 | 10.65 |
| ATOM | 1499 | CB | LYS | 154 | 13.571 | 28.129 | 28.322 | 1.00 | 12.32 |
| ATOM | 1500 | CG | LYS | 154 | 12.405 | 28.650 | 29.100 | 1.00 | 14.64 |
| ATOM | 1501 | CD | LYS | 154 | 12.336 | 30.169 | 29.040 | 1.00 | 20.28 |
| ATOM | 1502 | CE | LYS | 154 | 11.104 | 30.667 | 29.794 | 1.00 | 23.54 |
| ATOM | 1503 | NZ | LYS | 154 | 11.069 | 30.150 | 31.208 | 1.00 | 27.22 |
| ATOM | 1507 | C | LYS | 154 | 12.620 | 25.803 | 28.091 | 1.00 | 28.84 |
| ATOM | 1508 | O | LYS | 154 | 11.847 | 25.360 | 28.938 | 1.00 | 12.89 |
| ATOM | 1509 | N | SER | 155 | 12.499 | 25.520 | 26.797 | 1.00 | 12.44 |
| ATOM | 1511 | CA | SER | 155 | 11.372 | 24.732 | 26.298 | 1.00 | 13.31 |
| ATOM | 1512 | CB | SER | 155 | 11.358 | 24.706 | 24.770 | 1.00 | 14.63 |
| ATOM | 1513 | OG | SER | 155 | 12.315 | 23.786 | 24.267 | 1.00 | 16.22 |
| ATOM | 1515 | C | SER | 155 | 11.375 | 23.302 | 26.835 | 1.00 | 18.53 |
| ATOM | 1516 | O | SER | 155 | 10.352 | 22.612 | 26.796 | 1.00 | 15.94 |
| ATOM | 1517 | N | HIS | 156 | 12.530 | 22.847 | 27.316 | 1.00 | 16.03 |
| ATOM | 1519 | CA | HIS | 156 | 12.653 | 21.502 | 27.865 | 1.00 | 15.14 |
| ATOM | 1520 | CB | HIS | 156 | 13.846 | 20.777 | 27.243 | 1.00 | 15.16 |
| ATOM | 1521 | CG | HIS | 156 | 13.660 | 20.483 | 25.795 | 1.00 | 16.18 |
| ATOM | 1522 | CD2 | HIS | 156 | 12.918 | 19.540 | 25.170 | 1.00 | 17.56 |
| ATOM | 1523 | ND1 | HIS | 156 | 14.220 | 21.251 | 24.799 | 1.00 | 17.74 |

-continued

| | | | | | | | | | |
|---|---|---|---|---|---|---|---|---|---|
| | | | | | | | | 1.00 | 18.24 |
| ATOM | 1525 | CE1 | HIS | 156 | 13.832 | 20.795 | 23.622 | 1.00 | 17.83 |
| ATOM | 1526 | NE2 | HIS | 156 | 13.041 | 19.758 | 23.821 | 1.00 | 19.83 |
| ATOM | 1528 | C | HIS | 156 | 12.765 | 21.504 | 29.377 | 1.00 | 14.84 |
| ATOM | 1529 | O | HIS | 156 | 13.220 | 20.525 | 29.973 | 1.00 | 15.74 |
| ATOM | 1530 | N | GLY | 157 | 12.349 | 22.607 | 29.991 | 1.00 | 13.35 |
| ATOM | 1532 | CA | GLY | 157 | 12.404 | 22.719 | 31.438 | 1.00 | 13.68 |
| ATOM | 1533 | C | GLY | 157 | 13.801 | 22.895 | 32.022 | 1.00 | 13.89 |
| ATOM | 1534 | O | GLY | 157 | 14.016 | 22.658 | 33.204 | 1.00 | 15.37 |
| ATOM | 1535 | N | MET | 158 | 14.746 | 23.333 | 31.202 | 1.00 | 11.75 |
| ATOM | 1537 | CA | MET | 158 | 16.114 | 23.548 | 31.651 | 1.00 | 11.51 |
| ATOM | 1538 | CB | MET | 158 | 17.083 | 23.009 | 30.598 | 1.00 | 9.86 |
| ATOM | 1539 | CG | MET | 158 | 17.075 | 21.493 | 30.479 | 1.00 | 9.83 |
| ATOM | 1540 | SD | MET | 158 | 17.768 | 20.929 | 28.919 | 1.00 | 11.15 |
| ATOM | 1541 | CE | MET | 158 | 19.481 | 21.502 | 29.063 | 1.00 | 9.64 |
| ATOM | 1542 | C | MET | 158 | 16.297 | 25.047 | 31.839 | 1.00 | 11.30 |
| ATOM | 1543 | O | MET | 158 | 16.681 | 25.756 | 30.915 | 1.00 | 11.61 |
| ATOM | 1544 | N | ASN | 159 | 15.965 | 25.529 | 33.029 | 1.00 | 12.08 |
| ATOM | 1546 | CA | ASN | 159 | 16.067 | 26.948 | 33.337 | 1.00 | 12.87 |
| ATOM | 1547 | CB | ASN | 159 | 14.883 | 27.387 | 34.197 | 1.00 | 16.49 |
| ATOM | 1548 | CG | ASN | 159 | 13.557 | 27.198 | 33.486 | 1.00 | 18.00 |
| ATOM | 1549 | OD1 | ASN | 159 | 12.757 | 26.340 | 33.857 | 1.00 | 22.78 |
| ATOM | 1550 | ND2 | ASN | 159 | 13.344 | 27.961 | 32.425 | 1.00 | 20.94 |
| ATOM | 1553 | C | ASN | 159 | 17.367 | 27.289 | 34.039 | 1.00 | 12.90 |
| ATOM | 1554 | O | ASN | 159 | 17.803 | 26.584 | 34.955 | 1.00 | 12.75 |
| ATOM | 1555 | N | LEU | 160 | 17.982 | 28.378 | 33.603 | 1.00 | 12.27 |
| ATOM | 1557 | CA | LEU | 160 | 19.239 | 28.825 | 34.178 | 1.00 | 13.44 |
| ATOM | 1558 | CB | LEU | 160 | 19.997 | 29.674 | 33.152 | 1.00 | 13.40 |
| ATOM | 1559 | CG | LEU | 160 | 20.564 | 28.838 | 32.002 | 1.00 | 13.30 |
| ATOM | 1560 | CD1 | LEU | 160 | 20.954 | 29.739 | 30.855 | 1.00 | 14.40 |
| ATOM | 1561 | CD2 | LEU | 160 | 21.758 | 28.020 | 32.482 | 1.00 | 13.55 |
| ATOM | 1562 | C | LEU | 160 | 19.007 | 29.596 | 35.480 | 1.00 | 14.33 |
| ATOM | 1563 | O | LEU | 160 | 17.882 | 30.024 | 35.763 | 1.00 | 14.67 |
| ATOM | 1564 | N | GLY | 161 | 20.060 | 29.740 | 36.278 | 1.00 | 14.47 |
| ATOM | 1566 | CA | GLY | 161 | 19.953 | 30.465 | 37.529 | 1.00 | 15.47 |
| ATOM | 1567 | C | GLY | 161 | 19.784 | 31.954 | 37.290 | 1.00 | 16.15 |
| ATOM | 1568 | O | GLY | 161 | 19.999 | 32.452 | 36.171 | 1.00 | 16.60 |
| ATOM | 1569 | N | SER | 162 | 19.445 | 32.683 | 38.347 | 1.00 | 17.37 |
| ATOM | 1571 | CA | SER | 162 | 19.239 | 34.121 | 38.230 | 1.00 | 17.84 |
| ATOM | 1572 | CB | SER | 162 | 18.170 | 34.576 | 39.223 | 1.00 | 19.00 |
| ATOM | 1573 | OG | SER | 162 | 18.500 | 34.145 | 40.530 | 1.00 | 21.73 |
| ATOM | 1575 | C | SER | 162 | 20.505 | 34.953 | 38.413 | | |

| | | | | | | | | Occupancy | B-factor |
|---|---|---|---|---|---|---|---|---|---|
| | | | | | | | | 1.00 | 17.19 |
| ATOM | 1576 | O | SER | 162 | 20.538 | 36.123 | 38.041 | 1.00 | 17.92 |
| ATOM | 1577 | N | ASN | 163 | 21.541 | 34.362 | 38.995 | 1.00 | 16.21 |
| ATOM | 1579 | CA | ASN | 163 | 22.784 | 35.087 | 39.219 | 1.00 | 15.87 |
| ATOM | 1580 | CB | ASN | 163 | 23.260 | 34.871 | 40.661 | 1.00 | 19.24 |
| ATOM | 1581 | CG | ASN | 163 | 24.477 | 35.718 | 41.020 | 1.00 | 23.45 |
| ATOM | 1582 | OD1 | ASN | 163 | 25.295 | 35.326 | 41.860 | 1.00 | 27.11 |
| ATOM | 1583 | ND2 | ASN | 163 | 24.590 | 36.894 | 40.410 | 1.00 | 25.66 |
| ATOM | 1586 | C | ASN | 163 | 23.816 | 34.580 | 38.219 | 1.00 | 14.67 |
| ATOM | 1587 | O | ASN | 163 | 24.280 | 33.454 | 38.320 | 1.00 | 15.00 |
| ATOM | 1588 | N | TRP | 164 | 24.144 | 35.402 | 37.233 | 1.00 | 12.77 |
| ATOM | 1590 | CA | TRP | 164 | 25.106 | 35.017 | 36.205 | 1.00 | 12.67 |
| ATOM | 1591 | CB | TRP | 164 | 24.802 | 35.764 | 34.902 | 1.00 | 12.97 |
| ATOM | 1592 | CG | TRP | 164 | 23.523 | 35.331 | 34.250 | 1.00 | 13.93 |
| ATOM | 1593 | CD2 | TRP | 164 | 23.393 | 34.489 | 33.098 | 1.00 | 13.58 |
| ATOM | 1594 | CE2 | TRP | 164 | 22.015 | 34.297 | 32.871 | 1.00 | 14.09 |
| ATOM | 1595 | CE3 | TRP | 164 | 24.308 | 33.876 | 32.238 | 1.00 | 13.32 |
| ATOM | 1596 | CD1 | TRP | 164 | 22.253 | 35.620 | 34.659 | 1.00 | 15.26 |
| ATOM | 1597 | NE1 | TRP | 164 | 21.340 | 34.996 | 33.837 | 1.00 | 15.80 |
| ATOM | 1599 | CZ2 | TRP | 164 | 21.534 | 33.518 | 31.825 | 1.00 | 14.29 |
| ATOM | 1600 | CZ3 | TRP | 164 | 23.829 | 33.107 | 31.204 | 1.00 | 13.95 |
| ATOM | 1601 | CH2 | TRP | 164 | 22.456 | 32.932 | 31.004 | 1.00 | 13.84 |
| ATOM | 1602 | C | TRP | 164 | 26.576 | 35.218 | 36.569 | 1.00 | 12.17 |
| ATOM | 1603 | O | TRP | 164 | 26.990 | 36.300 | 37.001 | 1.00 | 12.76 |
| ATOM | 1604 | N | ALA | 165 | 27.365 | 34.173 | 36.360 | 1.00 | 10.88 |
| ATOM | 1606 | CA | ALA | 165 | 28.796 | 34.233 | 36.611 | 1.00 | 9.93 |
| ATOM | 1607 | CB | ALA | 165 | 29.275 | 32.979 | 37.333 | 1.00 | 12.00 |
| ATOM | 1608 | C | ALA | 165 | 29.486 | 34.396 | 35.246 | 1.00 | 9.94 |
| ATOM | 1609 | O | ALA | 165 | 28.846 | 34.822 | 34.275 | 1.00 | 10.07 |
| ATOM | 1610 | N | TYR | 166 | 30.759 | 34.027 | 35.145 | 1.00 | 8.78 |
| ATOM | 1612 | CA | TYR | 166 | 31.474 | 34.207 | 33.881 | 1.00 | 8.27 |
| ATOM | 1613 | CB | TYR | 166 | 32.982 | 34.002 | 34.069 | 1.00 | 8.85 |
| ATOM | 1614 | CG | TYR | 166 | 33.384 | 32.610 | 34.503 | 1.00 | 10.16 |
| ATOM | 1615 | CD1 | TYR | 166 | 33.438 | 31.567 | 33.588 | 1.00 | 10.41 |
| ATOM | 1616 | CE1 | TYR | 166 | 33.821 | 30.302 | 33.964 | 1.00 | 12.25 |
| ATOM | 1617 | CD2 | TYR | 166 | 33.726 | 32.344 | 35.827 | 1.00 | 9.77 |
| ATOM | 1618 | CE2 | TYR | 166 | 34.111 | 31.073 | 36.220 | 1.00 | 11.27 |
| ATOM | 1619 | CZ | TYR | 166 | 34.157 | 30.061 | 35.283 | 1.00 | 11.58 |
| ATOM | 1620 | OH | TYR | 166 | 34.553 | 28.803 | 35.642 | 1.00 | 13.25 |
| ATOM | 1622 | C | TYR | 166 | 30.941 | 33.364 | 32.717 | 1.00 | 8.20 |
| ATOM | 1623 | O | TYR | 166 | 30.242 | 32.355 | 32.915 | 1.00 | 8.68 |
| ATOM | 1624 | N | GLN | 167 | 31.327 | 33.765 | 31.509 | | |

-continued

| ATOM | | | | | | | |
|---|---|---|---|---|---|---|---|
| 1.00 | 8.01 | | | | | | |
| ATOM | | 1626 | CA | GLN | 167 | 30.894 | 33.122 | 30.272 |
| 1.00 | 7.76 | | | | | | |
| ATOM | | 1627 | CB | GLN | 167 | 29.687 | 33.897 | 29.742 |
| 1.00 | 8.57 | | | | | | |
| ATOM | | 1628 | CG | GLN | 167 | 29.059 | 33.379 | 28.465 |
| 1.00 | 9.03 | | | | | | |
| ATOM | | 1629 | CD | GLN | 167 | 27.822 | 34.189 | 28.116 |
| 1.00 | 9.86 | | | | | | |
| ATOM | | 1630 | OE1 | GLN | 167 | 27.896 | 35.405 | 27.941 |
| 1.00 | 9.96 | | | | | | |
| ATOM | | 1631 | NE2 | GLN | 167 | 26.674 | 33.531 | 28.081 |
| 1.00 | 11.48 | | | | | | |
| ATOM | | 1634 | C | GLN | 167 | 32.084 | 33.233 | 29.322 |
| 1.00 | 7.37 | | | | | | |
| ATOM | | 1635 | O | GLN | 167 | 32.463 | 34.340 | 28.940 |
| 1.00 | 7.66 | | | | | | |
| ATOM | | 1636 | N | VAL | 168 | 32.684 | 32.103 | 28.961 |
| 1.00 | 6.64 | | | | | | |
| ATOM | | 1638 | CA | VAL | 168 | 33.871 | 32.126 | 28.109 |
| 1.00 | 6.81 | | | | | | |
| ATOM | | 1639 | CB | VAL | 168 | 35.152 | 31.861 | 28.970 |
| 1.00 | 7.79 | | | | | | |
| ATOM | | 1640 | CG1 | VAL | 168 | 35.294 | 32.912 | 30.062 |
| 1.00 | 7.77 | | | | | | |
| ATOM | | 1641 | CG2 | VAL | 168 | 35.093 | 30.475 | 29.599 |
| 1.00 | 8.95 | | | | | | |
| ATOM | | 1642 | C | VAL | 168 | 33.857 | 31.097 | 26.992 |
| 1.00 | 6.72 | | | | | | |
| ATOM | | 1643 | O | VAL | 168 | 33.087 | 30.141 | 27.034 |
| 1.00 | 7.62 | | | | | | |
| ATOM | | 1644 | N | MET | 169 | 34.671 | 31.325 | 25.962 |
| 1.00 | 6.24 | | | | | | |
| ATOM | | 1646 | CA | MET | 169 | 34.822 | 30.353 | 24.875 |
| 1.00 | 7.10 | | | | | | |
| ATOM | | 1647 | CB | MET | 169 | 35.078 | 31.020 | 23.527 |
| 1.00 | 7.60 | | | | | | |
| ATOM | | 1648 | CG | MET | 169 | 35.016 | 30.028 | 22.389 |
| 1.00 | 9.98 | | | | | | |
| ATOM | | 1649 | SD | MET | 169 | 33.355 | 29.295 | 22.243 |
| 1.00 | 10.60 | | | | | | |
| ATOM | | 1650 | CE | MET | 169 | 33.759 | 27.805 | 21.363 |
| 1.00 | 11.26 | | | | | | |
| ATOM | | 1651 | C | MET | 169 | 36.066 | 29.618 | 25.357 |
| 1.00 | 7.23 | | | | | | |
| ATOM | | 1652 | O | MET | 169 | 37.175 | 30.167 | 25.347 |
| 1.00 | 7.62 | | | | | | |
| ATOM | | 1653 | N | ALA | 170 | 35.871 | 28.375 | 25.750 |
| 1.00 | 6.93 | | | | | | |
| ATOM | | 1655 | CA | ALA | 170 | 36.920 | 27.585 | 26.367 |
| 1.00 | 7.05 | | | | | | |
| ATOM | | 1656 | CB | ALA | 170 | 36.453 | 27.205 | 27.778 |
| 1.00 | 8.93 | | | | | | |
| ATOM | | 1657 | C | ALA | 170 | 37.436 | 26.334 | 25.706 |
| 1.00 | 7.41 | | | | | | |
| ATOM | | 1658 | O | ALA | 170 | 36.823 | 25.752 | 24.806 |
| 1.00 | 6.87 | | | | | | |
| ATOM | | 1659 | N | THR | 171 | 38.585 | 25.920 | 26.230 |
| 1.00 | 7.05 | | | | | | |
| ATOM | | 1661 | CA | THR | 171 | 39.218 | 24.668 | 25.892 |
| 1.00 | 6.62 | | | | | | |
| ATOM | | 1662 | CB | THR | 171 | 40.690 | 24.847 | 25.497 |
| 1.00 | 7.70 | | | | | | |
| ATOM | | 1663 | OG1 | THR | 171 | 40.771 | 25.554 | 24.258 |
| 1.00 | 8.40 | | | | | | |
| ATOM | | 1665 | CG2 | THR | 171 | 41.363 | 23.476 | 25.341 |
| 1.00 | 8.06 | | | | | | |
| ATOM | | 1666 | C | THR | 171 | 39.195 | 23.916 | 27.237 |
| 1.00 | 7.48 | | | | | | |
| ATOM | | 1667 | O | THR | 171 | 39.717 | 24.420 | 28.242 |
| 1.00 | 7.78 | | | | | | |
| ATOM | | 1668 | N | GLU | 172 | 38.507 | 22.778 | 27.290 |
| 1.00 | 7.60 | | | | | | |
| ATOM | | 1670 | CA | GLU | 172 | 38.473 | 21.968 | 28.510 |
| 1.00 | 7.72 | | | | | | |
| ATOM | | 1671 | CB | GLU | 172 | 37.040 | 21.751 | 29.035 |
| 1.00 | 8.64 | | | | | | |
| ATOM | | 1672 | CG | GLU | 172 | 37.010 | 20.705 | 30.165 |
| 1.00 | 10.82 | | | | | | |
| ATOM | | 1673 | CD | GLU | 172 | 35.722 | 20.667 | 30.977 |
| 1.00 | 13.27 | | | | | | |
| ATOM | | 1674 | OE1 | GLU | 172 | 35.663 | 19.872 | 31.946 |

-continued

| | | | | | | | | Occupancy | Temp |
|---|---|---|---|---|---|---|---|---|---|
| ATOM | 1675 | OE2 | GLU | 172 | 34.785 | 21.428 | 30.667 | 1.00 | 14.50 |
| ATOM | 1676 | C | GLU | 172 | 39.085 | 20.613 | 28.180 | 1.00 | 13.18 |
| ATOM | 1677 | O | GLU | 172 | 38.843 | 20.069 | 27.101 | 1.00 | 8.52 |
| ATOM | 1678 | N | GLY | 173 | 39.909 | 20.089 | 29.077 | 1.00 | 9.45 |
| ATOM | 1680 | CA | GLY | 173 | 40.501 | 18.792 | 28.830 | 1.00 | 7.84 |
| ATOM | 1681 | C | GLY | 173 | 40.389 | 17.910 | 30.046 | 1.00 | 8.42 |
| ATOM | 1682 | O | GLY | 173 | 40.196 | 18.403 | 31.164 | 1.00 | 9.01 |
| ATOM | 1683 | N | TYR | 174 | 40.442 | 16.602 | 29.817 | 1.00 | 9.09 |
| ATOM | 1685 | CA | TYR | 174 | 40.389 | 15.626 | 30.896 | 1.00 | 9.90 |
| ATOM | 1686 | CB | TYR | 174 | 38.969 | 15.103 | 31.125 | 1.00 | 10.77 |
| ATOM | 1687 | CG | TYR | 174 | 38.914 | 14.153 | 32.296 | 1.00 | 13.07 |
| ATOM | 1688 | CD1 | TYR | 174 | 38.603 | 12.811 | 32.115 | 1.00 | 16.61 |
| ATOM | 1689 | CE1 | TYR | 174 | 38.619 | 11.926 | 33.181 | 1.00 | 18.40 |
| ATOM | 1690 | CD2 | TYR | 174 | 39.236 | 14.586 | 33.579 | 1.00 | 19.66 |
| ATOM | 1691 | CE2 | TYR | 174 | 39.258 | 13.709 | 34.648 | 1.00 | 18.49 |
| ATOM | 1692 | CZ | TYR | 174 | 38.948 | 12.383 | 34.443 | 1.00 | 20.51 |
| ATOM | 1693 | OH | TYR | 174 | 38.970 | 11.506 | 35.508 | 1.00 | 20.34 |
| ATOM | 1695 | C | TYR | 174 | 41.311 | 14.466 | 30.552 | 1.00 | 24.58 |
| ATOM | 1696 | O | TYR | 174 | 41.107 | 13.773 | 29.553 | 1.00 | 10.26 |
| ATOM | 1697 | N | GLN | 175 | 42.359 | 14.308 | 31.359 | 1.00 | 10.33 |
| ATOM | 1699 | CA | GLN | 175 | 43.354 | 13.248 | 31.184 | 1.00 | 9.98 |
| ATOM | 1700 | CB | GLN | 175 | 42.837 | 11.937 | 31.787 | 1.00 | 10.93 |
| ATOM | 1701 | CG | GLN | 175 | 42.566 | 12.065 | 33.283 | 1.00 | 13.41 |
| ATOM | 1702 | CD | GLN | 175 | 42.419 | 10.732 | 34.001 | 1.00 | 16.14 |
| ATOM | 1703 | OE1 | GLN | 175 | 42.573 | 10.665 | 35.228 | 1.00 | 19.68 |
| ATOM | 1704 | NE2 | GLN | 175 | 42.110 | 9.673 | 33.258 | 1.00 | 21.27 |
| ATOM | 1707 | C | GLN | 175 | 43.781 | 13.073 | 29.720 | 1.00 | 20.43 |
| ATOM | 1708 | O | GLN | 175 | 43.726 | 11.976 | 29.151 | 1.00 | 10.40 |
| ATOM | 1709 | N | SER | 176 | 44.279 | 14.155 | 29.137 | 1.00 | 10.98 |
| ATOM | 1711 | CA | SER | 176 | 44.680 | 14.133 | 27.746 | 1.00 | 10.43 |
| ATOM | 1712 | CB | SER | 176 | 43.467 | 14.513 | 26.879 | 1.00 | 9.15 |
| ATOM | 1713 | OG | SER | 176 | 43.042 | 15.847 | 27.130 | 1.00 | 10.20 |
| ATOM | 1715 | C | SER | 176 | 45.840 | 15.101 | 27.489 | 1.00 | 9.79 |
| ATOM | 1716 | O | SER | 176 | 46.427 | 15.654 | 28.426 | 1.00 | 9.26 |
| ATOM | 1717 | N | SER | 177 | 46.178 | 15.264 | 26.216 | 1.00 | 9.17 |
| ATOM | 1719 | CA | SER | 177 | 47.240 | 16.164 | 25.776 | 1.00 | 9.64 |
| ATOM | 1720 | CB | SER | 177 | 48.507 | 15.375 | 25.461 | 1.00 | 9.15 |
| ATOM | 1721 | OG | SER | 177 | 48.928 | 14.633 | 26.596 | 1.00 | 10.09 |
| ATOM | 1723 | C | SER | 177 | 46.745 | 16.829 | 24.508 | 1.00 | 12.00 |
| ATOM | 1724 | O | SER | 177 | 45.803 | 16.341 | 23.883 | 1.00 | 10.02 |
| ATOM | 1725 | N | GLY | 178 | 47.317 | 17.972 | 24.157 | 1.00 | 9.82 |

| | | | | | | | | Occ | B |
|---|---|---|---|---|---|---|---|---|---|
| ATOM | 1727 | CA | GLY | 178 | 46.893 | 18.632 | 22.935 | 1.00 | 9.77 |
| ATOM | 1728 | C | GLY | 178 | 47.289 | 20.089 | 22.869 | 1.00 | 9.38 |
| ATOM | 1729 | O | GLY | 178 | 48.044 | 20.569 | 23.714 | 1.00 | 9.30 |
| ATOM | 1730 | N | SER | 179 | 46.757 | 20.785 | 21.870 | 1.00 | 8.99 |
| ATOM | 1732 | CA | SER | 179 | 47.028 | 22.206 | 21.674 | 1.00 | 9.17 |
| ATOM | 1733 | CB | SER | 179 | 48.177 | 22.408 | 20.671 | 1.00 | 9.44 |
| ATOM | 1734 | OG | SER | 179 | 49.424 | 22.073 | 21.243 | 1.00 | 11.55 |
| ATOM | 1736 | C | SER | 179 | 45.804 | 22.901 | 21.104 | 1.00 | 19.58 |
| ATOM | 1737 | O | SER | 179 | 45.009 | 22.284 | 20.394 | 1.00 | 8.63 |
| ATOM | 1738 | N | SER | 180 | 45.636 | 24.164 | 21.463 | 1.00 | 9.53 |
| ATOM | 1740 | CA | SER | 180 | 44.563 | 24.989 | 20.937 | 1.00 | 8.95 |
| ATOM | 1741 | CB | SER | 180 | 43.263 | 24.866 | 21.750 | 1.00 | 8.51 |
| ATOM | 1742 | OG | SER | 180 | 43.365 | 25.508 | 23.006 | 1.00 | 9.65 |
| ATOM | 1744 | C | SER | 180 | 45.026 | 26.441 | 20.912 | 1.00 | 11.87 |
| ATOM | 1745 | O | SER | 180 | 45.920 | 26.848 | 21.674 | 1.00 | 8.80 |
| ATOM | 1746 | N | ASN | 181 | 44.454 | 27.202 | 19.993 | 1.00 | 9.51 |
| ATOM | 1748 | CA | ASN | 181 | 44.750 | 28.619 | 19.850 | 1.00 | 8.43 |
| ATOM | 1749 | CB | ASN | 181 | 45.837 | 28.845 | 18.792 | 1.00 | 8.44 |
| ATOM | 1750 | CG | ASN | 181 | 46.374 | 30.257 | 18.808 | 1.00 | 9.20 |
| ATOM | 1751 | OD1 | ASN | 181 | 47.577 | 30.476 | 19.001 | 1.00 | 10.45 |
| ATOM | 1752 | ND2 | ASN | 181 | 45.504 | 31.221 | 18.607 | 1.00 | 14.84 |
| ATOM | 1755 | C | ASN | 181 | 43.406 | 29.157 | 19.385 | 1.00 | 9.73 |
| ATOM | 1756 | O | ASN | 181 | 42.912 | 28.774 | 18.322 | 1.00 | 8.65 |
| ATOM | 1757 | N | VAL | 182 | 42.802 | 30.003 | 20.211 | 1.00 | 8.58 |
| ATOM | 1759 | CA | VAL | 182 | 41.474 | 30.535 | 19.940 | 1.00 | 7.83 |
| ATOM | 1760 | CB | VAL | 182 | 40.449 | 29.879 | 20.899 | 1.00 | 7.20 |
| ATOM | 1761 | CG1 | VAL | 182 | 39.018 | 30.269 | 20.525 | 1.00 | 8.34 |
| ATOM | 1762 | CG2 | VAL | 182 | 40.612 | 28.362 | 20.910 | 1.00 | 9.23 |
| ATOM | 1763 | C | VAL | 182 | 41.411 | 32.046 | 20.158 | 1.00 | 8.07 |
| ATOM | 1764 | O | VAL | 182 | 42.013 | 32.576 | 21.097 | 1.00 | 8.01 |
| ATOM | 1765 | N | THR | 183 | 40.646 | 32.728 | 19.311 | 1.00 | 7.62 |
| ATOM | 1767 | CA | THR | 183 | 40.459 | 34.173 | 19.418 | 1.00 | 7.00 |
| ATOM | 1768 | CB | THR | 183 | 40.973 | 34.877 | 18.146 | 1.00 | 7.39 |
| ATOM | 1769 | OG1 | THR | 183 | 42.362 | 34.565 | 17.995 | 1.00 | 8.24 |
| ATOM | 1771 | CG2 | THR | 183 | 40.799 | 36.398 | 18.245 | 1.00 | 9.42 |
| ATOM | 1772 | C | THR | 183 | 38.964 | 34.373 | 19.603 | 1.00 | 8.99 |
| ATOM | 1773 | O | THR | 183 | 38.166 | 33.828 | 18.834 | 1.00 | 7.65 |
| ATOM | 1774 | N | VAL | 184 | 38.595 | 35.121 | 20.634 | 1.00 | 7.43 |
| ATOM | 1776 | CA | VAL | 184 | 37.194 | 35.351 | 20.999 | 1.00 | 7.62 |
| ATOM | 1777 | CB | VAL | 184 | 36.979 | 34.886 | 22.464 | 1.00 | 8.26 |
| ATOM | 1778 | CG1 | VAL | 184 | 35.502 | 34.914 | 22.837 | 1.00 | 9.19 |

-continued

| | | | | | | | | | |
|---|---|---|---|---|---|---|---|---|---|
| ATOM | 1779 | CG2 | VAL | 184 | 37.576 | 33.502 | 22.672 | 1.00 | 9.70 |
| ATOM | 1780 | C | VAL | 184 | 36.829 | 36.832 | 20.938 | 1.00 | 9.78 |
| ATOM | 1781 | O | VAL | 184 | 37.637 | 37.674 | 21.330 | 1.00 | 8.76 |
| ATOM | 1782 | N | TRP | 185 | 35.619 | 37.144 | 20.461 | 1.00 | 8.92 |
| ATOM | 1784 | CA | TRP | 185 | 35.142 | 38.525 | 20.401 | 1.00 | 8.50 |
| ATOM | 1785 | CB | TRP | 185 | 35.755 | 39.295 | 19.212 | 1.00 | 9.38 |
| ATOM | 1786 | CG | TRP | 185 | 35.302 | 38.875 | 17.840 | 1.00 | 9.55 |
| ATOM | 1787 | CD2 | TRP | 185 | 35.814 | 37.791 | 17.055 | 1.00 | 10.25 |
| ATOM | 1788 | CE2 | TRP | 185 | 35.150 | 37.825 | 15.808 | 1.00 | 10.55 |
| ATOM | 1789 | CE3 | TRP | 185 | 36.769 | 36.797 | 17.281 | 1.00 | 10.75 |
| ATOM | 1790 | CD1 | TRP | 185 | 34.367 | 39.497 | 17.061 | 1.00 | 10.39 |
| ATOM | 1791 | NE1 | TRP | 185 | 34.272 | 38.876 | 15.840 | 1.00 | 11.62 |
| ATOM | 1793 | CZ2 | TRP | 185 | 35.410 | 36.903 | 14.794 | 1.00 | 12.03 |
| ATOM | 1794 | CZ3 | TRP | 185 | 37.025 | 35.883 | 16.266 | 1.00 | 11.32 |
| ATOM | 1795 | CH2 | TRP | 185 | 36.346 | 35.944 | 15.040 | 1.00 | 11.87 |
| ATOM | 1796 | C | TRP | 185 | 33.611 | 38.581 | 20.364 | 1.00 | 11.03 |
| ATOM | 1797 | O | TRP | 185 | 32.974 | 37.509 | 20.372 | 1.00 | 9.55 |
| ATOM | 1798 | OXT | TRP | 185 | 33.062 | 39.698 | 20.362 | 1.00 | 9.75 |
| | | | | | | | | 1.00 | 12.79 |

The three-dimensional crystal structure of the *T. harzianum* xylanase shows a great degree of similarity to the structure of the *B. circulans* xylanase (FIG. 3), although the *T. harzianum* xylanase contains two extra strands at the beginning of sheets I and II, and a few small insertions and deletions (see also FIG. 1). While the structures are similar at 89% of the residues of the *B. circulans* xylanase, the sequences are identical at only 51% of the 185 residues. The x-ray co-ordinates of the structure is given below.

| | | | | | | | | |
|---|---|---|---|---|---|---|---|---|
| ATOM | 1 | CB | GLN | 1 | 15.828 | 12.804 | 3.943 | 1.00 26.76 |
| ATOM | 2 | CG | GLN | 1 | 14.520 | 12.576 | 3.185 | 1.00 31.36 |
| ATOM | 3 | CD | GLN | 1 | 13.427 | 13.621 | 3.366 | 1.00 32.78 |
| ATOM | 4 | OE1 | GLN | 1 | 13.524 | 14.505 | 4.210 | 1.00 35.55 |
| ATOM | 5 | NE2 | GLN | 1 | 12.296 | 13.583 | 2.708 | 1.00 35.11 |
| ATOM | 6 | C | GLN | 1 | 17.269 | 13.179 | 5.908 | 1.00 24.81 |
| ATOM | 7 | O | GLN | 1 | 18.126 | 13.319 | 5.064 | 1.00 27.64 |
| ATOM | 8 | N | GLN | 1 | 15.208 | 13.707 | 6.190 | 1.00 24.75 |
| ATOM | 9 | CA | GLN | 1 | 15.926 | 12.688 | 5.486 | 1.00 25.70 |
| ATOM | 10 | N | THR | 2 | 17.472 | 13.314 | 7.213 | 1.00 25.76 |
| ATOM | 11 | CA | THR | 2 | 18.554 | 14.044 | 7.875 | 1.00 24.44 |
| ATOM | 12 | CB | THR | 2 | 19.855 | 13.864 | 7.084 | 1.00 25.32 |
| ATOM | 13 | OG1 | THR | 2 | 20.017 | 12.431 | 7.146 | 1.00 26.72 |
| ATOM | 14 | CG2 | THR | 2 | 21.104 | 14.549 | 7.600 | 1.00 27.32 |
| ATOM | 15 | C | THR | 2 | 17.847 | 15.388 | 7.733 | 1.00 21.71 |
| ATOM | 16 | O | THR | 2 | 17.768 | 16.039 | 6.692 | 1.00 20.85 |
| ATOM | 17 | N | ILE | 3 | 17.002 | 15.542 | 8.751 | 1.00 18.32 |
| ATOM | 18 | CA | ILE | 3 | 16.196 | 16.735 | 8.873 | | |

-continued

| | | | | | | | | | |
|---|---|---|---|---|---|---|---|---|---|
| | | | | | | | | 1.00 | 17.14 |
| ATOM | 19 | CB | ILE | 3 | 14.723 | 16.216 | 8.640 | 1.00 | 17.94 |
| ATOM | 20 | CG2 | ILE | 3 | 13.680 | 16.289 | 9.744 | 1.00 | 16.71 |
| ATOM | 21 | CG1 | ILE | 3 | 14.269 | 17.095 | 7.557 | 1.00 | 18.00 |
| ATOM | 22 | CD1 | ILE | 3 | 14.803 | 16.716 | 6.179 | 1.00 | 20.15 |
| ATOM | 23 | C | ILE | 3 | 16.568 | 17.281 | 10.229 | 1.00 | 16.13 |
| ATOM | 24 | O | ILE | 3 | 17.085 | 16.584 | 11.119 | 1.00 | 16.34 |
| ATOM | 25 | N | GLY | 4 | 16.451 | 18.588 | 10.370 | 1.00 | 14.88 |
| ATOM | 26 | CA | GLY | 4 | 16.674 | 19.198 | 11.659 | 1.00 | 11.55 |
| ATOM | 27 | C | GLY | 4 | 15.299 | 19.349 | 12.251 | 1.00 | 12.16 |
| ATOM | 28 | O | GLY | 4 | 14.314 | 18.938 | 11.628 | 1.00 | 11.77 |
| ATOM | 29 | N | PRO | 5 | 15.134 | 19.926 | 13.445 | 1.00 | 11.94 |
| ATOM | 30 | CD | PRO | 5 | 16.159 | 20.593 | 14.231 | 1.00 | 12.27 |
| ATOM | 31 | CA | PRO | 5 | 13.887 | 19.803 | 14.160 | 1.00 | 12.67 |
| ATOM | 32 | CB | PRO | 5 | 14.208 | 20.405 | 15.490 | 1.00 | 12.77 |
| ATOM | 33 | CG | PRO | 5 | 15.703 | 20.207 | 15.627 | 1.00 | 12.89 |
| ATOM | 34 | C | PRO | 5 | 12.754 | 20.463 | 13.391 | 1.00 | 13.39 |
| ATOM | 35 | O | PRO | 5 | 12.974 | 21.493 | 12.764 | 1.00 | 14.17 |
| ATOM | 36 | N | GLY | 6 | 11.583 | 19.867 | 13.377 | 1.00 | 12.31 |
| ATOM | 37 | CA | GLY | 6 | 10.494 | 20.387 | 12.606 | 1.00 | 13.71 |
| ATOM | 38 | C | GLY | 6 | 9.260 | 19.487 | 12.636 | 1.00 | 14.99 |
| ATOM | 39 | O | GLY | 6 | 9.172 | 18.391 | 13.233 | 1.00 | 14.55 |
| ATOM | 40 | N | THR | 7 | 8.292 | 19.986 | 11.875 | 1.00 | 15.50 |
| ATOM | 41 | CA | THR | 7 | 6.963 | 19.390 | 11.753 | 1.00 | 15.99 |
| ATOM | 42 | CB | THR | 7 | 6.093 | 20.345 | 12.625 | 1.00 | 16.25 |
| ATOM | 43 | OG1 | THR | 7 | 5.671 | 19.625 | 13.799 | 1.00 | 16.71 |
| ATOM | 44 | CG2 | THR | 7 | 4.986 | 20.941 | 11.844 | 1.00 | 16.56 |
| ATOM | 45 | C | THR | 7 | 6.671 | 19.383 | 10.249 | 1.00 | 17.13 |
| ATOM | 46 | O | THR | 7 | 7.171 | 20.278 | 9.526 | 1.00 | 16.03 |
| ATOM | 47 | N | GLY | 8 | 5.941 | 18.369 | 9.742 | 1.00 | 18.40 |
| ATOM | 48 | CA | GLY | 8 | 5.511 | 18.374 | 8.345 | 1.00 | 19.41 |
| ATOM | 49 | C | GLY | 8 | 4.948 | 17.020 | 7.930 | 1.00 | 20.80 |
| ATOM | 50 | O | GLY | 8 | 4.664 | 16.135 | 8.751 | 1.00 | 20.52 |
| ATOM | 51 | N | TYR | 9 | 4.868 | 16.856 | 6.621 | 1.00 | 23.10 |
| ATOM | 52 | CA | TYR | 9 | 4.319 | 15.669 | 5.985 | 1.00 | 24.71 |
| ATOM | 53 | CB | TYR | 9 | 3.106 | 15.980 | 5.152 | 1.00 | 23.68 |
| ATOM | 54 | CG | TYR | 9 | 1.919 | 16.159 | 6.053 | 1.00 | 23.21 |
| ATOM | 55 | CD1 | TYR | 9 | 1.098 | 15.072 | 6.302 | 1.00 | 24.08 |
| ATOM | 56 | CE1 | TYR | 9 | 0.066 | 15.221 | 7.201 | 1.00 | 24.07 |
| ATOM | 57 | CD2 | TYR | 9 | 1.719 | 17.380 | 6.663 | 1.00 | 23.62 |
| ATOM | 58 | CE2 | TYR | 9 | 0.686 | 17.525 | 7.566 | 1.00 | 24.15 |
| ATOM | 59 | CZ | TYR | 9 | −0.118 | 16.437 | 7.827 | | |

-continued

| | | | | | | | | | |
|---|---|---|---|---|---|---|---|---|---|
| ATOM | 60 | OH | TYR | 9 | −1.099 | 16.569 | 8.790 | 1.00 | 23.90 |
| ATOM | 61 | C | TYR | 9 | 5.307 | 15.026 | 5.047 | 1.00 | 24.93 |
| ATOM | 62 | O | TYR | 9 | 6.094 | 15.819 | 4.503 | 1.00 | 26.87 |
| ATOM | 63 | N | SER | 10 | 5.354 | 13.666 | 4.903 | 1.00 | 26.77 |
| ATOM | 64 | CA | SER | 10 | 6.074 | 13.019 | 3.786 | 1.00 | 29.24 |
| ATOM | 65 | CB | SER | 10 | 7.578 | 12.994 | 4.132 | 1.00 | 31.30 |
| ATOM | 66 | OG | SER | 10 | 8.099 | 14.175 | 3.415 | 1.00 | 33.29 |
| ATOM | 67 | C | SER | 10 | 5.687 | 11.658 | 3.167 | 1.00 | 36.05 |
| ATOM | 68 | O | SER | 10 | 6.443 | 10.761 | 2.742 | 1.00 | 31.30 |
| ATOM | 69 | N | ASN | 11 | 4.369 | 11.565 | 3.067 | 1.00 | 32.28 |
| ATOM | 70 | CA | ASN | 11 | 3.633 | 10.727 | 2.104 | 1.00 | 31.13 |
| ATOM | 71 | CB | ASN | 11 | 4.369 | 9.574 | 1.411 | 1.00 | 29.54 |
| ATOM | 72 | CG | ASN | 11 | 3.862 | 9.653 | −0.044 | 1.00 | 31.69 |
| ATOM | 73 | OD1 | ASN | 11 | 2.642 | 9.754 | −0.339 | 1.00 | 34.14 |
| ATOM | 74 | ND2 | ASN | 11 | 4.801 | 9.795 | −0.993 | 1.00 | 33.69 |
| ATOM | 75 | C | ASN | 11 | 2.473 | 10.070 | 2.756 | 1.00 | 34.10 |
| ATOM | 76 | O | ASN | 11 | 2.349 | 8.838 | 2.987 | 1.00 | 27.90 |
| ATOM | 77 | N | GLY | 12 | 1.757 | 11.137 | 3.151 | 1.00 | 28.07 |
| ATOM | 78 | CA | GLY | 12 | 0.547 | 10.965 | 3.909 | 1.00 | 24.30 |
| ATOM | 79 | C | GLY | 12 | 0.839 | 10.928 | 5.400 | 1.00 | 22.09 |
| ATOM | 80 | O | GLY | 12 | −0.117 | 10.901 | 6.189 | 1.00 | 19.23 |
| ATOM | 81 | N | TYR | 13 | 2.112 | 10.925 | 5.828 | 1.00 | 19.87 |
| ATOM | 82 | CA | TYR | 13 | 2.364 | 10.901 | 7.256 | 1.00 | 16.68 |
| ATOM | 83 | CB | TYR | 13 | 3.311 | 9.730 | 7.672 | 1.00 | 13.96 |
| ATOM | 84 | CG | TYR | 13 | 2.641 | 8.380 | 7.359 | 1.00 | 14.86 |
| ATOM | 85 | CD1 | TYR | 13 | 1.913 | 7.701 | 8.331 | 1.00 | 16.63 |
| ATOM | 86 | CE1 | TYR | 13 | 1.274 | 6.499 | 7.999 | 1.00 | 18.73 |
| ATOM | 87 | CD2 | TYR | 13 | 2.730 | 7.866 | 6.084 | 1.00 | 19.94 |
| ATOM | 88 | CE2 | TYR | 13 | 2.101 | 6.680 | 5.740 | 1.00 | 16.53 |
| ATOM | 89 | CZ | TYR | 13 | 1.384 | 6.020 | 6.710 | 1.00 | 17.13 |
| ATOM | 90 | OH | TYR | 13 | 0.758 | 4.855 | 6.377 | 1.00 | 18.35 |
| ATOM | 91 | C | TYR | 13 | 2.988 | 12.206 | 7.686 | 1.00 | 19.27 |
| ATOM | 92 | O | TYR | 13 | 3.768 | 12.869 | 7.013 | 1.00 | 12.85 |
| ATOM | 93 | N | TYR | 14 | 2.469 | 12.560 | 8.828 | 1.00 | 11.47 |
| ATOM | 94 | CA | TYR | 14 | 2.901 | 13.680 | 9.583 | 1.00 | 14.13 |
| ATOM | 95 | CB | TYR | 14 | 1.785 | 13.965 | 10.526 | 1.00 | 12.57 |
| ATOM | 96 | CG | TYR | 14 | 2.119 | 15.111 | 11.446 | 1.00 | 13.51 |
| ATOM | 97 | CD1 | TYR | 14 | 2.055 | 16.416 | 10.949 | 1.00 | 15.53 |
| ATOM | 98 | CE1 | TYR | 14 | 2.374 | 17.464 | 11.785 | 1.00 | 16.07 |
| ATOM | 99 | CD2 | TYR | 14 | 2.497 | 14.849 | 12.762 | 1.00 | 15.89 |
| ATOM | 100 | CE2 | TYR | 14 | 2.827 | 15.898 | 13.594 | 1.00 | 16.13 |

-continued

| | | | | | | | | | |
|---|---|---|---|---|---|---|---|---|---|
| | | | | | | | | 1.00 | 16.08 |
| ATOM | 101 | CZ | TYR | 14 | 2.748 | 17.186 | 13.077 | 1.00 | 16.73 |
| ATOM | 102 | OH | TYR | 14 | 3.055 | 18.266 | 13.866 | 1.00 | 18.42 |
| ATOM | 103 | C | TYR | 14 | 4.165 | 13.171 | 10.274 | 1.00 | 13.04 |
| ATOM | 104 | O | TYR | 14 | 4.290 | 11.986 | 10.656 | 1.00 | 11.98 |
| ATOM | 105 | N | TYR | 15 | 5.107 | 14.068 | 10.452 | 1.00 | 11.94 |
| ATOM | 106 | CA | TYR | 15 | 6.302 | 13.775 | 11.193 | 1.00 | 12.73 |
| ATOM | 107 | CB | TYR | 15 | 7.551 | 13.590 | 10.265 | 1.00 | 15.06 |
| ATOM | 108 | CG | TYR | 15 | 8.113 | 14.812 | 9.520 | 1.00 | 17.13 |
| ATOM | 109 | CD1 | TYR | 15 | 7.729 | 15.025 | 8.221 | 1.00 | 17.27 |
| ATOM | 110 | CE1 | TYR | 15 | 8.165 | 16.146 | 7.558 | 1.00 | 18.57 |
| ATOM | 111 | CD2 | TYR | 15 | 8.954 | 15.714 | 10.164 | 1.00 | 18.44 |
| ATOM | 112 | CE2 | TYR | 15 | 9.389 | 16.845 | 9.506 | 1.00 | 18.53 |
| ATOM | 113 | CZ | TYR | 15 | 8.983 | 17.056 | 8.207 | 1.00 | 19.40 |
| ATOM | 114 | OH | TYR | 15 | 9.324 | 18.241 | 7.554 | 1.00 | 21.86 |
| ATOM | 115 | C | TYR | 15 | 6.470 | 14.984 | 12.096 | 1.00 | 12.96 |
| ATOM | 116 | O | TYR | 15 | 6.048 | 16.114 | 11.732 | 1.00 | 10.33 |
| ATOM | 117 | N | SER | 16 | 7.095 | 14.681 | 13.245 | 1.00 | 11.29 |
| ATOM | 118 | CA | SER | 16 | 7.450 | 15.700 | 14.199 | 1.00 | 11.41 |
| ATOM | 119 | CB | SER | 16 | 6.416 | 15.772 | 15.316 | 1.00 | 9.89 |
| ATOM | 120 | OG | SER | 16 | 6.764 | 16.764 | 16.281 | 1.00 | 10.30 |
| ATOM | 121 | C | SER | 16 | 8.790 | 15.268 | 14.773 | 1.00 | 12.00 |
| ATOM | 122 | O | SER | 16 | 8.944 | 14.112 | 15.217 | 1.00 | 13.12 |
| ATOM | 123 | N | TYR | 17 | 9.787 | 16.126 | 14.795 | 1.00 | 10.82 |
| ATOM | 124 | CA | TYR | 17 | 11.047 | 15.823 | 15.405 | 1.00 | 8.67 |
| ATOM | 125 | CB | TYR | 17 | 12.079 | 15.633 | 14.307 | 1.00 | 7.15 |
| ATOM | 126 | CG | TYR | 17 | 13.533 | 15.647 | 14.771 | 1.00 | 7.03 |
| ATOM | 127 | CD1 | TYR | 17 | 13.886 | 15.191 | 16.039 | 1.00 | 7.12 |
| ATOM | 128 | CE1 | TYR | 17 | 15.186 | 15.210 | 16.456 | 1.00 | 7.12 |
| ATOM | 129 | CD2 | TYR | 17 | 14.502 | 16.123 | 13.920 | 1.00 | 6.69 |
| ATOM | 130 | CE2 | TYR | 17 | 15.808 | 16.140 | 14.325 | 1.00 | 7.74 |
| ATOM | 131 | CZ | TYR | 17 | 16.131 | 15.685 | 15.596 | 1.00 | 7.93 |
| ATOM | 132 | OH | TYR | 17 | 17.422 | 15.747 | 16.038 | 1.00 | 7.83 |
| ATOM | 133 | C | TYR | 17 | 11.329 | 17.058 | 16.262 | 1.00 | 10.23 |
| ATOM | 134 | O | TYR | 17 | 11.442 | 18.156 | 15.702 | 1.00 | 11.78 |
| ATOM | 135 | N | TRP | 18 | 11.511 | 16.898 | 17.564 | 1.00 | 11.36 |
| ATOM | 136 | CA | TRP | 18 | 11.782 | 17.983 | 18.516 | 1.00 | 13.34 |
| ATOM | 137 | CB | TRP | 18 | 10.624 | 18.138 | 19.571 | 1.00 | 13.58 |
| ATOM | 138 | CG | TRP | 18 | 11.022 | 19.043 | 20.770 | 1.00 | 16.90 |
| ATOM | 139 | CD2 | TRP | 18 | 11.668 | 18.676 | 21.973 | 1.00 | 15.25 |
| ATOM | 140 | CE2 | TRP | 18 | 11.923 | 19.930 | 22.560 | 1.00 | 14.76 |
| ATOM | 141 | CE3 | TRP | 18 | 12.079 | 17.518 | 22.620 | | |

| | | | | | | | | | |
|---|---|---|---|---|---|---|---|---|---|
| ATOM | 142 | CD1 | TRP | 18 | 10.884 | 20.432 | 20.676 | 1.00 | 14.38 |
| ATOM | 143 | NE1 | TRP | 18 | 11.444 | 20.923 | 21.780 | 1.00 | 15.60 |
| ATOM | 144 | CZ2 | TRP | 18 | 12.581 | 20.047 | 23.752 | 1.00 | 15.81 |
| ATOM | 145 | CZ3 | TRP | 18 | 12.739 | 17.626 | 23.821 | 1.00 | 12.46 |
| ATOM | 146 | CH2 | TRP | 18 | 12.988 | 18.880 | 24.379 | 1.00 | 14.47 |
| ATOM | 147 | C | TRP | 18 | 13.076 | 17.609 | 19.261 | 1.00 | 15.27 |
| ATOM | 148 | O | TRP | 18 | 13.287 | 16.436 | 19.642 | 1.00 | 14.41 |
| ATOM | 149 | N | ASN | 19 | 13.984 | 18.545 | 19.526 | 1.00 | 13.85 |
| ATOM | 150 | CA | ASN | 19 | 15.035 | 18.250 | 20.451 | 1.00 | 12.84 |
| ATOM | 151 | CB | ASN | 19 | 16.224 | 17.600 | 19.699 | 1.00 | 13.21 |
| ATOM | 152 | CG | ASN | 19 | 17.151 | 18.440 | 18.894 | 1.00 | 14.57 |
| ATOM | 153 | OD1 | ASN | 19 | 17.244 | 19.629 | 19.124 | 1.00 | 15.06 |
| ATOM | 154 | ND2 | ASN | 19 | 17.864 | 17.941 | 17.903 | 1.00 | 18.68 |
| ATOM | 155 | C | ASN | 19 | 15.396 | 19.550 | 21.166 | 1.00 | 16.80 |
| ATOM | 156 | O | ASN | 19 | 14.989 | 20.636 | 20.741 | 1.00 | 12.55 |
| ATOM | 157 | N | ASP | 20 | 16.131 | 19.441 | 22.251 | 1.00 | 13.22 |
| ATOM | 158 | CA | ASP | 20 | 16.504 | 20.540 | 23.135 | 1.00 | 11.88 |
| ATOM | 159 | CB | ASP | 20 | 16.797 | 19.893 | 24.518 | 1.00 | 11.46 |
| ATOM | 160 | CG | ASP | 20 | 18.025 | 18.968 | 24.621 | 1.00 | 10.44 |
| ATOM | 161 | OD1 | ASP | 20 | 18.718 | 18.720 | 23.650 | 1.00 | 9.88 |
| ATOM | 162 | OD2 | ASP | 20 | 18.310 | 18.428 | 25.678 | 1.00 | 10.13 |
| ATOM | 163 | C | ASP | 20 | 17.695 | 21.403 | 22.637 | 1.00 | 10.16 |
| ATOM | 164 | O | ASP | 20 | 18.103 | 22.388 | 23.291 | 1.00 | 11.25 |
| ATOM | 165 | N | GLY | 21 | 18.234 | 21.045 | 21.466 | 1.00 | 13.63 |
| ATOM | 166 | CA | GLY | 21 | 19.380 | 21.652 | 20.875 | 1.00 | 9.37 |
| ATOM | 167 | C | GLY | 21 | 20.648 | 20.856 | 21.103 | 1.00 | 8.25 |
| ATOM | 168 | O | GLY | 21 | 21.648 | 21.119 | 20.438 | 1.00 | 9.30 |
| ATOM | 169 | N | HIS | 22 | 20.741 | 19.936 | 22.053 | 1.00 | 8.94 |
| ATOM | 170 | CA | HIS | 22 | 21.960 | 19.155 | 22.258 | 1.00 | 9.49 |
| ATOM | 171 | CB | HIS | 22 | 21.741 | 18.177 | 23.358 | 1.00 | 8.32 |
| ATOM | 172 | CG | HIS | 22 | 22.979 | 17.601 | 23.957 | 1.00 | 8.11 |
| ATOM | 173 | CD2 | HIS | 22 | 23.428 | 18.016 | 25.187 | 1.00 | 6.81 |
| ATOM | 174 | ND1 | HIS | 22 | 23.803 | 16.685 | 23.489 | 1.00 | 6.67 |
| ATOM | 175 | CE1 | HIS | 22 | 24.747 | 16.526 | 24.386 | 1.00 | 8.56 |
| ATOM | 176 | NE2 | HIS | 22 | 24.505 | 17.334 | 25.395 | 1.00 | 8.59 |
| ATOM | 177 | C | HIS | 22 | 22.310 | 18.377 | 20.984 | 1.00 | 8.33 |
| ATOM | 178 | O | HIS | 22 | 21.423 | 17.986 | 20.218 | 1.00 | 8.28 |
| ATOM | 179 | N | ALA | 23 | 23.598 | 18.178 | 20.750 | 1.00 | 9.57 |
| ATOM | 180 | CA | ALA | 23 | 24.077 | 17.456 | 19.601 | 1.00 | 6.80 |
| ATOM | 181 | CB | ALA | 23 | 25.543 | 17.722 | 19.414 | 1.00 | 8.20 |
| ATOM | 182 | C | ALA | 23 | 23.884 | 15.951 | 19.853 | 1.00 | 6.23 |

-continued

| | | | | | | | | | |
|---|---|---|---|---|---|---|---|---|---|
| | | | | | | | | 1.00 | 9.20 |
| ATOM | 183 | O | ALA | 23 | 23.555 | 15.546 | 20.983 | 1.00 | 9.54 |
| ATOM | 184 | N | GLY | 24 | 24.053 | 15.132 | 18.813 | 1.00 | 11.67 |
| ATOM | 185 | CA | GLY | 24 | 24.056 | 13.696 | 19.026 | 1.00 | 11.28 |
| ATOM | 186 | C | GLY | 24 | 23.003 | 12.932 | 18.274 | 1.00 | 12.70 |
| ATOM | 187 | O | GLY | 24 | 23.144 | 11.705 | 18.119 | 1.00 | 14.05 |
| ATOM | 188 | N | VAL | 25 | 21.954 | 13.601 | 17.782 | 1.00 | 11.17 |
| ATOM | 189 | CA | VAL | 25 | 20.870 | 12.933 | 17.087 | 1.00 | 11.42 |
| ATOM | 190 | CB | VAL | 25 | 19.513 | 13.475 | 17.632 | 1.00 | 10.39 |
| ATOM | 191 | CG1 | VAL | 25 | 18.430 | 12.519 | 17.220 | 1.00 | 9.36 |
| ATOM | 192 | CG2 | VAL | 25 | 19.568 | 13.692 | 19.147 | 1.00 | 10.78 |
| ATOM | 193 | C | VAL | 25 | 20.893 | 13.113 | 15.566 | 1.00 | 11.41 |
| ATOM | 194 | O | VAL | 25 | 21.215 | 14.214 | 15.055 | 1.00 | 10.88 |
| ATOM | 195 | N | THR | 26 | 20.545 | 12.071 | 14.797 | 1.00 | 12.50 |
| ATOM | 196 | CA | THR | 26 | 20.256 | 12.290 | 13.397 | 1.00 | 12.14 |
| ATOM | 197 | CB | THR | 26 | 21.498 | 11.864 | 12.462 | 1.00 | 13.95 |
| ATOM | 198 | OG1 | THR | 26 | 21.030 | 10.946 | 11.485 | 1.00 | 16.06 |
| ATOM | 199 | CG2 | THR | 26 | 22.706 | 11.411 | 13.230 | 1.00 | 12.20 |
| ATOM | 200 | C | THR | 26 | 18.959 | 11.552 | 13.126 | 1.00 | 12.76 |
| ATOM | 201 | O | THR | 26 | 18.758 | 10.385 | 13.519 | 1.00 | 13.16 |
| ATOM | 202 | N | TYR | 27 | 17.998 | 12.359 | 12.665 | 1.00 | 10.77 |
| ATOM | 203 | CA | TYR | 27 | 16.665 | 11.919 | 12.311 | 1.00 | 10.37 |
| ATOM | 204 | CB | TYR | 27 | 15.581 | 12.842 | 12.861 | 1.00 | 9.29 |
| ATOM | 205 | CG | TYR | 27 | 14.148 | 12.477 | 12.477 | 1.00 | 8.75 |
| ATOM | 206 | CD1 | TYR | 27 | 13.599 | 12.815 | 11.240 | 1.00 | 9.08 |
| ATOM | 207 | CE1 | TYR | 27 | 12.306 | 12.458 | 10.929 | 1.00 | 10.58 |
| ATOM | 208 | CD2 | TYR | 27 | 13.378 | 11.789 | 13.377 | 1.00 | 8.03 |
| ATOM | 209 | CE2 | TYR | 27 | 12.077 | 11.427 | 13.078 | 1.00 | 8.62 |
| ATOM | 210 | CZ | TYR | 27 | 11.547 | 11.760 | 11.854 | 1.00 | 10.33 |
| ATOM | 211 | OH | TYR | 27 | 10.269 | 11.337 | 11.544 | 1.00 | 11.41 |
| ATOM | 212 | C | TYR | 27 | 16.526 | 11.902 | 10.789 | 1.00 | 10.52 |
| ATOM | 213 | O | TYR | 27 | 16.581 | 12.905 | 10.043 | 1.00 | 9.97 |
| ATOM | 214 | N | THR | 28 | 16.226 | 10.719 | 10.289 | 1.00 | 10.67 |
| ATOM | 215 | CA | THR | 28 | 15.990 | 10.624 | 8.866 | 1.00 | 13.02 |
| ATOM | 216 | CB | THR | 28 | 17.060 | 9.679 | 8.276 | 1.00 | 12.93 |
| ATOM | 217 | OG1 | THR | 28 | 18.323 | 10.097 | 8.775 | 1.00 | 14.75 |
| ATOM | 218 | CG2 | THR | 28 | 17.051 | 9.700 | 6.740 | 1.00 | 12.92 |
| ATOM | 219 | C | THR | 28 | 14.577 | 10.154 | 8.537 | 1.00 | 13.28 |
| ATOM | 220 | O | THR | 28 | 14.095 | 9.159 | 9.058 | 1.00 | 11.76 |
| ATOM | 221 | N | ASN | 29 | 13.877 | 10.924 | 7.712 | 1.00 | 15.11 |
| ATOM | 222 | CA | ASN | 29 | 12.610 | 10.493 | 7.127 | 1.00 | 17.11 |
| ATOM | 223 | CB | ASN | 29 | 11.759 | 11.680 | 6.583 | | |

-continued

| | | | | | | | |
|---|---|---|---|---|---|---|---|
| ATOM | 224 | CG | ASN | 29 | 10.957 | 11.330 | 5.310 |
| 1.00 | 20.17 | | | | | | |
| ATOM | 225 | OD1 | ASN | 29 | 9.752 | 11.006 | 5.349 |
| 1.00 | 23.95 | | | | | | |
| ATOM | 226 | ND2 | ASN | 29 | 11.595 | 11.263 | 4.123 |
| 1.00 | 25.19 | | | | | | |
| ATOM | 227 | C | ASN | 29 | 12.949 | 9.585 | 5.931 |
| 1.00 | 26.04 | | | | | | |
| ATOM | 228 | O | ASN | 29 | 13.733 | 9.976 | 5.034 |
| 1.00 | 17.45 | | | | | | |
| ATOM | 229 | N | GLY | 30 | 12.292 | 8.430 | 5.973 |
| 1.00 | 13.40 | | | | | | |
| ATOM | 230 | CA | GLY | 30 | 12.366 | 7.507 | 4.876 |
| 1.00 | 17.19 | | | | | | |
| ATOM | 231 | C | GLY | 30 | 11.061 | 7.603 | 4.091 |
| 1.00 | 20.59 | | | | | | |
| ATOM | 232 | O | GLY | 30 | 10.149 | 8.393 | 4.394 |
| 1.00 | 20.60 | | | | | | |
| ATOM | 233 | N | GLY | 31 | 10.880 | 6.783 | 3.065 |
| 1.00 | 21.82 | | | | | | |
| ATOM | 234 | CA | GLY | 31 | 9.593 | 6.864 | 2.353 |
| 1.00 | 20.69 | | | | | | |
| ATOM | 235 | C | GLY | 31 | 8.379 | 6.433 | 3.198 |
| 1.00 | 21.04 | | | | | | |
| ATOM | 236 | O | GLY | 31 | 8.534 | 5.626 | 4.140 |
| 1.00 | 20.17 | | | | | | |
| ATOM | 237 | N | GLY | 32 | 7.192 | 7.004 | 2.901 |
| 1.00 | 21.45 | | | | | | |
| ATOM | 238 | CA | GLY | 32 | 5.921 | 6.633 | 3.522 |
| 1.00 | 17.60 | | | | | | |
| ATOM | 239 | C | GLY | 32 | 5.950 | 6.688 | 5.053 |
| 1.00 | 15.29 | | | | | | |
| ATOM | 240 | O | GLY | 32 | 6.228 | 7.744 | 5.678 |
| 1.00 | 13.27 | | | | | | |
| ATOM | 241 | N | GLY | 33 | 5.743 | 5.536 | 5.682 |
| 1.00 | 14.99 | | | | | | |
| ATOM | 242 | CA | GLY | 33 | 5.684 | 5.504 | 7.127 |
| 1.00 | 10.93 | | | | | | |
| ATOM | 243 | C | GLY | 33 | 7.020 | 5.351 | 7.849 |
| 1.00 | 9.50 | | | | | | |
| ATOM | 244 | O | GLY | 33 | 7.024 | 5.171 | 9.070 |
| 1.00 | 7.59 | | | | | | |
| ATOM | 245 | N | SER | 34 | 8.144 | 5.399 | 7.165 |
| 1.00 | 6.40 | | | | | | |
| ATOM | 246 | CA | SER | 34 | 9.433 | 5.095 | 7.768 |
| 1.00 | 7.69 | | | | | | |
| ATOM | 247 | CB | SER | 34 | 10.348 | 4.331 | 6.832 |
| 1.00 | 9.77 | | | | | | |
| ATOM | 248 | OG | SER | 34 | 9.840 | 3.098 | 6.383 |
| 1.00 | 9.92 | | | | | | |
| ATOM | 249 | C | SER | 34 | 10.278 | 6.253 | 8.213 |
| 1.00 | 11.79 | | | | | | |
| ATOM | 250 | O | SER | 34 | 10.312 | 7.296 | 7.519 |
| 1.00 | 8.85 | | | | | | |
| ATOM | 251 | N | PHE | 35 | 10.938 | 6.029 | 9.340 |
| 1.00 | 11.44 | | | | | | |
| ATOM | 252 | CA | PHE | 35 | 11.958 | 6.938 | 9.798 |
| 1.00 | 8.14 | | | | | | |
| ATOM | 253 | CB | PHE | 35 | 11.353 | 8.045 | 10.667 |
| 1.00 | 7.22 | | | | | | |
| ATOM | 254 | CG | PHE | 35 | 10.780 | 7.622 | 11.990 |
| 1.00 | 5.37 | | | | | | |
| ATOM | 255 | CD1 | PHE | 35 | 9.482 | 7.189 | 12.055 |
| 1.00 | 4.40 | | | | | | |
| ATOM | 256 | CD2 | PHE | 35 | 11.578 | 7.664 | 13.111 |
| 1.00 | 5.29 | | | | | | |
| ATOM | 257 | CE1 | PHE | 35 | 8.972 | 6.789 | 13.273 |
| 1.00 | 2.70 | | | | | | |
| ATOM | 258 | CE2 | PHE | 35 | 11.073 | 7.267 | 14.314 |
| 1.00 | 5.43 | | | | | | |
| ATOM | 259 | CZ | PHE | 35 | 9.772 | 6.828 | 14.399 |
| 1.00 | 4.23 | | | | | | |
| ATOM | 260 | C | PHE | 35 | 12.974 | 6.128 | 10.596 |
| 1.00 | 5.42 | | | | | | |
| ATOM | 261 | O | PHE | 35 | 12.624 | 5.078 | 11.148 |
| 1.00 | 7.01 | | | | | | |
| ATOM | 262 | N | THR | 36 | 14.193 | 6.657 | 10.651 |
| 1.00 | 7.90 | | | | | | |
| ATOM | 263 | CA | THR | 36 | 15.346 | 6.181 | 11.379 |
| 1.00 | 6.93 | | | | | | |
| ATOM | 264 | CB | THR | 36 | 16.530 | 5.882 | 10.407 |
| 1.00 | 8.26 | | | | | | |

| | | | | | | | | |
|---|---|---|---|---|---|---|---|---|
| 1.00 | 9.23 | | | | | | | |
| ATOM | | 265 | OG1 | THR | 36 | 15.996 | 5.076 | 9.379 |
| 1.00 | 10.78 | | | | | | | |
| ATOM | | 266 | CG2 | THR | 36 | 17.701 | 5.125 | 11.030 |
| 1.00 | 10.22 | | | | | | | |
| ATOM | | 267 | C | THR | 36 | 15.758 | 7.312 | 12.343 |
| 1.00 | 9.84 | | | | | | | |
| ATOM | | 268 | O | THR | 36 | 15.537 | 8.507 | 12.050 |
| 1.00 | 9.61 | | | | | | | |
| ATOM | | 269 | N | VAL | 37 | 16.298 | 6.977 | 13.520 |
| 1.00 | 9.80 | | | | | | | |
| ATOM | | 270 | CA | VAL | 37 | 16.826 | 7.961 | 14.439 |
| 1.00 | 9.70 | | | | | | | |
| ATOM | | 271 | CB | VAL | 37 | 15.976 | 8.312 | 15.692 |
| 1.00 | 10.77 | | | | | | | |
| ATOM | | 272 | CG1 | VAL | 37 | 16.624 | 9.555 | 16.323 |
| 1.00 | 10.77 | | | | | | | |
| ATOM | | 273 | CG2 | VAL | 37 | 14.509 | 8.571 | 15.389 |
| 1.00 | 10.75 | | | | | | | |
| ATOM | | 274 | C | VAL | 37 | 18.010 | 7.180 | 14.958 |
| 1.00 | 10.19 | | | | | | | |
| ATOM | | 275 | O | VAL | 37 | 17.903 | 5.987 | 15.292 |
| 1.00 | 12.44 | | | | | | | |
| ATOM | | 276 | N | ASN | 38 | 19.154 | 7.842 | 15.003 |
| 1.00 | 9.51 | | | | | | | |
| ATOM | | 277 | CA | ASN | 38 | 20.363 | 7.273 | 15.517 |
| 1.00 | 10.83 | | | | | | | |
| ATOM | | 278 | CB | ASN | 38 | 21.351 | 7.007 | 14.392 |
| 1.00 | 13.08 | | | | | | | |
| ATOM | | 279 | CG | ASN | 38 | 20.884 | 5.745 | 13.683 |
| 1.00 | 18.12 | | | | | | | |
| ATOM | | 280 | OD1 | ASN | 38 | 20.079 | 5.762 | 12.722 |
| 1.00 | 18.42 | | | | | | | |
| ATOM | | 281 | ND2 | ASN | 38 | 21.365 | 4.580 | 14.159 |
| 1.00 | 18.73 | | | | | | | |
| ATOM | | 282 | C | ASN | 38 | 20.878 | 8.342 | 16.455 |
| 1.00 | 10.89 | | | | | | | |
| ATOM | | 283 | O | ASN | 38 | 20.817 | 9.510 | 16.083 |
| 1.00 | 10.36 | | | | | | | |
| ATOM | | 284 | N | TRP | 39 | 21.339 | 8.018 | 17.651 |
| 1.00 | 8.76 | | | | | | | |
| ATOM | | 285 | CA | TRP | 39 | 21.772 | 9.048 | 18.577 |
| 1.00 | 10.30 | | | | | | | |
| ATOM | | 286 | CB | TRP | 39 | 20.583 | 9.478 | 19.449 |
| 1.00 | 8.23 | | | | | | | |
| ATOM | | 287 | CG | TRP | 39 | 19.943 | 8.426 | 20.359 |
| 1.00 | 7.73 | | | | | | | |
| ATOM | | 288 | CD2 | TRP | 39 | 19.034 | 7.452 | 19.994 |
| 1.00 | 7.65 | | | | | | | |
| ATOM | | 289 | CE2 | TRP | 39 | 18.728 | 6.903 | 21.234 |
| 1.00 | 7.27 | | | | | | | |
| ATOM | | 290 | CE3 | TRP | 39 | 18.410 | 6.956 | 18.835 |
| 1.00 | 8.18 | | | | | | | |
| ATOM | | 291 | CD1 | TRP | 39 | 20.183 | 8.466 | 21.706 |
| 1.00 | 5.84 | | | | | | | |
| ATOM | | 292 | NE1 | TRP | 39 | 19.425 | 7.538 | 22.200 |
| 1.00 | 5.45 | | | | | | | |
| ATOM | | 293 | CZ2 | TRP | 39 | 17.805 | 5.847 | 21.320 |
| 1.00 | 6.19 | | | | | | | |
| ATOM | | 294 | CZ3 | TRP | 39 | 17.487 | 5.910 | 18.934 |
| 1.00 | 6.98 | | | | | | | |
| ATOM | | 295 | CH2 | TRP | 39 | 17.194 | 5.367 | 20.174 |
| 1.00 | 6.37 | | | | | | | |
| ATOM | | 296 | C | TRP | 39 | 22.898 | 8.504 | 19.411 |
| 1.00 | 10.96 | | | | | | | |
| ATOM | | 297 | O | TRP | 39 | 22.879 | 7.317 | 19.771 |
| 1.00 | 13.55 | | | | | | | |
| ATOM | | 298 | N | SER | 40 | 23.916 | 9.328 | 19.631 |
| 1.00 | 13.07 | | | | | | | |
| ATOM | | 299 | CA | SER | 40 | 25.061 | 9.010 | 20.463 |
| 1.00 | 13.74 | | | | | | | |
| ATOM | | 300 | CB | SER | 40 | 26.357 | 8.815 | 19.658 |
| 1.00 | 14.37 | | | | | | | |
| ATOM | | 301 | OG | SER | 40 | 26.111 | 7.978 | 18.518 |
| 1.00 | 20.42 | | | | | | | |
| ATOM | | 302 | C | SER | 40 | 25.227 | 10.244 | 21.326 |
| 1.00 | 12.72 | | | | | | | |
| ATOM | | 303 | O | SER | 40 | 25.357 | 11.332 | 20.770 |
| 1.00 | 10.52 | | | | | | | |
| ATOM | | 304 | N | ASN | 41 | 25.165 | 10.040 | 22.646 |
| 1.00 | 13.35 | | | | | | | |
| ATOM | | 305 | CA | ASN | 41 | 25.338 | 11.092 | 23.656 |

-continued

| | | | | | | | | | |
|---|---|---|---|---|---|---|---|---|---|
| ATOM | 306 | CB | ASN | 41 | 26.757 | 11.568 | 23.695 | 1.00 | 13.53 |
| ATOM | 307 | CG | ASN | 41 | 27.771 | 10.495 | 24.008 | 1.00 | 15.67 |
| ATOM | 308 | OD1 | ASN | 41 | 28.757 | 10.358 | 23.282 | 1.00 | 18.65 |
| ATOM | 309 | ND2 | ASN | 41 | 27.653 | 9.675 | 25.050 | 1.00 | 22.59 |
| ATOM | 310 | C | ASN | 41 | 24.441 | 12.287 | 23.350 | 1.00 | 19.49 |
| ATOM | 311 | O | ASN | 41 | 24.873 | 13.422 | 23.078 | 1.00 | 12.66 |
| ATOM | 312 | N | SER | 42 | 23.155 | 11.974 | 23.365 | 1.00 | 11.83 |
| ATOM | 313 | CA | SER | 42 | 22.156 | 12.925 | 22.935 | 1.00 | 10.43 |
| ATOM | 314 | CB | SER | 42 | 20.894 | 12.124 | 22.555 | 1.00 | 10.63 |
| ATOM | 315 | OG | SER | 42 | 20.288 | 11.609 | 23.751 | 1.00 | 9.58 |
| ATOM | 316 | C | SER | 42 | 21.856 | 13.905 | 24.087 | 1.00 | 8.86 |
| ATOM | 317 | O | SER | 42 | 22.501 | 13.874 | 25.146 | 1.00 | 9.67 |
| ATOM | 318 | N | GLY | 43 | 20.855 | 14.769 | 23.867 | 1.00 | 11.35 |
| ATOM | 319 | CA | GLY | 43 | 20.215 | 15.460 | 24.946 | 1.00 | 9.05 |
| ATOM | 320 | C | GLY | 43 | 18.840 | 14.815 | 25.018 | 1.00 | 6.67 |
| ATOM | 321 | O | GLY | 43 | 18.694 | 13.583 | 24.897 | 1.00 | 7.83 |
| ATOM | 322 | N | ASN | 44 | 17.809 | 15.616 | 25.181 | 1.00 | 9.11 |
| ATOM | 323 | CA | ASN | 44 | 16.450 | 15.160 | 25.134 | 1.00 | 6.80 |
| ATOM | 324 | CB | ASN | 44 | 15.643 | 15.843 | 26.251 | 1.00 | 8.62 |
| ATOM | 325 | CG | ASN | 44 | 14.239 | 15.305 | 26.407 | 1.00 | 9.32 |
| ATOM | 326 | OD1 | ASN | 44 | 13.395 | 16.034 | 26.942 | 1.00 | 11.76 |
| ATOM | 327 | ND2 | ASN | 44 | 13.867 | 14.062 | 26.021 | 1.00 | 14.29 |
| ATOM | 328 | C | ASN | 44 | 15.906 | 15.528 | 23.737 | 1.00 | 12.06 |
| ATOM | 329 | O | ASN | 44 | 16.070 | 16.664 | 23.240 | 1.00 | 8.95 |
| ATOM | 330 | N | PHE | 45 | 15.358 | 14.499 | 23.068 | 1.00 | 7.76 |
| ATOM | 331 | CA | PHE | 45 | 14.723 | 14.592 | 21.745 | 1.00 | 8.42 |
| ATOM | 332 | CB | PHE | 45 | 15.707 | 14.187 | 20.598 | 1.00 | 8.92 |
| ATOM | 333 | CG | PHE | 45 | 16.041 | 12.710 | 20.589 | 1.00 | 6.83 |
| ATOM | 334 | CD1 | PHE | 45 | 15.274 | 11.836 | 19.819 | 1.00 | 7.80 |
| ATOM | 335 | CD2 | PHE | 45 | 17.051 | 12.228 | 21.403 | 1.00 | 7.09 |
| ATOM | 336 | CE1 | PHE | 45 | 15.515 | 10.477 | 19.875 | 1.00 | 7.62 |
| ATOM | 337 | CE2 | PHE | 45 | 17.274 | 10.857 | 21.433 | 1.00 | 7.59 |
| ATOM | 338 | CZ | PHE | 45 | 16.510 | 9.994 | 20.678 | 1.00 | 7.17 |
| ATOM | 339 | C | PHE | 45 | 13.491 | 13.660 | 21.684 | 1.00 | 5.89 |
| ATOM | 340 | O | PHE | 45 | 13.435 | 12.692 | 22.478 | 1.00 | 8.27 |
| ATOM | 341 | N | VAL | 46 | 12.541 | 13.912 | 20.755 | 1.00 | 9.67 |
| ATOM | 342 | CA | VAL | 46 | 11.346 | 13.130 | 20.533 | 1.00 | 7.23 |
| ATOM | 343 | CB | VAL | 46 | 10.076 | 13.715 | 21.179 | 1.00 | 7.92 |
| ATOM | 344 | CG1 | VAL | 46 | 8.860 | 12.823 | 20.921 | 1.00 | 8.74 |
| ATOM | 345 | CG2 | VAL | 46 | 10.226 | 13.721 | 22.656 | 1.00 | 9.06 |
| ATOM | 346 | C | VAL | 46 | 11.179 | 13.174 | 19.034 | 1.00 | 8.48 |

| | | | | | | | | | |
|---|---|---|---|---|---|---|---|---|---|
| | | | | | | | | 1.00 | 9.06 |
| ATOM | 347 | O | VAL | 46 | 11.069 | 14.250 | 18.422 | 1.00 | 7.02 |
| ATOM | 348 | N | ALA | 47 | 11.148 | 11.984 | 18.423 | 1.00 | 10.19 |
| ATOM | 349 | CA | ALA | 47 | 11.088 | 11.923 | 16.970 | 1.00 | 11.40 |
| ATOM | 350 | CB | ALA | 47 | 12.487 | 11.628 | 16.548 | 1.00 | 14.35 |
| ATOM | 351 | C | ALA | 47 | 10.115 | 10.894 | 16.379 | 1.00 | 11.87 |
| ATOM | 352 | O | ALA | 47 | 10.126 | 9.770 | 16.905 | 1.00 | 11.08 |
| ATOM | 353 | N | GLY | 48 | 9.315 | 11.134 | 15.349 | 1.00 | 9.25 |
| ATOM | 354 | CA | GLY | 48 | 8.396 | 10.089 | 14.949 | 1.00 | 11.87 |
| ATOM | 355 | C | GLY | 48 | 7.493 | 10.425 | 13.794 | 1.00 | 11.00 |
| ATOM | 356 | O | GLY | 48 | 7.513 | 11.559 | 13.316 | 1.00 | 11.18 |
| ATOM | 357 | N | LYS | 49 | 6.712 | 9.448 | 13.324 | 1.00 | 9.47 |
| ATOM | 358 | CA | LYS | 49 | 5.783 | 9.700 | 12.233 | 1.00 | 8.49 |
| ATOM | 359 | CB | LYS | 49 | 6.156 | 8.995 | 10.959 | 1.00 | 7.23 |
| ATOM | 360 | CG | LYS | 49 | 7.203 | 9.663 | 10.124 | 1.00 | 7.71 |
| ATOM | 361 | CD | LYS | 49 | 7.411 | 8.921 | 8.809 | 1.00 | 8.83 |
| ATOM | 362 | CE | LYS | 49 | 8.141 | 9.814 | 7.800 | 1.00 | 9.61 |
| ATOM | 363 | NZ | LYS | 49 | 8.376 | 9.080 | 6.554 | 1.00 | 11.96 |
| ATOM | 364 | C | LYS | 49 | 4.398 | 9.237 | 12.597 | 1.00 | 8.57 |
| ATOM | 365 | O | LYS | 49 | 4.248 | 8.384 | 13.486 | 1.00 | 9.28 |
| ATOM | 366 | N | GLY | 50 | 3.361 | 9.766 | 11.960 | 1.00 | 8.33 |
| ATOM | 367 | CA | GLY | 50 | 2.000 | 9.425 | 12.301 | 1.00 | 8.35 |
| ATOM | 368 | C | GLY | 50 | 0.963 | 10.342 | 11.663 | 1.00 | 10.55 |
| ATOM | 369 | O | GLY | 50 | 0.966 | 10.545 | 10.442 | 1.00 | 10.22 |
| ATOM | 370 | N | TRP | 51 | 0.070 | 10.906 | 12.511 | 1.00 | 11.01 |
| ATOM | 371 | CA | TRP | 51 | −1.118 | 11.652 | 12.085 | 1.00 | 12.06 |
| ATOM | 372 | CB | TRP | 51 | −2.423 | 10.864 | 12.333 | 1.00 | 11.79 |
| ATOM | 373 | CG | TRP | 51 | −2.333 | 9.504 | 11.635 | 1.00 | 13.30 |
| ATOM | 374 | CD2 | TRP | 51 | −1.674 | 8.392 | 12.124 | 1.00 | 13.13 |
| ATOM | 375 | CE2 | TRP | 51 | −1.810 | 7.489 | 11.080 | 1.00 | 14.19 |
| ATOM | 376 | CE3 | TRP | 51 | −0.996 | 8.040 | 13.282 | 1.00 | 12.35 |
| ATOM | 377 | CD1 | TRP | 51 | −2.848 | 9.301 | 10.393 | 1.00 | 13.99 |
| ATOM | 378 | NE1 | TRP | 51 | −2.494 | 8.051 | 10.078 | 1.00 | 14.34 |
| ATOM | 379 | CZ2 | TRP | 51 | −1.271 | 6.217 | 11.162 | 1.00 | 15.05 |
| ATOM | 380 | CZ3 | TRP | 51 | −0.457 | 6.769 | 13.365 | 1.00 | 14.41 |
| ATOM | 381 | CH2 | TRP | 51 | −0.595 | 5.873 | 12.316 | 1.00 | 14.24 |
| ATOM | 382 | C | TRP | 51 | −1.291 | 12.983 | 12.788 | 1.00 | 11.13 |
| ATOM | 383 | O | TRP | 51 | −0.968 | 13.135 | 13.964 | 1.00 | 9.97 |
| ATOM | 384 | N | GLN | 52 | −1.795 | 13.962 | 12.028 | 1.00 | 13.14 |
| ATOM | 385 | CA | GLN | 52 | −2.174 | 15.267 | 12.560 | 1.00 | 14.01 |
| ATOM | 386 | CB | GLN | 52 | −1.088 | 16.284 | 12.168 | 1.00 | 13.62 |
| ATOM | 387 | CG | GLN | 52 | −1.328 | 17.699 | 12.606 | | |

| | | | | | | | | | |
|---|---|---|---|---|---|---|---|---|---|
| | | | | | | | | 1.00 | 15.07 |
| ATOM | 388 | CD | GLN | 52 | −1.494 | 17.915 | 14.104 | 1.00 | 14.27 |
| ATOM | 389 | OE1 | GLN | 52 | −0.629 | 18.407 | 14.830 | 1.00 | 16.02 |
| ATOM | 390 | NE2 | GLN | 52 | −2.657 | 17.626 | 14.635 | 1.00 | 13.08 |
| ATOM | 391 | C | GLN | 52 | −3.559 | 15.701 | 12.054 | 1.00 | 13.05 |
| ATOM | 392 | O | GLN | 52 | −3.704 | 16.030 | 10.868 | 1.00 | 14.72 |
| ATOM | 393 | N | PRO | 53 | −4.628 | 15.721 | 12.866 | 1.00 | 13.11 |
| ATOM | 394 | CD | PRO | 53 | −5.967 | 16.150 | 12.469 | 1.00 | 13.04 |
| ATOM | 395 | CA | PRO | 53 | −4.680 | 15.205 | 14.223 | 1.00 | 12.06 |
| ATOM | 396 | CB | PRO | 53 | −5.876 | 15.851 | 14.828 | 1.00 | 12.56 |
| ATOM | 397 | CG | PRO | 53 | −6.846 | 15.722 | 13.670 | 1.00 | 12.67 |
| ATOM | 398 | C | PRO | 53 | −4.799 | 13.691 | 14.254 | 1.00 | 12.14 |
| ATOM | 399 | O | PRO | 53 | −5.135 | 13.011 | 13.248 | 1.00 | 10.91 |
| ATOM | 400 | N | GLY | 54 | −4.607 | 13.246 | 15.484 | 1.00 | 12.13 |
| ATOM | 401 | CA | GLY | 54 | −4.869 | 11.866 | 15.739 | 1.00 | 13.75 |
| ATOM | 402 | C | GLY | 54 | −6.346 | 11.663 | 16.041 | 1.00 | 15.01 |
| ATOM | 403 | O | GLY | 54 | −7.172 | 12.582 | 16.005 | 1.00 | 15.77 |
| ATOM | 404 | N | THR | 55 | −6.740 | 10.453 | 16.400 | 1.00 | 15.56 |
| ATOM | 405 | CA | THR | 55 | −8.135 | 10.178 | 16.694 | 1.00 | 16.04 |
| ATOM | 406 | CB | THR | 55 | −8.827 | 9.410 | 15.572 | 1.00 | 15.48 |
| ATOM | 407 | OG1 | THR | 55 | −8.200 | 8.132 | 15.474 | 1.00 | 15.49 |
| ATOM | 408 | CG2 | THR | 55 | −8.800 | 10.183 | 14.265 | 1.00 | 15.96 |
| ATOM | 409 | C | THR | 55 | −8.258 | 9.350 | 17.937 | 1.00 | 16.77 |
| ATOM | 410 | O | THR | 55 | −7.322 | 8.644 | 18.310 | 1.00 | 16.68 |
| ATOM | 411 | N | LYS | 56 | −9.438 | 9.279 | 18.531 | 1.00 | 19.29 |
| ATOM | 412 | CA | LYS | 56 | −9.564 | 8.452 | 19.725 | 1.00 | 21.92 |
| ATOM | 413 | CB | LYS | 56 | −10.675 | 9.096 | 20.595 | 1.00 | 23.92 |
| ATOM | 414 | CG | LYS | 56 | −10.234 | 10.565 | 20.893 | 1.00 | 26.95 |
| ATOM | 415 | CD | LYS | 56 | −10.828 | 11.213 | 22.151 | 1.00 | 29.47 |
| ATOM | 416 | CE | LYS | 56 | −10.528 | 12.739 | 22.187 | 1.00 | 31.18 |
| ATOM | 417 | NZ | LYS | 56 | −10.775 | 13.356 | 23.492 | 1.00 | 32.24 |
| ATOM | 418 | C | LYS | 56 | −9.831 | 6.988 | 19.365 | 1.00 | 22.96 |
| ATOM | 419 | O | LYS | 56 | −10.122 | 6.137 | 20.230 | 1.00 | 24.28 |
| ATOM | 420 | N | ASN | 57 | −9.656 | 6.581 | 18.102 | 1.00 | 22.55 |
| ATOM | 421 | CA | ASN | 57 | −10.009 | 5.214 | 17.735 | 1.00 | 22.75 |
| ATOM | 422 | CB | ASN | 57 | −11.479 | 5.164 | 17.184 | 1.00 | 24.35 |
| ATOM | 423 | CG | ASN | 57 | −11.671 | 5.923 | 15.848 | 1.00 | 27.06 |
| ATOM | 424 | OD1 | ASN | 57 | −11.050 | 6.960 | 15.544 | 1.00 | 27.62 |
| ATOM | 425 | ND2 | ASN | 57 | −12.539 | 5.461 | 14.955 | 1.00 | 27.78 |
| ATOM | 426 | C | ASN | 57 | −9.048 | 4.680 | 16.679 | 1.00 | 21.44 |
| ATOM | 427 | O | ASN | 57 | −9.397 | 3.777 | 15.896 | 1.00 | 22.71 |
| ATOM | 428 | N | LYS | 58 | −7.821 | 5.193 | 16.624 | | |

-continued

| | | | | | | | | | |
|---|---|---|---|---|---|---|---|---|---|
| ATOM | 429 | CA | LYS | 58 | −6.950 | 4.785 | 15.552 | 1.00 | 18.17 |
| ATOM | 430 | CB | LYS | 58 | −5.911 | 5.860 | 15.363 | 1.00 | 15.67 |
| ATOM | 431 | CG | LYS | 58 | −5.278 | 5.787 | 13.998 | 1.00 | 16.07 |
| ATOM | 432 | CD | LYS | 58 | −4.526 | 7.069 | 13.607 | 1.00 | 17.83 |
| ATOM | 433 | CE | LYS | 58 | −5.410 | 8.299 | 13.205 | 1.00 | 18.91 |
| ATOM | 434 | NZ | LYS | 58 | −6.249 | 8.140 | 11.995 | 1.00 | 18.54 |
| ATOM | 435 | C | LYS | 58 | −6.334 | 3.476 | 15.978 | 1.00 | 19.60 |
| ATOM | 436 | O | LYS | 58 | −6.086 | 3.300 | 17.171 | 1.00 | 13.93 |
| ATOM | 437 | N | VAL | 59 | −6.174 | 2.474 | 15.131 | 1.00 | 15.02 |
| ATOM | 438 | CA | VAL | 59 | −5.364 | 1.313 | 15.506 | 1.00 | 13.40 |
| ATOM | 439 | CB | VAL | 59 | −6.203 | −0.053 | 15.388 | 1.00 | 12.92 |
| ATOM | 440 | CG1 | VAL | 59 | −7.120 | −0.117 | 14.200 | 1.00 | 14.48 |
| ATOM | 441 | CG2 | VAL | 59 | −5.192 | −1.198 | 15.311 | 1.00 | 16.35 |
| ATOM | 442 | C | VAL | 59 | −4.138 | 1.408 | 14.583 | 1.00 | 13.23 |
| ATOM | 443 | O | VAL | 59 | −4.167 | 1.542 | 13.343 | 1.00 | 11.86 |
| ATOM | 444 | N | ILE | 60 | −3.061 | 1.577 | 15.346 | 1.00 | 12.38 |
| ATOM | 445 | CA | ILE | 60 | −1.749 | 1.915 | 14.826 | 1.00 | 10.27 |
| ATOM | 446 | CB | ILE | 60 | −1.119 | 3.011 | 15.700 | 1.00 | 9.01 |
| ATOM | 447 | CG2 | ILE | 60 | 0.280 | 3.326 | 15.213 | 1.00 | 8.58 |
| ATOM | 448 | CG1 | ILE | 60 | −2.000 | 4.252 | 15.663 | 1.00 | 8.04 |
| ATOM | 449 | CD1 | ILE | 60 | −1.611 | 5.192 | 16.759 | 1.00 | 7.60 |
| ATOM | 450 | C | ILE | 60 | −0.851 | 0.725 | 14.800 | 1.00 | 9.90 |
| ATOM | 451 | O | ILE | 60 | −0.680 | 0.059 | 15.822 | 1.00 | 9.88 |
| ATOM | 452 | N | ASN | 61 | −0.270 | 0.546 | 13.616 | 1.00 | 9.11 |
| ATOM | 453 | CA | ASN | 61 | 0.671 | −0.545 | 13.341 | 1.00 | 11.11 |
| ATOM | 454 | CB | ASN | 61 | 0.366 | −1.204 | 12.006 | 1.00 | 10.36 |
| ATOM | 455 | CG | ASN | 61 | −1.072 | −1.619 | 11.996 | 1.00 | 12.63 |
| ATOM | 456 | OD1 | ASN | 61 | −1.478 | −2.378 | 12.874 | 1.00 | 14.76 |
| ATOM | 457 | ND2 | ASN | 61 | −1.921 | −1.111 | 11.095 | 1.00 | 16.78 |
| ATOM | 458 | C | ASN | 61 | 2.088 | −0.032 | 13.291 | 1.00 | 15.45 |
| ATOM | 459 | O | ASN | 61 | 2.338 | 1.095 | 12.867 | 1.00 | 9.66 |
| ATOM | 460 | N | PHE | 62 | 3.042 | −0.806 | 13.765 | 1.00 | 9.13 |
| ATOM | 461 | CA | PHE | 62 | 4.422 | −0.405 | 13.688 | 1.00 | 9.56 |
| ATOM | 462 | CB | PHE | 62 | 4.865 | 0.454 | 14.933 | 1.00 | 10.44 |
| ATOM | 463 | CG | PHE | 62 | 4.657 | −0.145 | 16.314 | 1.00 | 9.48 |
| ATOM | 464 | CD1 | PHE | 62 | 5.751 | −0.618 | 17.021 | 1.00 | 9.74 |
| ATOM | 465 | CD2 | PHE | 62 | 3.371 | −0.259 | 16.828 | 1.00 | 10.19 |
| ATOM | 466 | CE1 | PHE | 62 | 5.546 | −1.224 | 18.250 | 1.00 | 10.24 |
| ATOM | 467 | CE2 | PHE | 62 | 3.176 | −0.867 | 18.054 | 1.00 | 9.20 |
| ATOM | 468 | CZ | PHE | 62 | 4.274 | −1.347 | 18.757 | 1.00 | 9.66 |
| ATOM | 469 | C | PHE | 62 | 5.348 | −1.590 | 13.570 | 1.00 | 9.91 |

-continued

| | serial | atom | res | seq | x | y | z | occ | temp |
|---|---|---|---|---|---|---|---|---|---|
| ATOM | 470 | O | PHE | 62 | 5.066 | −2.608 | 14.200 | 1.00 | 9.69 |
| ATOM | 471 | N | SER | 63 | 6.404 | −1.538 | 12.767 | 1.00 | 11.84 |
| ATOM | 472 | CA | SER | 63 | 7.449 | −2.547 | 12.847 | 1.00 | 11.03 |
| ATOM | 473 | CB | SER | 63 | 7.328 | −3.650 | 11.765 | 1.00 | 11.59 |
| ATOM | 474 | OG | SER | 63 | 7.114 | −3.195 | 10.463 | 1.00 | 12.00 |
| ATOM | 475 | C | SER | 63 | 8.819 | −1.923 | 12.715 | 1.00 | 12.51 |
| ATOM | 476 | O | SER | 63 | 8.928 | −0.727 | 12.379 | 1.00 | 11.22 |
| ATOM | 477 | N | GLY | 64 | 9.823 | −2.781 | 12.942 | 1.00 | 12.00 |
| ATOM | 478 | CA | GLY | 64 | 11.193 | −2.372 | 12.823 | 1.00 | 10.23 |
| ATOM | 479 | C | GLY | 64 | 11.988 | −2.761 | 14.029 | 1.00 | 8.33 |
| ATOM | 480 | O | GLY | 64 | 11.615 | −3.676 | 14.751 | 1.00 | 7.41 |
| ATOM | 481 | N | SER | 65 | 13.077 | −2.058 | 14.222 | 1.00 | 8.00 |
| ATOM | 482 | CA | SER | 65 | 13.961 | −2.346 | 15.314 | 1.00 | 7.92 |
| ATOM | 483 | CB | SER | 65 | 15.240 | −2.865 | 14.680 | 1.00 | 10.77 |
| ATOM | 484 | OG | SER | 65 | 15.702 | −2.010 | 13.636 | 1.00 | 12.34 |
| ATOM | 485 | C | SER | 65 | 14.215 | −1.151 | 16.250 | 1.00 | 12.01 |
| ATOM | 486 | O | SER | 65 | 14.393 | −0.010 | 15.791 | 1.00 | 10.66 |
| ATOM | 487 | N | TYR | 66 | 14.338 | −1.407 | 17.535 | 1.00 | 11.27 |
| ATOM | 488 | CA | TYR | 66 | 14.573 | −0.359 | 18.514 | 1.00 | 8.76 |
| ATOM | 489 | CB | TYR | 66 | 13.258 | −0.091 | 19.279 | 1.00 | 8.36 |
| ATOM | 490 | CG | TYR | 66 | 13.429 | 0.738 | 20.539 | 1.00 | 6.60 |
| ATOM | 491 | CD1 | TYR | 66 | 13.005 | 0.198 | 21.732 | 1.00 | 5.88 |
| ATOM | 492 | CE1 | TYR | 66 | 13.053 | 0.928 | 22.894 | 1.00 | 3.88 |
| ATOM | 493 | CD2 | TYR | 66 | 13.932 | 2.032 | 20.506 | 1.00 | 3.78 |
| ATOM | 494 | CE2 | TYR | 66 | 13.982 | 2.780 | 21.677 | 1.00 | 5.67 |
| ATOM | 495 | CZ | TYR | 66 | 13.533 | 2.217 | 22.851 | 1.00 | 3.65 |
| ATOM | 496 | OH | TYR | 66 | 13.501 | 2.961 | 24.006 | 1.00 | 4.38 |
| ATOM | 497 | C | TYR | 66 | 15.667 | −0.905 | 19.416 | 1.00 | 5.96 |
| ATOM | 498 | O | TYR | 66 | 15.539 | −1.954 | 20.045 | 1.00 | 8.49 |
| ATOM | 499 | N | ASN | 67 | 16.768 | −0.197 | 19.470 | 1.00 | 8.59 |
| ATOM | 500 | CA | ASN | 67 | 17.951 | −0.686 | 20.156 | 1.00 | 10.09 |
| ATOM | 501 | CB | ASN | 67 | 18.968 | −1.158 | 19.130 | 1.00 | 11.81 |
| ATOM | 502 | CG | ASN | 67 | 18.427 | −2.110 | 18.028 | 1.00 | 15.94 |
| ATOM | 503 | OD1 | ASN | 67 | 18.079 | −3.269 | 18.260 | 1.00 | 20.43 |
| ATOM | 504 | ND2 | ASN | 67 | 18.287 | −1.681 | 16.767 | 1.00 | 21.28 |
| ATOM | 505 | C | ASN | 67 | 18.556 | 0.438 | 21.016 | 1.00 | 22.48 |
| ATOM | 506 | O | ASN | 67 | 19.512 | 1.103 | 20.618 | 1.00 | 11.16 |
| ATOM | 507 | N | PRO | 68 | 17.937 | 0.733 | 22.173 | 1.00 | 8.26 |
| ATOM | 508 | CD | PRO | 68 | 16.694 | 0.131 | 22.659 | 1.00 | 10.94 |
| ATOM | 509 | CA | PRO | 68 | 18.378 | 1.755 | 23.099 | 1.00 | 10.82 |
| ATOM | 510 | CB | PRO | 68 | 17.103 | 2.066 | 23.890 | 1.00 | 11.97 |

-continued

| | | | | | | | | | |
|---|---|---|---|---|---|---|---|---|---|
| ATOM | 511 | CG | PRO | 68 | 16.437 | 0.732 | 24.019 | 1.00 | 11.53 |
| ATOM | 512 | C | PRO | 68 | 19.561 | 1.340 | 23.957 | 1.00 | 10.89 |
| ATOM | 513 | O | PRO | 68 | 19.689 | 0.209 | 24.442 | 1.00 | 11.57 |
| ATOM | 514 | N | ASN | 69 | 20.429 | 2.277 | 24.207 | 1.00 | 10.78 |
| ATOM | 515 | CA | ASN | 69 | 21.523 | 2.025 | 25.094 | 1.00 | 9.77 |
| ATOM | 516 | CB | ASN | 69 | 22.744 | 2.036 | 24.242 | 1.00 | 11.79 |
| ATOM | 517 | CG | ASN | 69 | 23.967 | 1.656 | 25.041 | 1.00 | 13.60 |
| ATOM | 518 | OD1 | ASN | 69 | 25.063 | 1.812 | 24.504 | 1.00 | 17.40 |
| ATOM | 519 | ND2 | ASN | 69 | 24.006 | 1.089 | 26.244 | 1.00 | 21.47 |
| ATOM | 520 | C | ASN | 69 | 21.484 | 3.117 | 26.179 | 1.00 | 17.05 |
| ATOM | 521 | O | ASN | 69 | 22.208 | 4.144 | 26.160 | 1.00 | 12.60 |
| ATOM | 522 | N | GLY | 70 | 20.491 | 2.932 | 27.046 | 1.00 | 13.38 |
| ATOM | 523 | CA | GLY | 70 | 20.226 | 3.850 | 28.114 | 1.00 | 8.91 |
| ATOM | 524 | C | GLY | 70 | 18.795 | 4.357 | 28.073 | 1.00 | 8.37 |
| ATOM | 525 | O | GLY | 70 | 17.842 | 3.663 | 27.670 | 1.00 | 8.21 |
| ATOM | 526 | N | ASN | 71 | 18.656 | 5.595 | 28.502 | 1.00 | 9.06 |
| ATOM | 527 | CA | ASN | 71 | 17.347 | 6.161 | 28.701 | 1.00 | 7.03 |
| ATOM | 528 | CB | ASN | 71 | 17.448 | 7.409 | 29.589 | 1.00 | 7.69 |
| ATOM | 529 | CG | ASN | 71 | 16.104 | 7.886 | 30.142 | 1.00 | 7.29 |
| ATOM | 530 | OD1 | ASN | 71 | 15.032 | 7.684 | 29.577 | 1.00 | 8.85 |
| ATOM | 531 | ND2 | ASN | 71 | 16.047 | 8.491 | 31.329 | 1.00 | 9.56 |
| ATOM | 532 | C | ASN | 71 | 16.668 | 6.525 | 27.391 | 1.00 | 7.50 |
| ATOM | 533 | O | ASN | 71 | 17.072 | 7.537 | 26.762 | 1.00 | 8.37 |
| ATOM | 534 | N | SER | 72 | 15.643 | 5.733 | 27.043 | 1.00 | 9.29 |
| ATOM | 535 | CA | SER | 72 | 14.864 | 5.953 | 25.837 | 1.00 | 6.66 |
| ATOM | 536 | CB | SER | 72 | 15.699 | 5.398 | 24.662 | 1.00 | 7.05 |
| ATOM | 537 | OG | SER | 72 | 15.191 | 5.543 | 23.349 | 1.00 | 7.68 |
| ATOM | 538 | C | SER | 72 | 13.483 | 5.286 | 25.932 | 1.00 | 8.77 |
| ATOM | 539 | O | SER | 72 | 13.292 | 4.335 | 26.722 | 1.00 | 8.50 |
| ATOM | 540 | N | TYR | 73 | 12.520 | 5.701 | 25.110 | 1.00 | 8.19 |
| ATOM | 541 | CA | TYR | 73 | 11.190 | 5.154 | 25.058 | 1.00 | 7.79 |
| ATOM | 542 | CB | TYR | 73 | 10.094 | 6.073 | 25.659 | 1.00 | 7.74 |
| ATOM | 543 | CG | TYR | 73 | 10.319 | 6.583 | 27.099 | 1.00 | 7.66 |
| ATOM | 544 | CD1 | TYR | 73 | 10.919 | 5.817 | 28.103 | 1.00 | 10.11 |
| ATOM | 545 | CE1 | TYR | 73 | 11.121 | 6.358 | 29.366 | 1.00 | 9.07 |
| ATOM | 546 | CD2 | TYR | 73 | 9.920 | 7.881 | 27.376 | 1.00 | 9.86 |
| ATOM | 547 | CE2 | TYR | 73 | 10.116 | 8.418 | 28.625 | 1.00 | 10.46 |
| ATOM | 548 | CZ | TYR | 73 | 10.709 | 7.668 | 29.607 | 1.00 | 9.86 |
| ATOM | 549 | OH | TYR | 73 | 10.868 | 8.246 | 30.846 | 1.00 | 10.88 |
| ATOM | 550 | C | TYR | 73 | 10.796 | 4.932 | 23.600 | 1.00 | 10.66 |
| ATOM | 551 | O | TYR | 73 | 11.244 | 5.627 | 22.676 | 1.00 | 8.12 |

| | | | | | | | | | |
|---|---|---|---|---|---|---|---|---|---|
| | | | | | | | | 1.00 | 8.31 |
| ATOM | 552 | N | LEU | 74 | 9.946 | 3.942 | 23.394 | 1.00 | 6.70 |
| ATOM | 553 | CA | LEU | 74 | 9.292 | 3.736 | 22.104 | 1.00 | 7.34 |
| ATOM | 554 | CB | LEU | 74 | 9.677 | 2.388 | 21.485 | 1.00 | 7.37 |
| ATOM | 555 | CG | LEU | 74 | 8.939 | 1.937 | 20.190 | 1.00 | 8.67 |
| ATOM | 556 | CD1 | LEU | 74 | 9.182 | 2.886 | 19.023 | 1.00 | 8.01 |
| ATOM | 557 | CD2 | LEU | 74 | 9.430 | 0.523 | 19.850 | 1.00 | 8.15 |
| ATOM | 558 | C | LEU | 74 | 7.805 | 3.752 | 22.500 | 1.00 | 6.80 |
| ATOM | 559 | O | LEU | 74 | 7.359 | 2.918 | 23.297 | 1.00 | 6.53 |
| ATOM | 560 | N | SER | 75 | 7.030 | 4.688 | 21.973 | 1.00 | 5.87 |
| ATOM | 561 | CA | SER | 75 | 5.669 | 4.839 | 22.425 | 1.00 | 5.53 |
| ATOM | 562 | CB | SER | 75 | 5.555 | 5.907 | 23.516 | 1.00 | 6.86 |
| ATOM | 563 | OG | SER | 75 | 6.582 | 5.955 | 24.476 | 1.00 | 11.37 |
| ATOM | 564 | C | SER | 75 | 4.770 | 5.295 | 21.297 | 1.00 | 4.71 |
| ATOM | 565 | O | SER | 75 | 5.235 | 5.772 | 20.263 | 1.00 | 4.19 |
| ATOM | 566 | N | ILE | 76 | 3.485 | 5.121 | 21.489 | 1.00 | 3.93 |
| ATOM | 567 | CA | ILE | 76 | 2.508 | 5.857 | 20.711 | 1.00 | 5.49 |
| ATOM | 568 | CB | ILE | 76 | 1.190 | 5.090 | 20.679 | 1.00 | 7.40 |
| ATOM | 569 | CG2 | ILE | 76 | 0.068 | 6.005 | 20.340 | 1.00 | 8.03 |
| ATOM | 570 | CG1 | ILE | 76 | 1.184 | 4.029 | 19.557 | 1.00 | 8.58 |
| ATOM | 571 | CD1 | ILE | 76 | 2.241 | 2.921 | 19.633 | 1.00 | 9.45 |
| ATOM | 572 | C | ILE | 76 | 2.465 | 7.108 | 21.600 | 1.00 | 6.93 |
| ATOM | 573 | O | ILE | 76 | 2.370 | 6.973 | 22.829 | 1.00 | 7.49 |
| ATOM | 574 | N | TYR | 77 | 2.627 | 8.295 | 21.020 | 1.00 | 6.57 |
| ATOM | 575 | CA | TYR | 77 | 2.811 | 9.555 | 21.724 | 1.00 | 5.67 |
| ATOM | 576 | CB | TYR | 77 | 4.299 | 9.948 | 21.647 | 1.00 | 4.54 |
| ATOM | 577 | CG | TYR | 77 | 4.686 | 11.364 | 22.139 | 1.00 | 4.19 |
| ATOM | 578 | CD1 | TYR | 77 | 4.668 | 11.654 | 23.497 | 1.00 | 4.75 |
| ATOM | 579 | CE1 | TYR | 77 | 4.991 | 12.901 | 23.966 | 1.00 | 4.71 |
| ATOM | 580 | CD2 | TYR | 77 | 5.044 | 12.363 | 21.240 | 1.00 | 4.76 |
| ATOM | 581 | CE2 | TYR | 77 | 5.373 | 13.638 | 21.694 | 1.00 | 3.95 |
| ATOM | 582 | CZ | TYR | 77 | 5.341 | 13.894 | 23.060 | 1.00 | 5.09 |
| ATOM | 583 | OH | TYR | 77 | 5.641 | 15.159 | 23.541 | 1.00 | 6.11 |
| ATOM | 584 | C | TYR | 77 | 1.961 | 10.639 | 21.098 | 1.00 | 5.81 |
| ATOM | 585 | O | TYR | 77 | 1.888 | 10.741 | 19.856 | 1.00 | 6.39 |
| ATOM | 586 | N | GLY | 78 | 1.359 | 11.509 | 21.898 | 1.00 | 5.96 |
| ATOM | 587 | CA | GLY | 78 | 0.615 | 12.588 | 21.278 | 1.00 | 6.69 |
| ATOM | 588 | C | GLY | 78 | 0.156 | 13.586 | 22.288 | 1.00 | 7.28 |
| ATOM | 589 | O | GLY | 78 | 0.537 | 13.494 | 23.466 | 1.00 | 7.84 |
| ATOM | 590 | N | TRP | 79 | −0.672 | 14.528 | 21.822 | 1.00 | 7.76 |
| ATOM | 591 | CA | TRP | 79 | −1.234 | 15.560 | 22.707 | 1.00 | 7.51 |
| ATOM | 592 | CB | TRP | 79 | −0.598 | 16.949 | 22.555 | | |

-continued

| | | | | | | | |
|---|---|---|---|---|---|---|---|
| 1.00 | 6.56 | | | | | | |
| ATOM | | 593 | CG | TRP | 79 | 0.876 | 17.041 | 22.832 |
| 1.00 | 5.50 | | | | | | |
| ATOM | | 594 | CD2 | TRP | 79 | 1.419 | 17.620 | 23.935 |
| 1.00 | 5.87 | | | | | | |
| ATOM | | 595 | CE2 | TRP | 79 | 2.774 | 17.469 | 23.695 |
| 1.00 | 5.84 | | | | | | |
| ATOM | | 596 | CE3 | TRP | 79 | 0.951 | 18.249 | 25.072 |
| 1.00 | 5.83 | | | | | | |
| ATOM | | 597 | CD1 | TRP | 79 | 1.819 | 16.560 | 21.962 |
| 1.00 | 6.72 | | | | | | |
| ATOM | | 598 | NE1 | TRP | 79 | 2.963 | 16.842 | 22.524 |
| 1.00 | 5.73 | | | | | | |
| ATOM | | 599 | CZ2 | TRP | 79 | 3.695 | 1.7.950 | 24.600 |
| 1.00 | 5.70 | | | | | | |
| ATOM | | 600 | CZ3 | TRP | 79 | 1.867 | 18.733 | 25.972 |
| 1.00 | 5.50 | | | | | | |
| ATOM | | 601 | CH2 | TRP | 79 | 3.226 | 18.581 | 25.742 |
| 1.00 | 5.81 | | | | | | |
| ATOM | | 602 | C | TRP | 79 | −2.702 | 15.796 | 22.434 |
| 1.00 | 7.13 | | | | | | |
| ATOM | | 603 | O | TRP | 79 | −3.219 | 15.434 | 21.365 |
| 1.00 | 6.19 | | | | | | |
| ATOM | | 604 | N | SER | 80 | −3.360 | 16.381 | 23.440 |
| 1.00 | 8.56 | | | | | | |
| ATOM | | 605 | CA | SER | 80 | −4.683 | 16.933 | 23.242 |
| 1.00 | 11.11 | | | | | | |
| ATOM | | 606 | CB | SER | 80 | −5.761 | 16.138 | 23.974 |
| 1.00 | 10.43 | | | | | | |
| ATOM | | 607 | OG | SER | 80 | −5.890 | 16.355 | 25.385 |
| 1.00 | 16.05 | | | | | | |
| ATOM | | 608 | C | SER | 80 | −4.643 | 18.381 | 23.781 |
| 1.00 | 10.31 | | | | | | |
| ATOM | | 609 | O | SER | 80 | −3.732 | 18.753 | 24.528 |
| 1.00 | 9.07 | | | | | | |
| ATOM | | 610 | N | ARG | 81 | −5.593 | 19.225 | 23.392 |
| 1.00 | 12.84 | | | | | | |
| ATOM | | 611 | CA | ARG | 81 | −5.732 | 20.562 | 23.953 |
| 1.00 | 15.11 | | | | | | |
| ATOM | | 612 | CB | ARG | 81 | −5.614 | 21.564 | 22.851 |
| 1.00 | 18.41 | | | | | | |
| ATOM | | 613 | CG | ARG | 81 | −4.205 | 21.639 | 22.307 |
| 1.00 | 22.70 | | | | | | |
| ATOM | | 614 | CD | ARG | 81 | −4.381 | 22.114 | 20.897 |
| 1.00 | 25.52 | | | | | | |
| ATOM | | 615 | NE | ARG | 81 | −3.063 | 22.554 | 20.439 |
| 1.00 | 29.78 | | | | | | |
| ATOM | | 616 | CZ | ARG | 81 | −2.811 | 22.897 | 19.179 |
| 1.00 | 30.17 | | | | | | |
| ATOM | | 617 | NH1 | ARG | 81 | −3.810 | 22.847 | 18.270 |
| 1.00 | 32.23 | | | | | | |
| ATOM | | 618 | NH2 | ARG | 81 | −1.547 | 23.168 | 18.822 |
| 1.00 | 30.78 | | | | | | |
| ATOM | | 619 | C | ARG | 81 | −7.071 | 20.736 | 24.659 |
| 1.00 | 13.57 | | | | | | |
| ATOM | | 620 | O | ARG | 81 | −8.067 | 20.129 | 24.261 |
| 1.00 | 12.68 | | | | | | |
| ATOM | | 621 | N | ASN | 82 | −7.100 | 21.628 | 25.667 |
| 1.00 | 13.97 | | | | | | |
| ATOM | | 622 | CA | ASN | 82 | −8.284 | 21.968 | 26.448 |
| 1.00 | 13.79 | | | | | | |
| ATOM | | 623 | CB | ASN | 82 | −9.250 | 22.793 | 25.588 |
| 1.00 | 14.31 | | | | | | |
| ATOM | | 624 | CG | ASN | 82 | −8.645 | 24.103 | 25.115 |
| 1.00 | 15.90 | | | | | | |
| ATOM | | 625 | OD1 | ASN | 82 | −8.695 | 24.391 | 23.929 |
| 1.00 | 18.55 | | | | | | |
| ATOM | | 626 | ND2 | ASN | 82 | −7.998 | 24.954 | 25.904 |
| 1.00 | 16.49 | | | | | | |
| ATOM | | 627 | C | ASN | 82 | −9.012 | 20.744 | 27.004 |
| 1.00 | 13.02 | | | | | | |
| ATOM | | 628 | O | ASN | 82 | −10.109 | 20.409 | 26.570 |
| 1.00 | 13.95 | | | | | | |
| ATOM | | 629 | N | PRO | 83 | −8.490 | 19.988 | 27.956 |
| 1.00 | 11.90 | | | | | | |
| ATOM | | 630 | CD | PRO | 83 | −9.129 | 18.759 | 28.468 |
| 1.00 | 12.28 | | | | | | |
| ATOM | | 631 | CA | PRO | 83 | −7.228 | 20.233 | 28.616 |
| 1.00 | 10.88 | | | | | | |
| ATOM | | 632 | CB | PRO | 83 | −7.374 | 19.477 | 29.921 |
| 1.00 | 11.28 | | | | | | |
| ATOM | | 633 | CG | PRO | 83 | −8.168 | 18.254 | 29.514 |

-continued

| | | | | | | | |
|---|---|---|---|---|---|---|---|
| 1.00 | 12.43 | | | | | | |
| ATOM | | 634 | C | PRO | 83 | −6.020 | 19.812 | 27.806 |
| 1.00 | 9.55 | | | | | | |
| ATOM | | 635 | O | PRO | 83 | −6.065 | 18.925 | 26.941 |
| 1.00 | 10.93 | | | | | | |
| ATOM | | 636 | N | LEU | 84 | −4.949 | 20.487 | 28.139 |
| 1.00 | 9.55 | | | | | | |
| ATOM | | 637 | CA | LEU | 84 | −3.650 | 20.212 | 27.575 |
| 1.00 | 10.04 | | | | | | |
| ATOM | | 638 | CB | LEU | 84 | −2.725 | 21.373 | 27.908 |
| 1.00 | 9.09 | | | | | | |
| ATOM | | 639 | CG | LEU | 84 | −1.343 | 21.354 | 27.288 |
| 1.00 | 9.70 | | | | | | |
| ATOM | | 640 | CD1 | LEU | 84 | −1.402 | 21.496 | 25.777 |
| 1.00 | 8.76 | | | | | | |
| ATOM | | 641 | CD2 | LEU | 84 | −0.580 | 22.526 | 27.836 |
| 1.00 | 10.04 | | | | | | |
| ATOM | | 642 | C | LEU | 84 | −3.170 | 18.903 | 28.205 |
| 1.00 | 9.91 | | | | | | |
| ATOM | | 643 | O | LEU | 84 | −3.002 | 18.839 | 29.428 |
| 1.00 | 10.98 | | | | | | |
| ATOM | | 644 | N | ILE | 85 | −2.966 | 17.863 | 27.375 |
| 1.00 | 10.87 | | | | | | |
| ATOM | | 645 | CA | ILE | 85 | −2.538 | 16.538 | 27.873 |
| 1.00 | 11.93 | | | | | | |
| ATOM | | 646 | CB | ILE | 85 | −3.711 | 15.489 | 27.812 |
| 1.00 | 11.72 | | | | | | |
| ATOM | | 647 | CG2 | ILE | 85 | −3.226 | 14.128 | 28.360 |
| 1.00 | 12.89 | | | | | | |
| ATOM | | 648 | CG1 | ILE | 85 | −4.909 | 15.932 | 28.663 |
| 1.00 | 11.57 | | | | | | |
| ATOM | | 649 | CD1 | ILE | 85 | −4.578 | 16.047 | 30.178 |
| 1.00 | 11.61 | | | | | | |
| ATOM | | 650 | C | ILE | 85 | −1.393 | 16.023 | 27.028 |
| 1.00 | 10.50 | | | | | | |
| ATOM | | 651 | O | ILE | 85 | −1.481 | 16.104 | 25.799 |
| 1.00 | 12.37 | | | | | | |
| ATOM | | 652 | N | GLU | 86 | −0.310 | 15.580 | 27.654 |
| 1.00 | 10.70 | | | | | | |
| ATOM | | 653 | CA | GLU | 86 | 0.725 | 14.868 | 26.909 |
| 1.00 | 10.27 | | | | | | |
| ATOM | | 654 | CB | GLU | 86 | 2.072 | 15.269 | 27.364 |
| 1.00 | 8.12 | | | | | | |
| ATOM | | 655 | CG | GLU | 86 | 3.207 | 14.580 | 26.675 |
| 1.00 | 6.80 | | | | | | |
| ATOM | | 656 | CD | GLU | 86 | 4.537 | 15.107 | 27.134 |
| 1.00 | 8.51 | | | | | | |
| ATOM | | 657 | OE1 | GLU | 86 | 5.414 | 15.338 | 26.303 |
| 1.00 | 9.55 | | | | | | |
| ATOM | | 658 | OE2 | GLU | 86 | 4.717 | 15.329 | 28.333 |
| 1.00 | 11.97 | | | | | | |
| ATOM | | 659 | C | GLU | 86 | 0.491 | 13.405 | 27.268 |
| 1.00 | 9.41 | | | | | | |
| ATOM | | 660 | O | GLU | 86 | 0.386 | 13.100 | 28.464 |
| 1.00 | 10.26 | | | | | | |
| ATOM | | 661 | N | TYR | 87 | 0.324 | 12.484 | 26.315 |
| 1.00 | 7.81 | | | | | | |
| ATOM | | 662 | CA | TYR | 87 | 0.083 | 11.088 | 26.705 |
| 1.00 | 7.22 | | | | | | |
| ATOM | | 663 | CB | TYR | 87 | −1.380 | 10.679 | 26.368 |
| 1.00 | 5.93 | | | | | | |
| ATOM | | 664 | CG | TYR | 87 | −1.738 | 10.658 | 24.884 |
| 1.00 | 7.18 | | | | | | |
| ATOM | | 665 | CD1 | TYR | 87 | −1.474 | 9.535 | 24.099 |
| 1.00 | 8.82 | | | | | | |
| ATOM | | 666 | CE1 | TYR | 87 | −1.766 | 9.541 | 22.758 |
| 1.00 | 7.19 | | | | | | |
| ATOM | | 667 | CD2 | TYR | 87 | −2.307 | 11.750 | 24.278 |
| 1.00 | 6.85 | | | | | | |
| ATOM | | 668 | CE2 | TYR | 87 | −2.612 | 11.756 | 22.941 |
| 1.00 | 5.57 | | | | | | |
| ATOM | | 669 | CZ | TYR | 87 | −2.335 | 10.650 | 22.181 |
| 1.00 | 7.53 | | | | | | |
| ATOM | | 670 | OH | TYR | 87 | −2.601 | 10.636 | 20.820 |
| 1.00 | 7.92 | | | | | | |
| ATOM | | 671 | C | TYR | 87 | 1.089 | 10.145 | 26.007 |
| 1.00 | 7.60 | | | | | | |
| ATOM | | 672 | O | TYR | 87 | 1.593 | 10.460 | 24.914 |
| 1.00 | 6.22 | | | | | | |
| ATOM | | 673 | N | TYR | 88 | 1.277 | 8.961 | 26.612 |
| 1.00 | 7.31 | | | | | | |
| ATOM | | 674 | CA | TYR | 88 | 2.217 | 7.936 | 26.154 |

-continued

| | serial | name | resName | resSeq | x | y | z | occ | temp |
|---|---|---|---|---|---|---|---|---|---|
| ATOM | 675 | CB | TYR | 88 | 3.528 | 7.871 | 26.929 | 1.00 | 7.13 |
| ATOM | 676 | CG | TYR | 88 | 4.468 | 9.042 | 27.007 | 1.00 | 8.10 |
| ATOM | 677 | CD1 | TYR | 88 | 4.116 | 10.234 | 27.638 | 1.00 | 7.71 |
| ATOM | 678 | CE1 | TYR | 88 | 5.051 | 11.255 | 27.679 | 1.00 | 9.49 |
| ATOM | 679 | CD2 | TYR | 88 | 5.718 | 8.892 | 26.443 | 1.00 | 9.02 |
| ATOM | 680 | CE2 | TYR | 88 | 6.648 | 9.911 | 26.481 | 1.00 | 9.73 |
| ATOM | 681 | CZ | TYR | 88 | 6.293 | 11.080 | 27.099 | 1.00 | 8.95 |
| ATOM | 682 | OH | TYR | 88 | 7.201 | 12.087 | 27.106 | 1.00 | 10.51 |
| ATOM | 683 | C | TYR | 88 | 1.650 | 6.523 | 26.351 | 1.00 | 8.02 |
| ATOM | 684 | O | TYR | 88 | 1.044 | 6.170 | 27.392 | 1.00 | 9.02 |
| ATOM | 685 | N | ILE | 89 | 1.732 | 5.702 | 25.323 | 1.00 | 8.56 |
| ATOM | 686 | CA | ILE | 89 | 1.416 | 4.327 | 25.590 | 1.00 | 8.75 |
| ATOM | 687 | CB | ILE | 89 | 0.027 | 3.839 | 24.820 | 1.00 | 11.11 |
| ATOM | 688 | CG2 | ILE | 89 | −1.015 | 4.940 | 24.514 | 1.00 | 11.61 |
| ATOM | 689 | CG1 | ILE | 89 | 0.325 | 3.284 | 23.516 | 1.00 | 14.51 |
| ATOM | 690 | CD1 | ILE | 89 | 0.188 | 1.799 | 23.814 | 1.00 | 14.55 |
| ATOM | 691 | C | ILE | 89 | 2.753 | 3.699 | 25.133 | 1.00 | 7.56 |
| ATOM | 692 | O | ILE | 89 | 3.184 | 3.694 | 23.968 | 1.00 | 7.22 |
| ATOM | 693 | N | VAL | 90 | 3.532 | 3.345 | 26.134 | 1.00 | 5.27 |
| ATOM | 694 | CA | VAL | 90 | 4.871 | 2.849 | 25.887 | 1.00 | 7.56 |
| ATOM | 695 | CB | VAL | 90 | 5.825 | 3.471 | 27.042 | 1.00 | 8.16 |
| ATOM | 696 | CG1 | VAL | 90 | 5.051 | 3.700 | 28.284 | 1.00 | 11.52 |
| ATOM | 697 | CG2 | VAL | 90 | 7.017 | 2.585 | 27.388 | 1.00 | 9.08 |
| ATOM | 698 | C | VAL | 90 | 4.978 | 1.309 | 25.703 | 1.00 | 7.15 |
| ATOM | 699 | O | VAL | 90 | 4.665 | 0.486 | 26.563 | 1.00 | 5.67 |
| ATOM | 700 | N | GLU | 91 | 5.408 | 0.986 | 24.489 | 1.00 | 7.73 |
| ATOM | 701 | CA | GLU | 91 | 5.615 | −0.376 | 24.005 | 1.00 | 6.96 |
| ATOM | 702 | CB | GLU | 91 | 5.524 | −0.319 | 22.468 | 1.00 | 6.72 |
| ATOM | 703 | CG | GLU | 91 | 4.117 | 0.109 | 21.997 | 1.00 | 6.68 |
| ATOM | 704 | CD | GLU | 91 | 2.997 | −0.826 | 22.456 | 1.00 | 7.56 |
| ATOM | 705 | OE1 | GLU | 91 | 2.351 | −0.578 | 23.452 | 1.00 | 6.34 |
| ATOM | 706 | OE2 | GLU | 91 | 2.725 | −1.823 | 21.810 | 1.00 | 7.24 |
| ATOM | 707 | C | GLU | 91 | 6.930 | −1.017 | 24.472 | 1.00 | 8.03 |
| ATOM | 708 | O | GLU | 91 | 7.030 | −2.224 | 24.753 | 1.00 | 8.58 |
| ATOM | 709 | N | ASN | 92 | 7.982 | −0.202 | 24.624 | 1.00 | 6.40 |
| ATOM | 710 | CA | ASN | 92 | 9.301 | −0.640 | 24.993 | 1.00 | 5.56 |
| ATOM | 711 | CB | ASN | 92 | 9.971 | −1.242 | 23.777 | 1.00 | 7.20 |
| ATOM | 712 | CG | ASN | 92 | 11.086 | −2.249 | 24.078 | 1.00 | 4.55 |
| ATOM | 713 | OD1 | ASN | 92 | 11.508 | −2.921 | 23.158 | 1.00 | 8.31 |
| ATOM | 714 | ND2 | ASN | 92 | 11.658 | −2.485 | 25.235 | 1.00 | 4.54 |
| ATOM | 715 | C | ASN | 92 | 10.101 | 0.567 | 25.492 | | |

5,405,769

-continued

| | | | | | | | |
|---|---|---|---|---|---|---|---|
| 1.00 | 6.87 | | | | | | |
| ATOM | | 716 | O | ASN | 92 | 9.730 | 1.715 | 25.226 |
| 1.00 | 6.30 | | | | | | |
| ATOM | | 717 | N | PHE | 93 | 11.178 | 0.358 | 26.247 |
| 1.00 | 6.43 | | | | | | |
| ATOM | | 718 | CA | PHE | 93 | 12.014 | 1.435 | 26.793 |
| 1.00 | 7.21 | | | | | | |
| ATOM | | 719 | CB | PHE | 93 | 11.316 | 2.114 | 27.994 |
| 1.00 | 5.14 | | | | | | |
| ATOM | | 720 | CG | PHE | 93 | 10.879 | 1.272 | 29.174 |
| 1.00 | 5.75 | | | | | | |
| ATOM | | 721 | CD1 | PHE | 93 | 11.782 | 0.935 | 30.168 |
| 1.00 | 5.51 | | | | | | |
| ATOM | | 722 | CD2 | PHE | 93 | 9.551 | 0.889 | 29.272 |
| 1.00 | 5.97 | | | | | | |
| ATOM | | 723 | CE1 | PHE | 93 | 11.341 | 0.209 | 31.274 |
| 1.00 | 6.76 | | | | | | |
| ATOM | | 724 | CE2 | PHE | 93 | 9.115 | 0.163 | 30.383 |
| 1.00 | 6.85 | | | | | | |
| ATOM | | 725 | CZ | PHE | 93 | 10.013 | −0.176 | 31.378 |
| 1.00 | 6.45 | | | | | | |
| ATOM | | 726 | C | PHE | 93 | 13.343 | 0.843 | 27.218 |
| 1.00 | 7.46 | | | | | | |
| ATOM | | 727 | O | PHE | 93 | 13.439 | −0.393 | 27.217 |
| 1.00 | 8.45 | | | | | | |
| ATOM | | 728 | N | GLY | 94 | 14.326 | 1.659 | 27.611 |
| 1.00 | 9.27 | | | | | | |
| ATOM | | 729 | CA | GLY | 94 | 15.674 | 1.230 | 27.935 |
| 1.00 | 9.67 | | | | | | |
| ATOM | | 730 | C | GLY | 94 | 15.826 | 1.048 | 29.440 |
| 1.00 | 10.54 | | | | | | |
| ATOM | | 731 | O | GLY | 94 | 14.938 | 0.537 | 30.111 |
| 1.00 | 11.63 | | | | | | |
| ATOM | | 732 | N | THR | 95 | 16.920 | 1.556 | 29.966 |
| 1.00 | 8.02 | | | | | | |
| ATOM | | 733 | CA | THR | 95 | 17.305 | 1.389 | 31.345 |
| 1.00 | 9.56 | | | | | | |
| ATOM | | 734 | CB | THR | 95 | 18.812 | 1.747 | 31.485 |
| 1.00 | 10.30 | | | | | | |
| ATOM | | 735 | OG1 | THR | 95 | 18.950 | 3.144 | 31.160 |
| 1.00 | 12.79 | | | | | | |
| ATOM | | 736 | CG2 | THR | 95 | 19.687 | 0.913 | 30.581 |
| 1.00 | 11.07 | | | | | | |
| ATOM | | 737 | C | THR | 95 | 16.493 | 2.215 | 32.339 |
| 1.00 | 9.93 | | | | | | |
| ATOM | | 738 | O | THR | 95 | 16.646 | 2.037 | 33.545 |
| 1.00 | 7.89 | | | | | | |
| ATOM | | 739 | N | TYR | 96 | 15.683 | 3.177 | 31.892 |
| 1.00 | 9.40 | | | | | | |
| ATOM | | 740 | CA | TYR | 96 | 15.008 | 4.021 | 32.850 |
| 1.00 | 7.32 | | | | | | |
| ATOM | | 741 | CB | TYR | 96 | 15.273 | 5.509 | 32.531 |
| 1.00 | 8.01 | | | | | | |
| ATOM | | 742 | CG | TYR | 96 | 14.506 | 6.456 | 33.440 |
| 1.00 | 8.66 | | | | | | |
| ATOM | | 743 | CD1 | TYR | 96 | 15.004 | 6.750 | 34.690 |
| 1.00 | 11.35 | | | | | | |
| ATOM | | 744 | CE1 | TYR | 96 | 14.312 | 7.595 | 35.549 |
| 1.00 | 12.60 | | | | | | |
| ATOM | | 745 | CD2 | TYR | 96 | 13.322 | 7.013 | 33.043 |
| 1.00 | 9.65 | | | | | | |
| ATOM | | 746 | CE2 | TYR | 96 | 12.629 | 7.862 | 33.892 |
| 1.00 | 12.25 | | | | | | |
| ATOM | | 747 | CZ | TYR | 96 | 13.125 | 8.140 | 35.144 |
| 1.00 | 12.02 | | | | | | |
| ATOM | | 748 | OH | TYR | 96 | 12.398 | 8.947 | 36.037 |
| 1.00 | 16.30 | | | | | | |
| ATOM | | 749 | C | TYR | 96 | 13.547 | 3.703 | 32.772 |
| 1.00 | 7.36 | | | | | | |
| ATOM | | 750 | O | TYR | 96 | 12.891 | 3.804 | 31.729 |
| 1.00 | 7.79 | | | | | | |
| ATOM | | 751 | N | ASN | 97 | 13.023 | 3.350 | 33.925 |
| 1.00 | 6.69 | | | | | | |
| ATOM | | 752 | CA | ASN | 97 | 11.637 | 2.945 | 33.955 |
| 1.00 | 8.46 | | | | | | |
| ATOM | | 753 | CB | ASN | 97 | 11.378 | 2.061 | 35.197 |
| 1.00 | 6.22 | | | | | | |
| ATOM | | 754 | CG | ASN | 97 | 10.028 | 1.337 | 35.187 |
| 1.00 | 8.71 | | | | | | |
| ATOM | | 755 | OD1 | ASN | 97 | 9.902 | 0.092 | 35.210 |
| 1.00 | 8.88 | | | | | | |
| ATOM | | 756 | ND2 | ASN | 97 | 8.950 | 2.081 | 35.177 |

-continued

| | | | | | | | | | |
|---|---|---|---|---|---|---|---|---|---|
| ATOM | 757 | C | ASN | 97 | 10.775 | 4.208 | 33.979 | 1.00 | 9.04 |
| ATOM | 758 | O | ASN | 97 | 10.891 | 5.009 | 34.918 | 1.00 | 10.16 |
| ATOM | 759 | N | PRO | 98 | 9.864 | 4.383 | 33.017 | 1.00 | 9.73 |
| ATOM | 760 | CD | PRO | 98 | 9.616 | 3.413 | 31.965 | 1.00 | 10.11 |
| ATOM | 761 | CA | PRO | 98 | 8.929 | 5.503 | 32.905 | 1.00 | 11.05 |
| ATOM | 762 | CB | PRO | 98 | 8.134 | 5.233 | 31.671 | 1.00 | 10.57 |
| ATOM | 763 | CG | PRO | 98 | 8.894 | 4.168 | 30.909 | 1.00 | 11.36 |
| ATOM | 764 | C | PRO | 98 | 7.999 | 5.746 | 34.094 | 1.00 | 12.84 |
| ATOM | 765 | O | PRO | 98 | 7.553 | 6.881 | 34.328 | 1.00 | 12.98 |
| ATOM | 766 | N | SER | 99 | 7.635 | 4.699 | 34.852 | 1.00 | 11.41 |
| ATOM | 767 | CA | SER | 99 | 6.808 | 4.887 | 36.009 | 1.00 | 12.40 |
| ATOM | 768 | CB | SER | 99 | 6.193 | 3.565 | 36.411 | 1.00 | 11.96 |
| ATOM | 769 | OG | SER | 99 | 7.223 | 2.731 | 36.896 | 1.00 | 13.35 |
| ATOM | 770 | C | SER | 99 | 7.561 | 5.483 | 37.229 | 1.00 | 13.13 |
| ATOM | 771 | O | SER | 99 | 6.887 | 5.667 | 38.238 | 1.00 | 12.90 |
| ATOM | 772 | N | THR | 100 | 8.872 | 5.814 | 37.202 | 1.00 | 12.61 |
| ATOM | 773 | CA | THR | 100 | 9.570 | 6.319 | 38.373 | 1.00 | 14.31 |
| ATOM | 774 | CB | THR | 100 | 11.053 | 6.616 | 37.908 | 1.00 | 14.57 |
| ATOM | 775 | OG1 | THR | 100 | 11.681 | 5.381 | 37.513 | 1.00 | 13.39 |
| ATOM | 776 | CG2 | THR | 100 | 11.872 | 7.330 | 39.000 | 1.00 | 13.16 |
| ATOM | 777 | C | THR | 100 | 8.855 | 7.562 | 38.979 | 1.00 | 15.95 |
| ATOM | 778 | O | THR | 100 | 8.704 | 7.778 | 40.199 | 1.00 | 16.24 |
| ATOM | 779 | N | GLY | 101 | 8.283 | 8.459 | 38.197 | 1.00 | 16.98 |
| ATOM | 780 | CA | GLY | 101 | 7.638 | 9.603 | 38.908 | 1.00 | 22.81 |
| ATOM | 781 | C | GLY | 101 | 6.275 | 9.277 | 39.557 | 1.00 | 22.53 |
| ATOM | 782 | O | GLY | 101 | 5.846 | 9.799 | 40.603 | 1.00 | 24.30 |
| ATOM | 783 | N | ALA | 102 | 5.687 | 8.272 | 38.943 | 1.00 | 21.22 |
| ATOM | 784 | CA | ALA | 102 | 4.281 | 8.251 | 38.892 | 1.00 | 20.59 |
| ATOM | 785 | CB | ALA | 102 | 3.987 | 7.618 | 37.568 | 1.00 | 22.27 |
| ATOM | 786 | C | ALA | 102 | 3.361 | 7.726 | 39.918 | 1.00 | 20.55 |
| ATOM | 787 | O | ALA | 102 | 3.672 | 6.926 | 40.813 | 1.00 | 21.31 |
| ATOM | 788 | N | THR | 103 | 2.136 | 8.214 | 39.718 | 1.00 | 19.36 |
| ATOM | 789 | CA | THR | 103 | 1.096 | 7.726 | 40.572 | 1.00 | 18.69 |
| ATOM | 790 | CB | THR | 103 | 0.225 | 8.936 | 40.951 | 1.00 | 19.51 |
| ATOM | 791 | OG1 | THR | 103 | 1.084 | 9.806 | 41.743 | 1.00 | 20.44 |
| ATOM | 792 | CG2 | THR | 103 | −1.075 | 8.498 | 41.648 | 1.00 | 18.11 |
| ATOM | 793 | C | THR | 103 | 0.371 | 6.668 | 39.775 | 1.00 | 16.70 |
| ATOM | 794 | O | THR | 103 | −0.096 | 7.016 | 38.695 | 1.00 | 15.70 |
| ATOM | 795 | N | LYS | 104 | 0.313 | 5.418 | 40.253 | 1.00 | 15.07 |
| ATOM | 796 | CA | LYS | 104 | −0.377 | 4.378 | 39.528 | 1.00 | 14.87 |
| ATOM | 797 | CB | LYS | 104 | 0.040 | 2.976 | 40.009 | | |

| | | | | | | | |
|---|---|---|---|---|---|---|---|
| 1.00 | 15.19 | | | | | | |
| ATOM | | 798 | CG | LYS | 104 | −0.609 | 1.894 | 39.106 |
| 1.00 | 14.18 | | | | | | |
| ATOM | | 799 | CD | LYS | 104 | −0.270 | 0.443 | 39.507 |
| 1.00 | 13.52 | | | | | | |
| ATOM | | 800 | CE | LYS | 104 | −1.134 | −0.507 | 38.694 |
| 1.00 | 13.51 | | | | | | |
| ATOM | | 801 | NZ | LYS | 104 | −0.693 | −1.884 | 38.679 |
| 1.00 | 14.08 | | | | | | |
| ATOM | | 802 | C | LYS | 104 | −1.865 | 4.540 | 39.739 |
| 1.00 | 15.06 | | | | | | |
| ATOM | | 803 | O | LYS | 104 | −2.343 | 4.776 | 40.852 |
| 1.00 | 16.27 | | | | | | |
| ATOM | | 804 | N | LEU | 105 | −2.604 | 4.497 | 38.663 |
| 1.00 | 14.64 | | | | | | |
| ATOM | | 805 | CA | LEU | 105 | −4.012 | 4.642 | 38.765 |
| 1.00 | 16.10 | | | | | | |
| ATOM | | 806 | CB | LEU | 105 | −4.554 | 5.692 | 37.835 |
| 1.00 | 18.74 | | | | | | |
| ATOM | | 807 | CG | LEU | 105 | −4.239 | 7.181 | 38.163 |
| 1.00 | 21.39 | | | | | | |
| ATOM | | 808 | CD1 | LEU | 105 | −2.801 | 7.479 | 37.844 |
| 1.00 | 21.27 | | | | | | |
| ATOM | | 809 | CD2 | LEU | 105 | −5.016 | 8.118 | 37.214 |
| 1.00 | 22.30 | | | | | | |
| ATOM | | 810 | C | LEU | 105 | −4.735 | 3.403 | 38.415 |
| 1.00 | 17.33 | | | | | | |
| ATOM | | 811 | O | LEU | 105 | −5.958 | 3.403 | 38.613 |
| 1.00 | 18.71 | | | | | | |
| ATOM | | 812 | N | GLY | 106 | −4.142 | 2.420 | 37.716 |
| 1.00 | 16.78 | | | | | | |
| ATOM | | 813 | CA | GLY | 106 | −4.924 | 1.256 | 37.323 |
| 1.00 | 14.69 | | | | | | |
| ATOM | | 814 | C | GLY | 106 | −4.212 | 0.434 | 36.268 |
| 1.00 | 14.81 | | | | | | |
| ATOM | | 815 | O | GLY | 106 | −2.996 | 0.602 | 36.101 |
| 1.00 | 14.33 | | | | | | |
| ATOM | | 816 | N | GLU | 107 | −4.969 | −0.468 | 35.612 |
| 1.00 | 14.31 | | | | | | |
| ATOM | | 817 | CA | GLU | 107 | −4.471 | −1.347 | 34.563 |
| 1.00 | 14.01 | | | | | | |
| ATOM | | 818 | CB | GLU | 107 | −4.139 | −2.724 | 35.141 |
| 1.00 | 17.27 | | | | | | |
| ATOM | | 819 | CG | GLU | 107 | −3.101 | −2.650 | 36.288 |
| 1.00 | 19.43 | | | | | | |
| ATOM | | 820 | CD | GLU | 107 | −3.045 | −3.847 | 37.242 |
| 1.00 | 21.27 | | | | | | |
| ATOM | | 821 | OE1 | GLU | 107 | −3.493 | −4.937 | 36.863 |
| 1.00 | 20.90 | | | | | | |
| ATOM | | 822 | OE2 | GLU | 107 | −2.507 | −3.677 | 38.362 |
| 1.00 | 22.15 | | | | | | |
| ATOM | | 823 | C | GLU | 107 | −5.503 | −1.522 | 33.465 |
| 1.00 | 12.12 | | | | | | |
| ATOM | | 824 | O | GLU | 107 | −6.703 | −1.267 | 33.664 |
| 1.00 | 11.04 | | | | | | |
| ATOM | | 825 | N | VAL | 108 | −5.003 | −1.974 | 32.315 |
| 1.00 | 11.87 | | | | | | |
| ATOM | | 826 | CA | VAL | 108 | −5.812 | −2.265 | 31.129 |
| 1.00 | 13.37 | | | | | | |
| ATOM | | 827 | CB | VAL | 108 | −6.069 | −0.940 | 30.283 |
| 1.00 | 12.75 | | | | | | |
| ATOM | | 828 | CG1 | VAL | 108 | −4.742 | −0.406 | 29.730 |
| 1.00 | 13.07 | | | | | | |
| ATOM | | 829 | CG2 | VAL | 108 | −6.925 | −1.184 | 29.045 |
| 1.00 | 13.15 | | | | | | |
| ATOM | | 830 | C | VAL | 108 | −5.034 | −3.299 | 30.306 |
| 1.00 | 11.86 | | | | | | |
| ATOM | | 831 | O | VAL | 108 | −3.796 | −3.269 | 30.185 |
| 1.00 | 12.43 | | | | | | |
| ATOM | | 832 | N | THR | 109 | −5.786 | −4.210 | 29.734 |
| 1.00 | 12.65 | | | | | | |
| ATOM | | 833 | CA | THR | 109 | −5.255 | −5.257 | 28.889 |
| 1.00 | 12.30 | | | | | | |
| ATOM | | 834 | CB | THR | 109 | −5.935 | −6.599 | 29.286 |
| 1.00 | 14.44 | | | | | | |
| ATOM | | 835 | OG1 | THR | 109 | −5.674 | −6.816 | 30.697 |
| 1.00 | 15.40 | | | | | | |
| ATOM | | 836 | CG2 | THR | 109 | −5.415 | −7.780 | 28.462 |
| 1.00 | 13.97 | | | | | | |
| ATOM | | 837 | C | THR | 109 | −5.579 | −4.839 | 27.469 |
| 1.00 | 11.75 | | | | | | |
| ATOM | | 838 | O | THR | 109 | −6.711 | −4.454 | 27.199 |

| | Serial | Atom | Res | ResNum | X | Y | Z | Occ | B |
|---|---|---|---|---|---|---|---|---|---|
| | | | | | | | | 1.00 | 12.42 |
| ATOM | 839 | N | SER | 110 | −4.630 | −4.859 | 26.538 | 1.00 | 11.20 |
| ATOM | 840 | CA | SER | 110 | −4.879 | −4.532 | 25.155 | 1.00 | 10.80 |
| ATOM | 841 | CB | SER | 110 | −4.941 | −3.031 | 24.965 | 1.00 | 10.12 |
| ATOM | 842 | OG | SER | 110 | −5.204 | −2.682 | 23.632 | 1.00 | 11.48 |
| ATOM | 843 | C | SER | 110 | −3.690 | −5.105 | 24.405 | 1.00 | 11.32 |
| ATOM | 844 | O | SER | 110 | −2.547 | −5.207 | 24.920 | 1.00 | 12.50 |
| ATOM | 845 | N | ASP | 111 | −4.042 | −5.590 | 23.213 | 1.00 | 10.79 |
| ATOM | 846 | CA | ASP | 111 | −3.119 | −6.087 | 22.199 | 1.00 | 12.25 |
| ATOM | 847 | CB | ASP | 111 | −2.447 | −4.890 | 21.486 | 1.00 | 13.12 |
| ATOM | 848 | CG | ASP | 111 | −3.520 | −3.986 | 20.911 | 1.00 | 13.55 |
| ATOM | 849 | OD1 | ASP | 111 | −4.270 | −4.400 | 20.041 | 1.00 | 13.05 |
| ATOM | 850 | OD2 | ASP | 111 | −3.631 | −2.862 | 21.377 | 1.00 | 14.27 |
| ATOM | 851 | C | ASP | 111 | −2.044 | −7.029 | 22.706 | 1.00 | 13.33 |
| ATOM | 852 | O | ASP | 111 | −0.825 | −6.910 | 22.477 | 1.00 | 14.68 |
| ATOM | 853 | N | GLY | 112 | −2.491 | −7.933 | 23.566 | 1.00 | 13.67 |
| ATOM | 854 | CA | GLY | 112 | −1.595 | −8.956 | 24.072 | 1.00 | 10.73 |
| ATOM | 855 | C | GLY | 112 | −0.959 | −8.664 | 25.418 | 1.00 | 9.91 |
| ATOM | 856 | O | GLY | 112 | −0.094 | −9.437 | 25.783 | 1.00 | 9.84 |
| ATOM | 857 | N | SER | 113 | −1.218 | −7.600 | 26.180 | 1.00 | 9.51 |
| ATOM | 858 | CA | SER | 113 | −0.518 | −7.452 | 27.424 | 1.00 | 8.66 |
| ATOM | 859 | CB | SER | 113 | 0.851 | −6.812 | 27.189 | 1.00 | 6.40 |
| ATOM | 860 | OG | SER | 113 | 1.712 | −6.818 | 28.313 | 1.00 | 5.69 |
| ATOM | 861 | C | SER | 113 | −1.350 | −6.588 | 28.292 | 1.00 | 8.88 |
| ATOM | 862 | O | SER | 113 | −2.213 | −5.874 | 27.803 | 1.00 | 11.46 |
| ATOM | 863 | N | VAL | 114 | −1.190 | −6.691 | 29.594 | 1.00 | 10.48 |
| ATOM | 864 | CA | VAL | 114 | −1.787 | −5.641 | 30.395 | 1.00 | 9.89 |
| ATOM | 865 | CB | VAL | 114 | −2.304 | −6.209 | 31.826 | 1.00 | 11.18 |
| ATOM | 866 | CG1 | VAL | 114 | −1.870 | −7.641 | 32.032 | 1.00 | 10.85 |
| ATOM | 867 | CG2 | VAL | 114 | −1.853 | −5.324 | 32.981 | 1.00 | 10.22 |
| ATOM | 868 | C | VAL | 114 | −0.666 | −4.581 | 30.466 | 1.00 | 10.04 |
| ATOM | 869 | O | VAL | 114 | 0.535 | −4.838 | 30.231 | 1.00 | 9.80 |
| ATOM | 870 | N | TYR | 115 | −1.145 | −3.368 | 30.683 | 1.00 | 9.29 |
| ATOM | 871 | CA | TYR | 115 | −0.390 | −2.144 | 30.797 | 1.00 | 9.53 |
| ATOM | 872 | CB | TYR | 115 | −0.789 | −1.113 | 29.736 | 1.00 | 8.60 |
| ATOM | 873 | CG | TYR | 115 | −0.417 | −1.372 | 28.281 | 1.00 | 8.75 |
| ATOM | 874 | CD1 | TYR | 115 | 0.505 | −0.554 | 27.607 | 1.00 | 7.26 |
| ATOM | 875 | CE1 | TYR | 115 | 0.788 | −0.783 | 26.275 | 1.00 | 7.31 |
| ATOM | 876 | CD2 | TYR | 115 | −1.043 | −2.408 | 27.631 | 1.00 | 8.71 |
| ATOM | 877 | CE2 | TYR | 115 | −0.778 | −2.646 | 26.312 | 1.00 | 9.10 |
| ATOM | 878 | CZ | TYR | 115 | 0.126 | −1.843 | 25.640 | 1.00 | 8.99 |
| ATOM | 879 | OH | TYR | 115 | 0.311 | −2.161 | 24.309 | | |

-continued

| | | | | | | | |
|---|---|---|---|---|---|---|---|
| 1.00 | 9.97 | | | | | | |
| ATOM | | 880 | C | TYR | 115 | −0.747 | −1.545 | 32.151 |
| 1.00 | 10.03 | | | | | | |
| ATOM | | 881 | O | TYR | 115 | −1.874 | −1.667 | 32.641 |
| 1.00 | 10.65 | | | | | | |
| ATOM | | 882 | N | ASP | 116 | 0.206 | −0.895 | 32.794 |
| 1.00 | 10.05 | | | | | | |
| ATOM | | 883 | CA | ASP | 116 | −0.094 | −0.187 | 34.027 |
| 1.00 | 10.95 | | | | | | |
| ATOM | | 884 | CB | ASP | 116 | 1.092 | −0.386 | 34.982 |
| 1.00 | 10.88 | | | | | | |
| ATOM | | 885 | CG | ASP | 116 | 1.153 | −1.800 | 35.539 |
| 1.00 | 12.59 | | | | | | |
| ATOM | | 886 | OD1 | ASP | 116 | 2.085 | −2.539 | 35.245 |
| 1.00 | 12.09 | | | | | | |
| ATOM | | 887 | OD2 | ASP | 116 | 0.281 | −2.189 | 36.298 |
| 1.00 | 13.31 | | | | | | |
| ATOM | | 888 | C | ASP | 116 | −0.323 | 1.296 | 33.610 |
| 1.00 | 10.73 | | | | | | |
| ATOM | | 889 | O | ASP | 116 | 0.307 | 1.792 | 32.656 |
| 1.00 | 9.98 | | | | | | |
| ATOM | | 890 | N | ILE | 117 | −1.259 | 1.980 | 34.272 |
| 1.00 | 10.31 | | | | | | |
| ATOM | | 891 | CA | ILE | 117 | −1.768 | 3.320 | 33.944 |
| 1.00 | 11.24 | | | | | | |
| ATOM | | 892 | CB | ILE | 117 | −3.316 | 3.226 | 33.891 |
| 1.00 | 11.80 | | | | | | |
| ATOM | | 893 | CG2 | ILE | 117 | −3.969 | 4.626 | 33.919 |
| 1.00 | 12.99 | | | | | | |
| ATOM | | 894 | CG1 | ILE | 117 | −3.714 | 2.409 | 32.671 |
| 1.00 | 11.14 | | | | | | |
| ATOM | | 895 | CD1 | ILE | 117 | −5.195 | 2.011 | 32.763 |
| 1.00 | 11.30 | | | | | | |
| ATOM | | 896 | C | ILE | 117 | −1.287 | 4.285 | 35.037 |
| 1.00 | 11.21 | | | | | | |
| ATOM | | 897 | O | ILE | 117 | −1.484 | 4.007 | 36.236 |
| 1.00 | 11.16 | | | | | | |
| ATOM | | 898 | N | TYR | 118 | −0.646 | 5.368 | 34.631 |
| 1.00 | 9.67 | | | | | | |
| ATOM | | 899 | CA | TYR | 118 | −0.039 | 6.351 | 35.530 |
| 1.00 | 10.44 | | | | | | |
| ATOM | | 900 | CB | TYR | 118 | 1.481 | 6.226 | 35.585 |
| 1.00 | 8.83 | | | | | | |
| ATOM | | 901 | CG | TYR | 118 | 1.994 | 4.842 | 35.959 |
| 1.00 | 9.45 | | | | | | |
| ATOM | | 902 | CD1 | TYR | 118 | 2.210 | 3.919 | 34.944 |
| 1.00 | 9.25 | | | | | | |
| ATOM | | 903 | CE1 | TYR | 118 | 2.696 | 2.663 | 35.241 |
| 1.00 | 10.55 | | | | | | |
| ATOM | | 904 | CD2 | TYR | 118 | 2.261 | 4.524 | 37.284 |
| 1.00 | 9.83 | | | | | | |
| ATOM | | 905 | CE2 | TYR | 118 | 2.756 | 3.269 | 37.601 |
| 1.00 | 11.19 | | | | | | |
| ATOM | | 906 | CZ | TYR | 118 | 2.969 | 2.341 | 36.566 |
| 1.00 | 11.73 | | | | | | |
| ATOM | | 907 | OH | TYR | 118 | 3.484 | 1.078 | 36.857 |
| 1.00 | 11.26 | | | | | | |
| ATOM | | 908 | C | TYR | 118 | −0.329 | 7.801 | 35.103 |
| 1.00 | 10.46 | | | | | | |
| ATOM | | 909 | O | TYR | 118 | −0.521 | 8.073 | 33.914 |
| 1.00 | 9.48 | | | | | | |
| ATOM | | 910 | N | ARG | 119 | −0.335 | 8.724 | 36.053 |
| 1.00 | 11.66 | | | | | | |
| ATOM | | 911 | CA | ARG | 119 | −0.553 | 10.155 | 35.779 |
| 1.00 | 14.61 | | | | | | |
| ATOM | | 912 | CB | ARG | 119 | −1.973 | 10.621 | 36.265 |
| 1.00 | 17.40 | | | | | | |
| ATOM | | 913 | CG | ARG | 119 | −2.089 | 12.021 | 36.952 |
| 1.00 | 23.37 | | | | | | |
| ATOM | | 914 | CD | ARG | 119 | −3.471 | 12.483 | 37.490 |
| 1.00 | 26.18 | | | | | | |
| ATOM | | 915 | NE | ARG | 119 | −4.356 | 12.883 | 36.371 |
| 1.00 | 30.66 | | | | | | |
| ATOM | | 916 | CZ | ARG | 119 | −5.263 | 13.922 | 36.488 |
| 1.00 | 33.03 | | | | | | |
| ATOM | | 917 | NH1 | ARG | 119 | −5.325 | 14.574 | 37.682 |
| 1.00 | 34.14 | | | | | | |
| ATOM | | 918 | NH2 | ARG | 119 | −6.085 | 14.337 | 35.453 |
| 1.00 | 32.49 | | | | | | |
| ATOM | | 919 | C | ARG | 119 | 0.546 | 10.899 | 36.536 |
| 1.00 | 14.29 | | | | | | |
| ATOM | | 920 | O | ARG | 119 | 0.866 | 10.575 | 37.684 |

-continued

| | | | | | | | | |
|---|---|---|---|---|---|---|---|---|
| 1.00 | 12.19 | | | | | | | |
| ATOM | | 921 | N | THR | 120 | 1.155 | 11.881 | 35.873 |
| 1.00 | 15.13 | | | | | | | |
| ATOM | | 922 | CA | THR | 120 | 2.243 | 12.707 | 36.395 |
| 1.00 | 16.87 | | | | | | | |
| ATOM | | 923 | CB | THR | 120 | 3.620 | 12.350 | 35.730 |
| 1.00 | 19.15 | | | | | | | |
| ATOM | | 924 | OG1 | THR | 120 | 3.353 | 12.150 | 34.313 |
| 1.00 | 22.72 | | | | | | | |
| ATOM | | 925 | CG2 | THR | 120 | 4.277 | 11.062 | 36.276 |
| 1.00 | 21.25 | | | | | | | |
| ATOM | | 926 | C | THR | 120 | 1.859 | 14.152 | 35.996 |
| 1.00 | 15.72 | | | | | | | |
| ATOM | | 927 | O | THR | 120 | 0.915 | 14.327 | 35.236 |
| 1.00 | 11.42 | | | | | | | |
| ATOM | | 928 | N | GLN | 121 | 2.510 | 15.213 | 36.480 |
| 1.00 | 18.27 | | | | | | | |
| ATOM | | 929 | CA | GLN | 121 | 2.180 | 16.591 | 36.057 |
| 1.00 | 18.87 | | | | | | | |
| ATOM | | 930 | CB | GLN | 121 | 1.490 | 17.333 | 37.150 |
| 1.00 | 20.46 | | | | | | | |
| ATOM | | 931 | CG | GLN | 121 | 0.818 | 18.647 | 36.686 |
| 1.00 | 22.49 | | | | | | | |
| ATOM | | 932 | CD | GLN | 121 | 0.528 | 19.470 | 37.910 |
| 1.00 | 23.15 | | | | | | | |
| ATOM | | 933 | OE1 | GLN | 121 | −0.609 | 19.866 | 38.201 |
| 1.00 | 24.23 | | | | | | | |
| ATOM | | 934 | NE2 | GLN | 121 | 1.566 | 19.744 | 38.711 |
| 1.00 | 25.37 | | | | | | | |
| ATOM | | 935 | C | GLN | 121 | 3.469 | 17.311 | 35.724 |
| 1.00 | 17.45 | | | | | | | |
| ATOM | | 936 | O | GLN | 121 | 4.483 | 17.265 | 36.429 |
| 1.00 | 17.70 | | | | | | | |
| ATOM | | 937 | N | ARG | 122 | 3.507 | 17.884 | 34.557 |
| 1.00 | 16.86 | | | | | | | |
| ATOM | | 938 | CA | ARG | 122 | 4.666 | 18.646 | 34.205 |
| 1.00 | 17.38 | | | | | | | |
| ATOM | | 939 | CB | ARG | 122 | 4.919 | 18.431 | 32.738 |
| 1.00 | 17.17 | | | | | | | |
| ATOM | | 940 | CG | ARG | 122 | 4.983 | 16.936 | 32.371 |
| 1.00 | 17.66 | | | | | | | |
| ATOM | | 941 | CD | ARG | 122 | 6.035 | 16.268 | 33.234 |
| 1.00 | 19.91 | | | | | | | |
| ATOM | | 942 | NE | ARG | 122 | 7.405 | 16.749 | 33.155 |
| 1.00 | 20.83 | | | | | | | |
| ATOM | | 943 | CZ | ARG | 122 | 8.060 | 17.199 | 32.061 |
| 1.00 | 21.20 | | | | | | | |
| ATOM | | 944 | NH1 | ARG | 122 | 7.485 | 17.275 | 30.834 |
| 1.00 | 24.32 | | | | | | | |
| ATOM | | 945 | NH2 | ARG | 122 | 9.359 | 17.539 | 32.223 |
| 1.00 | 21.52 | | | | | | | |
| ATOM | | 946 | C | ARG | 122 | 4.285 | 20.099 | 34.550 |
| 1.00 | 18.00 | | | | | | | |
| ATOM | | 947 | O | ARG | 122 | 3.127 | 20.529 | 34.309 |
| 1.00 | 15.92 | | | | | | | |
| ATOM | | 948 | N | VAL | 123 | 5.264 | 20.778 | 35.187 |
| 1.00 | 17.31 | | | | | | | |
| ATOM | | 949 | CA | VAL | 123 | 5.100 | 22.174 | 35.581 |
| 1.00 | 17.49 | | | | | | | |
| ATOM | | 950 | CB | VAL | 123 | 5.204 | 22.292 | 37.118 |
| 1.00 | 18.68 | | | | | | | |
| ATOM | | 951 | CG1 | VAL | 123 | 5.057 | 23.752 | 37.578 |
| 1.00 | 18.13 | | | | | | | |
| ATOM | | 952 | CG2 | VAL | 123 | 4.025 | 21.495 | 37.756 |
| 1.00 | 17.08 | | | | | | | |
| ATOM | | 953 | C | VAL | 123 | 6.132 | 23.037 | 34.888 |
| 1.00 | 18.01 | | | | | | | |
| ATOM | | 954 | O | VAL | 123 | 7.348 | 22.820 | 34.956 |
| 1.00 | 19.01 | | | | | | | |
| ATOM | | 955 | N | ASN | 124 | 5.550 | 23.905 | 34.058 |
| 1.00 | 18.77 | | | | | | | |
| ATOM | | 956 | CA | ASN | 124 | 6.246 | 24.856 | 33.204 |
| 1.00 | 18.46 | | | | | | | |
| ATOM | | 957 | CB | ASN | 124 | 6.839 | 25.978 | 34.049 |
| 1.00 | 18.90 | | | | | | | |
| ATOM | | 958 | CG | ASN | 124 | 5.688 | 26.871 | 34.516 |
| 1.00 | 19.83 | | | | | | | |
| ATOM | | 959 | OD1 | ASN | 124 | 5.841 | 27.521 | 35.548 |
| 1.00 | 21.50 | | | | | | | |
| ATOM | | 960 | ND2 | ASN | 124 | 4.457 | 26.916 | 33.966 |
| 1.00 | 18.83 | | | | | | | |
| ATOM | | 961 | C | ASN | 124 | 7.288 | 24.274 | 32.301 |

| | | | | | | | |
|---|---|---|---|---|---|---|---|
| 1.00 | 17.97 | | | | | | |
| ATOM | | 962 | O | ASN | 124 | 8.485 | 24.580 | 32.249 |
| 1.00 | 19.21 | | | | | | |
| ATOM | | 963 | N | GLN | 125 | 6.718 | 23.436 | 31.457 |
| 1.00 | 17.42 | | | | | | |
| ATOM | | 964 | CA | GLN | 125 | 7.513 | 22.692 | 30.522 |
| 1.00 | 15.95 | | | | | | |
| ATOM | | 965 | CB | GLN | 125 | 7.340 | 21.162 | 30.781 |
| 1.00 | 18.71 | | | | | | |
| ATOM | | 966 | CG | GLN | 125 | 7.771 | 20.765 | 32.189 |
| 1.00 | 20.97 | | | | | | |
| ATOM | | 967 | CD | GLN | 125 | 9.279 | 20.949 | 32.484 |
| 1.00 | 23.57 | | | | | | |
| ATOM | | 968 | OE1 | GLN | 125 | 10.114 | 20.190 | 31.977 |
| 1.00 | 24.89 | | | | | | |
| ATOM | | 969 | NE2 | GLN | 125 | 9.737 | 21.872 | 33.335 |
| 1.00 | 24.87 | | | | | | |
| ATOM | | 970 | C | GLN | 125 | 6.994 | 23.068 | 29.153 |
| 1.00 | 14.36 | | | | | | |
| ATOM | | 971 | O | GLN | 125 | 5.828 | 23.466 | 28.999 |
| 1.00 | 13.68 | | | | | | |
| ATOM | | 972 | N | PRO | 126 | 7.847 | 22.921 | 28.138 |
| 1.00 | 13.24 | | | | | | |
| ATOM | | 973 | CD | PRO | 126 | 9.304 | 22.804 | 28.272 |
| 1.00 | 13.21 | | | | | | |
| ATOM | | 974 | CA | PRO | 126 | 7.444 | 22.936 | 26.773 |
| 1.00 | 11.98 | | | | | | |
| ATOM | | 975 | CB | PRO | 126 | 8.686 | 22.587 | 25.972 |
| 1.00 | 12.53 | | | | | | |
| ATOM | | 976 | CG | PRO | 126 | 9.718 | 22.098 | 26.983 |
| 1.00 | 12.93 | | | | | | |
| ATOM | | 977 | C | PRO | 126 | 6.291 | 22.004 | 26.506 |
| 1.00 | 11.75 | | | | | | |
| ATOM | | 978 | O | PRO | 126 | 6.115 | 20.913 | 27.073 |
| 1.00 | 11.75 | | | | | | |
| ATOM | | 979 | N | SER | 127 | 5.462 | 22.567 | 25.667 |
| 1.00 | 11.03 | | | | | | |
| ATOM | | 980 | CA | SER | 127 | 4.315 | 21.866 | 25.199 |
| 1.00 | 10.71 | | | | | | |
| ATOM | | 981 | CB | SER | 127 | 3.081 | 22.230 | 26.043 |
| 1.00 | 10.39 | | | | | | |
| ATOM | | 982 | OG | SER | 127 | 2.618 | 23.555 | 25.769 |
| 1.00 | 11.05 | | | | | | |
| ATOM | | 983 | C | SER | 127 | 4.178 | 22.399 | 23.787 |
| 1.00 | 12.20 | | | | | | |
| ATOM | | 984 | O | SER | 127 | 4.895 | 23.295 | 23.342 |
| 1.00 | 12.63 | | | | | | |
| ATOM | | 985 | N | ILE | 128 | 3.221 | 21.771 | 23.145 |
| 1.00 | 10.76 | | | | | | |
| ATOM | | 986 | CA | ILE | 128 | 2.628 | 22.112 | 21.877 |
| 1.00 | 12.75 | | | | | | |
| ATOM | | 987 | CB | ILE | 128 | 1.518 | 20.968 | 21.777 |
| 1.00 | 11.99 | | | | | | |
| ATOM | | 988 | CG2 | ILE | 128 | 0.710 | 20.959 | 23.097 |
| 1.00 | 13.03 | | | | | | |
| ATOM | | 989 | CG1 | ILE | 128 | 0.526 | 21.141 | 20.704 |
| 1.00 | 13.86 | | | | | | |
| ATOM | | 990 | CD1 | ILE | 128 | −0.807 | 20.429 | 21.073 |
| 1.00 | 11.79 | | | | | | |
| ATOM | | 991 | C | ILE | 128 | 2.166 | 23.616 | 21.786 |
| 1.00 | 12.49 | | | | | | |
| ATOM | | 992 | O | ILE | 128 | 2.010 | 24.160 | 20.689 |
| 1.00 | 11.61 | | | | | | |
| ATOM | | 993 | N | ILE | 129 | 1.911 | 24.268 | 22.923 |
| 1.00 | 11.55 | | | | | | |
| ATOM | | 994 | CA | ILE | 129 | 1.335 | 25.625 | 23.051 |
| 1.00 | 12.87 | | | | | | |
| ATOM | | 995 | CB | ILE | 129 | 0.050 | 25.264 | 23.942 |
| 1.00 | 12.77 | | | | | | |
| ATOM | | 996 | CG2 | ILE | 129 | 0.063 | 25.810 | 25.372 |
| 1.00 | 12.19 | | | | | | |
| ATOM | | 997 | CG1 | ILE | 129 | −1.129 | 25.730 | 23.208 |
| 1.00 | 13.88 | | | | | | |
| ATOM | | 998 | CD1 | ILE | 129 | −1.556 | 24.732 | 22.166 |
| 1.00 | 13.59 | | | | | | |
| ATOM | | 999 | C | ILE | 129 | 2.414 | 26.584 | 23.628 |
| 1.00 | 12.93 | | | | | | |
| ATOM | | 1000 | O | ILE | 129 | 2.195 | 27.795 | 23.818 |
| 1.00 | 15.68 | | | | | | |
| ATOM | | 1001 | N | GLY | 130 | 3.595 | 26.061 | 24.001 |
| 1.00 | 12.43 | | | | | | |
| ATOM | | 1002 | CA | GLY | 130 | 4.647 | 26.814 | 24.669 |

-continued

| | | | | | | | | |
|---|---|---|---|---|---|---|---|---|
| 1.00 | 11.72 | | | | | | | |
| ATOM | | 1003 | C | GLY | 130 | 4.752 | 26.447 | 26.146 |
| 1.00 | 10.71 | | | | | | | |
| ATOM | | 1004 | O | GLY | 130 | 4.105 | 25.502 | 26.558 |
| 1.00 | 11.85 | | | | | | | |
| ATOM | | 1005 | N | THR | 131 | 5.552 | 27.094 | 26.999 |
| 1.00 | 10.63 | | | | | | | |
| ATOM | | 1006 | CA | THR | 131 | 5.633 | 26.774 | 28.422 |
| 1.00 | 10.32 | | | | | | | |
| ATOM | | 1007 | CB | THR | 131 | 6.507 | 27.778 | 29.134 |
| 1.00 | 10.53 | | | | | | | |
| ATOM | | 1008 | OG1 | THR | 131 | 7.632 | 27.883 | 28.294 |
| 1.00 | 13.71 | | | | | | | |
| ATOM | | 1009 | CG2 | THR | 131 | 6.969 | 27.382 | 30.523 |
| 1.00 | 9.71 | | | | | | | |
| ATOM | | 1010 | C | THR | 131 | 4.284 | 26.743 | 29.108 |
| 1.00 | 10.05 | | | | | | | |
| ATOM | | 1011 | O | THR | 131 | 3.512 | 27.720 | 29.121 |
| 1.00 | 9.35 | | | | | | | |
| ATOM | | 1012 | N | ALA | 132 | 4.066 | 25.560 | 29.667 |
| 1.00 | 9.69 | | | | | | | |
| ATOM | | 1013 | CA | ALA | 132 | 2.783 | 25.208 | 30.228 |
| 1.00 | 10.33 | | | | | | | |
| ATOM | | 1014 | CB | ALA | 132 | 1.913 | 24.574 | 29.134 |
| 1.00 | 8.89 | | | | | | | |
| ATOM | | 1015 | C | ALA | 132 | 2.850 | 24.229 | 31.413 |
| 1.00 | 10.62 | | | | | | | |
| ATOM | | 1016 | O | ALA | 132 | 3.926 | 23.711 | 31.762 |
| 1.00 | 11.81 | | | | | | | |
| ATOM | | 1017 | N | THR | 133 | 1.721 | 24.123 | 32.100 |
| 1.00 | 11.01 | | | | | | | |
| ATOM | | 1018 | CA | THR | 133 | 1.541 | 23.113 | 33.134 |
| 1.00 | 12.77 | | | | | | | |
| ATOM | | 1019 | CB | THR | 133 | 1.145 | 23.789 | 34.478 |
| 1.00 | 13.67 | | | | | | | |
| ATOM | | 1020 | OG1 | THR | 133 | 2.360 | 24.447 | 34.897 |
| 1.00 | 15.23 | | | | | | | |
| ATOM | | 1021 | CG2 | THR | 133 | 0.651 | 22.835 | 35.592 |
| 1.00 | 13.85 | | | | | | | |
| ATOM | | 1022 | C | THR | 133 | 0.457 | 22.171 | 32.632 |
| 1.00 | 12.16 | | | | | | | |
| ATOM | | 1023 | O | THR | 133 | −0.628 | 22.577 | 32.176 |
| 1.00 | 12.10 | | | | | | | |
| ATOM | | 1024 | N | PHE | 134 | 0.737 | 20.871 | 32.678 |
| 1.00 | 12.04 | | | | | | | |
| ATOM | | 1025 | CA | PHE | 134 | −0.191 | 19.880 | 32.118 |
| 1.00 | 10.26 | | | | | | | |
| ATOM | | 1026 | CB | PHE | 134 | 0.014 | 19.753 | 30.593 |
| 1.00 | 9.74 | | | | | | | |
| ATOM | | 1027 | CG | PHE | 134 | 1.450 | 19.497 | 30.158 |
| 1.00 | 10.10 | | | | | | | |
| ATOM | | 1028 | CD1 | PHE | 134 | 2.345 | 20.538 | 30.021 |
| 1.00 | 9.16 | | | | | | | |
| ATOM | | 1029 | CD2 | PHE | 134 | 1.867 | 18.209 | 29.908 |
| 1.00 | 9.83 | | | | | | | |
| ATOM | | 1030 | CE1 | PHE | 134 | 3.652 | 20.313 | 29.647 |
| 1.00 | 10.74 | | | | | | | |
| ATOM | | 1031 | CE2 | PHE | 134 | 3.177 | 17.977 | 29.532 |
| 1.00 | 10.39 | | | | | | | |
| ATOM | | 1032 | CZ | PHE | 134 | 4.074 | 19.013 | 29.401 |
| 1.00 | 11.34 | | | | | | | |
| ATOM | | 1033 | C | PHE | 134 | 0.017 | 18.520 | 32.763 |
| 1.00 | 10.97 | | | | | | | |
| ATOM | | 1034 | O | PHE | 134 | 1.072 | 18.261 | 33.334 |
| 1.00 | 9.19 | | | | | | | |
| ATOM | | 1035 | N | TYR | 135 | −1.010 | 17.700 | 32.729 |
| 1.00 | 10.76 | | | | | | | |
| ATOM | | 1036 | CA | TYR | 135 | −0.896 | 16.327 | 33.212 |
| 1.00 | 11.10 | | | | | | | |
| ATOM | | 1037 | CB | TYR | 135 | −2.247 | 15.786 | 33.699 |
| 1.00 | 11.88 | | | | | | | |
| ATOM | | 1038 | CG | TYR | 135 | −2.575 | 16.298 | 35.090 |
| 1.00 | 15.19 | | | | | | | |
| ATOM | | 1039 | CD1 | TYR | 135 | −1.816 | 15.890 | 36.171 |
| 1.00 | 17.24 | | | | | | | |
| ATOM | | 1040 | CE1 | TYR | 135 | −2.054 | 16.351 | 37.457 |
| 1.00 | 17.77 | | | | | | | |
| ATOM | | 1041 | CD2 | TYR | 135 | −3.607 | 17.183 | 35.298 |
| 1.00 | 17.57 | | | | | | | |
| ATOM | | 1042 | CE2 | TYR | 135 | −3.862 | 17.655 | 36.594 |
| 1.00 | 18.71 | | | | | | | |
| ATOM | | 1043 | CZ | TYR | 135 | −3.082 | 17.237 | 37.661 |

-continued

| | | | | | | | | Occ | B |
|---|---|---|---|---|---|---|---|---|---|
| ATOM | 1044 | OH | TYR | 135 | −3.300 | 17.720 | 38.949 | 1.00 | 18.40 |
| ATOM | 1045 | C | TYR | 135 | −0.420 | 15.448 | 32.070 | 1.00 | 21.11 |
| ATOM | 1046 | O | TYR | 135 | −0.785 | 15.621 | 30.892 | 1.00 | 11.69 |
| ATOM | 1047 | N | GLN | 136 | 0.343 | 14.419 | 32.467 | 1.00 | 9.54 |
| ATOM | 1048 | CA | GLN | 136 | 0.927 | 13.498 | 31.514 | 1.00 | 10.85 |
| ATOM | 1049 | CB | GLN | 136 | 2.404 | 13.687 | 31.779 | 1.00 | 10.50 |
| ATOM | 1050 | CG | GLN | 136 | 3.383 | 13.299 | 30.739 | 1.00 | 10.66 |
| ATOM | 1051 | CD | GLN | 136 | 4.796 | 13.457 | 31.286 | 1.00 | 11.87 |
| ATOM | 1052 | OE1 | GLN | 136 | 5.081 | 13.041 | 32.405 | 1.00 | 12.64 |
| ATOM | 1053 | NE2 | GLN | 136 | 5.779 | 13.990 | 30.586 | 1.00 | 14.21 |
| ATOM | 1054 | C | GLN | 136 | 0.324 | 12.109 | 31.805 | 1.00 | 13.11 |
| ATOM | 1055 | O | GLN | 136 | 0.386 | 11.631 | 32.935 | 1.00 | 10.27 |
| ATOM | 1056 | N | TYR | 137 | −0.377 | 11.467 | 30.878 | 1.00 | 8.17 |
| ATOM | 1057 | CA | TYR | 137 | −0.971 | 10.159 | 31.163 | 1.00 | 11.70 |
| ATOM | 1058 | CB | TYR | 137 | −2.397 | 10.001 | 30.623 | 1.00 | 12.76 |
| ATOM | 1059 | CG | TYR | 137 | −3.416 | 11.066 | 30.980 | 1.00 | 15.14 |
| ATOM | 1060 | CD1 | TYR | 137 | −3.310 | 11.813 | 32.136 | 1.00 | 17.31 |
| ATOM | 1061 | CE1 | TYR | 137 | −4.280 | 12.773 | 32.443 | 1.00 | 20.43 |
| ATOM | 1062 | CD2 | TYR | 137 | −4.483 | 11.262 | 30.111 | 1.00 | 22.42 |
| ATOM | 1063 | CE2 | TYR | 137 | −5.460 | 12.203 | 30.402 | 1.00 | 20.69 |
| ATOM | 1064 | CZ | TYR | 137 | −5.354 | 12.951 | 31.583 | 1.00 | 22.72 |
| ATOM | 1065 | OH | TYR | 137 | −6.404 | 13.809 | 31.984 | 1.00 | 23.68 |
| ATOM | 1066 | C | TYR | 137 | −0.113 | 9.085 | 30.487 | 1.00 | 26.30 |
| ATOM | 1067 | O | TYR | 137 | 0.402 | 9.271 | 29.361 | 1.00 | 13.36 |
| ATOM | 1068 | N | TRP | 138 | 0.043 | 7.923 | 31.137 | 1.00 | 14.35 |
| ATOM | 1069 | CA | TRP | 138 | 0.942 | 6.879 | 30.640 | 1.00 | 11.84 |
| ATOM | 1070 | CB | TRP | 138 | 2.273 | 6.810 | 31.444 | 1.00 | 8.71 |
| ATOM | 1071 | CG | TRP | 138 | 3.238 | 8.005 | 31.558 | 1.00 | 8.01 |
| ATOM | 1072 | CD2 | TRP | 138 | 4.474 | 8.150 | 30.977 | 1.00 | 8.31 |
| ATOM | 1073 | CE2 | TRP | 138 | 4.909 | 9.361 | 31.532 | 1.00 | 7.73 |
| ATOM | 1074 | CE3 | TRP | 138 | 5.287 | 7.474 | 30.094 | 1.00 | 8.67 |
| ATOM | 1075 | CD1 | TRP | 138 | 2.949 | 9.072 | 32.391 | 1.00 | 7.01 |
| ATOM | 1076 | NE1 | TRP | 138 | 3.986 | 9.872 | 32.348 | 1.00 | 9.63 |
| ATOM | 1077 | CZ2 | TRP | 138 | 6.134 | 9.919 | 31.237 | 1.00 | 9.33 |
| ATOM | 1078 | CZ3 | TRP | 138 | 6.516 | 8.026 | 29.791 | 1.00 | 7.84 |
| ATOM | 1079 | CH2 | TRP | 138 | 6.935 | 9.224 | 30.349 | 1.00 | 9.01 |
| ATOM | 1080 | C | TRP | 138 | 0.270 | 5.502 | 30.768 | 1.00 | 8.58 |
| ATOM | 1081 | O | TRP | 138 | −0.484 | 5.232 | 31.709 | 1.00 | 9.46 |
| ATOM | 1082 | N | SER | 139 | 0.417 | 4.664 | 29.751 | 1.00 | 8.88 |
| ATOM | 1083 | CA | SER | 139 | 0.116 | 3.213 | 29.806 | 1.00 | 11.22 |
| ATOM | 1084 | CB | SER | 139 | −0.762 | 2.735 | 28.692 | 1.00 | 11.52 |

| | | | | | | | |
|---|---|---|---|---|---|---|---|
| 1.00 | 11.35 | | | | | | |
| ATOM | | 1085 | OG | SER | 139 | −2.138 | 2.978 | 28.917 |
| 1.00 | 13.26 | | | | | | |
| ATOM | | 1086 | C | SER | 139 | 1.477 | 2.565 | 29.547 |
| 1.00 | 10.74 | | | | | | |
| ATOM | | 1087 | O | SER | 139 | 2.063 | 2.824 | 28.486 |
| 1.00 | 11.43 | | | | | | |
| ATOM | | 1088 | N | VAL | 140 | 2.027 | 1.780 | 30.460 |
| 1.00 | 9.74 | | | | | | |
| ATOM | | 1089 | CA | VAL | 140 | 3.306 | 1.139 | 30.256 |
| 1.00 | 9.29 | | | | | | |
| ATOM | | 1090 | CB | VAL | 140 | 4.191 | 1.381 | 31.514 |
| 1.00 | 9.45 | | | | | | |
| ATOM | | 1091 | CG1 | VAL | 140 | 5.580 | 0.791 | 31.315 |
| 1.00 | 9.67 | | | | | | |
| ATOM | | 1092 | CG2 | VAL | 140 | 4.329 | 2.918 | 31.750 |
| 1.00 | 9.25 | | | | | | |
| ATOM | | 1093 | C | VAL | 140 | 3.057 | −0.352 | 30.005 |
| 1.00 | 9.37 | | | | | | |
| ATOM | | 1094 | O | VAL | 140 | 2.461 | −1.081 | 30.830 |
| 1.00 | 8.14 | | | | | | |
| ATOM | | 1095 | N | ARG | 141 | 3.521 | −0.782 | 28.835 |
| 1.00 | 10.69 | | | | | | |
| ATOM | | 1096 | CA | ARG | 141 | 3.404 | −2.199 | 28.443 |
| 1.00 | 11.96 | | | | | | |
| ATOM | | 1097 | CB | ARG | 141 | 3.757 | −2.391 | 26.945 |
| 1.00 | 11.92 | | | | | | |
| ATOM | | 1098 | CG | ARG | 141 | 3.431 | −3.843 | 26.522 |
| 1.00 | 12.57 | | | | | | |
| ATOM | | 1099 | CD | ARG | 141 | 3.684 | −4.280 | 25.085 |
| 1.00 | 11.72 | | | | | | |
| ATOM | | 1100 | NE | ARG | 141 | 2.351 | −4.384 | 24.581 |
| 1.00 | 15.48 | | | | | | |
| ATOM | | 1101 | CZ | ARG | 141 | 1.620 | −5.350 | 24.013 |
| 1.00 | 13.58 | | | | | | |
| ATOM | | 1102 | NH1 | ARG | 141 | 1.970 | −6.616 | 23.698 |
| 1.00 | 12.83 | | | | | | |
| ATOM | | 1103 | NH2 | ARG | 141 | 0.361 | −4.935 | 23.852 |
| 1.00 | 13.32 | | | | | | |
| ATOM | | 1104 | C | ARG | 141 | 4.314 | −3.116 | 29.302 |
| 1.00 | 9.52 | | | | | | |
| ATOM | | 1105 | O | ARG | 141 | 5.544 | −2.998 | 29.343 |
| 1.00 | 8.68 | | | | | | |
| ATOM | | 1106 | N | ARG | 142 | 3.671 | −4.076 | 30.002 |
| 1.00 | 10.19 | | | | | | |
| ATOM | | 1107 | CA | ARG | 142 | 4.421 | −5.006 | 30.855 |
| 1.00 | 10.06 | | | | | | |
| ATOM | | 1108 | CB | ARG | 142 | 3.456 | −5.843 | 31.649 |
| 1.00 | 9.21 | | | | | | |
| ATOM | | 1109 | CG | ARG | 142 | 2.846 | −5.061 | 32.777 |
| 1.00 | 9.22 | | | | | | |
| ATOM | | 1110 | CD | ARG | 142 | 2.254 | −5.997 | 33.780 |
| 1.00 | 8.97 | | | | | | |
| ATOM | | 1111 | NE | ARG | 142 | 1.440 | −5.256 | 34.689 |
| 1.00 | 8.70 | | | | | | |
| ATOM | | 1112 | CZ | ARG | 142 | 0.517 | −5.842 | 35.463 |
| 1.00 | 9.47 | | | | | | |
| ATOM | | 1113 | NH1 | ARG | 142 | 0.338 | −7.202 | 35.422 |
| 1.00 | 9.32 | | | | | | |
| ATOM | | 1114 | NH2 | ARG | 142 | −0.249 | −5.019 | 36.194 |
| 1.00 | 9.02 | | | | | | |
| ATOM | | 1115 | C | ARG | 142 | 5.337 | −5.888 | 30.030 |
| 1.00 | 9.64 | | | | | | |
| ATOM | | 1116 | O | ARG | 142 | 6.540 | −5.988 | 30.280 |
| 1.00 | 11.41 | | | | | | |
| ATOM | | 1117 | N | ASN | 143 | 4.786 | −6.349 | 28.929 |
| 1.00 | 9.44 | | | | | | |
| ATOM | | 1118 | CA | ASN | 143 | 5.490 | −7.214 | 27.997 |
| 1.00 | 11.07 | | | | | | |
| ATOM | | 1119 | CB | ASN | 143 | 4.523 | −8.194 | 27.420 |
| 1.00 | 15.18 | | | | | | |
| ATOM | | 1120 | CG | ASN | 143 | 4.798 | −9.487 | 28.077 |
| 1.00 | 19.83 | | | | | | |
| ATOM | | 1121 | OD1 | ASN | 143 | 4.354 | −9.693 | 29.224 |
| 1.00 | 21.43 | | | | | | |
| ATOM | | 1122 | ND2 | ASN | 143 | 5.589 | −10.295 | 27.336 |
| 1.00 | 21.58 | | | | | | |
| ATOM | | 1123 | C | ASN | 143 | 6.111 | −6.441 | 26.874 |
| 1.00 | 9.46 | | | | | | |
| ATOM | | 1124 | O | ASN | 143 | 5.418 | −6.281 | 25.886 |
| 1.00 | 7.69 | | | | | | |
| ATOM | | 1125 | N | HIS | 144 | 7.379 | −6.024 | 26.936 |

| | | | | | | | | |
|---|---|---|---|---|---|---|---|---|
| | | | | | | | 1.00 | 8.08 |
| ATOM | 1126 | CA | HIS | 144 | 7.902 | −5.078 | 25.959 | | |
| | | | | | | | 1.00 | 8.77 |
| ATOM | 1127 | CB | HIS | 144 | 9.257 | −4.577 | 26.418 | | |
| | | | | | | | 1.00 | 9.04 |
| ATOM | 1128 | CG | HIS | 144 | 9.304 | −3.876 | 27.793 | | |
| | | | | | | | 1.00 | 10.00 |
| ATOM | 1129 | CD2 | HIS | 144 | 10.469 | −3.373 | 28.345 | | |
| | | | | | | | 1.00 | 9.60 |
| ATOM | 1130 | ND1 | HIS | 144 | 8.353 | −3.647 | 28.706 | | |
| | | | | | | | 1.00 | 12.26 |
| ATOM | 1131 | CE1 | HIS | 144 | 8.904 | −3.055 | 29.762 | | |
| | | | | | | | 1.00 | 10.72 |
| ATOM | 1132 | NE2 | HIS | 144 | 10.191 | −2.893 | 29.533 | | |
| | | | | | | | 1.00 | 9.65 |
| ATOM | 1133 | C | HIS | 144 | 8.017 | −5.649 | 24.551 | | |
| | | | | | | | 1.00 | 11.38 |
| ATOM | 1134 | O | HIS | 144 | 8.203 | −6.861 | 24.375 | | |
| | | | | | | | 1.00 | 10.85 |
| ATOM | 1135 | N | ARG | 145 | 7.844 | −4.832 | 23.505 | | |
| | | | | | | | 1.00 | 10.56 |
| ATOM | 1136 | CA | ARG | 145 | 7.940 | −5.277 | 22.118 | | |
| | | | | | | | 1.00 | 9.42 |
| ATOM | 1137 | CB | ARG | 145 | 6.587 | −5.753 | 21.574 | | |
| | | | | | | | 1.00 | 8.54 |
| ATOM | 1138 | CG | ARG | 145 | 5.436 | −4.936 | 22.132 | | |
| | | | | | | | 1.00 | 9.46 |
| ATOM | 1139 | CD | ARG | 145 | 4.240 | −4.414 | 21.384 | | |
| | | | | | | | 1.00 | 10.47 |
| ATOM | 1140 | NE | ARG | 145 | 3.196 | −5.305 | 20.989 | | |
| | | | | | | | 1.00 | 8.83 |
| ATOM | 1141 | CZ | ARG | 145 | 1.931 | −4.970 | 20.643 | | |
| | | | | | | | 1.00 | 8.35 |
| ATOM | 1142 | NH1 | ARG | 145 | 1.339 | −3.775 | 20.631 | | |
| | | | | | | | 1.00 | 7.40 |
| ATOM | 1143 | NH2 | ARG | 145 | 1.255 | −5.917 | 20.002 | | |
| | | | | | | | 1.00 | 9.04 |
| ATOM | 1144 | C | ARG | 145 | 8.377 | −4.136 | 21.243 | | |
| | | | | | | | 1.00 | 9.13 |
| ATOM | 1145 | O | ARG | 145 | 8.135 | −2.979 | 21.592 | | |
| | | | | | | | 1.00 | 10.52 |
| ATOM | 1146 | N | SER | 146 | 8.954 | −4.467 | 20.093 | | |
| | | | | | | | 1.00 | 8.90 |
| ATOM | 1147 | CA | SER | 146 | 9.332 | −3.505 | 19.086 | | |
| | | | | | | | 1.00 | 9.55 |
| ATOM | 1148 | CB | SER | 146 | 10.781 | −3.760 | 18.716 | | |
| | | | | | | | 1.00 | 8.66 |
| ATOM | 1149 | OG | SER | 146 | 11.646 | −3.526 | 19.809 | | |
| | | | | | | | 1.00 | 10.90 |
| ATOM | 1150 | C | SER | 146 | 8.452 | −3.487 | 17.826 | | |
| | | | | | | | 1.00 | 9.89 |
| ATOM | 1151 | O | SER | 146 | 8.698 | −2.675 | 16.921 | | |
| | | | | | | | 1.00 | 11.00 |
| ATOM | 1152 | N | SER | 147 | 7.456 | −4.366 | 17.671 | | |
| | | | | | | | 1.00 | 9.25 |
| ATOM | 1153 | CA | SER | 147 | 6.519 | −4.300 | 16.562 | | |
| | | | | | | | 1.00 | 10.93 |
| ATOM | 1154 | CB | SER | 147 | 7.027 | −5.161 | 15.395 | | |
| | | | | | | | 1.00 | 13.60 |
| ATOM | 1155 | OG | SER | 147 | 7.396 | −6.472 | 15.843 | | |
| | | | | | | | 1.00 | 17.36 |
| ATOM | 1156 | C | SER | 147 | 5.134 | −4.781 | 16.995 | | |
| | | | | | | | 1.00 | 10.10 |
| ATOM | 1157 | O | SER | 147 | 5.045 | −5.529 | 17.975 | | |
| | | | | | | | 1.00 | 11.84 |
| ATOM | 1158 | N | GLY | 148 | 4.025 | −4.387 | 16.384 | | |
| | | | | | | | 1.00 | 9.36 |
| ATOM | 1159 | CA | GLY | 148 | 2.718 | −4.855 | 16.790 | | |
| | | | | | | | 1.00 | 8.24 |
| ATOM | 1160 | C | GLY | 148 | 1.658 | −3.894 | 16.327 | | |
| | | | | | | | 1.00 | 8.56 |
| ATOM | 1161 | O | GLY | 148 | 1.885 | −3.108 | 15.405 | | |
| | | | | | | | 1.00 | 10.71 |
| ATOM | 1162 | N | SER | 149 | 0.482 | −3.983 | 16.909 | | |
| | | | | | | | 1.00 | 9.40 |
| ATOM | 1163 | CA | SER | 149 | −0.602 | −3.056 | 16.648 | | |
| | | | | | | | 1.00 | 10.95 |
| ATOM | 1164 | CB | SER | 149 | −1.780 | −3.739 | 16.037 | | |
| | | | | | | | 1.00 | 12.62 |
| ATOM | 1165 | OG | SER | 149 | −1.203 | −4.402 | 14.925 | | |
| | | | | | | | 1.00 | 20.18 |
| ATOM | 1166 | C | SER | 149 | −1.039 | −2.529 | 18.002 | | |

| | | | | | | | | |
|---|---|---|---|---|---|---|---|---|
| 1.00 | 11.07 | | | | | | | |
| ATOM | | 1167 | O | SER | 149 | −0.827 | −3.223 | 19.016 |
| 1.00 | 10.99 | | | | | | | |
| ATOM | | 1168 | N | VAL | 150 | −1.551 | −1.292 | 18.042 |
| 1.00 | 10.64 | | | | | | | |
| ATOM | | 1169 | CA | VAL | 150 | −2.081 | −0.728 | 19.273 |
| 1.00 | 10.28 | | | | | | | |
| ATOM | | 1170 | CB | VAL | 150 | −1.224 | 0.457 | 19.813 |
| 1.00 | 10.28 | | | | | | | |
| ATOM | | 1171 | CG1 | VAL | 150 | −1.893 | 1.108 | 20.981 |
| 1.00 | 8.88 | | | | | | | |
| ATOM | | 1172 | CG2 | VAL | 150 | 0.152 | −0.067 | 20.216 |
| 1.00 | 10.04 | | | | | | | |
| ATOM | | 1173 | C | VAL | 150 | −3.475 | −0.217 | 18.919 |
| 1.00 | 11.39 | | | | | | | |
| ATOM | | 1174 | O | VAL | 150 | −3.657 | 0.510 | 17.936 |
| 1.00 | 11.90 | | | | | | | |
| ATOM | | 1175 | N | ASN | 151 | −4.456 | −0.661 | 19.661 |
| 1.00 | 11.61 | | | | | | | |
| ATOM | | 1176 | CA | ASN | 151 | −5.782 | −0.144 | 19.539 |
| 1.00 | 13.38 | | | | | | | |
| ATOM | | 1177 | CB | ASN | 151 | −6.745 | −1.312 | 19.809 |
| 1.00 | 15.35 | | | | | | | |
| ATOM | | 1178 | CG | ASN | 151 | −8.191 | −0.831 | 19.729 |
| 1.00 | 19.10 | | | | | | | |
| ATOM | | 1179 | OD1 | ASN | 151 | −8.500 | 0.361 | 19.505 |
| 1.00 | 21.76 | | | | | | | |
| ATOM | | 1180 | ND2 | ASN | 151 | −9.156 | −1.690 | 20.022 |
| 1.00 | 19.23 | | | | | | | |
| ATOM | | 1181 | C | ASN | 151 | −5.885 | 1.011 | 20.561 |
| 1.00 | 13.32 | | | | | | | |
| ATOM | | 1182 | O | ASN | 151 | −6.102 | 0.814 | 21.778 |
| 1.00 | 13.06 | | | | | | | |
| ATOM | | 1183 | N | THR | 152 | −5.744 | 2.285 | 20.109 |
| 1.00 | 12.70 | | | | | | | |
| ATOM | | 1184 | CA | THR | 152 | −5.670 | 3.429 | 21.041 |
| 1.00 | 10.80 | | | | | | | |
| ATOM | | 1185 | CB | THR | 152 | −5.402 | 4.741 | 20.273 |
| 1.00 | 9.08 | | | | | | | |
| ATOM | | 1186 | OG1 | THR | 152 | −6.506 | 5.026 | 19.423 |
| 1.00 | 9.66 | | | | | | | |
| ATOM | | 1187 | CG2 | THR | 152 | −4.107 | 4.646 | 19.511 |
| 1.00 | 8.63 | | | | | | | |
| ATOM | | 1188 | C | THR | 152 | −6.908 | 3.610 | 21.922 |
| 1.00 | 12.10 | | | | | | | |
| ATOM | | 1189 | O | THR | 152 | −6.824 | 3.983 | 23.109 |
| 1.00 | 12.41 | | | | | | | |
| ATOM | | 1190 | N | ALA | 153 | −8.062 | 3.223 | 21.362 |
| 1.00 | 12.52 | | | | | | | |
| ATOM | | 1191 | CA | ALA | 153 | −9.365 | 3.291 | 22.021 |
| 1.00 | 13.18 | | | | | | | |
| ATOM | | 1192 | CB | ALA | 153 | −10.422 | 2.571 | 21.212 |
| 1.00 | 14.11 | | | | | | | |
| ATOM | | 1193 | C | AIA | 153 | −9.390 | 2.663 | 23.410 |
| 1.00 | 13.55 | | | | | | | |
| ATOM | | 1194 | O | AIA | 153 | −9.868 | 3.237 | 24.389 |
| 1.00 | 11.50 | | | | | | | |
| ATOM | | 1195 | N | ASN | 154 | −8.688 | 1.526 | 23.512 |
| 1.00 | 13.78 | | | | | | | |
| ATOM | | 1196 | CA | ASN | 154 | −8.642 | 0.814 | 24.781 |
| 1.00 | 13.58 | | | | | | | |
| ATOM | | 1197 | CB | ASN | 154 | −7.924 | −0.499 | 24.613 |
| 1.00 | 14.46 | | | | | | | |
| ATOM | | 1198 | CG | ASN | 154 | −8.774 | −1.450 | 23.787 |
| 1.00 | 15.29 | | | | | | | |
| ATOM | | 1199 | OD1 | ASN | 154 | −8.242 | −2.299 | 23.070 |
| 1.00 | 16.38 | | | | | | | |
| ATOM | | 1200 | ND2 | ASN | 154 | −10.098 | −1.363 | 23.743 |
| 1.00 | 15.71 | | | | | | | |
| ATOM | | 1201 | C | ASN | 154 | −7.982 | 1.583 | 25.887 |
| 1.00 | 13.14 | | | | | | | |
| ATOM | | 1202 | O | ASN | 154 | −8.449 | 1.613 | 27.026 |
| 1.00 | 12.59 | | | | | | | |
| ATOM | | 1203 | N | HIS | 155 | −6.889 | 2.234 | 25.498 |
| 1.00 | 12.89 | | | | | | | |
| ATOM | | 1204 | CA | HIS | 155 | −6.134 | 3.043 | 26.440 |
| 1.00 | 13.28 | | | | | | | |
| ATOM | | 1205 | CB | HIS | 155 | −4.802 | 3.434 | 25.858 |
| 1.00 | 12.80 | | | | | | | |
| ATOM | | 1206 | CG | HIS | 155 | −3.934 | 2.210 | 25.718 |
| 1.00 | 11.42 | | | | | | | |
| ATOM | | 1207 | CD2 | HIS | 155 | −3.836 | 1.416 | 24.591 |

| | | | | | | | | |
|---|---|---|---|---|---|---|---|---|
| ATOM | 1208 | ND1 | HIS | 155 | −3.200 | 1.700 | 26.674 | 1.00 10.81 |
| ATOM | 1209 | CE1 | HIS | 155 | −2.651 | 0.622 | 26.199 | 1.00 9.77 |
| ATOM | 1210 | NE2 | HIS | 155 | −3.033 | 0.454 | 24.962 | 1.00 9.97 |
| ATOM | 1211 | C | HIS | 155 | −6.908 | 4.318 | 26.755 | 1.00 11.54 |
| ATOM | 1212 | O | HIS | 155 | −7.062 | 4.658 | 27.932 | 1.00 13.91 |
| ATOM | 1213 | N | PHE | 156 | −7.439 | 5.021 | 25.752 | 1.00 14.83 |
| ATOM | 1214 | CA | PHE | 156 | −8.141 | 6.257 | 26.072 | 1.00 14.01 |
| ATOM | 1215 | CB | PHE | 156 | −8.592 | 6.997 | 24.827 | 1.00 14.84 |
| ATOM | 1216 | CG | PHE | 156 | −7.473 | 7.369 | 23.896 | 1.00 14.21 |
| ATOM | 1217 | CD1 | PHE | 156 | −6.201 | 7.640 | 24.371 | 1.00 14.75 |
| ATOM | 1218 | CD2 | PHE | 156 | −7.723 | 7.428 | 22.544 | 1.00 16.50 |
| ATOM | 1219 | CE1 | PHE | 156 | −5.187 | 7.970 | 23.480 | 1.00 15.81 |
| ATOM | 1220 | CE2 | PHE | 156 | −6.705 | 7.762 | 21.658 | 1.00 16.11 |
| ATOM | 1221 | CZ | PHE | 156 | −5.435 | 8.039 | 22.124 | 1.00 15.84 |
| ATOM | 1222 | C | PHE | 156 | −9.382 | 5.954 | 26.906 | 1.00 15.88 |
| ATOM | 1223 | O | PHE | 156 | −9.769 | 6.777 | 27.733 | 1.00 15.07 |
| ATOM | 1224 | N | ASN | 157 | −9.998 | 4.775 | 26.741 | 1.00 14.39 |
| ATOM | 1225 | CA | ASN | 157 | −11.188 | 4.463 | 27.487 | 1.00 15.95 |
| ATOM | 1226 | CB | ASN | 157 | −11.947 | 3.247 | 26.911 | 1.00 16.78 |
| ATOM | 1227 | CG | ASN | 157 | −12.692 | 3.666 | 25.658 | 1.00 19.91 |
| ATOM | 1228 | OD1 | ASN | 157 | −12.844 | 2.871 | 24.723 | 1.00 21.97 |
| ATOM | 1229 | ND2 | ASN | 157 | −13.152 | 4.918 | 25.484 | 1.00 23.02 |
| ATOM | 1230 | C | ASN | 157 | −10.865 | 4.175 | 28.900 | 1.00 22.77 |
| ATOM | 1231 | O | ASN | 157 | −11.579 | 4.674 | 29.773 | 1.00 16.15 |
| ATOM | 1232 | N | AlA | 158 | −9.781 | 3.426 | 29.138 | 1.00 16.04 |
| ATOM | 1233 | CA | ALA | 158 | −9.319 | 3.129 | 30.494 | 1.00 16.31 |
| ATOM | 1234 | CB | ALA | 158 | −8.057 | 2.270 | 30.451 | 1.00 15.97 |
| ATOM | 1235 | C | ALA | 158 | −8.968 | 4.411 | 31.265 | 1.00 16.14 |
| ATOM | 1236 | O | ALA | 158 | −9.334 | 4.645 | 32.446 | 1.00 15.64 |
| ATOM | 1237 | N | TRP | 159 | −8.223 | 5.257 | 30.544 | 1.00 15.58 |
| ATOM | 1238 | CA | TRP | 159 | −7.821 | 6.552 | 31.114 | 1.00 15.76 |
| ATOM | 1239 | CB | TRP | 159 | −6.966 | 7.314 | 30.077 | 1.00 15.15 |
| ATOM | 1240 | CG | TRP | 159 | −5.581 | 6.715 | 29.752 | 1.00 14.73 |
| ATOM | 1241 | CD2 | TRP | 159 | −4.763 | 7.058 | 28.689 | 1.00 15.51 |
| ATOM | 1242 | CE2 | TRP | 159 | −3.698 | 6.146 | 28.818 | 1.00 15.24 |
| ATOM | 1243 | CE3 | TRP | 159 | −4.769 | 7.967 | 27.653 | 1.00 15.37 |
| ATOM | 1244 | CD1 | TRP | 159 | −5.023 | 5.673 | 30.479 | 1.00 14.42 |
| ATOM | 1245 | NE1 | TRP | 159 | −3.886 | 5.350 | 29.897 | 1.00 16.38 |
| ATOM | 1246 | CZ2 | TRP | 159 | −2.648 | 6.129 | 27.922 | 1.00 14.73 |
| ATOM | 1247 | CZ3 | TRP | 159 | −3.718 | 7.949 | 26.765 | 1.00 12.93 |
| ATOM | 1248 | CH2 | TRP | 159 | −2.678 | 7.043 | 26.901 | 1.00 14.15 |

-continued

| | | | | | | | |
|---|---|---|---|---|---|---|---|
| 1.00 | 14.30 | | | | | | |
| ATOM | | 1249 | C | TRP | 159 | −9.063 | 7.367 | 31.526 |
| 1.00 | 14.08 | | | | | | |
| ATOM | | 1250 | O | TRP | 159 | −9.173 | 7.852 | 32.677 |
| 1.00 | 13.42 | | | | | | |
| ATOM | | 1251 | N | ALA | 160 | −10.062 | 7.392 | 30.651 |
| 1.00 | 13.53 | | | | | | |
| ATOM | | 1252 | CA | ALA | 160 | −11.307 | 8.092 | 30.906 |
| 1.00 | 15.69 | | | | | | |
| ATOM | | 1253 | CB | ALA | 160 | −12.248 | 7.868 | 29.726 |
| 1.00 | 16.17 | | | | | | |
| ATOM | | 1254 | C | ALA | 160 | −12.001 | 7.663 | 32.188 |
| 1.00 | 17.30 | | | | | | |
| ATOM | | 1255 | O | ALA | 160 | −12.385 | 8.505 | 33.015 |
| 1.00 | 16.76 | | | | | | |
| ATOM | | 1256 | N | SER | 161 | −12.076 | 6.354 | 32.474 |
| 1.00 | 19.40 | | | | | | |
| ATOM | | 1257 | CA | SER | 161 | −12.799 | 5.887 | 33.642 |
| 1.00 | 21.24 | | | | | | |
| ATOM | | 1258 | CB | SER | 161 | −13.287 | 4.489 | 33.431 |
| 1.00 | 21.88 | | | | | | |
| ATOM | | 1259 | OG | SER | 161 | −12.407 | 3.847 | 32.515 |
| 1.00 | 24.44 | | | | | | |
| ATOM | | 1260 | C | SER | 161 | −11.964 | 5.918 | 34.877 |
| 1.00 | 21.71 | | | | | | |
| ATOM | | 1261 | O | SER | 161 | −12.392 | 5.514 | 35.946 |
| 1.00 | 24.49 | | | | | | |
| ATOM | | 1262 | N | HIS | 162 | −10.712 | 6.282 | 34.759 |
| 1.00 | 23.09 | | | | | | |
| ATOM | | 1263 | CA | HIS | 162 | −9.899 | 6.476 | 35.932 |
| 1.00 | 24.28 | | | | | | |
| ATOM | | 1264 | CB | HIS | 162 | −8.462 | 5.957 | 35.756 |
| 1.00 | 26.20 | | | | | | |
| ATOM | | 1265 | CG | HIS | 162 | −8.372 | 4.525 | 36.263 |
| 1.00 | 27.93 | | | | | | |
| ATOM | | 1266 | CD2 | HIS | 162 | −8.372 | 3.431 | 35.418 |
| 1.00 | 29.19 | | | | | | |
| ATOM | | 1267 | ND1 | HIS | 162 | −8.356 | 4.063 | 37.523 |
| 1.00 | 27.81 | | | | | | |
| ATOM | | 1268 | CE1 | HIS | 162 | −8.362 | 2.734 | 37.460 |
| 1.00 | 29.60 | | | | | | |
| ATOM | | 1269 | NE2 | HIS | 162 | −8.366 | 2.358 | 36.196 |
| 1.00 | 30.08 | | | | | | |
| ATOM | | 1270 | C | HIS | 162 | −9.870 | 7.965 | 36.145 |
| 1.00 | 24.43 | | | | | | |
| ATOM | | 1271 | O | HIS | 162 | −9.187 | 8.427 | 37.059 |
| 1.00 | 25.01 | | | | | | |
| ATOM | | 1272 | N | GLY | 163 | −10.594 | 8.702 | 35.302 |
| 1.00 | 24.39 | | | | | | |
| ATOM | | 1273 | CA | GLY | 163 | −10.836 | 10.108 | 35.509 |
| 1.00 | 24.50 | | | | | | |
| ATOM | | 1274 | C | GLY | 163 | −9.860 | 10.930 | 34.735 |
| 1.00 | 26.12 | | | | | | |
| ATOM | | 1275 | O | GLY | 163 | −9.693 | 12.118 | 35.003 |
| 1.00 | 27.42 | | | | | | |
| ATOM | | 1276 | N | LEU | 164 | −9.231 | 10.416 | 33.695 |
| 1.00 | 26.82 | | | | | | |
| ATOM | | 1277 | CA | LEU | 164 | −8.277 | 11.191 | 32.910 |
| 1.00 | 27.23 | | | | | | |
| ATOM | | 1278 | CB | LEU | 164 | −7.044 | 10.365 | 32.732 |
| 1.00 | 28.71 | | | | | | |
| ATOM | | 1279 | CG | LEU | 164 | −5.870 | 10.394 | 33.748 |
| 1.00 | 28.96 | | | | | | |
| ATOM | | 1280 | CD1 | LEU | 164 | −6.313 | 10.578 | 35.218 |
| 1.00 | 29.11 | | | | | | |
| ATOM | | 1281 | CD2 | LEU | 164 | −5.109 | 9.096 | 33.505 |
| 1.00 | 29.11 | | | | | | |
| ATOM | | 1282 | C | LEU | 164 | −8.824 | 11.631 | 31.569 |
| 1.00 | 27.74 | | | | | | |
| ATOM | | 1283 | O | LEU | 164 | −8.570 | 11.052 | 30.519 |
| 1.00 | 27.52 | | | | | | |
| ATOM | | 1284 | N | THR | 165 | −9.577 | 12.737 | 31.598 |
| 1.00 | 29.28 | | | | | | |
| ATOM | | 1285 | CA | THR | 165 | −10.232 | 13.318 | 30.432 |
| 1.00 | 29.12 | | | | | | |
| ATOM | | 1286 | CB | THR | 165 | −11.074 | 14.530 | 30.985 |
| 1.00 | 30.69 | | | | | | |
| ATOM | | 1287 | OG1 | THR | 165 | −11.760 | 15.097 | 29.861 |
| 1.00 | 31.47 | | | | | | |
| ATOM | | 1288 | CG2 | THR | 165 | −10.227 | 15.686 | 31.634 |
| 1.00 | 30.40 | | | | | | |
| ATOM | | 1289 | C | THR | 165 | −9.218 | 13.719 | 29.337 |

-continued

| | | | | | | | | |
|---|---|---|---|---|---|---|---|---|
| ATOM | 1290 | O | THR | 165 | −8.017 | 13.858 | 29.623 | 1.00 28.99 |
| ATOM | 1291 | N | LEU | 166 | −9.641 | 13.898 | 28.072 | 1.00 29.54 |
| ATOM | 1292 | CA | LEU | 166 | −8.746 | 14.319 | 26.983 | 1.00 27.70 |
| ATOM | 1293 | CB | LEU | 166 | −8.422 | 13.284 | 25.835 | 1.00 27.24 |
| ATOM | 1294 | CG | LEU | 166 | −7.481 | 12.109 | 26.084 | 1.00 27.12 |
| ATOM | 1295 | CD1 | LEU | 166 | −7.435 | 11.307 | 24.774 | 1.00 27.81 |
| ATOM | 1296 | CD2 | LEU | 166 | −6.070 | 12.560 | 26.494 | 1.00 28.93 |
| ATOM | 1297 | C | LEU | 166 | −9.593 | 15.334 | 26.271 | 1.00 27.08 |
| ATOM | 1298 | O | LEU | 166 | −10.797 | 15.041 | 26.120 | 1.00 25.11 |
| ATOM | 1299 | N | GLY | 167 | −8.932 | 16.364 | 25.727 | 1.00 24.48 |
| ATOM | 1300 | CA | GLY | 167 | −9.610 | 17.412 | 24.968 | 1.00 23.38 |
| ATOM | 1301 | C | GLY | 167 | −9.629 | 17.078 | 23.482 | 1.00 21.60 |
| ATOM | 1302 | O | GLY | 167 | −9.760 | 15.889 | 23.095 | 1.00 21.20 |
| ATOM | 1303 | N | THR | 168 | −9.432 | 18.098 | 22.645 | 1.00 22.34 |
| ATOM | 1304 | CA | THR | 168 | −9.390 | 17.997 | 21.191 | 1.00 19.20 |
| ATOM | 1305 | CB | THR | 168 | −9.760 | 19.453 | 20.735 | 1.00 17.79 |
| ATOM | 1306 | OG1 | THR | 168 | −10.323 | 19.282 | 19.441 | 1.00 19.15 |
| ATOM | 1307 | CG2 | THR | 168 | −8.613 | 20.458 | 20.690 | 1.00 21.89 |
| ATOM | 1308 | C | THR | 168 | −7.986 | 17.461 | 20.832 | 1.00 18.08 |
| ATOM | 1309 | O | THR | 168 | −6.987 | 17.903 | 21.384 | 1.00 15.71 |
| ATOM | 1310 | N | MET | 169 | −7.843 | 16.481 | 19.953 | 1.00 14.65 |
| ATOM | 1311 | CA | MET | 169 | −6.576 | 15.814 | 19.662 | 1.00 14.44 |
| ATOM | 1312 | CB | MET | 169 | −6.836 | 14.483 | 18.935 | 1.00 14.83 |
| ATOM | 1313 | CG | MET | 169 | −7.727 | 13.517 | 19.684 | 1.00 15.04 |
| ATOM | 1314 | SD | MET | 169 | −7.005 | 13.060 | 21.275 | 1.00 16.43 |
| ATOM | 1315 | CE | MET | 169 | −6.344 | 11.447 | 20.893 | 1.00 20.33 |
| ATOM | 1316 | C | MET | 169 | −5.637 | 16.648 | 18.797 | 1.00 18.80 |
| ATOM | 1317 | O | MET | 169 | −6.024 | 17.252 | 17.775 | 1.00 14.85 |
| ATOM | 1318 | N | ASP | 170 | −4.409 | 16.773 | 19.220 | 1.00 17.21 |
| ATOM | 1319 | CA | ASP | 170 | −3.401 | 17.330 | 18.307 | 1.00 13.83 |
| ATOM | 1320 | C | ASP | 170 | −2.670 | 16.197 | 17.581 | 1.00 13.73 |
| ATOM | 1321 | O | ASP | 170 | −3.383 | 15.283 | 17.156 | 1.00 10.96 |
| ATOM | 1322 | CB | ASP | 170 | −2.365 | 18.025 | 18.072 | 1.00 12.91 |
| ATOM | 1323 | CG | ASP | 170 | −1.803 | 19.443 | 18.160 | 1.00 14.89 |
| ATOM | 1324 | OD1 | ASP | 170 | −2.595 | 20.457 | 18.060 | 1.00 17.35 |
| ATOM | 1325 | OD2 | ASP | 170 | −0.538 | 19.626 | 18.333 | 1.00 20.00 |
| ATOM | 1326 | N | TYR | 171 | −1.371 | 16.150 | 17.418 | 1.00 20.00 |
| ATOM | 1327 | CA | TYR | 171 | −0.722 | 15.072 | 16.692 | 1.00 10.61 |
| ATOM | 1328 | CB | TYR | 171 | 0.658 | 15.560 | 16.280 | 1.00 11.47 |
| ATOM | 1329 | CG | TYR | 171 | 1.776 | 15.763 | 17.280 | 1.00 10.30 |
| ATOM | 1330 | CD1 | TYR | 171 | 2.416 | 14.672 | 17.876 | 1.00 10.95 |

-continued

| | | | | | | | | Occ | B |
|---|---|---|---|---|---|---|---|---|---|
| | | | | | | | | 1.00 | 11.20 |
| ATOM | 1331 | CE1 | TYR | 171 | 3.502 | 14.868 | 18.710 | 1.00 | 11.22 |
| ATOM | 1332 | CD2 | TYR | 171 | 2.214 | 17.053 | 17.525 | 1.00 | 10.25 |
| ATOM | 1333 | CE2 | TYR | 171 | 3.298 | 17.256 | 18.365 | 1.00 | 11.78 |
| ATOM | 1334 | CZ | TYR | 171 | 3.942 | 16.171 | 18.954 | 1.00 | 10.98 |
| ATOM | 1335 | OH | TYR | 171 | 5.018 | 16.389 | 19.792 | 1.00 | 9.29 |
| ATOM | 1336 | C | TYR | 171 | −0.664 | 13.748 | 17.485 | 1.00 | 11.01 |
| ATOM | 1337 | O | TYR | 171 | −0.816 | 13.794 | 18.713 | 1.00 | 10.53 |
| ATOM | 1338 | N | GLN | 172 | −0.495 | 12.610 | 16.787 | 1.00 | 10.87 |
| ATOM | 1339 | CA | GLN | 172 | −0.503 | 11.246 | 17.332 | 1.00 | 9.53 |
| ATOM | 1340 | CB | GLN | 172 | −1.889 | 10.738 | 17.176 | 1.00 | 10.18 |
| ATOM | 1341 | CG | GLN | 172 | −2.244 | 9.357 | 17.630 | 1.00 | 9.79 |
| ATOM | 1342 | CD | GLN | 172 | −3.732 | 9.052 | 17.489 | 1.00 | 9.76 |
| ATOM | 1343 | OE1 | GLN | 172 | −4.267 | 8.939 | 16.379 | 1.00 | 10.99 |
| ATOM | 1344 | NE2 | GLN | 172 | −4.460 | 8.919 | 18.599 | 1.00 | 9.74 |
| ATOM | 1345 | C | GLN | 172 | 0.492 | 10.523 | 16.436 | 1.00 | 8.72 |
| ATOM | 1346 | O | GLN | 172 | 0.248 | 10.353 | 15.235 | 1.00 | 9.11 |
| ATOM | 1347 | N | ILE | 173 | 1.605 | 10.159 | 17.064 | 1.00 | 6.96 |
| ATOM | 1348 | CA | ILE | 173 | 2.851 | 9.711 | 16.474 | 1.00 | 6.99 |
| ATOM | 1349 | CB | ILE | 173 | 3.719 | 11.020 | 16.654 | 1.00 | 9.21 |
| ATOM | 1350 | CG2 | ILE | 173 | 4.913 | 11.022 | 17.588 | 1.00 | 8.02 |
| ATOM | 1351 | CG1 | ILE | 173 | 4.058 | 11.318 | 15.266 | 1.00 | 10.65 |
| ATOM | 1352 | CD1 | ILE | 173 | 2.845 | 12.113 | 14.728 | 1.00 | 11.75 |
| ATOM | 1353 | C | ILE | 173 | 3.439 | 8.426 | 17.059 | 1.00 | 5.19 |
| ATOM | 1354 | O | ILE | 173 | 3.197 | 8.136 | 18.232 | 1.00 | 5.97 |
| ATOM | 1355 | N | VAL | 174 | 4.168 | 7.610 | 16.319 | 1.00 | 5.30 |
| ATOM | 1356 | CA | VAL | 174 | 4.915 | 6.536 | 16.939 | 1.00 | 5.81 |
| ATOM | 1357 | CB | VAL | 174 | 5.054 | 5.263 | 16.052 | 1.00 | 5.74 |
| ATOM | 1358 | CG1 | VAL | 174 | 6.070 | 4.324 | 16.682 | 1.00 | 6.61 |
| ATOM | 1359 | CG2 | VAL | 174 | 3.714 | 4.576 | 15.922 | 1.00 | 4.99 |
| ATOM | 1360 | C | VAL | 174 | 6.265 | 7.190 | 17.103 | 1.00 | 4.60 |
| ATOM | 1361 | O | VAL | 174 | 6.897 | 7.637 | 16.138 | 1.00 | 6.58 |
| ATOM | 1362 | N | ALA | 175 | 6.711 | 7.294 | 18.342 | 1.00 | 6.06 |
| ATOM | 1363 | CA | ALA | 175 | 7.916 | 8.061 | 18.607 | 1.00 | 4.93 |
| ATOM | 1364 | CB | ALA | 175 | 7.557 | 9.318 | 19.381 | 1.00 | 6.89 |
| ATOM | 1365 | C | ALA | 175 | 9.029 | 7.410 | 19.367 | 1.00 | 3.97 |
| ATOM | 1366 | O | ALA | 175 | 8.739 | 6.644 | 20.319 | 1.00 | 8.33 |
| ATOM | 1367 | N | VAL | 176 | 10.275 | 7.682 | 18.999 | 1.00 | 3.82 |
| ATOM | 1368 | CA | VAL | 176 | 11.309 | 7.278 | 19.902 | 1.00 | 6.89 |
| ATOM | 1369 | CB | VAL | 176 | 12.544 | 6.510 | 19.224 | 1.00 | 9.34 |
| ATOM | 1370 | CG1 | VAL | 176 | 11.996 | 5.545 | 18.180 | 1.00 | 7.08 |
| ATOM | 1371 | CG2 | VAL | 176 | 13.562 | 7.396 | 18.645 | | |

-continued

| | | | | | | | | |
|---|---|---|---|---|---|---|---|---|
| ATOM | 1372 | C | VAL | 176 | 11.770 | 8.574 | 20.585 | 1.00 10.56 |
| ATOM | 1373 | O | VAL | 176 | 11.913 | 9.639 | 19.970 | 1.00 8.28 |
| ATOM | 1374 | N | GLU | 177 | 11.846 | 8.510 | 21.912 | 1.00 7.87 |
| ATOM | 1375 | CA | GLU | 177 | 12.231 | 9.635 | 22.760 | 1.00 9.10 |
| ATOM | 1376 | CB | GLU | 177 | 11.195 | 9.842 | 23.821 | 1.00 8.39 |
| ATOM | 1377 | CG | GLU | 177 | 11.585 | 10.946 | 24.816 | 1.00 8.89 |
| ATOM | 1378 | CD | GLU | 177 | 10.463 | 11.616 | 25.586 | 1.00 10.47 |
| ATOM | 1379 | OE1 | GLU | 177 | 10.780 | 12.349 | 26.527 | 1.00 12.55 |
| ATOM | 1380 | OE2 | GLU | 177 | 9.286 | 11.451 | 25.259 | 1.00 14.06 |
| ATOM | 1381 | C | GLU | 177 | 13.517 | 9.156 | 23.393 | 1.00 11.52 |
| ATOM | 1382 | O | GLU | 177 | 13.565 | 7.957 | 23.766 | 1.00 9.30 |
| ATOM | 1383 | N | GLY | 178 | 14.506 | 10.044 | 23.506 | 1.00 10.91 |
| ATOM | 1384 | CA | GLY | 178 | 15.748 | 9.766 | 24.177 | 1.00 7.47 |
| ATOM | 1385 | C | GLY | 178 | 16.025 | 10.868 | 25.187 | 1.00 6.20 |
| ATOM | 1386 | O | GLY | 178 | 15.621 | 12.042 | 25.010 | 1.00 8.83 |
| ATOM | 1387 | N | TYR | 179 | 16.693 | 10.485 | 26.273 | 1.00 8.10 |
| ATOM | 1388 | CA | TYR | 179 | 17.120 | 11.392 | 27.288 | 1.00 7.84 |
| ATOM | 1389 | CB | TYR | 179 | 16.265 | 11.279 | 28.515 | 1.00 8.12 |
| ATOM | 1390 | CG | TYR | 179 | 16.568 | 12.436 | 29.468 | 1.00 8.58 |
| ATOM | 1391 | CD1 | TYR | 179 | 17.399 | 12.215 | 30.546 | 1.00 12.04 |
| ATOM | 1392 | CE1 | TYR | 179 | 17.723 | 13.240 | 31.395 | 1.00 12.92 |
| ATOM | 1393 | CD2 | TYR | 179 | 16.046 | 13.693 | 29.239 | 1.00 14.76 |
| ATOM | 1394 | CE2 | TYR | 179 | 16.363 | 14.734 | 30.096 | 1.00 12.66 |
| ATOM | 1395 | CZ | TYR | 179 | 17.202 | 14.485 | 31.159 | 1.00 14.65 |
| ATOM | 1396 | OH | TYR | 179 | 17.565 | 15.497 | 32.006 | 1.00 15.49 |
| ATOM | 1397 | C | TYR | 179 | 18.550 | 11.061 | 27.639 | 1.00 18.12 |
| ATOM | 1398 | O | TYR | 179 | 18.855 | 10.147 | 28.414 | 1.00 9.22 |
| ATOM | 1399 | N | PHE | 180 | 19.425 | 11.865 | 27.019 | 1.00 10.38 |
| ATOM | 1400 | CA | PHE | 180 | 20.844 | 11.857 | 27.265 | 1.00 8.36 |
| ATOM | 1401 | CB | PHE | 180 | 21.070 | 12.542 | 28.622 | 1.00 9.15 |
| ATOM | 1402 | CG | PHE | 180 | 20.877 | 14.060 | 28.563 | 1.00 9.13 |
| ATOM | 1403 | CD1 | PHE | 180 | 19.621 | 14.613 | 28.705 | 1.00 9.20 |
| ATOM | 1404 | CD2 | PHE | 180 | 21.983 | 14.868 | 28.362 | 1.00 9.46 |
| ATOM | 1405 | CE1 | PHE | 180 | 19.455 | 15.988 | 28.651 | 1.00 11.38 |
| ATOM | 1406 | CE2 | PHE | 180 | 21.829 | 16.257 | 28.304 | 1.00 10.39 |
| ATOM | 1407 | CZ | PHE | 180 | 20.563 | 16.793 | 28.449 | 1.00 10.50 |
| ATOM | 1408 | C | PHE | 180 | 21.464 | 10.460 | 27.223 | 1.00 10.79 |
| ATOM | 1409 | O | PHE | 180 | 22.029 | 9.956 | 28.189 | 1.00 10.10 |
| ATOM | 1410 | N | SER | 181 | 21.345 | 9.832 | 26.067 | 1.00 10.49 |
| ATOM | 1411 | CA | SER | 181 | 21.791 | 8.442 | 25.903 | 1.00 12.63 |
| ATOM | 1412 | CB | SER | 181 | 20.605 | 7.545 | 26.290 | 1.00 11.89 |

| | | | | | | | | | |
|---|---|---|---|---|---|---|---|---|---|
| ATOM | 1413 | OG | SER | 181 | 19.481 | 7.785 | 25.454 | 1.00 | 10.63 |
| ATOM | 1414 | C | SER | 181 | 22.261 | 8.187 | 24.458 | 1.00 | 9.90 |
| ATOM | 1415 | O | SER | 181 | 22.630 | 9.127 | 23.718 | 1.00 | 11.07 |
| ATOM | 1416 | N | SER | 182 | 22.284 | 6.908 | 24.101 | 1.00 | 10.95 |
| ATOM | 1417 | CA | SER | 182 | 22.600 | 6.513 | 22.769 | 1.00 | 8.87 |
| ATOM | 1418 | CB | SER | 182 | 24.021 | 6.016 | 22.725 | 1.00 | 9.70 |
| ATOM | 1419 | OG | SER | 182 | 24.934 | 7.051 | 23.106 | 1.00 | 8.44 |
| ATOM | 1420 | C | SER | 182 | 21.630 | 5.414 | 22.351 | 1.00 | 11.70 |
| ATOM | 1421 | O | SER | 182 | 20.985 | 4.798 | 23.214 | 1.00 | 8.32 |
| ATOM | 1422 | N | GLY | 183 | 21.467 | 5.216 | 21.045 | 1.00 | 8.91 |
| ATOM | 1423 | CA | GLY | 183 | 20.679 | 4.114 | 20.539 | 1.00 | 8.19 |
| ATOM | 1424 | C | GLY | 183 | 20.553 | 4.164 | 19.022 | 1.00 | 9.01 |
| ATOM | 1425 | O | GLY | 183 | 21.209 | 4.956 | 18.319 | 1.00 | 11.09 |
| ATOM | 1426 | N | SER | 184 | 19.610 | 3.365 | 18.544 | 1.00 | 11.68 |
| ATOM | 1427 | CA | SER | 184 | 19.353 | 3.151 | 17.133 | 1.00 | 11.79 |
| ATOM | 1428 | CB | SER | 184 | 20.242 | 2.035 | 16.632 | 1.00 | 11.40 |
| ATOM | 1429 | OG | SER | 184 | 20.580 | 2.124 | 15.275 | 1.00 | 11.41 |
| ATOM | 1430 | C | SER | 184 | 17.911 | 2.693 | 17.021 | 1.00 | 15.69 |
| ATOM | 1431 | O | SER | 184 | 17.446 | 1.896 | 17.852 | 1.00 | 10.12 |
| ATOM | 1432 | N | ALA | 185 | 17.201 | 3.136 | 16.005 | 1.00 | 11.52 |
| ATOM | 1433 | CA | ALA | 185 | 15.890 | 2.616 | 15.747 | 1.00 | 8.63 |
| ATOM | 1434 | CB | ALA | 185 | 14.812 | 3.279 | 16.605 | 1.00 | 6.71 |
| ATOM | 1435 | C | ALA | 185 | 15.548 | 2.893 | 14.307 | 1.00 | 5.28 |
| ATOM | 1436 | O | ALA | 185 | 15.852 | 3.971 | 13.757 | 1.00 | 8.30 |
| ATOM | 1437 | N | SER | 186 | 14.890 | 1.908 | 13.712 | 1.00 | 8.44 |
| ATOM | 1438 | CA | SER | 186 | 14.334 | 2.079 | 12.414 | 1.00 | 8.21 |
| ATOM | 1439 | CB | SER | 186 | 15.201 | 1.275 | 11.479 | 1.00 | 7.45 |
| ATOM | 1440 | OG | SER | 186 | 14.672 | 1.319 | 10.175 | 1.00 | 8.66 |
| ATOM | 1441 | C | SER | 186 | 12.886 | 1.622 | 12.514 | 1.00 | 8.84 |
| ATOM | 1442 | O | SER | 186 | 12.620 | 0.477 | 12.885 | 1.00 | 9.02 |
| ATOM | 1443 | N | ILE | 187 | 11.875 | 2.493 | 12.354 | 1.00 | 7.60 |
| ATOM | 1444 | CA | ILE | 187 | 10.517 | 2.013 | 12.471 | 1.00 | 8.36 |
| ATOM | 1445 | CB | ILE | 187 | 9.933 | 2.345 | 13.963 | 1.00 | 9.26 |
| ATOM | 1446 | CG2 | ILE | 187 | 11.001 | 2.794 | 14.977 | 1.00 | 12.57 |
| ATOM | 1447 | CG1 | ILE | 187 | 8.893 | 3.361 | 13.908 | 1.00 | 10.66 |
| ATOM | 1448 | CD1 | ILE | 187 | 7.616 | 2.580 | 14.124 | 1.00 | 11.46 |
| ATOM | 1449 | C | ILE | 187 | 9.623 | 2.516 | 11.337 | 1.00 | 12.68 |
| ATOM | 1450 | O | ILE | 187 | 9.873 | 3.551 | 10.672 | 1.00 | 9.78 |
| ATOM | 1451 | N | THR | 188 | 8.595 | 1.714 | 11.054 | 1.00 | 10.18 |
| ATOM | 1452 | CA | THR | 188 | 7.617 | 2.008 | 10.005 | 1.00 | 7.46 |
| ATOM | 1453 | CB | THR | 188 | 7.753 | 0.972 | 8.796 | 1.00 | 8.18 |

-continued

| ATOM | 1454 | OG1 | THR | 188 | 9.078 | 1.119 | 8.291 | 1.00 | 5.82 |
|------|------|-----|-----|-----|-------|-------|-------|------|------|
| ATOM | 1455 | CG2 | THR | 188 | 6.704 | 1.165 | 7.675 | 1.00 | 5.98 |
| ATOM | 1456 | C | THR | 188 | 6.218 | 1.951 | 10.610 | 1.00 | 6.88 |
| ATOM | 1457 | O | THR | 188 | 5.864 | 1.006 | 11.312 | 1.00 | 7.67 |
| ATOM | 1458 | N | VAL | 189 | 5.464 | 2.989 | 10.331 | 1.00 | 7.06 |
| ATOM | 1459 | CA | VAL | 189 | 4.104 | 3.196 | 10.803 | 1.00 | 9.10 |
| ATOM | 1460 | CB | VAL | 189 | 3.913 | 4.657 | 11.335 | 1.00 | 9.32 |
| ATOM | 1461 | CG1 | VAL | 189 | 2.554 | 4.764 | 11.989 | 1.00 | 9.82 |
| ATOM | 1462 | CG2 | VAL | 189 | 4.969 | 5.015 | 12.359 | 1.00 | 7.64 |
| ATOM | 1463 | C | VAL | 189 | 3.135 | 2.976 | 9.664 | 1.00 | 8.74 |
| ATOM | 1464 | O | VAL | 189 | 3.432 | 3.326 | 8.514 | 1.00 | 9.63 |
| ATOM | 1465 | N | SER | 190 | 1.967 | 2.498 | 10.032 | 1.00 | 10.99 |
| ATOM | 1466 | CA | SER | 190 | 0.853 | 2.346 | 9.138 | 1.00 | 13.10 |
| ATOM | 1467 | CB | SER | 190 | 0.966 | 1.065 | 8.258 | 1.00 | 15.33 |
| ATOM | 1468 | OG | SER | 190 | 1.169 | −0.182 | 8.908 | 1.00 | 15.84 |
| ATOM | 1469 | C | SER | 190 | −0.415 | 2.271 | 9.950 | 1.00 | 14.43 |
| ATOM | 1470 | O | SER | 190 | −1.439 | 2.580 | 9.354 | 1.00 | 17.68 |
| ATOM | 1471 | OXT | SER | 190 | −0.392 | 1.975 | 11.150 | 1.00 | 12.62 |

A portion of the three-dimensional crystal structure of a mutant of the B. circulans xylanase containing an intramolecular disulfide bond is shown in FIG. 4. In this mutant serine 100 and asparagine 148 have been mutated to cysteine. The disulfide which is formed links the last strand of sheet III to the alpha-helix. The structure of this mutant is identical to the wild-type enzyme except for the side chains of residues 100 and 148 and some very minor shifts of nearby atoms. The same region of the superimposed structures of the B. circulans and T. harzianum xylanases is shown in FIG. 5. Further details of the analyses will be provide in the examples, however, one can see that although there are some sequence differences between the B. circulans and T. harzianum xylanases near the site of the manufactured disulfide and some small position differences at other nearby residues, the structure of the T. harzianum xylanase is virtually identical to the structure of the B. circulans xylanase at the positions of the mutations. The sequence alignment (FIG. 1) shows that the sequence homology of the various xylanases in the vicinity of residues 98 to 100 and 148 to 152 is very good. One would therefore expect that the structures of other related xylanases would be similar enough that they could be modified with the introduction of an intramolecular disulfide bond linking sheet III to the alpha-helix and that this disulfide bond would stabilize them in a similar manner as taught in the present invention. For some xylanases with the lowest sequence homology to the B. circulans xylanase it may be necessary to make other mutations to increase the homology in the vicinity of the introduced intramolecular disulfide bond. In other words it may be necessary to make another xylanase more like the B. circulans xylanase before the disulfide bond could be formed successfully.

In the modification of family G xylanases, the B. circulans xylanase (BCX) was chosen to exemplify the principles of the present invention. This enzyme is only moderately thermostable at temperatures up to 55° C. For application of this enzyme in pretreatment of kraftpulp to enhance bleaching, a higher thermostability is desirable. A more thermostable enzyme for use in the food industry would also be of value.

The starting point for the present invention was the solution of the three-dimensional structure of the enzyme (FIG. 2). By inspection of the structure, a prediction of the residues, which could be mutated to cysteine, and which would possibly oxidize to form an intramolecular SS bridge was made. This was accomplished by searching for pairs of residues for which the inter-C-alpha distance was less than 6.6 Å and the inter-C-beta distance was less than 4.5 Å. If either member of the pair was a glycine this pair was ignored because glycines are important for the backbone conformation. Some candidates were excluded because they were involved in the active site of the enzyme. In addition the distance algorithm had selected pairs of residues which were too close, as they were on adjacent strands of one of the beta sheets.

Two areas for the introduction of a cysteine residue were selected. These areas are the beta-sheet III and the alpha-helix. Although the alpha-helix itself ranges from amino acids 147 to 155, some residues on either side could potentially be used to form intra-molecular disulfide linkages. Accordingly, the amino acids in the alpha-helix ranging from 143 to 158 and the amino acids on the beta-sheet III ranging from 95 to 109 are potential sites for the introduction of cysteine residues for the formation of an intra-molecular disulphide bond between these two areas. Two pairs of residues were found (details will be provided in the Examples) and the corresponding mutants were constructed, and in both cases the intramolecular SS bond formed spontaneously.

In addition to the intra-molecular SS bond mutant, a second type of disulfide mutant was constructed by joining two protein molecules with an inter-molecular SS bond. For the production of this type of disulfide bond, a cysteine is introduced in each of the two xylanase protein molecules such that the cysteine is on the exterior of the molecule, thus the two molecules can be joined by an inter-molecular disulphide bond. Potential sites of interest include amino acid 15 to 31 of the beta-sheet I; amino acid 43 to 61 of the beta-sheet I; amino acid 87 to 104 of the loop and beta-sheet III; amino acid 133 to 163 of the alpha-helix and surrounding loops; and amino acids 177 to 185 of the beta-sheet I.

A third type of mutant unrelated to SS bond formation has also been found to confer some thermostability. These mutants were generated by specific mutagenesis of amino acids at the N-terminus of the xylanase molecule. In one embodiment of the present invention, amino acids 1 to 8 of the xylanase protein are selected for specific mutagenesis. These mutations introduce aromatic amino acids substitutions and they add thermostability when compared to the wild type protein.

The selected amino acids referred to above are based on the amino acid sequence of the B. circulans xylanase sequence. The present invention is not limited to producing a thermostable xylanase from this bacterial source, but includes the production of a thermostable xylanase for other sources, as listed in Table 1 for example. The choice of suitable amino acids to target for mutagenesis in xylanases from other sources will be obvious to those skilled in the art by comparing the sequences and choosing the amino acids corresponding to those identified for the B. circulans xylanase.

In the present invention, the mutant xylanases showed enhanced thermostability of 2°-15° C., possessing specific activity of at least 60% of that of the wild-type, while simultaneously maintaining significant (at least 60%) residual activity after incubation at the elevated temperature.

The present invention will be further illustrated by way of the following examples, which are not to be construed as limiting. In these examples the xylanase mutants, which were constructed, are summarized in Table 2.

TABLE 2

| Xylanase Mutants | | |
|---|---|---|
| Name | Mutation | Type of Mutation |
| TS1 | S100C N148C | intra-molecular SS bond |
| TS2 | V98C A152C | intra-molecular SS bond |
| TS3a | D4Y N8F | N-terminal Mutation |
| TS3 | S100C N148C D4Y N8F | intra-molecular SS bond + N-terminal |
| TS4a | S179C dimer | inter-molecular SS bond |
| TS4 | S100C N148C S179C monomer/dimer mix | intra- + inter-molecular SS bond |
| TS4M | S100C N148C S179C monomer | intra-molecular SS bond |
| TS4D | S100C N148C S179C dimer | intra- + inter-molecular SS bond |
| TS5a | N8Y | N-terminal mutation |
| TS6a | T3G D4Y N8Y | N-terminal mutation |

EXAMPLE 1

Construction of the Mutant TS1

The gene encoding the B. subtilis xylanase (see FIG. 6), is identical to the B. circulans xylanase except at position 147, where a serine (BSX) rather than threonine (BCX) is encoded, (Yang et al, 1988, Nucleic Acid Research 16:7187 and Paice et al, 1986, Archives of Microbiology 144:201-206; all references incorporated herein by reference). The xylanase gene encoded by pBSX was mutated by the uracil containing DNA (UDNA) method (Kunkle et al, 1987, Methods in Enzymology, 154:367-382, which is incorporated herein by reference) to produce the mutant S100C. The coding sequence for this mutant gene was then removed from the vector using PCR. The 5' portion of the resulting PCR product (codons 1-103) was combined with a synthetic gene fragment from the B. circulans gene (codons 104-185) to produce the plasmid pCWBCX::S100C. The region containing codons 136-153 of pCWBCX::S100C was replaced with synthetic oligonucleotides to introduce the second cysteine codon at position 148 (N148C). The resultant plasmid contained the S100C and N148C mutations and was called TS1.

All liquid cultures in this and other Examples were grown in either 2YT medium (16 g yeast extract, 10 g bacto-tryptone, 5 g NaCl, 1 L of $H_2O$), or TB medium (24 g yeast extract, 12 g bacto-tryptone, 10 ml 1M potassium phosphate buffer pH 7.5, 5 ml of 80% glycerol, 1 L $H_2O$). The antibiotic ampicillin was added at 150 μg/ml to all cultures of plasmid containing strains. The cultures were grown with shaking at 30° C. for protein and plasmid production, and 37° C. for the production of single stranded DNA containing particles.

Basic recombinant DNA methods like plasmid DNA isolation, restriction enzyme digestions, the purification of DNA fragments for cloning, ligations, transformations and DNA sequencing were performed as recommended by the enzyme supplier, or the manufacturer of the kit used for the particular procedure. Polyacrylamide gel electrophorsis of proteins was performed as recommended in the technical literature supplied by Bio-Rad laboratories, Mississauga Ont. Restriction and DNA modification enzymes were purchased from New England Biolabs LTD., Mississauga Ont. Prep-A-Gene DNA purification matrix was purchased from Bio-Rad laboratories, Mississauga Ont. Sequenase, a DNA sequencing kit, was purchased from US Biochemicals, Cleveland Ohio. Oligonucleotide 3' end labelling was performed with a kit from Boehringer Mannheim Canada, Laval PQ. Protein concentration was determined from the molar extinction coefficient of the xylanase: 81,790 L. $mol^{-1}$.

A 2 ml culture of Escherichia coli RZ1032 (HfrKL16PO/45 [lysA(61–62)], dut1, ung1, thi1, relA1, Zbd-279::Tn10,SupE44) harbouring pBSX was grown at 37° C. with vigourous shaking until the $A_{600}$ reached 0.5, at which time 10 μl of the helper phage, M13KO7, (titre $1 \times 10^{12}$/ml), was added. After 1 h, 0.5 ml of the culture was subcultured into 20 ml of fresh media containing 50 μg kanamycin/ml, and 100 μg ampicillin/ml. This culture was shaken at 200 rpm for 16 h at 37° C. The supernatant containing the single stranded DNA containing particles (SSDNAP) was collected after centrifugation of the culture at 4° C. for 20 min. at $7000 \times g$. The SSDNAP were precipitated by the addition of ¼ volume of 15% PEG-8000/14.6% NaCl. After 30 min. at room temperature the precipitate was collected by centrifugation at $7000 \times g$ for 20 min. The precipitate was resuspended in 0.5 ml TE buffer (10 mM Tris—HCl, 1 mM EDTA, pH 8), and left on ice for 30 min. Any insoluble material was removed by a brief centrifugation in a microcentrifuge. The supernatant was made up to 1% acetic acid and the resultant precipitate was collected on a 1 cm glass fibre filter by suction filtration. Protein was removed from the precipitated SSDNAP'S, and the DNA bound to the filter by washing the filter under vacuum, with 2 ml of 4M $NaClO_4$ in TE buffer. Excess $NaClO_4$ was removed by washing the filter with 2 ml of ice cold 70% ethanol. The filter was allowed to air dry for 5 min. at room temperature. The filter was placed into a 500 μl microcentrifuge tube with a hole in the bottom. This tube was placed inside a 1.5 ml microcentrifuge tube. The single stranded DNA was eluted by the addition of 50 μl of 0.1 X TE buffer to the filter and after 5 min centrifuging the two tubes to recover the liquid in the larger tube. The elution step was repeated. The single stranded DNA was quantified by analysis on agarose gel electrophoresis.

Oligonucleotides were synthesized using an Applied Biosystems model 380B DNA synthesizer. Synthetic oligonucleotides were purified by polyacrylamide gel electrophoresis (PAGE) in 15% gels containing 7M urea. Oligonucleotides were detected by UV shadowing, cut out and eluted from the gel slices in 1 ml of 0.5M ammonium acetate, 10 mM magnesium acetate. The oligonucleotides were desalted by passage through a Sep-Pak C18 reverse phase cartridge (Atkinson and Smith, 1984, In: Oligonucleotide synthesis a practical approach. Gait, N. J., editor. IRL press, Washington). The oligonucleotides were eluted with 20 % acetonitrile, and the concentration was determined by reading the $A_{260}$ of the solution. For the production of S100C the following oligonucleotide was synthesized:

SEQ ID NO: 4
Codons 96  97  98  99  100 101 102 103 104
5'-GGT ACT GTA AAA <u>TGT</u> GAT GGG GGT ACA-3'

The oligonucleotide was phosphorylated for use in mutagenesis. 100 to 200 pmol of the oligonucleotide was mixed with 2 μl of 10× kinase buffer (500 mM Tris-HCl, pH 7.6, 100 mM $MgCl_2$, 100 mM dithiothreitol (DTT), 1.0 mM spermidine, 10 mM adenosine triphosphate (ATP)), and the volume was adjusted with water to a final volume of 20 μl. The reaction was initiated by the addition of 10 U of T4 polynucleotide kinase. The reaction was performed at 37° C. for 1 h, after which the reaction was terminated by heating at 70° C. for 10 min. Oligonucleotides prepared in this fashion were ready for use in the UDNA mutagenesis method.

The phosphorylated mutagenic oligonucleotide primer (20 pmol, 2 μl), was mixed with the ssUDNA (0.5 pmol, 7 μl); 1 μl of 10× DNA synthesis buffer (200 mM Tris-HCl, pH 7.5, 100 mM $MgCl_2$, 500 mM NaCl, 10 mM DTT). The DNA's were annealed by heating the mixture to 70° C., and then slowly cooled to room temperature. The mutagenesis reaction was then performed by the addition of 10 μl of the DNA synthesis mixture (1 μl 10× synthesis buffer (200 mM Tris-HCl, pH 7.5, 100 mM $MgCl_2$, 100 mM DTT), 1 μl 5 mM deoxynucleotide triphosphates (dNTPs), 1 μl 10 mM ATP, 6 μl $H_2O$, 1 μl, 5U, T4 DNA ligase, 0.25 μl, 2.5U, T7 DNA polymerase). The reaction mixture was kept on ice for 5 min, then at room temperature for 5 min., and finally incubated at 37° C. for 60 to 90 min. The reaction was terminated by the addition of 3 μl 50 mM EDTA. The reaction products were analyzed by standard agarose gel electrophoresis (Sambrook et al, 1989, Molecular cloning: A laboratory manual, 2nd edition). A 5 μl portion of this mixture was used to transform the E. coli strain MV1190 (deletion (lac-proAB), thi, supE44, deletion (srl-recA) 306::Tn10(tet$^r$) [F':traD36, proAB, lacI$^q$deletion M15]) or BHM 71-18 (deletion (lac-proAB), thi, supE44, [mutS::Tn10(tet$^r$)]).

After transformation the bacteria were plated onto solid media (2YT) containing 150 μg ampicillin/ml. Individual colonies were picked and transferred to a fresh plate in a grid pattern of 100 colonies per plate. After overnight growth at 37° C., the colonies were transferred to Hybond-N nylon filter membranes (Amersham, Canada, Oakville Ont.), the colonies were lysed, and the DNA fixed to these filters by well established procedures (Sambrook et al, 1989, Molecular cloning: a laboratory manual).

Oligonucleotide probes were synthesized using a 3' end labelling kit from Boehringer Mannheim. 100 pmol of oligonucleotide were dissolved in 4 μl $H_2O$. The reaction mixture was completed as follows: 4 μl of 5× tailing buffer (1M potassium cacodylate, 0.125M Tris-HCl, bovine serum albumin (BSA) 1.25 mg/ml, pH 6.6), 4 μl 25 mM $CoCl_2$, 1 μl 1 mM digoxigenin-dideoxyuracil triphosphate (DIG-ddUTP), 6 μl $H_2O$, 1 μl terminal transferase (50U). The mixture was reacted at 37° C. for 15 min., then 2 μl of glycogen was added (0.2 μg/μl in 0.2M EDTA). The labelled oligonucleotide was precipitated by the addition of 2.5 μl of 4M LiCl, and 75 μl of ice cold, $-20°$ C., 95% ethanol After 2 h at $-20°$ C. the precipitate was collected by centrifugation at 12,000 g for 30 min. The pellet was washed with 100 μl ice cold 70% ethanol, and then air dried in a fume hood.

The filters containing the colonies were washed free of cell debris in 2× SSC (SSC buffer is 0.15M NaCl, 0.015M sodium citrate, pH 7.0), 0.1% SDS, by gently rubbing the surface of the filter with a wet tissue. After removal of the cell debris, the filters were pre-hybridized in hybridization buffer (5× SSC, 0.1% SDS, 0.02% N-laurylsarkosine, 1% blocking reagent, a commercial product from Boehringer Mannheim), for at least 5 h. After the pre-hybridization, the DIG-labelled oligonucleotide was dissolved in 100 μl $H_2O$, and added to 7 ml of hybridization buffer. The hybridization buffer-DIG labelled oligonucleotide mixture was poured onto the filter and the hybridization was then performed in plastic petri dishes at 37° C., with shaking overnight. Excess (unbound) probe was removed by washing the filters twice for 10 min, each time, with 2× SSC, 0.1% SDS at room temperature. Non-specifically bound probe was removed by washing the filters at 40°

C. with 0.5×SSC, 0.1% SDS, again twice for 10 min each time.

The filters were then washed in 25 ml of M buffer (0.1M maleic acid, 0.15M NaCl, pH adjusted to 7.5 with concentrated NaOH). The filter was then incubated in 20 ml M buffer containing 1% blocking reagent for 30 min. at room temperature. The solution was then discarded and then further incubated with 10 ml of fresh M buffer with 1% blocking reagent and 750 mU of anti-DIG-alkaline phosphatase-conjugate antibody. After 30 min., the filter was washed with 3×20 ml washes of M buffer with 0.3% Tween 20. The filter was then equilibrated in alkaline phosphatase buffer (0.1M Tris-HCl, 0.1M NaCl, 0.05M $MgCl_2$ pH 9.5). The filter was then dipped in a solution of Lumi-phos, a chemiluminescent alkaline phosphatase substrate (Boehringer Mannheim). The filter was sealed into a plastic bag, and incubated at 37° C. for 30 min. The filter in the bag was then exposed to x-ray film for 5 to 60 min. Positive colonies were further characterized by DNA sequencing. The clone chosen for subsequent work contained plasmid pBSXS100C.

Removal of the mature coding sequence of the *B. subtilis* xylanase gene from its leader sequence was accomplished using PCR with specific primers. The primers were designed so that the resulting amplification product would contain a new NdeI restriction site to allow the precise fusion of the coding region to the transcriptional signals present in pCWori+. An XbaI site was introduced at the 3' end to facilitate cloning into pCWori+.

The plasmid pBSXS100C was digested with EcoRI to linearize it, and then it was used as a template for PCR. The amplification reaction contained, 15 µl of template DNA (50 ng), 5 µl of 10× buffer (100 mM KCl, 100 mM ammonium sulfate, 200 mM Tris-HCl pH 8.8, 40 mM magnesium sulfate, 1% Triton X100, 100 µg/ml BSA), 5 µl of 5 mM dNTPs, 2.5 µl 5' primer solution (25 pmol), 2.5 µl 3' primer solution (25 pmol), 19 µl $H_2O$, 1 µl (1U) Vent DNA polymerase (New England Biolabs). The 5' and 3' primers are shown below:

nase gene when cloned into pCWori+. The xylanase gene was cloned into pCWori+ in two steps. First the 3' portion, codons 105–185 (FIG. 6) was inserted as a 330 bp NdeI—XbaI fragment. This fragment was generated by digesting 200 ng of the PCR product with NdeI and XbaI, and then was purified from an agarose gel. 50 ng of this fragment was ligated with 50 ng of NdeI—XbaI digested and gel purified pCWori+. The clone, pCW3', was identified by hybridization using a probe made by random priming labelling (Sambrook et al, 1989, Molecular cloning: a laboratory manual), with DIG-dUTP, of 50 ng of the PCR product. The second step was to digest the PCR product with NdeI to generate a 318 bp fragment which encodes codons 1–104. After gel electrophoresis and purification, 50 ng of this fragment was ligated to 50 ng of NdeI digested pCW3'. The clones containing a functional xylanase gene were identified by screening transformants on plates containing remazo-brilliant blue xylan (RBBX). Those colonies which made halos, were expressing the gene for xylanase (Kluepfel, 1988, Methods in Enzymology, 154:367–382, which is incorporated herein by reference). This clone was called pCWBSX::S100C.

A version of the *B. circulans* xylanase gene was synthesized to aid in subsequent mutagenesis studies, using the first 103 codons of the natural gene, and 82 codons derived from synthetic DNA fragments (pCWBCX3'SYN, FIG. 7). The synthetic gene portion is identical to the natural gene except codons were used, which reflect the frequency of usage for specific amino acid residues in the genes of *E. coli*. The 103 codon portion was replaced with the equivalent portion from pCWBSX::S100C, by isolating the NheI-NdeI restriction fragment of pCWBSX::S1OOC and ligating it to NheI-NdeI digested pCWBCX3'SYN. After ligation, the mixture was transformed into *E. coli* MV1190. Clones were analyzed by DNA sequencing to verify they carried the S1OOC mutation. The resultant plasmid was called pCWBCX::S100C.

The plasmid pCWBCX::S100C was purified and digested with the restriction enzymes EagI and NsiI to remove the portion encoding codons 136 to 153. The SEQ ID NO: 5
```
                   NdeI site
5' BSYSL GC CTG CAG CAT ATG GCT AGC ACA GAC TAC TGG CAA AAT TGG A
```

SEQ ID NO: 6
```
                   XbaI site
3' BSXYL GC AAG CTT TCT AGA CTT TAA CCA TTA CTA ACG ATT TTA ATA ATC
```

The reaction was covered with 50 µl of paraffin oil to prevent evaporation. The reaction mixture was pre-warmed to 94° C. without enzyme for 5 min., then the reaction mixture was cooled to 72° C., then the enzyme was added. The reaction was incubated in a temperature cycler for 30 cycles of 94° C. 1 min., 55° C. 2 min., 72° C. for 2 min. The yield of amplification product was approximately 1 µg of a 700 bp fragment. This fragment was purified from an agarose gel.

The resulting PCR product had an introduced NdeI site at the 5' end to provide a start codon for the xylalarge plasmid fragment was isolated from an agarose gel as described above. A set of synthetic oligonucleotides: Xyl146C TOP (SEQ ID NO:7); Xyl147C BOTTOM (SEQ ID NO:8) and Xyl148C BOTTOM (SEQ ID NO:9) (as shown below) was synthesized to replace the EagI to NsiI fragment these oligonucleotides encoded the mutations at F146C, T147C, and N148C.

```
      EagI                                                    NsiI
      137 138 139 140 141 142 143 144 145 146 147 148 149 150 151 152
      GG  CCG ACT GGT TCG AAC GCC ACC ATC ACT TGC ACT AAC CAT GTC AAT GCA   Xyl146c TOP
          C   TGA CCA AGC TTG CGG TGG TAG TGA AAG ACA TTG GTA CAG TT        Xyl147c BOTTOM
          C   TGA CCA AGC TTG CGG TGG TAG TGA AAG TGA ACG GTA CAG TT        Xyl148c BOTTOM
```

For the construction of restriction fragments for cassette mutagenesis, after kinase treatment, complementary oligonucleotides were mixed together (20 pmol of each oligonucleotide), and the mixture was heated to 80° C. for 10 min. The mixture was then allowed to slowly cool to room temperature. Portions from the annealed oligonucleotide mixture were then used directly in ligation reactions with the previously digested and purified pCWBCX::S1OOC. After ligation and transformation, clones carrying the modified EagI-NsiI fragment were identified by hybridization with a DIG-ddUTP labelled oligonucleotide. Once hybridization positive colonies were identified, plasmid DNA was isolated and *E. coli* was re-transformed, to ensure the purity of the clone. DNA sequencing was performed to verify changes at the desired codons.

EXAMPLE 2

Construction of the Mutant TS2

The plasmid pCWBCX3'SYN was used to transform *E. coli* RZ1032, and single stranded UDNA was prepared as previously described in Example 1. Two mutagenic oligonucleotides for making V98C, and A152C (see below) were used in an in vitro DNA synthesis reaction as described in Example 1.

SEQ ID NO: 10
Codons          101   100   99   98   97   96   95   94
pCW V98C 5'  C ATC  ACT  TTT  GCA  AGT  ACC  TTT  ATA 3'

SEQ ID NO: 11
Codons          155   154   153   152   151   150   149
pCW A152C 5' GGA  TTT  CCA  GCA  ATT  CAC  GTG 3'

After transformation, colonies were screened for hybridization to both mutagenic oligonucleotides. The xylanase gene from a hybridization positive clone, TS2, was completely sequenced to ensure only the desired mutations were present.

EXAMPLE 3

Construction of the Mutant TS4

An additional thermostable mutant containing an inter-molecular disulfide bridge was constructed by a mutation at amino acid position 179 to change the amino acid from a serine to a cysteine (S179C). This mutant was constructed using cassette mutagenesis to make TS4a using the oligonucleotides: S179C-1 (SEQ ID NO:12); S179C-2 (SEQ ID NO:13) and S179C-3 (SEQ ID NO:14) shown below:

an agarose gel. The oligonucleotides for S179C were processed as described in Example 1, for cassette mutagenesis. This protein contained a single active thiol, however the protein dimerizes spontaneously. It forms a mixture based on the amount of free sulfhydryl from Ellmans reagent testing, and from purification of both the monomer and dimer from the mixture. This mutation was then combined with TS1, by standard subcloning to produce a mutant called TS4. The mutant TS4M is the combined TS1+S179C monomeric species and the TS4D is the dimeric species of this mutant. The purity of the monomeric and dimeric species used in the thermostability assays is shown in FIG. 8.

EXAMPLE 4

Construction of Mutations at the N-Terminus of *B. Circulans Xylanase*

Several mutant xylanases with mutations in the N-terminal region, have been constructed via the method of cassette mutagenesis. These mutants are either single, double or triple amino acid changes at positions 3, 4 or 8. All of the gene constructions involved ligations of 2 pairs of oligonucleotides which contained the mutations, into the NheI/BspEI linearized plasmid pXYbc (FIG. 9), via the well established recombinant procedures of (i) phosphorylation of the oligonucleotides, (ii) their ligation with the linearized plasmid, (iii) transformation into the *E. coli* competent cells, (iv) identification of the mutant transformants via hybridization with the labelled oligonucleotide as probe, and (v) confirmation of the mutation through gene sequencing. These procedures have been fully described in the preceding Examples. The oligonucleotides used for the production of various N-terminus mutants are shown below.
(1) TS5a mutant, where the asparagine-8 (N-8) has been converted into tyrosine (Y).

The oligonucleotides for the cassette mutagenesis are XYSY-1 (SEQ ID NO:15), XYSY-2 (SEQ ID NO:16), Codons          178   179   180   181   182   183   184   185
s179c-1 5'           CT GGA  TGC  TCC  AATGTG ACA  GTG  TGG  TAA  AGA  TCT  TGA
s179c-2 3' TCG AGA  CCT  ACG  AGG  TTA  CAC
s179c-3 3'                              TGT  CAC  ACC  ATT  TCT  AGA  ACT The plasmid pCWBCX3'SYN was digested with SacI and HindIII. The large fragment was purified from XY-11-2 (SEQ ID NO:17) and XY-16-1 (SEQ ID NO:18), and are as show below:

```
        1   2   3   4   5   6   7   8   9   10  11  12  13  14  15  16  17  18  19  20  21  22 23
N-ter   A   S   T   D   Y   W   Q   Y   W   T   D   G   G   G   I   V   N   A   V   N   G   S  G
5'-    CT AGT ACA GAT TAT TGG CAA TAT TGG ACA GAC GGT GGC GGT ATC GTT AAT GCC GTG AAC GGC AGG CC
       ──                              ─────────────────────
        NheI          XY8T-1                                                                BspEI
        ──                                              XY-11-2
                       A TGT CTA ATA ACC GTT ATA ACC TGT CTG CCA CCG CCA TAG CAA TTA CGG CAC TTG CCG T
                                      XY8Y-2                           XY-16-1
```

(2) TS6a mutant, where threonine-3 (T-3), aspartic acid-4 (D-4) and asparagine-8 (N-8) have been converted to glycine (G), tyrosine (Y) and tyrosine (Y), respectively.

The oligonucleotides for cassette mutagenesis are XY3G4, 8Y-1; (SEQ ID NO:19) XY3G4, 8Y-2 (SEQ ID NO:20); XY-11-2 and XY-16-1 wherein the first two oligonucleotides are shown below:

```
                           XY3G4,8Y-1
         1   2    3    4    5    6    7    8    9   10   11   12   13
N-ter    A   S    G    Y    Y    W    Q    Y    W    T    D    G    G
5'-     CT AGT  GGA  TAC  TAT  TGG  CAA  TAT  TGG
         A     CCT  ATG  ATA  ACC  GTT  TAT  ACC  TGT  CTG  CCA  CCG
        NheI                  XY3G4,8Y-2
```

(3) TS3a mutant was prepared from a pair of oligonucleotides with mixed bases at codons-4 and 8. The oligonucleotides for cassette mutagenesis are XY(1-8)Mu-1 (SEQ ID NO:21), XY(1-8)Mu-2 (SEQ ID NO:22), XY-11-2 and XY-16-1 wherein the first two oligonucleotides are shown below:

```
                           XY(1-8)Mu-1
         1   2    3    4    5    6    7    8    9   10   11   12   13
N-ter    A   S    T   D/Y   Y    W    Q         W    T    D    G    G
5'-     CT AGT  ACA  TAC  TAC  TGG  CAA  Tkl  TGG
         A     TGT  CTG  ATG  ACC  GTT  Am1  ACC  TGT  CTG  CCA  CCG
        NheI                  XY(1-8)Mu-2
``` k, l, m are mixed bases used in synthesis of oligonucleotide.

k=T+A+G
l=C+G
m=T+A+C

4) TS3 mutant was constructed by combining the mutations from TS1 with that from TS3a. The plasmid pXYbc was digested with Ssp I, Hind III and Avr II. Two fragments from this digest were isolated, a 2 KB Ssp I—Hind III (the vector portion of pXYbc) and a 245 bp Ssp I (a small portion of the vector and the first 78 codons of TS3a). A second plasmid pCW::TS1 was digested with Ssp I and Hind III and a 345 bp fragment was isolated (codons 79–185 of TS1). These three fragments were mixed together and ligated. After transformation, clones were picked from RBBX-agar plates if they produced clearing zones (xylanase activity). A clone was analyzed by DNA sequencing and was found to contain the desired mutations. This cone was designated TS3.

CHARACTERIZATION OF THE PROTEIN PRODUCTS

Protein Purification

Protein samples were prepared from cells by first making an extract of the cells by grinding 10 g of the cell paste with 25 g of alumina powder. After grinding to a smooth mixture, small amounts (5 ml) of ice cold buffer A (10 mM sodium acetate, pM 5.5) were added and the mixture ground vigorously between additions. DNase, 10 μg/ml, was added to lower the viscosity of the extract. The alumina and cell debris were removed by centrifugation of the mixture at 8000×g for 30 min. The supernatant (25 ml) was then dialyzed overnight at 4° C. against 3 L buffer A, using dialysis tubing with a 3500 molecular weight cutoff. A slight precipitate formed in the dialysis bag, which is removed by centrifugation at 8000×g for 15 min.

The cell extract was then pumped onto a 50 ml bed volume, S-sepharose fast flow, cation exchange column (Kabi-Pharmacia, Canada), equilibrated in buffer A. The xylanase was eluted with a 300 ml linear gradient of 0 to 0.3M NaCl in buffer A at a flow rate of 3 ml/min. The xylanase elutes at 100 to 150 ml of the gradient. The fraction are checked on SDS-PAGE, and those fractions having most of the xylanase were pooled, and concentrated by ultrafiltration using 3000 dalton molecular weight cutoff membranes (Amicon YM3). The concentrated material, 5 ml, was then applied to a 1.5 cm×85 cm TSK-HW50S gel filtration column, equilibrated in 50 mM ammonium acetate pH 6. The xylanase eluted at a volume of 90 to 100 ml. These fractions were analyzed by SDS-PAGE, and the peaks pooled as pure xylanase. The protein was quantified using the extinction co-efficient at 280 nm. ε 0.1% solution=4.08. Typical purified yield from 10 g of cells was 25 mg of xylanase.

Detection of Free Thiol Groups

Two methods were used to indicate the presence of the SS bond. The first was shown in FIG. 10. The electrophoretic mobility of the mutant proteins is faster under non-reducing conditions since the reduced protein is fully denatured and binds more SDS. This has also been observed for other disulfide bond containing proteins (Mitchison and Wells, 1989, Biochemistry 28:4807–4815; Eder and Wilmanns, 1992, Biochemistry 31:4437–4444).

The second method checked for reactive sulfhydryl groups (SH groups). Approximately 200 μg of protein (10 nmol) were used for each determination. The reaction was performed in cuvettes at room temperature. The reaction mixture contained 6M urea, 50 mM Tris-HCl, pH 8, 1 mM EDTA, and 9–13 nmol of xylanase, in a final volume of 1 ml. The reaction was initiated by the addition of 10 μl of 10 mM 5,5'-dithiobis(2-nitrobenzoic acid), Ellmans reagent. The $A_{412}$ of the solution was monitored for 45 min. The amount of free thiol was calculated from the liberated 2-nitro-5-thiobenzoate anion, using a molar extinction coefficient of 13,700. A single thiol containing mutant (S100C) was the positive control.

Titration of these and other mutants with Ellman's reagent under denaturing conditions shows undetectable levels of SH groups in the SS bond mutants, but shows stoichiometric amounts in a control containing a single SH group (Table 3). This shows that two of the mutants of the present invention (TS1 and TS2) have their cysteine residues in SS bridges.

TABLE 3

Determination of free sulfhydryl groups in xylanase mutants

| PROTEIN | [PROTEIN] μM (A₂₈₀) | [SULFHYDRYL] μM | [SH]/ [PROTEIN] |
|---|---|---|---|
| BCX wild type | 9.4 | 0 | 0 |
| S100C | 9.55 | 10.6 | 1.10 |
| TS1 | 10.4 | 0 | |
| TS2 | 11.5 | 0 | 0 |
| Mixture of S179C monomer and dimer | 13.3 | 3 | 0.23 |

Measurement of Enzymatic Activity

The activity of the enzyme was measured two ways. The quantitative assay determined the number of reducing sugar ends generated from soluble xylan. The substrate for this assay was the fraction of birchwood xylan which dissolved in water from a 5% suspension of birchwood xylan (Sigma Chemical Co). After removing the insoluble fraction, the supernatant was freeze dried and stored in a desiccator. The measurement of specific activity was performed as follows. Reaction mixtures containing 100 μl of 30 mg/ml xylan in assay buffer (50 mM sodium citrate pH 5.5), 150 μl assay buffer, 50 μl of enzyme diluted in 1 mg/ml BSA, in assay buffer. The substrate and buffer were mixed and prewarmed at 40° C. The reaction was started by the addition of the enzyme. At various time intervals 50 μl portions were removed and the reaction stopped by diluting in 1 ml of 5 mM NaOH. The amount of reducing sugars was determined with the hydroxybenzoic acid hydrazide reagent (HBAH) (Lever, 1972, Analytical Biochem 47:273–279). A unit of enzyme activity was defined as that amount generating 1 μmol reducing sugar in 1 minute at 40° C. For the determination of kinetic parameters substrate concentrations from 0.4 mg/ml to 20 mg/ml were used. Kinetic parameters were calculated using the computer program Enzfitter (Leatherbarrow 1987, Enzfitter, a non-linear regression data analysis program for the IBM-PC. Elsevier Science Publishers BV. Amsterdam, The Netherlands. 1987).

The second assay for activity was used for relative measurement, i.e. residual activity after heat treatment. This assay was performed with RBBX (Remazol Brilliant Blue Xylan) as the substrate (Biely et al, 1987, Methods in Enzymology 160:536–541). 100 μl of 10 mg/ml RBBX in H₂O was mixed with 100 μl of 100 mM ammonium acetate pH 6, and the mixture prewarmed to 40° C. The reaction was started by the addition of suitably diluted enzyme. After a fixed length of time, 5 or 10 min, the reaction was stopped by the addition of 0.5 ml 95% ethanol. The mixture was inverted to mix, and then allowed to stand at least 10 min. at room temperature. The mixture was then centrifuged in a microcentrifuge for 3 min. at 12,000×g. The $A_{595}$ of the supernatant was measured.

Thermostability Assay

To determine the thermostability of the mutant and wild type enzyme, the following parameters were used. The proteins were diluted to between 100 to 150 μg/ml, in dilution buffer (50 mM ammonium acetate pH 6.0). 400 μl of this solution were incubated in a 1.5 ml microcentrifuge tube, in a heating block containing glycerol. Portions of the solution were removed at specified times and immediately diluted 1 to 20 in dilution buffer and kept at room temperature until all samples had been taken. Portions of these diluted samples were then assayed for residual enzyme activity, using the RBBX assay. Results were expressed as percent residual activity compared to the zero time point sample. Heating blocks were calibrated with a thermocouple and the measured temperature was that of the enzyme solution.

The data shown in FIGS. 11–16, clearly indicate the thermostabilizing effect of the introduction of non-native disulfide bridges into BCX. The mutant TS1 is clearly stable at 61° C. for up to 3 h. The second SS bond mutant TS2 is not quite as stable, but maintains some activity after 1 h at 61° C. (see FIG. 12). FIGS. 11 and 12 show curves for the mixed TS4 monomer/dimer preparation, which is more stable than wild type but less stable than TS1. It is however, more relevant to examine the individual components. The mutant which contains only the inter-molecular SS bond (TS4a) shows increased thermostability at 58° C. (FIG. 13), and at this temperature is as stable as the intra-molecular SS bond mutant TS1 (FIG. 14).

TS4 protein is produced as a mixture, but the monomer (TS4M) and the dimer (TS4D) are easily separated by rechromatographing the mixture on a cation exchange column. TS4M behaves very much like the TS1 mutant, whereas TS4D results in additive thermostability such that TS4D is more stable than TS1. (FIGS. 14, 15 and 16).

There has been another example of an artificial inter-molecular dimer using an SS bond, where the thermostability was increased, however this protein was not an enzyme, and the measurement of thermostability did not include a biological activity assay (Sauer et al, 1986, Biochemistry 25:5992–5998). The increase in thermostability seen in the intra-molecular SS bond mutants is similar to the effects seen in other proteins with an engineered intra-molecular SS bond; however, there is no significant decrease in specific activity, or change in kinetic parameters (Table 4), as is sometimes the case with SS bond mutants (Kanaya et al, 1991, Journal of Biological Chemistry 266(10):6038–6044).

TABLE 4

Kinetic Parameters of Thermostable Xylanase Mutants

| MUTANT | $K_m$ (mg/ml) | $V_{max}$ (μmol/min/mg) | $k_{cat}/K_m$ |
|---|---|---|---|
| Wild type BCX | 1.78 ± 0.08 | 364 ± 24 | 11.04 |
| Wild type BSX | 1.86 ± 0.07 | 386 ± 14 | 10.16 |
| TS1 | 1.72 ± 0.04 | 353 ± 5 | 10.07 |
| Wild type BCX* | 2.21 ± 0.27 | 456 ± 46 | 10.086 |
| TS2* | 2.14 ± 0.24 | 413 ± 20 | 9.359 |
| TS3* | 2.27 ± 0.22 | 269 ± 1.4 | 5.819 |

*These values were determined with a different batch of substrate, than the first 3 were, which accounts for the difference in $K_m$ and $V_{max}$ The decrease in the $k_{cat}/K_m$ for TS3 indicates that some effect on catalysis and/or substrate specificity has occurred (Table 4). There is also a decrease in specific activity seen in TS4a and TS4D but this is not likely a severe limitation because decrease in the ability to hydrolyze soluble xylan may not be indicative of how well the protein performs in pre-bleaching applications on pulp (Table 5). The activity of the thermostable mutants is higher at elevated temperatures (FIG. 17).

TABLE 5

Specific Activity of Thermostable Mutants of the
B. circulans Xylanase

| MUTATION | SPECIFIC ACTIVITY* (% OF WILD TYPE) |
|---|---|
| TS1 | 105 |
| TS2 | 86 |
| TS3a | 77 |
| TS3 | 61 |
| TS4a | 59 |
| TS4M | 97 |
| TS4D | 66 |
| TS5a | 93 |
| TS6a | 103 |

*These activities were determined using the reducing sugar assay (HBAH), and are the average of at least two determinations.

The N-terminal mutations, were found to confer thermostability, although less than that seen with the SS bond mutants. Thermostability of these mutants was determined in two ways: by a residual activity assay and by scanning calorimetry.

In the residual activity assay identical samples of a xylanase mutant were preheated in the assay buffer (50 mM sodium citrate, pH 6.2) in Eppendorf tubes at different temperatures. The Eppendorf tubes with samples were heated in small water baths with lids. The heating temperatures were determined by a digital thermometer with a thermocouple sensor which measured to 0.1° C. After 30 min., samples were cooled down to 20° C before being assayed at 40° C. The residual enzyme activity of the heated sample was expressed as a percentage of the activity of an unheated sample. This residual activity was plotted against the heating temperature (FIG. 18). From the plot, the $T_{\frac{1}{2}}$ the preheating temperature, at which the xylanase still retained 50% of its activity, was determined and is shown in Table 6.

TABLE 6

$T_{\frac{1}{2}}$ of pre-heating temperatures at which xylanase will retain 50% of activity

| Xylanase | $T_{\frac{1}{2}}$ (°C.) |
|---|---|
| BCX (wild type) | 53.5 |
| TS3a | 56.5 |
| TS5a | 55.5 |
| TS6a | 58.5 |

Samples of the xylanase were studied by scanning calorimetry to study the unfolding process of the xylanase structure as it relates to the rising temperature. Then $T_m$, the temperature at which half of the xylanase molecules have been denatured or melted, was determined. A higher $T_m$ reflects a more thermostable molecule. It should be emphasized that calorimetry is concerned with the maintenance of the molecular structure, not enzymatic activity. However, the loss of enzyme activity through heating is often associated with the collapse of the molecular structure. The melting temperatures, $T_m$ of wild type and mutant xylanases were determined from the calorimetric scans and are shown in Table 7.

TABLE 7

Melting temperature $T_m$ of xylanase

| Xylanase | $T_m$ (°C.) |
|---|---|
| BCX (wild type) | 59.7 |
| TS3a | 62.7 |
| TS5a | 62.0 |
| TS6a | 64.6 |

Residue-8 appears to be essential to the thermostability of the BCX. The mechanism of the effect of this mutation may be explained by the 3-dimensional structure which reveals that a space existed between asparagine-8 and the other residues (FIG. 19). This space was occupied by two water molecules in the wild-type enzyme (BCX). Molecular modelling indicated that substitution of asparagine-8 by phenylalanine or tyrosine could displace the water molecules (FIG. 20). Increased thermostability resulting from this substitution may be a result of increased hydrophobic interaction contributed by these larger hydrophobic side-chains. The aromatic ring may displace the buried water molecules thus gaining hydrophobic interaction. In addition, the phenolic hydroxy group may also form a hydrogen bond with the carbonyl of peptide linkage-16 on the main chain.

The mutations at the N-terminus, described above, in combination with one of the SS bond mutations, resulted in an additive thermostability (FIG. 14, 15 and 16). The combination of mutations in TS3 result in a protein with a thermostability of 64° C.

X-ray Crystallographic Structure of the Xylanases from Bacillus circulans and Trichoderma Harzianum Structure of the B. circulans xylanase Crystals of the B. circulans xylanase were grown by the hanging drop vapour diffusion method. The reservoir buffer was 40 mM Tris, pH 7.5, 22% saturated $(NH_4)_2SO_4$ and 100 mM NaCl. Droplets were seeded after one day of equilibration. The space group of the crystals was $P2_12_12_1$. The unit cell parameters for all structures are given in Table 8. The heavy-atom derivative was obtained by soaking crystals of the Ser100Cys mutant protein in 10 mM $HgCl_2$ for 6 days. All of the X-ray diffraction data sets for both the B. circulans and T. harzianum xylanase crystals were collected on a San Diego Multiwire Area Detector system on a Rigaku rotating anode generator.

All data reduction was performed using the San Diego software and the PHASES program package (Furey, W. & Swaminathan, S. (1990) "PHASES—A Program Package for the Processing and Analysis of Diffraction Data from Macromolecules", PA33, American Crystallographic Association Meeting Abstracts, Series 2, 18, pg 73). The initial electron density map for the B. circulans xylanase was calculated from phases based on the native (wild-type) data set and the positions of the mercury atoms found from the Patterson maps for the data collected on the $HgCl_2$ derivative of the Ser100Cys mutant protein. The initial electron density map was "skeletonized" using BONES (Greer, J. (1985) Methods in Enzymology 115, 206) and the initial model was built with TOM/FRODO (Jones, T. (1978) J. Appl. Cryst. 11, 268) and with 0 (Jones, T. A., Bergdoll, M., & Kjeldgaard, M. (1990) O: A macromolecular modelling environment. In "Crystallographic and Modelling Methods in Molecular Design" (Bugg, C. E. & Ealick, S. E., Editors). Springer-Verlag, New York). All refinements were carried out using the simulated annealing and minimization protocols of X-PLOR (Brunger, A. T. (1988) J. Mol. Biol. 203, 803).

Structure of TS1 Mutant of the B. circulans Xylanase

Crystals of the TS1 mutant were grown as for the wild-type enzyme and were isomorphous with the crystals of the wild-type enzyme. A model for the cysteine side-chains was built into a difference electron density map that was calculated with data measured from the TS1 crystals and with phases calculated from the refined model of the wild-type structure.

Structure of the *T. Harzianum* Xylanase

Crystals of the *T. harzianum* xylanase were grown by the hanging drop vapour diffusion method. The reservoir buffer was 16 mM Tris, pH 7.5, 20% saturated $(NH_4)_2SO_4$. Droplets were seeded after one day of equilibration. The space group of the crystals was also $P2_12_12_1$ but with different unit cell dimensions and with a different crystal packing arrangement than for the *B. circulans* crystals.

The structure was solved by standard molecular replacement methods with the programs MERLOT (Fitzgerald, P. M. D. (1988) J. Appl. Cryst. 21, 273–278) and BRUTE (Fujinaga, M. and Read, R. (1987) J. Appl. Crystallogr., 20, 517–521) using the *B. circulans* xylanase as the search model. Refinement statistics for all structures are given in Table 9 and plots of average main-chain B-factors for the three structures are shown in FIGS. 21, 22 and 23. Ramachandran diagrams indicating the stereochemical quality of the structures are shown in FIGS. 24 and 25.

TABLE 8

Data collection statistics

| Data Set | | B. circulans Wild-type | S100C mutant + $HgCl_2$ | TS1 | T. harzianum Wild-type |
|---|---|---|---|---|---|
| Unit cell | a | 44.00 | 43.96 | 43.90 | 43.67 |
| parameters | b | 52.78 | 52.71 | 52.88 | 94.65 |
| (Å) | c | 78.39 | 78.41 | 78.43 | 51.55 |
| Resolution | (Å) | 1.6 | 2.3 | 1.6 | 1.8 |
| Merging R-factor ($R_{sym}$) | | 0.028 | 0.062 | 0.062 | 0.111 |
| Completeness of data set to resolution limit | | 94% | 99% | 99% | 98% |
| Isomorphous difference ($R_{iso}$) | | n/a | 0.098 | 0.077 | n/a |
| Figure of merit | | n/a | 0.77 | n/a | n/a |

$$R_{sym} = \frac{\Sigma |<I> - I_{obs}|}{\Sigma |I_{obs}|}$$

$<I>$ is the average intensity for a particular reflection and $I_{obs}$ is one intensity measurement for that reflection.

$$R_{iso} = \frac{\Sigma |F_{deriv} - F_{nat}|}{\Sigma |F_{nat}|}$$

$F_{deriv}$ and $F_{nat}$ are the amplitudes of the structure factors for the derivative (S100C+$HgCl_2$ and TS1) and native (wild-type) data sets, respectively. n/a=not applicable to this data set.

Figure of merit is a measure of the quality of a derivative for calculating phases.

TABLE 9

Refinement statistics

| | B. circulans | | T. harzianum |
|---|---|---|---|
| Data Set | Wild-type | TS1 | Wild-type |
| Number of non-hydrogen protein atoms | 1448 | 1446 | 1473 |
| Solvent molecules | 141 waters + 1 sulfate | 152 waters | 59 waters |
| R-factor | 0.163 | 0.172 | 0.208 |
| RMS-deviations from ideality for | | | |
| bonds (Å): | 0.009 | 0.009 | 0.010 |
| angles (°): | 1.691 | 1.783 | 1.318 |
| dihedrals (°): | 27.371 | 27.525 | 30.016 |
| impropers (°): | 1.312 | 1.351 | 2.326 | where, $$R\text{-factor} = \frac{\Sigma |F_{calc} - F_{obs}|}{\Sigma |F_{obs}|}$$

$F_{calc}$ and $F_{obs}$ are the amplitudes of the structure factors that are calculated from the refined model structure and from the measured reflections, respectively.

The invention has been described with reference to particular embodiments, although it is understood that the specific details shown are merely illustrative, and the invention may be carried out in other ways without departing from the spirit and the scope of the following claims.

SEQUENCE LISTING ( 1 ) GENERAL INFORMATION:

( i i i ) NUMBER OF SEQUENCES: 37

( 2 ) INFORMATION FOR SEQ ID NO: 1:

( i ) SEQUENCE CHARACTERISTICS:
        ( A ) LENGTH: 720
        ( B ) TYPE: Nucleic Acid
        ( C ) STRANDEDNESS: Double- Stranded
        ( D ) TOPOLOGY: Circular ( i i ) MOLECULE TYPE: Genomic DNA ( i i i ) HYPOTHETICAL: No ( i v ) ANTI-SENSE: No ( v ) FRAGMENT TYPE:

( v i ) ORIGINAL SOURCE:
    ( A ) ORGANISM: Bacillus subtilis ( v i i ) IMMEDIATE SOURCE:
    ( A ) LIBRARY:
    ( B ) CLONE: plasmid pBSX ( v i i i ) POSITION IN GENOME:

( i x ) FEATURE:

( x ) PUBLICATION INFORMATION:
    ( A ) AUTHORS: Paice, M.G., Bourbonnais, R.,
        Desrochers, M., Jurasek, L., Yaguchi, M.
    ( B ) TITLE: A XYLANASE GENE FROM BACILLUS SUBTILIS:
        NUCLEOTIDE SEQUENCE AND COMPARISON WITH B. PUMILIS
    ( C ) JOURNAL: Archives of Microbiology
    ( D ) VOLUME: 144
    ( E ) ISSUE:
    ( F ) PAGES: 201-206
    ( G ) DATE: 1986
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO: 1:

```
GCT AGC ACA GAC TAC TGG CAA AAT TGG ACT GAT GGG GGC GGT ATA GTA      48
AAC GCT GTC AAT GGG TCT GGC GGG AAT TAC AGT GTT AAT TGG TCT AAT      96
ACC GGA AAT TTT GTT GTT GGT AAA GGT TGG ACT ACA GGT TCG CCA TTT     144
AGG ACG ATA AAC TAT AAT GCC GGA GTT TGG GCG CCG AAT GGC AAT GGA     192
TAT TTA ACT TTA TAT GGT TGG ACG AGA TCA CCT CTC ATA GAA TAT TAT     240
GTA GTG GAT TCA TGG GGT ACT TAT AGA CCT ACT GGA ACG TAT AAA GGT     288
ACT GTA AAA AGT GAT GGG GGT ACA TAT GAC ATA TAT ACA ACT ACA CGT     336
TAT AAC GCA CCT TCC ATT GAT GGC GAT CGC ACT ACT TTT ACG CAG TAC     384
TGG AGT GTT CGC CAG TCG AAG AGA CCA ACC GGA AGC AAC GCT ACA ATC     432
ACT TTC AGC AAT CAT GTG AAC GCA TGG AAG AGC CAT GGA ATG AAT CTG     480
GGC AGT AAT TGG GCT TAC CAA GTC ATG GCG ACA GAA GGA TAT CAA AGT     528
AGT GGA AGT TCT AAC GTA ACA GTG TGG TAA CAGATCATCC TTAATCAGGG       578
GTAGCTAACG GCTGCTGAT CGTTCCTTGA GAAGTTTTAT AATCAATGAT TATTAAAATC   638
GTTAGTAATG GTTAAAGGTT GTTTCTACT AGGTGAACGG CCTTGGAATT GCTGGAGGTA    698
GGGTATTCTC CATCTGGTTT TT                                            720
```

( 2 ) INFORMATION FOR SEQ ID NO: 2:

( i ) SEQUENCE CHARACTERISTICS:
        ( A ) LENGTH: 572
        ( B ) TYPE: Nucleic Acid
        ( C ) STRANDEDNESS: Double-Stranded
        ( D ) TOPOLOGY: Circular ( i i ) MOLECULE TYPE: Genomic DNA ( i i i ) HYPOTHETICAL: No ( i v ) ANTI-SENSE: No ( v ) FRAGMENT TYPE:

( v i ) ORIGINAL SOURCE:
        ( A ) ORGANISM: Bacillus circulans
        ( G ) CELL TYPE: Bacterial ( v i i ) IMMEDIATE SOURCE:

(A) LIBRARY:
(B) CLONE: plasmid pCWBCX3'SYN (viii) POSITION IN GENOME:

(ix) FEATURE:
(C) IDENTIFICATION METHOD: By experiment (x) PUBLICATION INFORMATION:

(xi) SEQUENCE DESCRIPTION: SEQ ID NO: 2:

| | | | | | | | | | | | | | | | |
|---|---|---|---|---|---|---|---|---|---|---|---|---|---|---|---|
| GCT | AGC | ACA | GAC | TAC | TGG | CAA | AAT | TGG | ACT | GAT | GGG | GGC | GGT | ATA | GTA | 48 |
| AAC | GCT | GTC | AAT | GGG | TCT | GGC | GGG | AAT | TAC | AGT | GTT | AAT | TGG | TCT | AAT | 96 |
| ACC | GGA | AAT | TTT | GTT | GTT | GGT | AAA | GGT | TGG | ACT | ACA | GGT | TCG | CCA | TTT | 144 |
| AGG | ACG | ATA | AAC | TAT | AAT | GCC | GGA | GTT | TGG | GCG | CCG | AAT | GGC | AAT | GGA | 192 |
| TAT | TTA | ACT | TTA | TAT | GGT | TGG | ACG | AGA | TCA | CCT | CTC | ATA | GAA | TAT | TAT | 240 |
| GTA | GTG | GAT | TCA | TGG | GGT | ACT | TAT | AGA | CCT | ACT | GGA | ACG | TAT | AAA | GGT | 288 |
| ACT | GTA | AAA | AGT | GAT | GGG | GGT | ACA | TAT | GAC | ATC | TAC | ACC | ACC | ACA | AGA | 336 |
| TAC | AAC | GCA | CCT | TCC | ATC | GAT | GGC | GAT | CGG | ACC | ACC | TTT | ACT | CAG | TAC | 384 |
| TGG | AGT | GTT | AGA | CAA | TCT | AAG | CGG | CCG | ACT | GGT | TCG | AAC | GCC | ACC | ATT | 432 |
| ACG | TTC | ACC | AAT | CAC | GTG | AAT | GCA | TGG | AAA | TCC | CAC | GGT | ATG | AAC | CTA | 480 |
| GGT | TCT | AAT | TGG | GCT | TAT | CAA | GTA | ATG | GCG | ACC | GAA | GGC | TAC | CAG | AGC | 528 |
| TCT | GGT | TCT | TCC | AAC | GTT | ACA | GTG | TGG | TAA | AGATCTTGAA | GCTT | | | | | 572 |

(2) INFORMATION FOR SEQ ID NO: 3:

(i) SEQUENCE CHARACTERISTICS:
(A) LENGTH: 572
(B) TYPE: Nucleic Acid
(C) STRANDEDNESS: Double-stranded
(D) TOPOLOGY: Circular (ii) MOLECULE TYPE: Genomic DNA (iii) HYPOTHETICAL: No (iv) ANTI-SENSE: No (v) FRAGMENT TYPE:

(vi) ORIGINAL SOURCE:
(A) ORGANISM:
(G) CELL TYPE: Bacterial (vii) IMMEDIATE SOURCE:
(A) LIBRARY:
(B) CLONE: plasmid pXYSYN (viii) POSITION IN GENOME:

(ix) FEATURE:
(C) IDENTIFICATION METHOD: By experiment (x) PUBLICATION INFORMATION:

(xi) SEQUENCE DESCRIPTION: SEQ ID NO: 3:

| | | | | | | | | | | | | | | | |
|---|---|---|---|---|---|---|---|---|---|---|---|---|---|---|---|
| GCT | AGC | ACA | GAT | TAC | TGG | CAA | AAC | TGG | ACA | GAC | GGT | GGC | GGT | ATC | GTT | 48 |
| AAT | GCC | GTG | AAC | GGC | TCC | GGA | GGC | AAC | TAC | AGC | GTG | AAT | TGG | TCT | AAT | 96 |
| ACT | GGG | AAC | TTC | GTA | GTC | GGA | AAA | GGT | TGG | ACG | ACA | GGA | TCC | CCG | TTC | 144 |
| CGT | ACG | ATC | AAC | TAC | AAC | GCT | GGC | GTT | TGG | GCC | CCG | AAT | GGT | AAC | GGT | 192 |
| TAC | CTG | ACA | CTG | TAT | GGC | TGG | ACG | CGT | TCG | CCA | CTG | ATT | GAA | TAT | TAC | 240 |
| GTT | GTC | GAC | TCT | TGG | GGA | ACG | TAC | CGT | CCG | ACT | GGA | ACC | TAC | AAA | GGC | 288 |

| | | | | | | | | | | | | | | | |
|---|---|---|---|---|---|---|---|---|---|---|---|---|---|---|---|
| ACA | GTC | AAA | AGC | GAT | GGT | GGT | ACC | TAC | GAC | ATC | TAC | ACC | ACC | ACA | AGA | 336 |
| TAC | AAC | GCA | CCT | TCC | ATC* | GAT | GGC | GAT | CGG | ACC | ACC | TTT | ACT | CAG | TAC | 384 |
| TGG | AGT | GTT | AGA | CAA | TCT | AAG | CGG | CCG | ACT | GGT | TCG | AAC | GCC | ACC | ATT | 432 |
| ACG | TTC | ACC | AAT | CAC | GTG | AAT | GCA | TGG | AAA | TCC | CAC | GGT | ATG | AAC | CTA | 480 |
| GGT | TCT | AAT | TGG | GCT | TAT | CAA | GTA | ATG | GCG | ACC | GAA | GGC | TAC | CAG | AGC | 528 |
| TCT | GGT | TCT | TCC | AAC | GTT | ACA | GTG | TGG | TAA | AGATCTTGAA | GCTT | | | | | 572 |

( 2 ) INFORMATION FOR SEQ ID NO: 4:

( i ) SEQUENCE CHARACTERISTICS:
        ( A ) LENGTH: 27
        ( B ) TYPE: Nucleic Acid
        ( C ) STRANDEDNESS: Single- Stranded
        ( D ) TOPOLOGY: Circular ( i i ) MOLECULE TYPE: DNA
        ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
        ( A ) ORGANISM:
        ( G ) CELL TYPE: Bacterial ( v i i ) IMMEDIATE SOURCE:
        ( A ) LIBRARY:
        ( B ) CLONE:

( v i i i ) POSITION IN GENOME:

( i x ) FEATURE:
        ( C ) IDENTIFICATION METHOD: By experiment ( x ) PUBLICATION INFORMATION:

( x i ) SEQUENCE DESCRIPTION: SEQ ID NO: 4:

| | | | | | | | | |
|---|---|---|---|---|---|---|---|---|
| GGT | ACT | GTA | AAA | TGT | GAT | GGG | GGT | ACA | 27 |

( 2 ) INFORMATION FOR SEQ ID NO: 5:

( i ) SEQUENCE CHARACTERISTICS:
        ( A ) LENGTH: 42
        ( B ) TYPE: Nucleic Acid
        ( C ) STRANDEDNESS: Single- Stranded
        ( D ) TOPOLOGY: Circular ( i i ) MOLECULE TYPE: DNA
        ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
        ( A ) ORGANISM:
        ( G ) CELL TYPE: Bacterial ( v i i ) IMMEDIATE SOURCE:
        ( A ) LIBRARY:
        ( B ) CLONE: BSYSL ( v i i i ) POSITION IN GENOME:

( i x ) FEATURE:
        ( C ) IDENTIFICATION METHOD: By experiment ( x ) PUBLICATION INFORMATION:

( x i ) SEQUENCE DESCRIPTION: SEQ ID NO: 5:

GC CTG CAG CAT ATG GCT AGC ACA GAC TAC TGG CAA AAT TGG A  42

( 2 ) INFORMATION FOR SEQ ID NO: 6:

( i ) SEQUENCE CHARACTERISTICS:
        ( A ) LENGTH: 44
        ( B ) TYPE: Nucleic Acid
        ( C ) STRANDEDNESS: Single- Stranded
        ( D ) TOPOLOGY: Circular ( i i ) MOLECULE TYPE: DNA
        ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
        ( A ) ORGANISM:
        ( G ) CELL TYPE: Bacterial ( v i i ) IMMEDIATE SOURCE:
        ( A ) LIBRARY:
        ( B ) CLONE: BSXYL ( v i i i ) POSITION IN GENOME:

( i x ) FEATURE:
        ( C ) IDENTIFICATION METHOD: By experiment ( x ) PUBLICATION INFORMATION:

( x i ) SEQUENCE DESCRIPTION: SEQ ID NO: 6:

GC AAG CTT TCT AGA CTT TAA CCA TTA CTA ACG ATT TTA ATA ATC  44

( 2 ) INFORMATION FOR SEQ ID NO: 7:

( i ) SEQUENCE CHARACTERISTICS:
        ( A ) LENGTH: 50
        ( B ) TYPE: Nucleic Acid
        ( C ) STRANDEDNESS: Single- Stranded
        ( D ) TOPOLOGY: Circular ( i i ) MOLECULE TYPE: DNA
        ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
        ( A ) ORGANISM:
        ( G ) CELL TYPE: Bacterial ( v i i ) IMMEDIATE SOURCE:
        ( A ) LIBRARY:
        ( B ) CLONE: Xyl46C ( v i i i ) POSITION IN GENOME:

( i x ) FEATURE:
        ( C ) IDENTIFICATION METHOD: By experiment ( x ) PUBLICATION INFORMATION:

( x i ) SEQUENCE DESCRIPTION: SEQ ID NO: 7:

GG CCG ACT GGT TCG AAC GCC ACC ATC ACT TGC ACT AAC CAT GTC AAT  47

GCA  50

( 2 ) INFORMATION FOR SEQ ID NO: 8:

( i ) SEQUENCE CHARACTERISTICS:
  ( A ) LENGTH: 42
  ( B ) TYPE: Nucleic Acid
  ( C ) STRANDEDNESS: Single- Stranded
  ( D ) TOPOLOGY: Circular ( i i ) MOLECULE TYPE: DNA
  ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
  ( A ) ORGANISM:
  ( G ) CELL TYPE: Bacterial ( v i i ) IMMEDIATE SOURCE:
  ( A ) LIBRARY:
  ( B ) CLONE: Xy147C ( v i i i ) POSITION IN GENOME:

( i x ) FEATURE:
  ( C ) IDENTIFICATION METHOD: By experiment ( x ) PUBLICATION INFORMATION:

( x i ) SEQUENCE DESCRIPTION: SEQ ID NO: 8:

C TGA CCA AGC TTG CGG TGG TAG TGA AAG ACA TTG GTA CAG TT    42

( 2 ) INFORMATION FOR SEQ ID NO: 9:

( i ) SEQUENCE CHARACTERISTICS:
  ( A ) LENGTH: 42
  ( B ) TYPE: Nucleic Acid
  ( C ) STRANDEDNESS: Single- Stranded
  ( D ) TOPOLOGY: Circular ( i i ) MOLECULE TYPE: DNA
  ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
  ( A ) ORGANISM:
  ( G ) CELL TYPE: Bacterial ( v i i ) IMMEDIATE SOURCE:
  ( A ) LIBRARY:
  ( B ) CLONE: Xy148C ( v i i i ) POSITION IN GENOME:

( i x ) FEATURE:
  ( C ) IDENTIFICATION METHOD: By experiment ( x ) PUBLICATION INFORMATION:
  ( A ) AUTHORS:

( x i ) SEQUENCE DESCRIPTION: SEQ ID NO: 9:

C TGA CCA AGC TTG CGG TGG TAG TGA AAG TGA ACG GTA CAG TT    42

( 2 ) INFORMATION FOR SEQ ID NO: 10:

( i ) SEQUENCE CHARACTERISTICS:
  ( A ) LENGTH: 25
  ( B ) TYPE: Nucleic Acid
  ( C ) STRANDEDNESS: Single- Stranded
  ( D ) TOPOLOGY: Circular (i i) MOLECULE TYPE: DNA
    (A) DESCRIPTION: Synthetic DNA (i i i) HYPOTHETICAL: No (i v) ANTI-SENSE: No (v) FRAGMENT TYPE:

(v i) ORIGINAL SOURCE:
    (A) ORGANISM:

(v i i) IMMEDIATE SOURCE:
    (A) LIBRARY:
    (B) CLONE: pCW V98C (v i i i) POSITION IN GENOME:

(i x) FEATURE:

(x) PUBLICATION INFORMATION:

(x i) SEQUENCE DESCRIPTION: SEQ ID NO: 10:

C ATC ACT TTT GCA AGT ACC TTT ATA        2 5

(2) INFORMATION FOR SEQ ID NO: 11:

(i) SEQUENCE CHARACTERISTICS:
        (A) LENGTH: 21
        (B) TYPE: Nucleic Acid
        (C) STRANDEDNESS: Single- Stranded
        (D) TOPOLOGY: Circular (i i) MOLECULE TYPE: DNA
        (A) DESCRIPTION: Synthetic DNA (i i i) HYPOTHETICAL: No (i v) ANTI-SENSE: No (v) FRAGMENT TYPE:

(v i) ORIGINAL SOURCE:
        (A) ORGANISM:
        (G) CELL TYPE: Bacterial (v i i) IMMEDIATE SOURCE:
        (A) LIBRARY:
        (B) CLONE: pCWA152C (v i i i) POSITION IN GENOME:

(i x) FEATURE:
        (C) IDENTIFICATION METHOD: By experiment (x) PUBLICATION INFORMATION:

(x i) SEQUENCE DESCRIPTION: SEQ ID NO: 11:

GGA TTT CCA GCA ATT CAC GTG        2 1

(2) INFORMATION FOR SEQ ID NO: 12:

(i) SEQUENCE CHARACTERISTICS:
        (A) LENGTH: 38
        (B) TYPE: Nucleic Acid
        (C) STRANDEDNESS: Single- Stranded
        (D) TOPOLOGY: Circular (i i) MOLECULE TYPE: DNA
        (A) DESCRIPTION: Synthetic DNA (i i i) HYPOTHETICAL: No (i v) ANTI-SENSE: No (v) FRAGMENT TYPE:

(v i) ORIGINAL SOURCE:

( A ) ORGANISM:
                    ( G ) CELL TYPE: Bacterial ( v i i ) IMMEDIATE SOURCE:
                    ( A ) LIBRARY:
                    ( B ) CLONE: S179C-1

( v i i i ) POSITION IN GENOME:

( i x ) FEATURE:
                    ( C ) IDENTIFICATION METHOD: By experiment ( x ) PUBLICATION INFORMATION:

( x i ) SEQUENCE DESCRIPTION: SEQ ID NO: 12:

CT GGA TGC TCC AAT GTG ACA GTG TGG TAA AGA TCT TGA  38

( 2 ) INFORMATION FOR SEQ ID NO: 13:

( i ) SEQUENCE CHARACTERISTICS:
                    ( A ) LENGTH: 21
                    ( B ) TYPE: Nucleic Acid
                    ( C ) STRANDEDNESS: Single- Stranded
                    ( D ) TOPOLOGY: Circular ( i i ) MOLECULE TYPE: DNA
                    ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
                    ( A ) ORGANISM:
                    ( G ) CELL TYPE: Bacterial ( v i i ) IMMEDIATE SOURCE:
                    ( A ) LIBRARY:
                    ( B ) CLONE: S179C-2

( v i i i ) POSITION IN GENOME:

( i x ) FEATURE:
                    ( C ) IDENTIFICATION METHOD: By experiment ( x ) PUBLICATION INFORMATION:

( x i ) SEQUENCE DESCRIPTION: SEQ ID NO: 13:

TCG AGA CCT ACG AGG TTA CAC  21

( 2 ) INFORMATION FOR SEQ ID NO: 14:

( i ) SEQUENCE CHARACTERISTICS:
                    ( A ) LENGTH: 21
                    ( B ) TYPE: Nucleic Acid
                    ( C ) STRANDEDNESS: Single- Stranded
                    ( D ) TOPOLOGY: Circular ( i i ) MOLECULE TYPE: DNA
                    ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
                    ( A ) ORGANISM:
                    ( G ) CELL TYPE: Bacterial ( v i i ) IMMEDIATE SOURCE:
                    ( A ) LIBRARY:
                    ( B ) CLONE: S179C-3

( v i i i ) POSITION IN GENOME:

( i x ) FEATURE:
    ( C ) IDENTIFICATION METHOD: By experiment ( x ) PUBLICATION INFORMATION:

( x i ) SEQUENCE DESCRIPTION: SEQ ID NO: 14:

TGT CAC ACC ATT TCT AGA ACT                                                          21

( 2 ) INFORMATION FOR SEQ ID NO: 15:

( i ) SEQUENCE CHARACTERISTICS:
        ( A ) LENGTH: 26
        ( B ) TYPE: Nucleic Acid
        ( C ) STRANDEDNESS: Single- Stranded
        ( D ) TOPOLOGY: Circular ( i i ) MOLECULE TYPE: DNA
        ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
        ( A ) ORGANISM:
        ( G ) CELL TYPE: Bacterial ( v i i ) IMMEDIATE SOURCE:
        ( A ) LIBRARY:
        ( B ) CLONE: XY8Y-1

( v i i i ) POSITION IN GENOME:

( i x ) FEATURE:
        ( C ) IDENTIFICATION METHOD: By experiment ( x ) PUBLICATION INFORMATION:

( x i ) SEQUENCE DESCRIPTION: SEQ ID NO: 15:

CT AGT ACA GAT TAT TGG CAA TAT TGG                                                   26

( 2 ) INFORMATION FOR SEQ ID NO: 16:

( i ) SEQUENCE CHARACTERISTICS:
        ( A ) LENGTH: 34
        ( B ) TYPE: Nucleic Acid
        ( C ) STRANDEDNESS: Single- Stranded
        ( D ) TOPOLOGY: Circular ( i i ) MOLECULE TYPE: DNA
        ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
        ( A ) ORGANISM:
        ( G ) CELL TYPE: Bacterial ( v i i ) IMMEDIATE SOURCE:
        ( A ) LIBRARY:
        ( B ) CLONE: XY8Y-2

( v i i i ) POSITION IN GENOME:

( i x ) FEATURE:
        ( C ) IDENTIFICATION METHOD: By experiment ( x ) PUBLICATION INFORMATION:

( x i ) SEQUENCE DESCRIPTION: SEQ ID NO: 16:

A TGT CTA ATA ACC GTT ATA ACC TGT CTG CCA CCG                     34

( 2 ) INFORMATION FOR SEQ ID NO: 17:

( i ) SEQUENCE CHARACTERISTICS:
        ( A ) LENGTH: 37
        ( B ) TYPE: Nucleic Acid
        ( C ) STRANDEDNESS: Single- Stranded
        ( D ) TOPOLOGY: Circular ( i i ) MOLECULE TYPE: DNA
        ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
        ( A ) ORGANISM:
        ( G ) CELL TYPE: Bacterial ( v i i ) IMMEDIATE SOURCE:
        ( A ) LIBRARY:
        ( B ) CLONE: XY-11-2

( v i i i ) POSITION IN GENOME:

( i x ) FEATURE:
        ( C ) IDENTIFICATION METHOD: By experiment ( x ) PUBLICATION INFORMATION:

( x i ) SEQUENCE DESCRIPTION: SEQ ID NO: 17:

ACA GAC GGT GGC GGT ATC GTT AAT GCC GTG AAC GGC T                     37

( 2 ) INFORMATION FOR SEQ ID NO: 18:

( i ) SEQUENCE CHARACTERISTICS:
        ( A ) LENGTH: 29
        ( B ) TYPE: Nucleic Acid
        ( C ) STRANDEDNESS: Single- Stranded
        ( D ) TOPOLOGY: Circular ( i i ) MOLECULE TYPE: DNA
        ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
        ( A ) ORGANISM:
        ( G ) CELL TYPE: Bacterial ( v i i ) IMMEDIATE SOURCE:
        ( A ) LIBRARY:
        ( B ) CLONE: XY-16-1

( v i i i ) POSITION IN GENOME:

( i x ) FEATURE:
        ( C ) IDENTIFICATION METHOD: By experiment ( x ) PUBLICATION INFORMATION:

( x i ) SEQUENCE DESCRIPTION: SEQ ID NO: 18:

CCA TAG CAA TTA CGG CAC TTG CCG AGG CC                     29

( 2 ) INFORMATION FOR SEQ ID NO: 19:

( i ) SEQUENCE CHARACTERISTICS:
        ( A ) LENGTH: 26
        ( B ) TYPE: Nucleic Acid (C) STRANDEDNESS: Single-Stranded
            (D) TOPOLOGY: Circular (ii) MOLECULE TYPE: DNA
            (A) DESCRIPTION: Synthetic DNA (iii) HYPOTHETICAL: No (iv) ANTI-SENSE: No (v) FRAGMENT TYPE:

(vi) ORIGINAL SOURCE:
            (A) ORGANISM:
            (G) CELL TYPE: Bacterial (vii) IMMEDIATE SOURCE:
            (A) LIBRARY:
            (B) CLONE: XY3G4, 8Y-1

(viii) POSITION IN GENOME:

(ix) FEATURE:
            (C) IDENTIFICATION METHOD: By experiment (x) PUBLICATION INFORMATION:

(xi) SEQUENCE DESCRIPTION: SEQ ID NO: 19:

CT  AGT  GGA  TAC  TAT  TGG  CAA  TAT  TGG                                      26

(2) INFORMATION FOR SEQ ID NO: 20:

(i) SEQUENCE CHARACTERISTICS:
            (A) LENGTH: 34
            (B) TYPE: Nucleic Acid
            (C) STRANDEDNESS: Single-Stranded
            (D) TOPOLOGY: Circular (ii) MOLECULE TYPE: DNA
            (A) DESCRIPTION: Synthetic DNA (iii) HYPOTHETICAL: No (iv) ANTI-SENSE: No (v) FRAGMENT TYPE:

(vi) ORIGINAL SOURCE:
            (A) ORGANISM:
            (G) CELL TYPE: Bacterial (vii) IMMEDIATE SOURCE:
            (A) LIBRARY:
            (B) CLONE: XY3G4, 8Y-2

(viii) POSITION IN GENOME:

(ix) FEATURE:
            (C) IDENTIFICATION METHOD: By experiment (x) PUBLICATION INFORMATION:

(xi) SEQUENCE DESCRIPTION: SEQ ID NO: 20:

A  CCT  ATG  ATA  ACC  GTT  ATA  ACC  TGT  CTG  CCA  CCG                        34

(2) INFORMATION FOR SEQ ID NO: 21:

(i) SEQUENCE CHARACTERISTICS:
            (A) LENGTH: 26
            (B) TYPE: Nucleic Acid
            (C) STRANDEDNESS: Single-Stranded
            (D) TOPOLOGY: Circular (ii) MOLECULE TYPE: DNA
            (A) DESCRIPTION: Synthetic DNA (iii) HYPOTHETICAL: No ( i v ) ANTI-SENSE: No ( v ) FRAGMENT TYPE:

( v i ) ORIGINAL SOURCE:
    ( A ) ORGANISM:
    ( G ) CELL TYPE: Bacterial ( v i i ) IMMEDIATE SOURCE:
    ( A ) LIBRARY:
    ( B ) CLONE: XY(I-8)Mu-1

( v i i i ) POSITION IN GENOME:

( i x ) FEATURE:
    ( C ) IDENTIFICATION METHOD: By experiment ( x ) PUBLICATION INFORMATION:

( x i ) SEQUENCE DESCRIPTION: SEQ ID NO: 21:

CT AGT ACA TAC TAC TGG CAA TDS TGG    26

( 2 ) INFORMATION FOR SEQ ID NO: 22:

( i ) SEQUENCE CHARACTERISTICS:
    ( A ) LENGTH: 34
    ( B ) TYPE: Nucleic Acid
    ( C ) STRANDEDNESS: Single- Stranded
    ( D ) TOPOLOGY: Circular ( i i ) MOLECULE TYPE: DNA
    ( A ) DESCRIPTION: Synthetic DNA ( i i i ) HYPOTHETICAL: No ( i v ) ANTI-SENSE: No ( v ) FRAGMENT TYPE:

( v i ) ORIGINAL SOURCE:
    ( A ) ORGANISM:
    ( G ) CELL TYPE: Bacterial ( v i i ) IMMEDIATE SOURCE:
    ( A ) LIBRARY:
    ( B ) CLONE: XY91-8)Mu-2

( v i i i ) POSITION IN GENOME:

( i x ) FEATURE:
    ( C ) IDENTIFICATION METHOD: By experiment ( x ) PUBLICATION INFORMATION:

( x i ) SEQUENCE DESCRIPTION: SEQ ID NO: 22:

A TGT CTG ATG ACC GTT AHS ACC TGT CTG CCA CCG    34

( 2 ) INFORMATION FOR SEQ ID NO: 23:

( i ) SEQUENCE CHARACTERISTICS:
    ( A ) LENGTH: 201
    ( B ) TYPE: Amino Acid
    ( C ) STRANDEDNESS: Not Relevant
    ( D ) TOPOLOGY: linear ( i i ) MOLECULE TYPE:
    ( A ) DESCRIPTION: protein ( i i i ) HYPOTHETICAL: No ( i v ) ANTI-SENSE: No ( v ) FRAGMENT TYPE: No ( v i ) ORIGINAL SOURCE:
    ( A ) ORGANISM: Bacillus pumilis ( v i i ) IMMEDIATE SOURCE:

( v i i i ) POSITION IN GENOME:

( i x ) FEATURE:

( x ) PUBLICATION INFORMATION:
- ( A ) AUTHORS: Fukusaki E., Panbangred W., Shinmyo A., & Okada, H.
- ( B ) TITLE:
- ( C ) JOURNAL: FEBS Letters
- ( D ) VOLUME: 171
- ( E ) ISSUE:
- ( F ) PAGES: 197-201
- ( G ) DATE: 1984
- ( H ) DOCUMENT NUMBER:
- ( I ) FILING DATE:
- ( J ) PUBLICATION DATE:
- ( K ) RELEVANT RESIDUES IN SEQ ID NO:

( x i ) SEQUENCE DESCRIPTION: SEQ ID NO: 23:

| ARG | THR | ILE | THR | ASN | ASN | GLU | MET | GLY | ASN | HIS | SER | GLY | TYR | ASP | TYR |
|---|---|---|---|---|---|---|---|---|---|---|---|---|---|---|---|
| 1 | | | | 5 | | | | | 10 | | | | | 15 | |
| GLU | LEU | TRP | LYS | ASP | TYR | GLY | ASN | THR | SER | MET | THR | LEU | ASN | ASN | GLY |
| | | | 20 | | | | | 25 | | | | | 30 | | |
| GLY | ALA | PHE | SER | ALA | GLY | TRP | ASN | ASN | ILE | GLY | ASN | ALA | LEU | PHE | ARG |
| | | 35 | | | | | 40 | | | | | 45 | | | |
| LYS | GLY | LYS | LYS | PHE | ASP | SER | THR | ARG | THR | HIS | HIS | GLN | LEU | GLY | ASN |
| | 50 | | | | | 55 | | | | | 60 | | | | |
| ILE | SER | ILE | ASN | TYR | ASN | ALA | SER | PHE | ASN | PRO | SER | GLY | ASN | SER | TYR |
| 65 | | | | | 70 | | | | | 75 | | | | | 80 |
| LEU | CYS | VAL | TYR | GLY | TRP | THR | GLN | SER | PRO | LEU | ALA | GLU | TYR | TYR | ILE |
| | | | | 85 | | | | | 90 | | | | | 95 | |
| VAL | ASP | SER | TRP | GLY | THR | TYR | ARG | PRO | THR | GLY | ALA | TYR | LYS | GLY | SER |
| | | | | 100 | | | | | 105 | | | | | 110 | |
| PHE | TYR | ALA | ASP | GLY | GLY | THR | TYR | ASP | ILE | TYR | GLU | THR | THR | ARG | VAL |
| | | | 115 | | | | | 120 | | | | | 125 | | |
| ASN | GLN | PRO | SER | ILE | ILE | GLY | ILE | ALA | THR | PHE | LYS | GLN | TYR | TRP | SER |
| | | 130 | | | | | 135 | | | | | 140 | | | |
| VAL | ARG | GLN | THR | LYS | ARG | THR | SER | GLY | THR | VAL | SER | VAL | SER | ALA | HIS |
| 145 | | | | | 150 | | | | | 155 | | | | | 160 |
| PHE | ARG | LYS | TRP | GLU | SER | LEU | GLY | MET | PRO | MET | GLY | LYS | MET | TYR | GLU |
| | | | | 165 | | | | | 170 | | | | | 175 | |
| THR | ALA | PHE | THR | VAL | GLU | GLY | TYR | GLN | SER | SER | GLY | SER | ALA | ASN | VAL |
| | | | 180 | | | | | 185 | | | | | 190 | | |
| MET | THR | ASN | GLN | LEU | PHE | ILE | GLY | ASN | | | | | | | |
| | | 195 | | | | | 200 | | | | | | | | |

( 2 ) INFORMATION FOR SEQ ID NO: 24:

- ( i ) SEQUENCE CHARACTERISTICS:
    - ( A ) LENGTH: 233
    - ( B ) TYPE: Amino Acid
    - ( C ) STRANDEDNESS: Not Relevant
    - ( D ) TOPOLOGY: linear

- ( i i ) MOLECULE TYPE:
    - ( A ) DESCRIPTION: protein

- ( i i i ) HYPOTHETICAL: No

- ( i v ) ANTI-SENSE: No

- ( v ) FRAGMENT TYPE: No

- ( v i ) ORIGINAL SOURCE:
    - ( A ) ORGANISM: Clostridium acetobutylicum
    - ( B ) STRAIN: Clostridium acetobutylicum xyn B (v i i) IMMEDIATE SOURCE:

(v i i i) POSITION IN GENOME:

(i x) FEATURE:

(x) PUBLICATION INFORMATION:
- (A) AUTHORS: Zappe H., Jones W.A., & Woods D.R.
- (B) TITLE:
- (C) JOURNAL: Nucleic Acids Research
- (D) VOLUME: 18
- (E) ISSUE:
- (F) PAGES: 2719
- (G) DATE: 1990
- (H) DOCUMENT NUMBER:
- (I) FILING DATE:
- (J) PUBLICATION DATE:
- (K) RELEVANT RESIDUES IN SEQ ID NO:

(x i) SEQUENCE DESCRIPTION: SEQ ID NO: 24:

```
ALA THR ASN LEU ASN THR THR GLU SER THR PHE SER LYS GLU VAL LEU
1               5                   10                  15

SER THR GLN LYS THR TYR SER ALA PHE ASN THR GLN ALA ALA PRO LYS
            20                  25                  30

THR ILE THR SER ASN GLU ILE GLY VAL ASN GLY GLY TYR ASP TYR GLU
        35                  40                  45

LEU TRP LYS ASP TYR GLY ASN THR SER MET THR LEU LYS ASN GLY GLY
    50                  55                  60

ALA PHE SER CYS GLN TRP SER ASN ILE GLY ASN ALA LEU PHE ARG LYS
65                  70                  75                  80

GLY LYS LYS PHE ASN ASP THR GLN THR TYR LYS GLN LEU GLY ASN ILE
                85                  90                  95

SER VAL ASN TYR ASP CYS ASN TYR GLN PRO TYR GLY ASN SER TYR LEU
                100                 105                 110

CYS VAL TYR GLY TRP THR SER SER PRO LEU VAL GLU TYR TYR ILE VAL
        115                 120                 125

ASP SER TRP GLY SER TRP ARG PRO PRO GLY GLY THR SER LYS GLY THR
    130                 135                 140

ILE THR VAL ASP GLY GLY ILE TYR ASP ILE TYR GLU THR THR ARG ILE
145                 150                 155                 160

ASN GLN PRO SER ILE GLN GLY ASN THR THR PHE LYS GLN TYR TRP SER
                165                 170                 175

VAL ARG ARG THR LYS ARG THR SER GLY THR ILE SER VAL SER LYS HIS
            180                 185                 190

PHE ALA ALA TRP GLU SER LYS GLY MET PRO LEU GLY LYS MET HIS GLU
            195                 200                 205

THR ALA PHE ASN ILE GLU GLY TYR GLN SER SER GLY LYS ALA ASP VAL
    210                 215                 220

ASN SER MET SER ILE ASN ILE GLY LYS
225                 230
```

(2) INFORMATION FOR SEQ ID NO: 25:

(i) SEQUENCE CHARACTERISTICS:
- (A) LENGTH: 211
- (B) TYPE: Amino Acid
- (C) STRANDEDNESS: Not Relevant
- (D) TOPOLOGY: linear (i i) MOLECULE TYPE:
- (A) DESCRIPTION: protein (i i i) HYPOTHETICAL: No (i v) ANTI-SENSE: No (v) FRAGMENT TYPE: No (vi) ORIGINAL SOURCE:
    (A) ORGANISM: Ruminococcus flavefaciens (vii) IMMEDIATE SOURCE:

(viii) POSITION IN GENOME:

(ix) FEATURE:

(x) PUBLICATION INFORMATION:
    (A) AUTHORS: Zhang, J. & Flint, H.J.
    (B) TITLE:
    (C) JOURNAL: EMBL database accession number Z11127
    (D) VOLUME:
    (E) ISSUE:
    (F) PAGES:
    (G) DATE: 1992
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO: 25:

| SER | ALA | ALA | ASP | GLN | GLN | THR | ARG | GLY | ASN | VAL | GLY | GLY | TYR | ASP | TYR |
| 1 | | | | 5 | | | | | 10 | | | | | | 15 |

| GLU | MET | TRP | ASN | GLN | ASN | GLY | GLN | GLY | GLN | ALA | SER | MET | ASN | PRO | GLY |
| | | | 20 | | | | | 25 | | | | | 30 | | |

| ALA | GLY | SER | PHE | THR | CYS | SER | TRP | SER | ASN | ILE | GLU | ASN | PHE | LEU | ALA |
| | | 35 | | | | | 40 | | | | | 45 | | | |

| ARG | MET | GLY | LYS | ASN | TYR | ASP | SER | GLN | LYS | LYS | ASN | TYR | LYS | ALA | PHE |
| | 50 | | | | | 55 | | | | | 60 | | | | |

| GLY | ASN | ILE | VAL | LEU | THR | TYR | ASP | VAL | GLU | TYR | THR | PRO | ARG | GLY | ASN |
| 65 | | | | | 70 | | | | | 75 | | | | | 80 |

| SER | TYR | MET | CYS | VAL | TYR | GLY | TRP | THR | ARG | ASN | PRO | LEU | MET | GLU | TYR |
| | | | | 85 | | | | | 90 | | | | | 95 | |

| TYR | ILE | VAL | GLU | GLY | TRP | GLY | ASP | TRP | ARG | PRO | PRO | GLY | ASN | ASP | GLY |
| | | | 100 | | | | | 105 | | | | | 110 | | |

| GLU | VAL | LYS | GLY | THR | VAL | SER | ALA | ASN | GLY | ASN | THR | TYR | ASP | ILE | ARG |
| | | 115 | | | | | 120 | | | | | 125 | | | |

| LYS | THR | MET | ARG | TYR | ASN | GLN | PRO | SER | LEU | ASP | GLY | THR | ALA | THR | PHE |
| | 130 | | | | | 135 | | | | | 140 | | | | |

| PRO | GLN | TYR | TRP | SER | VAL | ARG | GLN | THR | SER | GLY | SER | ALA | ASN | ASN | GLN |
| 145 | | | | | 150 | | | | | 155 | | | | | 160 |

| THR | ASN | TYR | MET | LYS | GLY | THR | ILE | ASP | VAL | SER | LYS | HIS | PHE | ASP | ALA |
| | | | | 165 | | | | | 170 | | | | | 175 | |

| TRP | SER | ALA | ALA | GLY | LEU | ASP | MET | SER | GLY | THR | LEU | TYR | GLU | VAL | SER |
| | | | 180 | | | | | 185 | | | | | 190 | | |

| LEU | ASN | ILE | GLU | GLY | TYR | ARG | SER | ASN | GLY | SER | ALA | ASN | VAL | LYS | SER |
| | | 195 | | | | | 200 | | | | | 205 | | | |

| VAL | SER | VAL |
| 210 | | |

(2) INFORMATION FOR SEQ ID NO: 26:

(i) SEQUENCE CHARACTERISTICS:
        (A) LENGTH: 190
        (B) TYPE: Amino Acid
        (C) STRANDEDNESS: Not Relevant
        (D) TOPOLOGY: linear (ii) MOLECULE TYPE:
        (A) DESCRIPTION: protein (iii) HYPOTHETICAL: No (iv) ANTI-SENSE: No (v) FRAGMENT TYPE: No (vi) ORIGINAL SOURCE:
  (A) ORGANISM: Trichoderma reesei
  (B) STRAIN: Trichoderma reesei, XYN II, 21kD, pI 9.0

(vii) IMMEDIATE SOURCE:

(viii) POSITION IN GENOME:

(ix) FEATURE:

(x) PUBLICATION INFORMATION:
  (A) AUTHORS: Torronene, A., Mach, R.L., Messner, R.,
       Gonzalez, R., Kalkkinen, N., Harkki, A.
       & Kubicek, C.P.
  (B) TITLE:
  (C) JOURNAL: Bio/Technology
  (D) VOLUME: 10
  (E) ISSUE:
  (F) PAGES: 1461-1465
  (G) DATE: 1992
  (H) DOCUMENT NUMBER:
  (I) FILING DATE:
  (J) PUBLICATION DATE:
  (K) RELEVANT RESIDUES IN SEQ ID NO:

(xi) SEQUENCE DESCRIPTION: SEQ ID NO: 26:

```
GLN THR ILE GLN PRO GLY THR GLY TYR ASN ASN GLY TYR PHE TYR SER
 1           5                  10                  15

TYR TRP ASN ASP GLY HIS GLY GLY VAL THR TYR THR ASN GLY PRO GLY
            20              25                  30

GLY GLN PHE SER VAL ASN TRP SER ASN SER GLY ASN PHE VAL GLY GLY
        35              40                  45

LYS GLY TRP GLN PRO GLY THR LYS ASN LYS VAL ILE ASN PHE SER GLY
    50                  55                  60

SER TYR ASN PRO ASN GLY ASN SER TYR LEU SER VAL TYR GLY TRP SER
 65              70                  75                      80

ARG ASN PRO LEU ILE GLU TYR TYR ILE VAL GLU ASN PHE GLY THR TYR
                85              90                  95

ASN PRO SER THR GLY ALA THR LYS LEU GLY GLU VAL THR SER ASP GLY
            100             105                 110

SER VAL TYR ASP ILE TYR ARG THR GLN ARG VAL ASN GLN PRO SER ILE
        115             120                 125

ILE GLY THR ALA THR PHE TYR GLN TYR TRP SER VAL ARG ARG ASN HIS
    130             135                 140

ARG SER SER GLY SER VAL ASN THR ALA ASN HIS PHE ASN ALA TRP ALA
145             150                 155                     160

GLN GLN GLY LEU THR LEU GLY THR MET ASP TYR GLN ILE VAL ALA VAL
                165             170                 175

GLU GLY TYR PHE SER SER GLY SER ALA SER ILE THR VAL SER
            180             185                 190
```

(2) INFORMATION FOR SEQ ID NO: 27:

(i) SEQUENCE CHARACTERISTICS:
    (A) LENGTH: 190
    (B) TYPE: Amino Acid
    (C) STRANDEDNESS: Not Relevant
    (D) TOPOLOGY: linear (ii) MOLECULE TYPE:
    (A) DESCRIPTION: protein (iii) HYPOTHETICAL: No (iv) ANTI-SENSE: No (v) FRAGMENT TYPE: No (vi) ORIGINAL SOURCE:
    (A) ORGANISM: Trichoderma viride
    (B) STRAIN: Trichoderma viride, 20kD (vii) IMMEDIATE SOURCE:

(viii) POSITION IN GENOME:

(ix) FEATURE:

(x) PUBLICATION INFORMATION:
    (A) AUTHORS: Yaguchi M., Roy C., Ujiie M., Watson D.C., & Wakarchuk W.
    (B) TITLE: Amino Acid Sequence of the Low-Molecular-Weight Xylanase from Trichoderma viride
    (C) JOURNAL: Xylans and Xylanases
    (D) VOLUME:
    (E) ISSUE:
    (F) PAGES: 149-154
    (G) DATE: 1992
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO: 27:

| GLN | THR | ILE | GLN | PRO | GLY | THR | GLY | PHE | ASN | ASN | GLY | TYR | PHE | TYR | SER |
|---|---|---|---|---|---|---|---|---|---|---|---|---|---|---|---|
| 1 | | | | 5 | | | | | 10 | | | | | 15 | |
| TYR | TRP | ASN | ASP | GLY | HIS | GLY | GLY | VAL | THR | TYR | THR | ASN | GLY | PRO | GLY |
| | | | 20 | | | | | 25 | | | | | 30 | | |
| GLY | GLN | PHE | SER | VAL | ASN | TRP | SER | ASN | SER | GLY | ASN | PHE | VAL | GLY | GLY |
| | | 35 | | | | | 40 | | | | | 45 | | | |
| LYS | GLY | TRP | GLN | PRO | GLY | THR | LYS | ASN | LYS | VAL | ILE | ASN | PHE | SER | GLY |
| | 50 | | | | | 55 | | | | | 60 | | | | |
| THR | TYR | ASN | PRO | ASN | GLY | ASN | SER | TYR | LEU | SER | VAL | TYR | GLY | TRP | SER |
| 65 | | | | | 70 | | | | 75 | | | | | | 80 |
| ARG | ASN | PRO | LEU | ILE | GLU | TYR | TYR | ILE | VAL | GLU | ASN | PHE | GLY | THR | TYR |
| | | | | 85 | | | | | 90 | | | | | 95 | |
| ASN | PRO | SER | THR | GLY | ALA | THR | LYS | LEU | GLY | GLU | VAL | THR | SER | ASP | GLY |
| | | | 100 | | | | | 105 | | | | | 110 | | |
| SER | VAL | TYR | ASP | ILE | TYR | ARG | THR | GLN | ARG | VAL | ASN | GLN | PRO | SER | ILE |
| | | 115 | | | | | 120 | | | | | 125 | | | |
| ILE | GLY | THR | ALA | THR | PHE | TYR | GLN | TYR | TRP | SER | VAL | ARG | ARG | THR | HIS |
| | 130 | | | | | 135 | | | | | 140 | | | | |
| ARG | SER | SER | GLY | SER | VAL | ASN | THR | ALA | ASN | HIS | PHE | ASN | ALA | TRP | ALA |
| 145 | | | | | 150 | | | | | 155 | | | | | 160 |
| GLN | GLN | GLY | LEU | THR | LEU | GLY | THR | MET | ASP | TYR | GLN | ILE | VAL | ALA | VAL |
| | | | | 165 | | | | | 170 | | | | | 175 | |
| GLU | GLY | TYR | PHE | SER | SER | GLY | SER | ALA | SER | ILE | THR | VAL | SER | | |
| | | | 180 | | | | | 185 | | | | | 190 | | |

(2) INFORMATION FOR SEQ ID NO: 28:

(i) SEQUENCE CHARACTERISTICS:
        (A) LENGTH: 190
        (B) TYPE: Amino Acid
        (C) STRANDEDNESS: Not Relevant
        (D) TOPOLOGY: linear (ii) MOLECULE TYPE:
        (A) DESCRIPTION: protein (iii) HYPOTHETICAL: No (iv) ANTI-SENSE: No (v) FRAGMENT TYPE: No (vi) ORIGINAL SOURCE:
(A) ORGANISM: Trichoderma harzianum
(B) STRAIN: Trichoderma harzianum, 20kD (vii) IMMEDIATE SOURCE:

(viii) POSITION IN GENOME:

(ix) FEATURE:

(x) PUBLICATION INFORMATION:
(A) AUTHORS: Yaguchi M., Roy C., Watson D.C., Rollin F., Tan L.U.L., Senior D.J., & Saddler J.N.
(B) TITLE:
(C) JOURNAL: Xylans and Xylanases
(D) VOLUME:
(E) ISSUE:
(F) PAGES: 435-438
(G) DATE: 1992
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 28:

| GLN | THR | ILE | GLY | PRO | GLY | THR | GLY | TYR | SER | ASN | GLY | TYR | TYR | TYR | SER |
|---|---|---|---|---|---|---|---|---|---|---|---|---|---|---|---|
| 1 | | | | 5 | | | | | 10 | | | | | 15 | |
| TYR | TRP | ASN | ASP | GLY | HIS | ALA | GLY | VAL | THR | TYR | THR | ASN | GLY | GLY | GLY |
| | | | 20 | | | | | 25 | | | | | 30 | | |
| GLY | SER | PHE | THR | VAL | ASN | TRP | SER | ASN | SER | GLY | ASN | PHE | VAL | GLY | GLY |
| | | 35 | | | | | 40 | | | | | 45 | | | |
| LYS | GLY | TRP | GLN | PRO | GLY | THR | LYS | ASN | LYS | VAL | ILE | ASN | PHE | SER | GLY |
| | 50 | | | | | 55 | | | | | 60 | | | | |
| SER | TYR | ASN | PRO | ASN | GLY | ASN | SER | TYR | LEU | SER | ILE | TYR | GLY | TRP | SER |
| 65 | | | | | 70 | | | | 75 | | | | | | 80 |
| ARG | ASN | PRO | LEU | ILE | GLU | TYR | TYR | ILE | VAL | GLU | ASN | PHE | GLY | THR | TYR |
| | | | | 85 | | | | | 90 | | | | | 95 | |
| ASN | PRO | SER | THR | GLY | ALA | THR | LYS | LEU | GLY | GLU | VAL | THR | SER | ASP | GLY |
| | | | 100 | | | | | 105 | | | | | 110 | | |
| SER | VAL | TYR | ASP | ILE | TYR | ARG | THR | GLN | ARG | VAL | ASN | GLN | PRO | SER | ILE |
| | | 115 | | | | | 120 | | | | | 125 | | | |
| ILE | GLY | THR | ALA | THR | PHE | TYR | GLN | TYR | TRP | SER | VAL | ARG | ARG | ASN | HIS |
| | 130 | | | | | 135 | | | | | 140 | | | | |
| ARG | SER | SER | GLY | SER | VAL | ASN | THR | ALA | ASN | HIS | PHE | ASN | ALA | TRP | ALA |
| 145 | | | | | 150 | | | | | 155 | | | | | 160 |
| SER | HIS | GLY | LEU | THR | LEU | GLY | THR | MET | ASP | TYR | GLN | ILE | VAL | ALA | VAL |
| | | | | 165 | | | | | 170 | | | | | 175 | |
| GLU | GLY | TYR | PHE | SER | SER | GLY | SER | ALA | SER | ILE | THR | VAL | SER | | |
| | | | 180 | | | | | 185 | | | | | 190 | | |

(2) INFORMATION FOR SEQ ID NO: 29:

(i) SEQUENCE CHARACTERISTICS:
(A) LENGTH: 197
(B) TYPE: Amino Acid
(C) STRANDEDNESS: Not Relevant
(D) TOPOLOGY: linear (ii) MOLECULE TYPE:
(A) DESCRIPTION: protein (iii) HYPOTHETICAL: No (iv) ANTI-SENSE: No (v) FRAGMENT TYPE: No (vi) ORIGINAL SOURCE:
    (A) ORGANISM: Schizophyllum commune
    (B) STRAIN: Schizophyllum commune, Xylanase A (vii) IMMEDIATE SOURCE:

(viii) POSITION IN GENOME:

(ix) FEATURE:

(x) PUBLICATION INFORMATION:
    (A) AUTHORS: Oku T., Yaguchi M., Paice M., & Jurasek L.
    (B) TITLE:
    (C) JOURNAL: Canadian Fed. Biol. Soc. Annu. Meet.
    (D) VOLUME:
    (E) ISSUE:
    (F) PAGES: Abstract 676
    (G) DATE: 1988
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO: 29:

| SER | GLY | THR | PRO | SER | SER | THR | GLY | THR | ASP | GLY | GLY | TYR | TYR | TYR | SER |
|---|---|---|---|---|---|---|---|---|---|---|---|---|---|---|---|
| 1 | | | | 5 | | | | | 10 | | | | | | 15 |
| TRP | TRP | THR | ASP | GLY | ALA | GLY | ASP | ALA | THR | TYR | GLN | ASN | ASN | GLY | GLY |
| | | | 20 | | | | | 25 | | | | | 30 | | |
| GLY | SER | TYR | THR | LEU | THR | TRP | SER | GLY | ASN | ASN | GLY | ASN | LEU | VAL | GLY |
| | | 35 | | | | | 40 | | | | | 45 | | | |
| GLY | LYS | GLY | TRP | ASN | PRO | GLY | ALA | ALA | SER | ARG | SER | ILE | SER | TYR | SER |
| | 50 | | | | | 55 | | | | | 60 | | | | |
| GLY | THR | TYR | GLN | PRO | ASN | GLY | ASN | SER | TYR | LEU | SER | VAL | TYR | GLY | TRP |
| 65 | | | | | 70 | | | | | 75 | | | | | 80 |
| THR | ARG | SER | SER | LEU | ILE | GLU | TYR | TYR | ILE | VAL | GLU | SER | TYR | GLY | SER |
| | | | | 85 | | | | | 90 | | | | | 95 | |
| TYR | ASP | PRO | SER | SER | ALA | ALA | SER | HIS | LYS | GLY | SER | VAL | THR | CYS | ASN |
| | | | 100 | | | | | 105 | | | | | 110 | | |
| GLY | ALA | THR | TYR | ASP | ILE | LEU | SER | THR | TRP | ARG | TYR | ASN | ALA | PRO | SER |
| | | 115 | | | | | 120 | | | | | 125 | | | |
| ILE | ASP | GLY | THR | GLN | THR | PHE | GLU | GLN | PHE | TRP | SER | VAL | ARG | ASN | PRO |
| | 130 | | | | | 135 | | | | | 140 | | | | |
| LYS | LYS | ALA | PRO | GLY | GLY | SER | ILE | SER | GLY | THR | VAL | ASP | VAL | GLN | CYS |
| 145 | | | | | 150 | | | | | 155 | | | | | 160 |
| HIS | PHE | ASP | ALA | TRP | LYS | GLY | LEU | GLY | MET | ASN | LEU | GLY | SER | GLU | HIS |
| | | | | 165 | | | | | 170 | | | | | 175 | |
| ASN | TYR | GLN | ILE | VAL | ALA | THR | GLU | GLY | TYR | GLN | SER | SER | GLY | THR | ALA |
| | | | 180 | | | | | 185 | | | | | 190 | | |
| THR | ILE | THR | VAL | THR | | | | | | | | | | | |
| | | 195 | | | | | | | | | | | | | |

(2) INFORMATION FOR SEQ ID NO: 30:

(i) SEQUENCE CHARACTERISTICS:
    (A) LENGTH: 184
    (B) TYPE: Amino Acid
    (C) STRANDEDNESS: Not Relevant
    (D) TOPOLOGY: linear (ii) MOLECULE TYPE:
    (A) DESCRIPTION: protein (iii) HYPOTHETICAL: No (iv) ANTI-SENSE: No ( v ) FRAGMENT TYPE: No ( v i ) ORIGINAL SOURCE:
( A ) ORGANISM: Aspergillus niger, var. awamori ( v i i ) IMMEDIATE SOURCE:

( v i i i ) POSITION IN GENOME:

( i x ) FEATURE:

( x ) PUBLICATION INFORMATION:
( A ) AUTHORS: Maat, J., Roza, M., Verbakel, J., Stam,
H., Santos da Silva, M.J., Egmond, M.R.,
Hagemans, M.L.D., Gorcom, R.F.M.v.,
Hessing, J.G.M., Hondel, C.A.M.J.J.v.d.
& Rotterdam, C.v.
( B ) TITLE:
( C ) JOURNAL: Xylans and Xylanases
( D ) VOLUME:
( E ) ISSUE:
( F ) PAGES: 349-360
( G ) DATE: 1992
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO: 30:

| SER | ALA | GLY | ILE | ASN | TYR | VAL | GLN | ASN | TYR | ASN | GLY | ASN | LEU | GLY | ASP |
|---|---|---|---|---|---|---|---|---|---|---|---|---|---|---|---|
| 1 | | | | 5 | | | | | 10 | | | | | 15 | |

| PHE | THR | TYR | ASP | GLU | SER | ALA | GLY | THR | PHE | SER | MET | TYR | TRP | GLU | ASP |
|---|---|---|---|---|---|---|---|---|---|---|---|---|---|---|---|
| | | | 20 | | | | | 25 | | | | | 30 | | |

| GLY | VAL | SER | SER | ASP | PHE | VAL | VAL | GLY | LEU | GLY | TRP | THR | THR | GLY | SER |
|---|---|---|---|---|---|---|---|---|---|---|---|---|---|---|---|
| | | | 35 | | | | 40 | | | | | 45 | | | |

| SER | ASN | ALA | ILE | THR | TYR | SER | ALA | GLU | TYR | SER | ALA | SER | GLY | SER | SER |
|---|---|---|---|---|---|---|---|---|---|---|---|---|---|---|---|
| | 50 | | | | | 55 | | | | | | 60 | | | |

| SER | TYR | LEU | ALA | VAL | TYR | GLY | TRP | VAL | ASN | TYR | PRO | GLY | ALA | GLU | TYR |
|---|---|---|---|---|---|---|---|---|---|---|---|---|---|---|---|
| 65 | | | | | 70 | | | | | 75 | | | | | 80 |

| TYR | ILE | VAL | GLU | ASP | TYR | GLY | ASP | TYR | ASN | PRO | CYS | SER | SER | ALA | THR |
|---|---|---|---|---|---|---|---|---|---|---|---|---|---|---|---|
| | | | | 85 | | | | | 90 | | | | | 95 | |

| SER | LEU | GLY | THR | VAL | TYR | SER | ASP | GLY | SER | THR | TYR | GLN | VAL | CYS | THR |
|---|---|---|---|---|---|---|---|---|---|---|---|---|---|---|---|
| | | | | 100 | | | | | 105 | | | | | 110 | |

| ASP | THR | ARG | ILE | ASN | GLU | PRO | SER | ILE | THR | GLY | THR | SER | THR | PHE | THR |
|---|---|---|---|---|---|---|---|---|---|---|---|---|---|---|---|
| | | 115 | | | | | 120 | | | | | 125 | | | |

| GLN | TYR | PHE | SER | VAL | ARG | GLU | SER | THR | ARG | THR | SER | GLY | THR | VAL | THR |
|---|---|---|---|---|---|---|---|---|---|---|---|---|---|---|---|
| | 130 | | | | | 135 | | | | | 140 | | | | |

| VAL | ALA | ASN | HIS | PHE | ASN | PHE | TRP | ALA | GLN | HIS | GLY | PHE | GLY | ASN | SER |
|---|---|---|---|---|---|---|---|---|---|---|---|---|---|---|---|
| 145 | | | | | 150 | | | | | 155 | | | | | 160 |

| ASP | PHE | ASN | TYR | GLN | VAL | MET | ALA | VAL | GLU | ALA | TRP | SER | GLY | ALA | GLY |
|---|---|---|---|---|---|---|---|---|---|---|---|---|---|---|---|
| | | | | 165 | | | | | 170 | | | | | 175 | |

| SER | ALA | SER | VAL | THR | ILE | SER | SER |
|---|---|---|---|---|---|---|---|
| | | | 180 | | | | |

( 2 ) INFORMATION FOR SEQ ID NO: 31:

( i ) SEQUENCE CHARACTERISTICS:
( A ) LENGTH: 184
( B ) TYPE: Amino Acid
( C ) STRANDEDNESS: Not Relevant
( D ) TOPOLOGY: linear ( i i ) MOLECULE TYPE:
( A ) DESCRIPTION: protein ( i i i ) HYPOTHETICAL: No ( i v ) ANTI-SENSE: No (v) FRAGMENT TYPE: No (vi) ORIGINAL SOURCE:
    (A) ORGANISM: Aspergillus tubigensis
    (B) STRAIN: Aspergillus tubigensis A (vii) IMMEDIATE SOURCE:

(viii) POSITION IN GENOME:

(ix) FEATURE:

(x) PUBLICATION INFORMATION:
    (A) AUTHORS: de Graaff, L.H., van den Broeck, H.C.,
        van Ooijan, A.J.J. & Visser, J.
    (B) TITLE:
    (C) JOURNAL: Xylans and Xylanases
    (D) VOLUME:
    (E) ISSUE:
    (F) PAGES: 235-246
    (G) DATE: 1992
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO: 31:

```
ALA GLY ILE ASN TYR VAL GLN ASN TYR ASN GLN ASN LEU GLY ASP PHE
 1               5                   10                  15
THR TYR ASP GLU SER ALA GLY THR PHE SER MET TYR TRP GLU ASP GLY
            20                  25                  30
VAL SER SER ASP PHE VAL VAL GLY LEU GLY GLY TRP THR THR GLY SER
        35                  40                  45
SER ASN ALA ILE THR TYR SER ALA GLU TYR SER ALA SER GLY SER ALA
    50                  55                  60
SER TYR LEU ALA VAL TYR GLY TRP VAL ASN TYR PRO GLN ALA GLU TYR
65                  70                  75                  80
TYR ILE VAL GLU ASP TYR GLY ASP TYR ASN PRO CYS SER SER ALA THR
            85                  90                  95
SER LEU GLY THR VAL TYR SER ASP GLY SER THR TYR GLN VAL CYS THR
            100                 105                 110
ASP THR ARG ILE ASN GLU PRO SER ILE THR GLY THR SER THR PHE THR
        115                 120                 125
GLN TYR PHE SER VAL ARG GLU SER THR ARG THR SER GLY THR VAL THR
    130                 135                 140
VAL ALA ASN HIS PHE ASN PHE TRP ALA HIS HIS GLY PHE HIS ASN SER
145                 150                 155                 160
ASP PHE ASN TYR GLN VAL VAL ALA VAL GLU ALA TRP SER GLY ALA GLY
            165                 170                 175
SER ALA ALA VAL THR ILE SER SER
            180
```

(2) INFORMATION FOR SEQ ID NO: 32:

(i) SEQUENCE CHARACTERISTICS:
        (A) LENGTH: 178
        (B) TYPE: Amino Acid
        (C) STRANDEDNESS: Not Relevant
        (D) TOPOLOGY: linear (ii) MOLECULE TYPE:
        (A) DESCRIPTION: protein (iii) HYPOTHETICAL: No (iv) ANTI-SENSE: No (v) FRAGMENT TYPE: No (vi) ORIGINAL SOURCE:
    (A) ORGANISM: Trichoderma reesei
    (B) STRAIN: Trichoderma reesei, XYN I, 19kD, pI 5.2
    (C) INDIVIDUAL ISOLATE:

(vii) IMMEDIATE SOURCE:

(viii) POSITION IN GENOME:

(ix) FEATURE:

(x) PUBLICATION INFORMATION:
    (A) AUTHORS: Torronene, A., Mach, R.L., Messner, R., Gonzalez, R., Kalkkinen, N., Harkki, A. & Kubicek, C.P.
    (B) TITLE:
    (C) JOURNAL: Bio/Technology
    (D) VOLUME: 10
    (E) ISSUE:
    (F) PAGES: 1461-1465
    (G) DATE: 1992
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO: 32:

```
ALA SER ILE ASN TYR ASP GLN ASN TYR GLN THR GLY GLY GLN VAL SER
 1           5                  10                      15
TYR SER PRO SER ASN THR GLY PHE SER VAL ASN TRP ASN THR GLN ASP
            20                  25                  30
ASP PHE VAL VAL GLY VAL GLY TRP THR THR GLY SER SER ALA PRO ILE
        35                  40                  45
ASN PHE GLY GLY SER PHE SER VAL ASN SER GLY THR GLY LEU LEU SER
        50              55                  60
VAL TYR GLY TRP SER THR ASN PRO LEU VAL GLU TYR TYR ILE MET GLU
 65              70                  75                      80
ASP ASN HIS ASN TYR PRO ALA GLN GLY THR VAL LYS GLY THR VAL THR
                85                  90                  95
SER ASP GLY ALA THR TYR THR ILE TRP GLU ASN THR ARG VAL ASN GLU
            100                 105                 110
PRO SER ILE GLN GLY THR ALA THR PHE ASN GLN TYR ILE SER VAL ARG
            115                 120                 125
ASN SER PRO ARG THR SER GLY THR VAL THR VAL GLN ASN HIS PHE ASN
        130                 135                 140
TRP ALA SER LEU GLY LEU HIS LEU GLY GLN MET MET ASN TYR GLN VAL
145                 150                 155                 160
VAL ALA VAL GLU GLY TRP GLY GLY SER GLY SER ALA SER GLN SER VAL
                165                 170                 175
SER ASN
```

(2) INFORMATION FOR SEQ ID NO: 33:

(i) SEQUENCE CHARACTERISTICS:
        (A) LENGTH: 189
        (B) TYPE: Amino Acid
        (C) STRANDEDNESS: Not Relevant
        (D) TOPOLOGY: linear (ii) MOLECULE TYPE:
        (A) DESCRIPTION: protein (iii) HYPOTHETICAL: No (iv) ANTI-SENSE: No (v) FRAGMENT TYPE: No (vi) ORIGINAL SOURCE:

(A) ORGANISM: Streptomyces sp.
(B) STRAIN: Streptomyces sp. #icrosoft Corp (vii) IMMEDIATE SOURCE:

(viii) POSITION IN GENOME:

(ix) FEATURE:

(x) PUBLICATION INFORMATION:
 (A) AUTHORS: Nagashima M., Okumoto Y. & Okanishi M.
 (B) TITLE:
 (C) JOURNAL: Trends in Actinomycetologia
 (D) VOLUME:
 (E) ISSUE:
 (F) PAGES: 91-96
 (G) DATE: 1989
 (H) DOCUMENT NUMBER:
 (I) FILING DATE:
 (J) PUBLICATION DATE:
 (K) RELEVANT RESIDUES IN SEQ ID NO:

(xi) SEQUENCE DESCRIPTION: SEQ ID NO: 33:

| | | | | | | | | | | | | | | |
|---|---|---|---|---|---|---|---|---|---|---|---|---|---|---|
| ALA | THR | THR | ILE | THR | ASN | GLU | THR | GLY | TYR | ASP | GLY | MET | TYR | TYR | SER |
| 1 | | | | 5 | | | | | 10 | | | | | 15 |
| PHE | TRP | THR | ASP | GLY | GLY | GLY | SER | VAL | SER | MET | THR | LEU | ASN | GLY | GLY |
| | | | 20 | | | | | 25 | | | | | 30 | | |
| GLY | SER | TYR | SER | THR | ARG | TRP | THR | ASN | CYS | GLY | ASN | PHE | VAL | ALA | GLY |
| | | 35 | | | | | 40 | | | | | 45 | | | |
| LYS | GLY | TRP | ALA | ASN | GLY | GLY | ARG | ARG | THR | VAL | ARG | TYR | THR | GLY | TRP |
| | 50 | | | | | 55 | | | | | 60 | | | | |
| PHE | ASN | PRO | SER | GLY | ASN | GLY | TYR | GLY | CYS | LEU | TYR | GLY | TRP | THR | SER |
| 65 | | | | | 70 | | | | | 75 | | | | | 80 |
| ASN | PRO | LEU | VAL | GLU | TYR | TYR | ILE | VAL | ASP | ASN | TRP | GLY | SER | TYR | ARG |
| | | | | 85 | | | | | 90 | | | | | 95 | |
| PRO | THR | GLY | GLU | THR | ARG | GLY | THR | VAL | HIS | SER | ASP | GLY | GLY | THR | TYR |
| | | | | 100 | | | | | 105 | | | | | 110 | |
| ASP | ILE | TYR | LYS | THR | THR | ARG | TYR | ASN | ALA | PRO | SER | VAL | GLU | ALA | PRO |
| | | | 115 | | | | | 120 | | | | | 125 | | |
| ALA | ALA | PHE | ASP | GLN | TYR | TRP | SER | VAL | ARG | GLN | SER | LYS | VAL | THR | SER |
| | 130 | | | | | 135 | | | | | 140 | | | | |
| GLY | THR | ILE | THR | THR | GLY | ASN | HIS | PHE | ASP | ALA | TRP | ALA | ARG | ALA | GLY |
| 145 | | | | | 150 | | | | | 155 | | | | | 160 |
| MET | ASN | MET | GLY | ASN | PHE | ARG | TYR | TYR | MET | ILE | MET | ALA | THR | GLU | GLY |
| | | | | 165 | | | | | 170 | | | | | 175 | |
| TYR | GLN | SER | SER | GLY | SER | SER | THR | ILE | THR | VAL | SER | GLY | | | |
| | | | 180 | | | | | 185 | | | | | | | |

(2) INFORMATION FOR SEQ ID NO: 34:

(i) SEQUENCE CHARACTERISTICS:
 (A) LENGTH: 215
 (B) TYPE: Amino Acid
 (C) STRANDEDNESS: Not Relevant
 (D) TOPOLOGY: linear (ii) MOLECULE TYPE:
 (A) DESCRIPTION: protein (iii) HYPOTHETICAL: No (iv) ANTI-SENSE: No (v) FRAGMENT TYPE: No (vi) ORIGINAL SOURCE:
 (A) ORGANISM: Streptomyces lividans
 (B) STRAIN: Streptomyces lividans, Xln B (vii) IMMEDIATE SOURCE:

(viii) POSITION IN GENOME:

(ix) FEATURE:

(x) PUBLICATION INFORMATION:
   (A) AUTHORS: Shareck, F., Roy, C., Yaguchi, M.,
        Morosoli, R. & Kluepfel, D.
   (B) TITLE:
   (C) JOURNAL: Gene
   (D) VOLUME: 107
   (E) ISSUE:
   (F) PAGES: 75-82
   (G) DATE: 1991
   (H) DOCUMENT NUMBER:
   (I) FILING DATE:
   (J) PUBLICATION DATE:
   (K) RELEVANT RESIDUES IN SEQ ID NO:

(xi) SEQUENCE DESCRIPTION: SEQ ID NO: 34:

```
ASP THR VAL VAL THR THR ASN GLN GLU GLY THR ASN ASN GLY TYR TYR
 1            5                  10                     15

TYR SER PHE TRP THR ASP SER GLN GLY THR VAL SER MET ASN MET GLY
            20              25                  30

SER GLY GLY GLN TYR SER THR SER TRP ARG ASN THR GLY ASN PHE VAL
        35              40                  45

ALA GLY LYS GLY TRP ALA ASN GLY GLY ARG ARG THR VAL GLN TYR SER
    50              55                  60

GLY SER PHE ASN PRO SER GLY ASN ALA TYR LEU ALA LEU TYR GLY TRP
 65              70              75                      80

THR SER ASN PRO LEU VAL GLU TYR TYR ILE VAL ASP ASN TRP GLY THR
                85                  90                  95

TYR ARG PRO THR GLY GLU TYR LYS GLY THR VAL THR SER ASP GLY GLY
            100             105                 110

THR TYR ASP ILE TYR LYS THR THR ARG VAL ASN LYS PRO SER VAL GLU
        115             120             125

GLY THR ARG THR PHE ASP GLN TYR TRP SER VAL ARG GLN SER LYS ARG
    130             135             140

THR GLY GLY THR ILE THR THR GLY ASN HIS PHE ASP ALA TRP ALA ARG
145             150             155                     160

ALA GLY MET PRO LEU GLY ASN PHE SER TYR TYR MET ILE MET ALA THR
            165             170                 175

GLU GLY TYR GLN SER SER GLY THR SER SER ILE ASN VAL GLY GLY THR
            180             185                 190

GLY GLY GLY ASP SER GLY GLY ALA THR THR GLY ALA VAL ALA ALA GLY
        195             200             205

ALA PRO THR VAL SER ALA GLY
    210             215
```

(2) INFORMATION FOR SEQ ID NO: 35:

(i) SEQUENCE CHARACTERISTICS:
       (A) LENGTH: 191
       (B) TYPE: Amino Acid
       (C) STRANDEDNESS: Not Relevant
       (D) TOPOLOGY: linear (ii) MOLECULE TYPE:
       (A) DESCRIPTION: protein (iii) HYPOTHETICAL: No (iv) ANTI-SENSE: No (v) FRAGMENT TYPE: No ( v i ) ORIGINAL SOURCE:
    ( A ) ORGANISM: Streptomyces lividans
    ( B ) STRAIN: Streptomyces lividans, Xln C ( v i i ) IMMEDIATE SOURCE:

( v i i i ) POSITION IN GENOME:

( i x ) FEATURE:

( x ) PUBLICATION INFORMATION:
    ( A ) AUTHORS: Shareck, F., Roy, C., Yaguchi, M.,
                Morosoli, R. & Kluepfel, D.
    ( B ) TITLE:
    ( C ) JOURNAL: Gene
    ( D ) VOLUME: 107
    ( E ) ISSUE:
    ( F ) PAGES: 75-82
    ( G ) DATE: 1991
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO: 35:

```
ALA THR THR ILE THR THR ASN GLN THR GLY THR ASP GLY MET TYR TYR
 1           5                  10                      15

SER PHE TRP THR ASP GLY GLY GLY SER VAL SER MET THR LEU ASN GLY
             20              25              30

GLY GLY SER TYR SER THR GLN TRP THR ASN CYS GLY ASN PHE VAL ALA
         35              40                  45

GLY LYS GLY TRP SER THR GLY ASP GLY ASN VAL ARG TYR ASN GLY TYR
     50                  55                  60

PHE ASN PRO VAL GLY ASN GLY TYR GLY CYS LEU TYR GLY TRP THR SER
 65                  70              75                      80

ASN PRO LEU VAL GLU TYR TYR ILE VAL ASP ASN TRP GLY SER TYR ARG
                 85                  90                  95

PRO THR GLY THR TYR LYS GLY THR VAL SER SER ASP GLY GLY THR TYR
             100                 105             110

ASP ILE TYR GLN THR THR ARG TYR ASN ALA PRO SER VAL GLU GLY THR
         115                 120             125

LYS THR PHE GLN GLN TYR TRP SER VAL ARG GLN SER LYS VAL THR SER
     130             135                 140

GLY SER GLY THR ILE THR THR GLY ASN HIS PHE ASP ALA TRP ALA ARG
145                 150             155                     160

ALA GLY MET ASN MET GLY GLN PHE ARG TYR TYR MET ILE MET ALA THR
             165                 170             175

GLU GLY TYR GLN SER SER GLY SER SER ASN ILE THR VAL SER GLY
             180             185             190
```

( 2 ) INFORMATION FOR SEQ ID NO: 36:

( i ) SEQUENCE CHARACTERISTICS:
        ( A ) LENGTH: 185
        ( B ) TYPE: Amino Acid
        ( C ) STRANDEDNESS: Not Relevant
        ( D ) TOPOLOGY: linear ( i i ) MOLECULE TYPE:
        ( A ) DESCRIPTION: protein ( i i i ) HYPOTHETICAL: No ( i v ) ANTI-SENSE: No ( v ) FRAGMENT TYPE: No ( v i ) ORIGINAL SOURCE:
        ( A ) ORGANISM: Bacillus circulans ( v i i ) IMMEDIATE SOURCE:

( v i i i ) POSITION IN GENOME:

( i x ) FEATURE:

( x ) PUBLICATION INFORMATION:
- ( A ) AUTHORS: Yang R.C.A., MacKenzie C.R. & Narang R.A.
- ( B ) TITLE:
- ( C ) JOURNAL: Nucleic Acids Res.
- ( D ) VOLUME: 16
- ( E ) ISSUE:
- ( F ) PAGES: 7187
- ( G ) DATE: 1988
- ( H ) DOCUMENT NUMBER:
- ( I ) FILING DATE:
- ( J ) PUBLICATION DATE:
- ( K ) RELEVANT RESIDUES IN SEQ ID NO:

( x i ) SEQUENCE DESCRIPTION: SEQ ID NO: 36:

| ALA | SER | THR | ASP | TYR | TRP | GLN | ASN | TRP | THR | ASP | GLY | GLY | GLY | ILE | VAL |
|---|---|---|---|---|---|---|---|---|---|---|---|---|---|---|---|
| 1 | | | | 5 | | | | | 10 | | | | | 15 | |
| ASN | ALA | VAL | ASN | GLY | SER | GLY | GLY | ASN | TYR | SER | VAL | ASN | TRP | SER | ASN |
| | | | 20 | | | | | 25 | | | | | 30 | | |
| THR | GLY | ASN | PHE | VAL | VAL | GLY | LYS | GLY | TRP | THR | THR | GLY | SER | PRO | PHE |
| | | 35 | | | | | 40 | | | | | 45 | | | |
| ARG | THR | ILE | ASN | TYR | ASN | ALA | GLY | VAL | TRP | ALA | PRO | ASN | GLY | ASN | GLY |
| | 50 | | | | 55 | | | | | 60 | | | | | |
| TYR | LEU | THR | LEU | TYR | GLY | TRP | THR | ARG | SER | PRO | LEU | ILE | GLU | TYR | TYR |
| 65 | | | | | 70 | | | | 75 | | | | | | 80 |
| VAL | VAL | ASP | SER | TRP | GLY | THR | TYR | ARG | PRO | THR | GLY | THR | TYR | LYS | GLY |
| | | | | 85 | | | | | 90 | | | | | 95 | |
| THR | VAL | LYS | SER | ASP | GLY | GLY | THR | TYR | ASP | ILE | TYR | THR | THR | THR | ARG |
| | | | | 100 | | | | | 105 | | | | | 110 | |
| TYR | ASN | ALA | PRO | SER | ILE | ASP | GLY | ASP | ARG | THR | THR | PHE | THR | GLN | TYR |
| | | | 115 | | | | | 120 | | | | | 125 | | |
| TRP | SER | VAL | ARG | GLN | SER | LYS | ARG | PRO | THR | GLY | SER | ASN | ALA | THR | ILE |
| | | | 130 | | | | 135 | | | | | 140 | | | |
| THR | PHE | THR | ASN | HIS | VAL | ASN | ALA | TRP | LYS | SER | HIS | GLY | MET | ASN | LEU |
| 145 | | | | | 150 | | | | | 155 | | | | | 160 |
| GLY | SER | ASN | TRP | ALA | TYR | GLN | VAL | MET | ALA | THR | GLU | GLY | TYR | GLN | SER |
| | | | | 165 | | | | | 170 | | | | | 175 | |
| SER | GLY | SER | SER | ASN | VAL | THR | VAL | TRP | | | | | | | |
| | | | | 180 | | | | 185 | | | | | | | |

( 2 ) INFORMATION FOR SEQ ID NO: 37:

( i ) SEQUENCE CHARACTERISTICS:
- ( A ) LENGTH: 185
- ( B ) TYPE: Amino Acid
- ( C ) STRANDEDNESS: Not Relevant
- ( D ) TOPOLOGY: linear ( i i ) MOLECULE TYPE:
- ( A ) DESCRIPTION: protein ( i i i ) HYPOTHETICAL: No ( i v ) ANTI-SENSE: No ( v ) FRAGMENT TYPE: No ( v i ) ORIGINAL SOURCE:
- ( A ) ORGANISM: Bacillus subtilis ( v i i ) IMMEDIATE SOURCE:

(viii) POSITION IN GENOME:

(ix) FEATURE:

(x) PUBLICATION INFORMATION:
(A) AUTHORS: Paice M.G., Bourbonnais R., Desrochers
M., Jurasek L., & Yaguchi M.
(B) TITLE:
(C) JOURNAL: Arch. Microbiol.
(D) VOLUME: 144
(E) ISSUE:
(F) PAGES: 201-206
(G) DATE: 1986
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 37:

```
ALA  SER  THR  ASP  TYR  TRP  GLN  ASN  TRP  THR  ASP  GLY  GLY  GLY  ILE  VAL
 1              5                        10                       15

ASN  ALA  VAL  ASN  GLY  SER  GLY  GLY  ASN  TYR  SER  VAL  ASN  TRP  SER  ASN
               20                        25                       30

THR  GLY  ASN  PHE  VAL  VAL  GLY  LYS  GLY  TRP  THR  THR  GLY  SER  PRO  PHE
               35                   40                       45

ARG  THR  ILE  ASN  TYR  ASN  ALA  GLY  VAL  TRP  ALA  PRO  ASN  GLY  ASN  GLY
      50                        55                  60

TYR  LEU  THR  LEU  TYR  GLY  TRP  THR  ARG  SER  PRO  LEU  ILE  GLU  TYR  TYR
 65                       70                        75                        80

VAL  VAL  ASP  SER  TRP  GLY  THR  TYR  ARG  PRO  THR  GLY  THR  TYR  LYS  GLY
                85                        90                        95

THR  VAL  LYS  SER  ASP  GLY  GLY  THR  TYR  ASP  ILE  TYR  THR  THR  THR  ARG
               100                       105                      110

TYR  ASN  ALA  PRO  SER  ILE  ASP  GLY  ASP  ARG  THR  THR  PHE  THR  GLN  TYR
               115                      120                      125

TRP  SER  VAL  ARG  GLN  SER  LYS  ARG  PRO  THR  GLY  SER  ASN  ALA  THR  ILE
      130                      135                       140

THR  PHE  SER  ASN  HIS  VAL  ASN  ALA  TRP  LYS  SER  HIS  GLY  MET  ASN  LEU
145                       150                      155                       160

GLY  SER  ASN  TRP  ALA  TYR  GLN  VAL  MET  ALA  THR  GLU  GLY  TYR  GLN  SER
                165                       170                      175

SER  GLY  SER  SER  ASN  VAL  THR  VAL  TRP
               180                      185
```

The embodiments of the invention in which an exclusive property of privilege is claimed are defined as follows:

1. A modified family G xylanase essentially having the structure of the *B. circulans* enzyme or mutated to essentially have this structure, wherein said xylanase has increased thermostability and wherein said xylanase is modified at least through either the introduction of a disulfide bridge, introduction of a N-terminal mutation, or both;

wherein the disulfide bridge is an intra-molecular bridge between two cysteine amino acids selected from the group consisting of 100 and 148, and 98 and 152, based on the amino acid numbering from *B. circulans*, or the disulphide bridge is an intermolecular bridge between two xylanase molecules, wherein a cysteine amino acid has been introduced in each of said two molecules at amino acid position 179, based on the amino acid numbering from *B. circulans* xylanase; and wherein the N-terminal mutation introduces a tyrosine or phenylalanine amino acid at amino acid position 3, 4 or 8 of the N-terminal region, or a combination thereof, based on the amino acid numbering from *B. circulans* xylanase.

2. The modified xylanase of claim 1 wherein the G family xylanase is selected from a bacterial or fungal xylanase.

3. The modified xylanase of claim 2 wherein the bacterial xylanase is from bacteria selected from the group consisting of *Bacillus pumilus*; *Clostridium acetobutylicum*; *Ruminococcus flavefaciens*; *Streptomyces* sp.; *Streptomyces lividans, B*; *Streptomyces lividans, C*; *Bacillus circulans*; and *Bacillus subtilis*.

4. The modified xylanase of claim 2 wherein the fungal xylanase is from fungi selected from the group consisting of *Trichoderma reesei, II*; *Trichoderma viride*; *Trichodenna harzianum*; *Schizophyllum commune*; *Aspergillus niger var. awamori*; *Aspergillus tubigensis, A*; and *Trichoderma reesei, I*.

5. The modified xylanase of claim 1 wherein the increased thermostability is represented by an increase of from 2° C. to 15° C.

6. The modified xylanase of claim 1 wherein said modified xylanase has an increased thermostability of 2° C. to 15° C., possesses specific activity of at least 60% of that of wild type xylanase and maintains at least 60% residual activity after incubation at an elevated temperature.

7. The modified xylanase of claim 1 wherein said modified xylanase is produced from clones selected from the group consisting of TS1, TS2, TS3a, TS3, TS4a, TS4, TS4M, TS4D, TS5a and TS6a.

8. The modified xylanase of claim 2 wherein said xylanase is modified by the introduction of an intra-molecular disulfide bridge.

9. The modified xylanase of claim 1 wherein said xylanase is modified by the introduction of an inter-molecular disulfide bridge.

10. The modified xylanase of claim 1 wherein said xylanase is modified by the introduction of an N-terminal mutation.

11. The modified xylanase of claim 1 wherein said xylanase is modified by the introduction of a intra-molecular disulfide bridge and an inter-molecular disulfide bridge.

12. The modified xylanase of claim 1 wherein said xylanase is modified through the introduction of an intra-molecular disulfide bridge; an inter-molecular disulfide bridge and an N-terminal mutation.

13. The modified xylanase of claim 1 wherein said xylanase is modified through the introduction of an intra-molecular disulfide bridge and an N-terminal mutation.

14. The modified xylanase of claim 1 wherein said xylanase is modified through the introduction of an inter-molecular disulfide bridge and an N-terminal mutation.

15. A modified family G xylanase essentially having the structure of the *B. circulans* enzyme or mutated to essentially have this structure, wherein said xylanase has increased thermostability and wherein said xylanase is modified at least through either the introduction of a disulfide bridge, introduction of a N-terminal mutation, or both; and wherein said modified xylanase is produced from clones selected from the group consisting of TS1, TS2, TS3a, TS3, TS4a, TS4, TS4M, TS4D, TS5a, and TS6a.

* * * * *